(12) United States Patent
Takatani et al.

(10) Patent No.: US 6,251,905 B1
(45) Date of Patent: Jun. 26, 2001

(54) TRICYCLIC COMPOUNDS, THEIR PRODUCTION AND USE

(75) Inventors: Muneo Takatani, Kyoto; Yumiko Shibouta, Suita; Kiminori Tomimatsu, Minoo; Tetsuji Kawamoto, Neyagawa, all of (JP)

(73) Assignee: Takeda Chemical Industries, Ltd., Osaka (JP)

( * ) Notice: Subject to any disclaimer, the term of this patent is extended or adjusted under 35 U.S.C. 154(b) by 0 days.

(21) Appl. No.: 09/234,876

(22) Filed: Jan. 21, 1999

Related U.S. Application Data

(62) Division of application No. 08/783,101, filed on Jan. 14, 1997, now Pat. No. 5,958,942, which is a continuation-in-part of application No. 08/500,945, filed as application No. PCT/JP95/01382 on Jul. 12, 1995, now abandoned.

(30) Foreign Application Priority Data

| Jul. 15, 1994 | (JP) | 6-163802 |
|---|---|---|
| Jul. 12, 1995 | (TH) | 027225 |
| Jul. 13, 1995 | (JP) | 7-177453 |
| Jul. 14, 1995 | (PH) | 50922 |
| Jul. 17, 1995 | (CN) | 84107355 |
| Jul. 17, 1995 | (ID) | P-951373 |
| Nov. 1, 1996 | (JP) | 8-292059 |

(51) Int. Cl.[7] ............ C07D 401/06; C07D 403/06; C07D 471/14; A61K 31/495; A61K 31/50

(52) U.S. Cl. ............ 514/253.03; 544/238; 544/333; 544/346

(58) Field of Search ............ 544/238, 333, 544/346; 514/253.03

(56) References Cited

PUBLICATIONS

Jazwinski et al.,Bulletin of the Polish Academy of Sciences Chemistry, 37(7–8),313–316 (1989).*
Sabljii et al.,Journal of Molecular Structure, 49(2), 415–420 (1978).*
Paudler et al.,The Journal of Heterocyclic Chemistry, 9 (1), 81–85 (Feb. 1972).*
Ceder et al., Journal of Heterocyclic Chemistry, 13 (5), 1029–1031 (Oct. 1976).*

* cited by examiner

Primary Examiner—Alan L. Rotman
(74) Attorney, Agent, or Firm—Wenderoth, Lind & Ponack, L.L.P.

(57) ABSTRACT

Tricyclic compound of the formula:

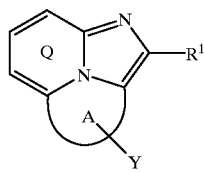

wherein ring A is a nitrogen-containing heterocyclic ring, having two nitrogen atoms as the hetero-atoms, which is optionally substituted with oxo or thioxo; ring Q may optionally be substituted;

Y is an optionally substituted hydrocarbon group, an optionally substituted hydroxyl group or an optionally substituted mecapto group, excluding for methyl group as Y; $R^1$ is a hydrogen atom, a halogen atom, an optionally substituted hydrocarbon group or an acyl group, or a salt thereof, having excellent PDGF-inhibiting activities, antihypertensive activities, activities of ameliorating renal diseases and activities of lowering lipid level.

47 Claims, No Drawings

TRICYCLIC COMPOUNDS, THEIR PRODUCTION AND USE

This application is a divisional of Ser. No. 08/783,101, filed Jan. 14, 1997, now U.S. Pat. No. 5,958,942, which is a continuation-in-part of Ser. No. 08/500,945, filed Aug. 7, 1995, now abandoned, which is a §371 application of PCT/JP95/01382, filed Jul. 12, 1995.

TECHNICAL FIELD

The present invention relates to a novel tricyclic compound, which is useful as a medicine having an excellent activity of inhibiting platelet-derived growth factor (PDGF), antihypertensive activity, ameliorating activity of renal diseases and lowering the cholesterol level, a process for producing the compound, and a pharmaceutical composition containing the compound.

BACKGROUND ART

With the progressive increase of aged population in recent years, various ischemic diseases in cerebral and cardiac vessels have been also increasing. As the therapeutic agents of these diseases, calcium channel blockers or angiotensin converting enzymes (ACE) inhibitors have been widely used in the clinical field and have served to decrease cerebrovascular disturbances due to hypertension. However, the mortality from ischemic heart diseases has not yet been decreased. For improving them, it has been considered that lowering blood pressure is not sufficient but improving lipid metabolism is necessary. And, the degree of antihypertensive action is important; namely, it has been considered that, the agents which keep the elasticity of blood vessels are more preferable even if their antihypertensive action is milder than the agents which lower blood pressure markedly. For keeping the elasticity of blood vessels, it is necessary to positively improve vascular hypertrophy or fibrosis. As the diseases causing vascular hypertrophy, there are mentioned, for example, hypertension, diabetes, glomerulosclerosis (chronic renal failure) and arteriosclerosis. Precutaneous transliminal coronary angioplasty (PTCA) is generally carried out in the case of coronary artery obstruction caused by platelet aggregation and accumulation. In this case, however, there is often observed that endothelium is injured to cause proliferation of vascular smooth muscle toward the inside of vessels and to lead to restoerosis.

As one of the common phenomena observed in these diseases mentioned above, the enhanced expression of platelet-derived growth factor (PDGF) or PDGF receptors (mRNA) has been reported.

More specifically stating; 1) In spontaneously hypertensive rats (SHR) and renal hypertensive animals, expression of PDGF or PDGF receptors is enhanced, or the tyrosine kinase activity associated with PDGF receptors is enhanced (R. Sarzani et al., Hypertension, 18, III 93/1991; P. Pauletto et al., 15th International Meeting of Hypertension, Melbourne, Abstract 1197/1994; M. D. Sauro and B. Thomas, Life Sci., 53, PL371/1993). 2) In the essential hypertensive patients with diabetes, it has been observed that blood concentration of PDGF in blood is higher than normal subjects. (P. Bolli et al., 15th International Meeting of Hypertension, Melbourne, Abstract 767/1994). 3) In human atherosclerotic plaques, expression of PDGF mRNA is enhanced (T. Barrett and P. Benditt, Proc. Natl. Acad. Sci. USA, 85, 2810/1988; J. N. Wilcox et al., J. Clin. Invest., 82, 1134/1988), in the vascular smooth muscle cells of diabetic rats with arteriosclerosis, expression of PDGF receptors is enhanced (T. Kanzaki, Y. Saitoh, Gendai Iryo (Modern Therapeutics), 23, 2614/1991). 4) In the blood vessels of balloon injured animals and humans after PTCA, the expression of PDGF or PDGF receptor is enhanced (M. W. Majesky et al., J. Cell Biol., 111, 2149/1990; M. Ueda et al., Circulation, 86 (Suppl.), 1/1992). 5) In renal mesangial cells of 5/6 nephrectomized rats, a model of focal glomerulosclerosis, expression of PDGF is enhanced (J. Floege et al., Kidney Int., 41, 297/1992). 6) In mesangium proliferative nephritis (IgA nephropathy) and a model of nephritis in rats, enhancement of PDGF in mesangial cells is observed (R. J. Johnson et al., J. Am. Soc. Nephrol., 4, 119/1993; H. E. Abboud et al., Kidney Int., 43, 252/1993). It is demonstrated that PDGF proliferates vascular smooth muscle cells or renal glomerular mesangial cells in vitro experiments (R. Ross et al., Cell, 46, 155/1986); J. Floege et al., Clin. Exp. Immunol., 86, 334/1991) and in vivo experiments (A. Jawien et al., J. Clin. Invest., 89, 507/1992; Y. Isaka et al., J. Clin. Invest., 92 2597/1993; J. Floege et al., J. Clin. Invest., 92, 2952/1993). It is also reported that the action of cytokine TGF-β (transforming growth factor β) is via the action of PDGF expressed by TGF-β (E. G. Battegay et al., Cell, 63, 515/1990). Furthermore, recently there have been a number of reports that hypertensive vascular hypertrophy and cardiac hypertrophy due to congestive heart failure are suppressed by administration of ACE inhibitors or angiotensin antagonistic agent. It is considered that, also in the angiotensin-mediated vascular hypertrophy and cardiac hypertrophy, PDGF plays a role (A. J. Naftilan et al., J. Clin. Invest., 83, 1419/1989; G. H. Gibbons et al., J. Clin. Invest., 90, 456/1992). Besides, it has been known that, in respect of the proliferation of vascular smooth muscle cells or renal mesangial cells, LDL-cholesterol and PDGF mutually cooperate to enhance the proliferation, which has been considered as one of factors causing arteriosclerosis. Therefore, drugs capable of specifically inhibiting the action of PDGF are expected to be useful therapeutic agents of various circulatory disturbances including arteriosclerosis.

On the other hand, as the tricyclic compounds, the following compounds are disclosed in the following literature references, namely, (1) J. Heterocycl. Chem., 1972, 9 (1), p.85, (2) J. Heterocycl. Chem., 1976, 13 (5), p.1029–1031, (3) J. Mol. Struct., Perkin Trans.1, 1978, 49 (2), p415–420, (4) J. Pharm. Soc. Jpn., 1978, 98 (5) p.631–635, (5) J. Crystallogr. Spectrosc. Res., 1989, 19 (1), p.159–166, (6) Bull. Pol. Acad. Sci., Chem., 1989, 37 (7–8), p.313–316, and (7) J. Chem. Soc., Perkin Trans. 1, 1987, (5), p.1159–1163. However, no reports concerning the therapeutic uses of these compounds has been found yet.

| Structural Formula | Symbol |
| --- | --- |
| [tricyclic structure with $R^1$ and X substituents] | $R^1$ = H or $CH_3$<br>X = O or $H_2$ |

| Structural Formula | Symbol |
| --- | --- |
| 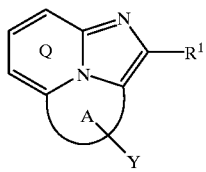 | $R^1$ = H or $CH_3$<br>$R^2$ = H or $CH_3$ |
| (structure) | $R^1$ = $SCH_3$<br>$R^2$ = H or $CH_3$ |
| (structure) | |
| (structure) | |

DISCLOSURE OF INVENTION

Circumstances being such as above, the development of novel and safely administrable therapeutic agents has been desired, which inhibit the action of PDGF.

The present inventors have made extensive and intensive studies, and succeeded in synthesizing, for the first time, a compound of the formula: (I')(hereinafter called the compound (I'))

(I')

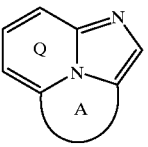

wherein ring A is a nitrogen-containing heterocyclic ring, having two nitrogen atoms as the hetero-atoms, which is optionally substituted with oxo or thioxo; ring Q may optionally be substituted;

Y is an optionally substituted hydrocarbon group, an optionally substituted hydroxyl group or an optionally substituted mercapto group, excluding methyl group as Y; and $R^1$ is a hydrogen atom, a halogen atom, an optionally substituted hydrocarbon group or an acyl group, or a salt thereof, whose characteristic feature of the chemical structure lies in the tricyclic condensed heterocyclic ring of the formula:

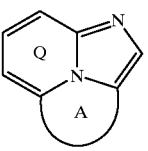

and the substituent on ring A, as the representative of the tricyclic condensed heterocyclic ring wherein the three kinds of rings of the pyridine ring Q, the imidazole ring and the heterocyclic ring A containing nitrogen-atom are condensed, comprising nitrogen-atom at the head of bridge in the condensed ring, especially a compound of the formula (I) (hereinafter called the compound (I)):

(I)

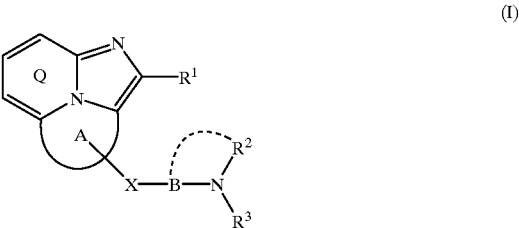

wherein ring A, ring Q and $R^1$ are as defined above;
B is an optionally substituted divalent hydrocarbon;
X is a bond, an oxygen atom or a sulfur atom;
$R^2$ is a hydrogen atom or an optionally substituted hydrocarbon group or, $R^2$ and B may form a ring together with the adjacent nitrogen atom; and
$R^3$ is an electron-withdrawing group, or a salt thereof, whose characteristic feature of the chemical structure lies in the tricyclic condensed heterocyclic ring of the formula:

(structure)

as mentioned above and the side-chain having an electron-withdrawing group at the terminal nitrogen, and found that the compound (I') or (I) produced thus above or a salt thereof has, unexpectedly, excellent PDGF-inhibiting action (e.g. actions of inhibiting cell proliferation or vascular constriction), antihypertensive action, action of ameliorating nephropathy and, further, action of lowering cholesterol level. The present inventors have further developed studies to accomplish the present invention.

More specifically, the present invention relates to
(1) a compound (I') or a salt thereof,
(2) a compound as described in (1) above, wherein Y is a hydrocarbon group, a hydroxyl group or a mercapto group, each of which optionally has a substituent comprising at least one nitrogen atom,
(3) a compound as described in (1) above, wherein Y is a hydrocarbon group, a hydroxyl group or a mercapto group, each of which optionally has a substituent comprising at least one electron-withdrawing group,
(4) a compound as defined in (1) above, wherein Y is a hydrocarbon group, a hydroxyl group or a mercapto group, each of which optionally has a substituent comprising an amino group which is substituted with at least one electron-withdrawing group, (5) a compound as defined in (1) above, wherein Y is group of the formula:

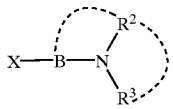

wherein B is an optionally substituted divalent hydrocarbon group;

X is a bond, an oxygen atom or a sulfur atom;

$R^2$ is a hydrogen atom or an optionally substituted hydrocarbon group, or $R^2$ and B may from a ring together with the adjacent nitrogen atom; and $R^{3a}$ is an electron-withdrawing group; or $R^2$ and $R^{3a}$ may form a ring together with the adjacent nitrogen atom, or a salt thereof, (6) a compound (I) or a salt thereof, (7) a compound as described in (1) above, wherein the nitrogen atom-containing heterocycleic ring is a 5- or 6-membered ring, (8) a compound as described in (1) above, wherein the ring Q may optionally be substituted with 1 to 3 substituents selected from the group consisting of (i) halogen atom, (ii) a $C_{1-4}$ alkyl group, (iii) a $C_{1-4}$ alkoxy group, (iv) a $C_{1-4}$ alkylthio group, (v) a hydroxyl group, (vi) a carboxyl group, (vii) a cyano group, (viii) a nitro group, (ix) a amino group, (x) a mono- or di-$C_{1-4}$ alkyl amino group, (xi) a formyl group, (xii) a mercapto group, (xiii) a $C_{1-4}$ alkyl-carbonyl group, (xiv) a $C_{1-4}$ alkoxy-carbonyl group, (xv) a sulfonyl group, (xvi) a $C_{1-4}$ alkyl sulfonyl group, (xvii) a carbamoyl group and (xviii) a mono- or di-$C_{1-4}$ alkyl-carbamoyl group, (9) a compound as described in (1) above, wherein the ring Q is unsubstituted,

(10) a compound as described in (1) above, wherein $R^1$ is a hydrogen atom, an optionally substituted alkyl group, an optionally substituted alkenyl group, an optionally substituted aralkyl group, an optionally substituted aryl group, an alkoxy carbonyl group, an alkyl carbamoyl group or an alkanoyl group,

(11) a compound as described in (1) above, wherein $R^1$ is a hydrogen atom, a $C_{1-6}$ alkyl group or a phenyl group,

(12) a compound as described in (5) above, wherein $R^2$ is a hydrogen atom, an optionally substituted alkyl group or an optionally substituted alkenyl group,

(13) a compound as described in (3) above, wherein the electron-withdrawing group is (i) —$SO_2R^4$ ($R^4$ is an optionally substituted hydrocarbon group), (ii) —CO—$R^5$ ($R^5$ is a hydrogen atom or an optionally substituted hydrocarbon group), (iii) —$COOR^6$ ($R^6$ is an optionally substituted hydrocarbon group) (iv) —$CON(R^7)R^8$ (wherein $R^7$ and $R^8$ respectively are a hydrogen atom or an optionally substituted hydrocarbon group, or, $R^7$ and $R^8$ form a ring together with the adjacent nitrogen atom), (v) a nitro group or (vi) a cyano group,

(14) a compound as described in (5) above, wherein B is a $C_{2-10}$ alkylene group,

(15) a compound as described in (5) above, wherein B is a group of the formula:

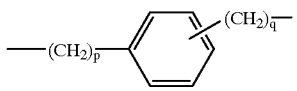

wherein p and q respectively are independently an integer of 0 to 5,

(16) a compound as described in (5) above, wherein B is a $C_{3-8}$ alkylene group,

(17) a compound as described in (6) above, which is one of the formula:

(II)

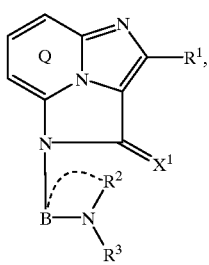

(III)

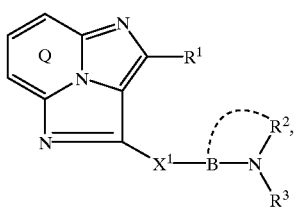

(IV)

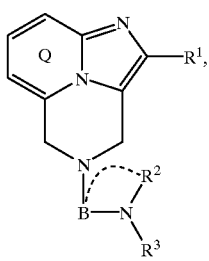

(V)

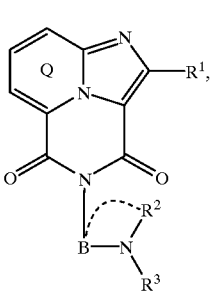

-continued

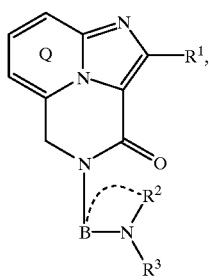
(VI)

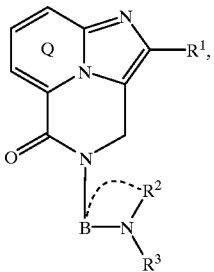
(VII)

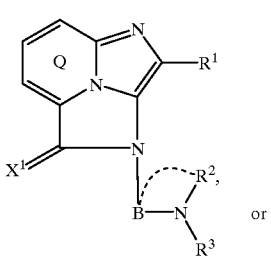
(VII')

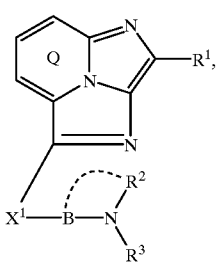
(VII")

wherein $X^1$ is an oxygen atom or a sulfur atom, and the other symbols are of the same meanings as defined in (6) or a salt thereof,

(18) a compound as described in (6) above, which is the compound (II) or (VI) or a salt thereof,

(19) a compound as described in (17) above, wherein the ring Q is unsubstituted,

(20) a compound as described in (17) above, wherein $R^1$ is a hydrogen atom, an optionally substituted alkyl group or an optionally substituted alkenyl group,

(21) a compound as described in (17) above, wherein $R^1$ is a hydrogen atom or a $C_{1-6}$ alkyl group,

(22) a compound as described in (17) above, wherein $R^2$ is a hydrogen atom or $C_{1-6}$ alkyl group,

(23) a compound as described in (17) above, wherein $R^2$ is a hydrogen atom,

(24) a compound as described in (17) above, wherein $X^1$ is an oxygen atom,

(25) a compound as described in (17) above, wherein $X^1$ is a sulfur atom,

(26) a compound as described in (17) above, wherein B is a $C_{2-10}$ alkylene group,

(27) a compound as described in (17) above, wherein B is a $C_{3-8}$ alkylene group,

(28) a compound as described in (17) above, wherein the electron-withdrawing group represented by $R^3$ is $-SO_2R^{4a}$ ($R^{4a}$ is an optionally substituted alkyl group, an optionally substituted alkenyl group, an optionally substituted aralkyl group or an optionally substituted aryl group),

(29) a compound as described in (28) above, wherein $R^{4a}$ is a halogeno-$C_{1-6}$ alkyl group,

(30) a compound as defined in (1) above represented by the formula:

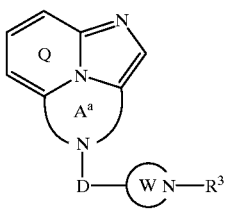

wherein ring $A^a$ is a nitrogen-containing heterocyclic ring which may have one oxo group, D is a bond or an optionally substituted divalent hydrocarbon, ring W is an optionally substituted nitrogen-containing heterocyclic ring, ring Q may optionally be substituted, and $R^3$ is an electron-withdrawing group, or a salt thereof,

(31) a compound as defined in (30) above, wherein ring $A^a$ is a 5- or 6-membered nitrogen-containing heterocyclic ring which may have one oxo group,

(32) a compound as defined in (30) above, wherein

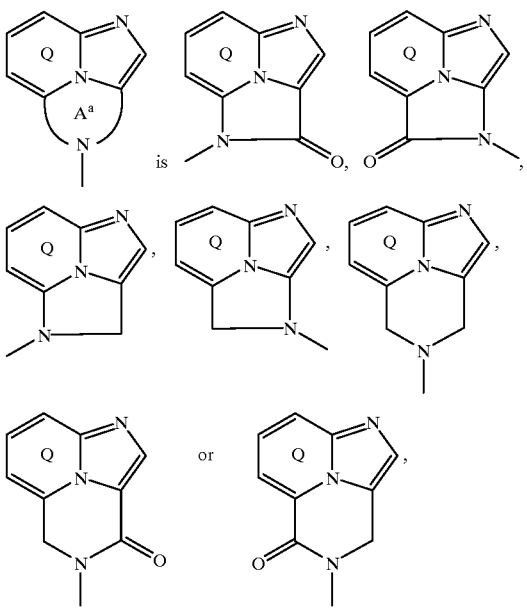

wherein Q is of the same meaning of (30) above,

(33) a compound as defined in (30) above, wherein D is an optionally substituted divalent hydrocarbon,

(34) a compound as defined in (30) above, wherein ring W is an optionally substituted 5- or 6-membered nitrogen-containing heterocyclic ring,

(35) a compound as defined in (30) above, wherein $R^3$ is $-SO_2R^4$ ($R^4$ is an optionally substituted hydrocarbon group), —COR⁵ (R⁵ is a hydrogen atom or an optionally substituted hydrocarbon group), —COOR⁶ (R⁶ is an optionally substituted hydrocarbon group) or —CON(R⁷)R⁸ (R⁷ and R⁸ respectively are a hydrogen atom or an optionally substituted hydrocarbon group, or R⁷ and R⁸ form a ring together with the adjacent nitrogen atom),

(36) a compound as defined in (30) above, wherein ring Q is unsubstituted,

(37) a compound as defined in (30) above, wherein ring W is

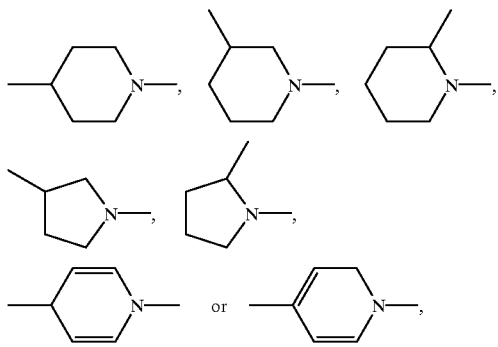

(38) a compound as defined in (30) above, wherein D is $C_{1-6}$ alkylene,

(39) a compound as defined in (1) above represented by the formula:

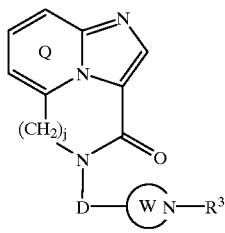

wherein j is 0 or 1, and the other symbols are of the same meanings as defined in (30) above, or a salt thereof,

(40) a compound as defined in (39) above, wherein R³ is —SO₂R⁴ (R⁴ is an optionally substituted hydrocarbon group), —COR⁵ (R⁵ is a hydrogen atom or an optionally substituted hydrocarbon group) or —COOR⁶ (R⁶ is an optionally substituted hydrocarbon group),

(41) a compound as defined in (40) above, wherein R⁴, R⁵ and R⁶ respectively are an optionally halogenated hydrocarbon group,

(42) a compound as defined in (39) above, wherein D is $C_{1-6}$ alkylene,

(43) a compound as defined in (39) above, wherein D is ethylene,

(44) a compound as defined in (39) above, wherein ring W is

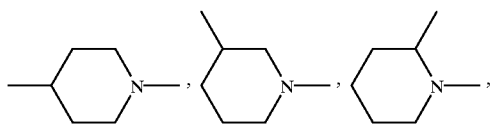

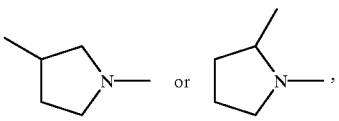

(45) a compound as defined in (39) above, wherein R³ is —SO₂R⁴ (R⁴ is an optionally substituted hydrocarbon group),

(46) a compound as defined in (45) above, wherein R⁴ is an optionally halogenated $C_{1-6}$ alkyl group,

(47) a compound as defined in (39) above, wherein ring W is

(48) a compound as defined in (39) above, wherein ring Q is unsubstituted,

(49) a compound as defined in (39) above, wherein j is 0,

(50) a compound as defined in (1) above, which is 1,2-dihydro-1-(1-trifluoromethanesulfonylpiperidin-4-ylmethyl)-1,4,7b-triazacyclopent[cd]inden-2-one, or a salt thereof,

(51) a compound as defined in (1) above, which is 1,2-dihydro-1-[2-(1-trifluoromethanesulfonylpiperidin-4-yl)ethane-1-yl]-1,4,7b-triazacyclopent[cd]inden-2-one, or a salt thereof,

(52) a compound as defined in (1) above, which is 1,2-dihydro-1-[3-(trifluoromethanesulfonylpiperidin-4-yl)propan-1-yl]-1,4,7b-triazacyclopent[cd]inden-2-one, or a salt thereof,

(53) a compound as defined in (1) above, which is 4,5-dihydro-4-(1-trifluoromethanesulfonylpiperidin-4-ylmethyl)-3H-1,4,8b-triazaacenaphthylen-3-one, or a salt thereof,

(54) a compound as defined in (1) above, which is 4,5-dihydro-4-[2-(1-trifluoromethanesulfonylpiperidin-4-ylmethyl)-3H-1,4,8b-triazaacenaphthylen-3-one, or a salt thereof,

(55) a compound as described in (1), which is 4,5-dihydro-4-[4-(trifluoromethanesulfonamido)butan-1-yl]-3H-1,4,8b-triazaacenaphthylen-3-one or a salt thereof, or 1,2-dihydro-3-methyl-1-[5-(trifluoromethanesulfonamido)pentan-1-yl]-1,4,7b-triazacylcopent[cd]inden-2-one or a salt thereof,

(56) a process for producing the compound as described in (1) above, which comprises reacting a compound of the formula:

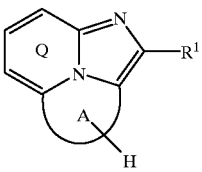

wherein the symbols are defined in (1) above, or a salt thereof, with a compound of the formula:

E¹—Y wherein E¹ is a leaving group and the other symbol is defined in (1) above, or a salt thereof,

(57) a compound of the formula:

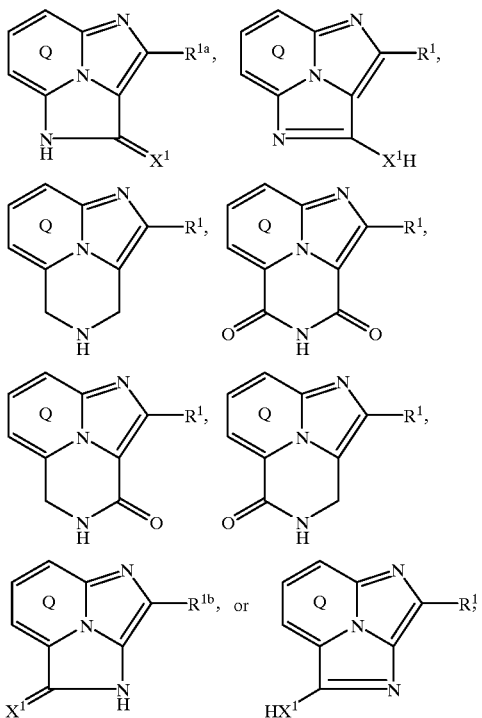

wherein $R^{1a}$ is a halogen atom, an optionally substituted hydrocarbon group or an acyl group, except for methyl group as $R^{1a}$;

$R^{1b}$ is a halogen atom, an optionally substituted hydrocarbon group or an acyl group; and the other symbols are of the same meanings as defind above, or a salt thereof,

(58) a composition which comprises the compound as described in (1) above,

(59) a pharmaceutical composition which comprises the compound as described in (1) above,

(60) a pharmaceutical composition for suppressing platelet-derived growth factor, which comprises the compound as described in (1) above,

(61) a therapeutic composition for hypertension, which comprises the compound as described in (1) above,

(62) a therapeutic composition for renal diseases, which comprises the compound as described in (1) above, and

(63) a composition for lowering lipid level, which comprises the compound as described in (1) above.

The term "nitrogen-containing heterocyclic ring" used in the present specification means, for example, 5- to 10-membered ring containing, two nitrogen atoms as heteroatoms. Among them, 5- or 6-membered ring is widely used. These ring may be saturated or unsaturated, and may contain 1 or 2 hetero atoms (e.g. sulfur atom, oxygen atom, nitrogen atom). More specifically, for example, the following ones

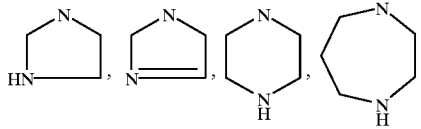

are employed. These "nitrogen-containing heterocyclic rings" may optionally be substituted with one or two of oxo or thioxo groups.

The term "divalent hydrocarbon group" used in the present specification means, for example, divalent chain-like hydrocarbon groups including $C_{1-15}$ alkylene groups (e.g. methylene, ethylene, propylene, butylene, pentamethylene, hexamethylene, heptamethylene and octamethylene), $C_{2-16}$ alkenylene groups (e.g. vinylene, propenylene, 1-butenylene, 2-butenylene, 1-pentenylene, 2-pentenylene and 3-pentenylene), $C_{2-16}$ alkynylene groups (e.g. ethynylene, propynylene, 1-butynylene, 2-butynylene, 1-pentynylene, 2-pentynylene and 3-pentynylene), phenylene group or a combination of them.

As substituents which the said "divalent hydrocarbon group" optionally has, mention is made of, for example, optionally substituted alkyl groups, optionally substituted aralkyl groups and optionally substituted aryl groups, and optionally substituted alkyl groups are preferable. The said "phenylene group" may be substituted.

As substituents which the said "phenylene group" optionally has, mention is made of one to four selected from, for example, halogen atoms (e.g. fluorine, chlorine, bromine and iodine), $C_{1-4}$ alkyl groups (e.g. methyl, ethyl, propyl, isopropyl and butyl), $C_{1-4}$ alkoxy groups (e.g. methoxy, ethoxy, propoxy and isopropoxy), $C_{1-4}$ alkylthio groups (e.g. methylthio, ethylthio, propylthio and isopropylthio), hydroxyl group, carboxyl group, cyano group, nitro group, amino group, mono- or di-$C_{1-4}$ amino groups (e.g. methylamino, ethylamino, dimethylamino and diethylamino), formyl group, mercapto group, $C_{1-4}$ alkyl-carbonyl groups (e.g. acetyl, propionyl and butyryl), $C_{1-4}$ alkoxy-carbonyl groups (e.g. methoxycarbonyl, ethoxycarbonyl and propoxycarbonyl), sulfo group, $C_{1-4}$ alkylsulfonyl groups (e.g. methylsulfonyl, ethylsulfonyl and propylsulfonyl), carbamoyl group and mono- or di-$C_{1-4}$ alkyl-carbamoyl groups (e.g. N-methylcarbamoyl, N-ethylcarbamoyl, N,N-dimethylcarbamoyl and N,N-diethylcarbamoyl).

The term "halogen atom" used in the present specification means, for example, fluorine, chlorine, bromine and iodine.

The "hydrocarbon group" of the term "optionally substituted hydrocarbon group" used in the present specification means, for example, alkyl group, cycloalkyl group, alkenyl group, aralkyl group and aryl group.

Examples of the substituents, which the said "hydrocarbon group" optionally has, use is made of the substituents which the said "alkyl group", "cycloalkyl group", "alkenyl group", "aralkyl group" and "aryl group" optionally have.

As said "alkyl group", use is made of, for example, "straight-chain or branched $C_{1-15}$ alkyl group" such as methyl, ethyl, propyl, isopropyl, butyl, isobutyl, sec-butyl, tert-butyl, pentyl, hexyl, heptyl, octyl, nonyl, decyl, undecyl, tridecyl, tetradecyl and pentadecyl.

As said "cycloalkyl group", use is made of, for example, "$C_{3-8}$ cycloalkyl group" such as cyclopropyl, cyclobutyl, cyclopentyl, cyclohexyl, cycloheptyl and cyclooctyl.

Examples of the substituents, which the said "alkyl group" and "cycloalkyl group" optionally have, include (i) nitro group, (ii) hydroxyl group, (iii) cyano group, (iv) carbamoyl group, (v) mono- or di-$C_{1-4}$ alkyl-carbamoyl groups (e.g. N-methylcarbamoyl, N-ethylcarbamoyl, N,N-dimethylcarbamoyl and N,N-diethylcarbamoyl), (vi) carboxyl group, (vii) $C_{1-4}$ alkoxy-carbonyl groups (e.g. methoxycarbonyl, ethoxycarbonyl, propoxycarbonyl and isopropoxycarbonyl), (viii) sulfo group, (ix) halogen atoms (e.g. fluorine, chlorine, bromine and iodine), (x) $C_{1-4}$ alkoxyl groups (e.g. methoxy, ethoxy, propoxy and isopropoxy), (xi) phenoxy group, (xii) halogenophenoxy groups (e.g. o-, m- or p-chlorophenoxy, and o-, m- or p-bromophenoxy), (xiii)

$C_{1-4}$ alkylthio groups (e.g. methylthio, ethylthio, n-propylthio, isopropylthio and n-butylthio), (xiv) mercapto group, (xv) phenylthio group, (xvi) pyridylthio group, (xvii) $C_{1-4}$ alkylsulfinyl groups (e.g. methylsulfinyl and ethylsulfinyl), (xviii) $C_{1-4}$ alkylsulfonyl groups (e.g. methylsulfonyl and ethylsulfonyl), (xix) amino group, (xx) $C_{1-3}$ acylamino groups (e.g. acetylamino and propionylamino), (xxi) mono- or di-$C_{1-4}$ alkylamino groups (e.g. methylamino, ethylamino, dimethylamino and diethylamino), (xxii) 4- to 6-membered cyclic amino groups (e.g. 1-azetidinyl, 1-pyrrolidinyl, piperidino, morpholino, thiomorpholino and 1-piperazinyl), (xxiii) $C_{1-3}$ acyl groups (e.g. formyl and acetyl), (xxiv) benzoyl group and (xxv) 5 to 10 membered heterocyclic groups (e.g. 2- or 3-thienyl, 2- or 3-furyl, 3-, 4- or 5-pyrazolyl, 2-, 4- or 5-thiazolyl, 3-, 4- or 5-isothiazolyl, 2, 4- or 5-oxazolyl, 1,2,3- or 1,2,4-triazolyl, 1H- or 2H-tetrazolyl, 2-, 3- or 4-pyridyl, 2-, 4- or 5-pyrimidyl, 3- or 4-pyridazinyl, quinolyl and isoquinolylindolyl). The said "alkyl group" and "cycloalkyl group" optionally have 1 to 5 of these substituents at any substituable positions.

Preferable examples of the said "alkyl group" include $C_{1-6}$ straight-chain or branched alkyl groups such as methyl, ethyl, propyl, isopropyl, butyl, isobutyl, sec-butyl, tert-butyl, pentyl and hexyl. As the substituents which the said "$C_{1-6}$ alkyl groups" optionally have, use is made of 1 to 3 of, for example, halogen atoms, $C_{1-4}$ alkoxyl group, hydroxyl group, $C_{1-4}$ alkoxy-carbonyl groups, carboxyl group, carbamoyyl group, mono- or di-$C_{1-4}$ alkylcarbamoyl groups and pyridylthio group.

Examples of the said "alkenyl group" include "$C_{2-18}$ alkenyl groups" such as vinyl, allyl, isopropenyl, 3-butenyl, 3-octenyl and 9-octadecenyl. As the substituents which the said "alkenyl groups" optionally have, use is made of, for example, the same ones as those which the above-mentioned "alkyl group" optionally has.

Preferable examples of the said "alkenyl group" include $C_{2-6}$ alkenyl groups such as vinyl, allyl, 2-butenyl and 3-butenyl. As the substituents which the said "$C_{2-6}$ alkenyl groups" optionally has, use is made of, for example, the same ones as those which the above-mentioned "$C_{1-6}$ alkyl group" optionally has.

As the said "aralkyl group", use is made of, for example, $C_{7-16}$ aralkyl groups, which are specifically exemplified by phenyl-$C_{1-6}$ alkyl groups such as benzyl, phenethyl, 3-phenylpropyl and 4-phenylbutyl, and naphthyl-$C_{1-6}$ alkyl group such as (1-naphthyl)methyl, 2-(1-naphthyl)ethyl and 2-(2-naphthyl)ethyl.

Examples of the substituents, which the said "aralkyl group" optionally has, include halogen atoms (e.g. fluorine, chlorine, bromine and iodine), $C_{1-4}$ alkyl groups (e.g. methyl, ethyl, propyl, isopropyl and butyl), halogeno-$C_{1-4}$ alkyl groups (e.g. trifluoromethyl, trichloromethyl), $C_{2-6}$ alkenyl groups (e.g. vinyl, allyl, 2-butenyl and 3-butenyl), $C_{1-3}$ acyl groups (e.g. formyl and acetyl), $C_{1-4}$ alkoxyl groups (e.g. methoxy, ethoxy, propoxy and isopropoxy), nitro group, cyano group, hydroxyl group, $C_{1-4}$ alkoxy-carbonyl groups (e.g. methoxycarbonyl, ethoxycarbonyl, propoxycarbonyl and isopropoxycarbonyl), carbamoyl group, mono- or di-$C_{1-4}$ alkyl-carbamoyl groups (e.g. N-methylcarbamoyl, N-ethylcarbamoyl, N,N-dimethylcarbamoyl and N,N-diethylcarbamoyl) and mono- or di-$C_{1-4}$ alkenyl-carbamoyl groups (e.g. N-vinylcarbamoyl). The said "aralkyl group" may optionally have 1 to 4 of these substituents at any substituable position.

As the said "aryl group", use is made of, for example, aromatic monocyclic, dicyclic or tricyclic $C_{6-14}$ aryl groups exemplified by phenyl, 1-naphthyl, 2-naphthyl, phenanthryl and anthryl.

As the substituents which the said "aryl group" optionally has, use is made of, besides the substituents which the said "aralkyl group" may optionally have, oxo group. The said "aryl group" may optionally have 1 to 4, preferably 1 or 2, of these substituents at any substitutable positions. Examples of the aryl group having oxo group include benzoquinonyl, naphthoquinolyl and anthraquinonyl.

The term "electron-withdrawing group" used in the present specification is exemplified by (i) —$SO_2R^4$, (ii) —$CO$—$R^5$, (iii) —$COOR^6$, (iv) —$CON(R^7)R^{8,}$ (v) a nitro group and (vi) a cyano group, preferably —$SO_2R^4$, —$CO$—$R^5$ and —$COOR^6$, especially —$SO_2R^4$ is commonly used. $R^4$ stands for an optionally substituted hydrocarbon group; $R^5$ stands for a hydrogen atom or an optionally substituted hydrocarbon group; $R^6$ stands for an optionally substituted hydrocarbon group; $R^7$ and $R^8$ independently stand for a hydrogen atom or an optionally substituted hydrocarbon group, or $R^7$ and $R^8$ form, combined with the adjacent nitrogen atom, an nitrogen atom-containing heterocyclic ring.

The term "acyl group" used in the present specification is exemplified by the acyl group derived from carboxylic acid, which is exemplified by alkoxycarbonyl group, alkylcarbamoyl group and alkanoyl group.

As the said "alkoxycarbonyl group", use is made of $C_{1-6}$ alkoxycarbonyl groups including, for example, methoxycarbonyl, ethoxycarbonyl, propoxycarbonyl, isopropoxycarbonyl, butoxycarbonyl, isobutoxycarbonyl, sec-butoxycarbonyl, tert-butoxycarbonyl, pentyloxycarbonyl, isopentyloxycarbonyl, neopentyloxycarbonyl and tert-pentyloxycarbonyl.

As the said "alkylcarbamoyl group", use is made of mono-$C_{1-6}$-N-alkylcarbamoyl groups, for example, N-methylcarbamoyl, N-ethylcarbamoyl, N-propylcarbamoyl and N-butylcarbamoyl, and di-$C_{1-6}$-N,N-dialkylcarbamoyl groups, for example, N,N-dimethylcarbamoyl, N,N-diethylcarbamoyl, N,N-dipropylcarbamoyl, N,N-dibutylcarbamoyl and N-ethyl-methylcarbamoyl, and 4- to 6-membered cyclic carbamoyl groups formed by combination of the dialkyl portions with each other (e.g. 1-azetidinylcarbonyl, morpholinocarbonyl, 1-pyrrolidinylcarbonyl, 1-piperidinocarbonyl and 1-piperazinylcarbonyl).

As the said "alkanoyl group", use is made of formyl, $C_{1-6}$ alkyl-carbonyl group (e.g. acetyl, propionyl).

In the above-mentioned formula, the ring A stands for a nitrogen-containing heterocyclic ring having two nitrogen atoms containing the nitrogen atom at the head of the bridge in the condensed ring, which be further substituted with oxo or thioxo.

Preferable examples of the ring A include 5- or 6-membered nitrogen-containing heterocyclic ring optionally substituted with one or two oxo groups. Especially, the following ones are commonly employed.

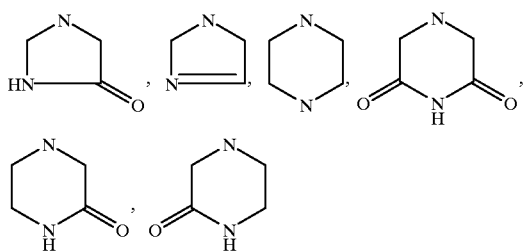

In the above-mentioned formula, the ring Q is optionally substituted.

Examples of the substituents, which the ring Q optionally has, include halogen atoms (e.g. fluorine, chlorine, bromine and iodine), $C_{1-4}$ alkyl groups (e.g. methyl, ethyl, propyl, isopropyl and butyl), halogeno-$C_{1-4}$ alkyl groups (e.g. trifluoromethyl, trichloromethyl), $C_{1-4}$ alkoxy groups (e.g. methoxy, ethoxy, propoxy and isopropoxy), halogeno-$C_{1-4}$ alkoxy groups (e.g. trifluoromethoxy, trichloromethoxy), $C_{1-4}$ alkylthio groups (e.g. methylthio, ethylthio, propylthio and isopropylthio), halogeno-$C_{1-4}$ alkylthio groups (e.g. trifluoromethylthio, trichloromethylthio), hydroxyl group, carboxyl group, cyano group, nitro group, amino group, mono- or di-$C_{1-4}$ alkyl amino groups (e.g. methylamino, ethylamino, dimethylamino and diethylamino), formyl group, mercapto group, $C_{1-4}$ alkyl-carbonyl groups (e.g. acetyl, propionyl and butyryl), $C_{1-4}$ alkoxy-carbonyl groups (e.g. methoxycarbonyl, ethoxycarbonyl and propoxycarbonyl), sulfo group, $C_{1-4}$ alkylsulfonyl groups (e.g. methylsulfonyl, ethylsulfonyl and propylsulfonyl), carbamoyl group and mono- or di-$C_{1-4}$ alkyl-carbamoyl groups (e.g. N-methylcarbamoyl, N-ethylcarbamoyl, N,N-dimethylcarbamoyl and N,N-diethylcarbamoyl). The ring Q may be substituted with one to three of these substituents on any substitutable position. The ring Q is preferably unsubstituted.

In the above-mentioned formulae, $R^1$ stands for a hydrogen atom, a halogen atom, an optionally substituted hydrocarbon group or acyl group.

Preferable examples of $R^1$ include a hydrogen atom, optionally substituted alkyl groups, optionally substituted alkenyl groups, optionally substituted aralkyl groups, optionally substituted aryl groups, alkoxycarbonyl groups, alkylcarbamoyl groups and alkanoyl groups; especially a hydrogen atom, $C_{1-6}$ alkyl groups (e.g. methyl, ethyl, propyl, isopropyl and butyl) or phenyl group are preferably used, and, a hydrogen atom is employed most preferably.

In the above-mentioned formula, Y stands for an optionally substituted hydrocarbon group, an optionally substituted hydroxyl group or an optionally substituted mercapto group, excluding methyl group as Y.

Examples of the optionally substituted hydrocarbon group shown by Y include those described in respect of the above-mentioned "optionally substituted hydrocarbon group", excluding unsubstituted methyl group.

Examples of the substituents, which the hydroxyl group or the mercapto group shown by Y optionally has, include optionally substituted hydrocarbon group, the groups containing at least one nitrogen atom and/or the groups containing at least one electron-withdrawing groups.

Preferable examples of the substituents, which the hydroxyl group or the mercapto group shown by Y optionally has, include optionally substituted hydrocarbon group. As the said "optionally substituted hydrocarbon group", use is made of the same ones as the above-mentioned "optionally substituted hydrocarbon group".

Preferable examples of the substituents, which the hydrocarbon group, the hydroxyl group and the mercapto group shown by Y optionally has, include the groups containing at least one nitrogen atom and/or the groups containing at least one electron-withdrawing group, especially the groups containing an amino group substituted with at least one electron-withdrawing group.

As "the group containing at least one nitrogen atom" mentioned above, use is made of, for example, alkylaminoalkyl groups aralkylaminoalkyl groups, arylaminoalkyl groups, alkylaminoaralkyl groups, aralkylaminoaralkyl groups, arylaminoaralkyl groups, alkylaminoaryl groups, aralkylaminoaryl groups, arylaminoaryl groups, aminoalkyl groups, aminoaralkyl group and aminoaryl groups.

As "the group containing at least one electron-withdrawing group", use is made of, for example, the hydrocarbon groups containing at least one "electron-withdrawing group as mentioned above".

As "the group containing an amino group which is substituted with at least one electron-withdrawing group", use is made of, for example, the hydrocarbon groups containing an amino group substituted with at least one "electron-withdrawing group as mentioned above".

The most preferable examples of Y include the groups represented by the formula

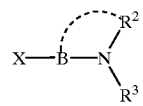

wherein the symbols are of the same meaning as defined above.

In the above-mentioned formula, B stands for an optionally substituted divalent hydrocarbon group. Specific examples of the group include those represented by (i)

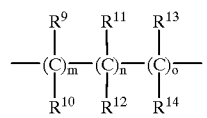

wherein m, n and o independently are integers of 0 to 5, $R^9$, $R^{10}$, $R^{11}$, $R^{12}$, $R^{13}$ and $R^{14}$ independently stand for a hydrogen atom, an optionally substituted alkyl group, an optionally substituted aralkyl group or an optionally substituted aryl group, and, $R^9$ and $R^{10}$; $R^{11}$ and $R^{12}$; $R^{13}$ and $R^{14}$; $R^9$ or $R^{10}$ and $R^2$; $R^{11}$ or $R^{12}$ and $R^2$; or, $R^{13}$ or $R^{14}$ and $R^2$ may respectively be combined to form rings, and $R^9$ or $R^{11}$ may be combined with $R^{13}$ or $R^{14}$ respectively to form rings, or (ii)

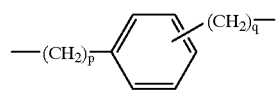

wherein phenylene group may be substituted, and, p and q are independently an integer of 0 to 5. Examples of the optionally substituted alkyl, aralkyl or aryl group shown by $R^9$ to $R^{14}$ include those described in respect of the above-mentioned "optionally substituted hydrocarbon groups". The rings formed by combination of $R^9$ and $R^{10}$, $R^{11}$ and $R^{12}$, and $R^{13}$ and $R^{14}$ are exemplified by $C_{3-8}$ cycloalkanes including cyclopropane, cyclobutane, cyclopentane and cyclohexane. The rings formed by combination of $R^9$ or $R^{10}$ and $R^2$; $R^{11}$ or $R^{12}$ and $R^2$; or $R^{13}$ or $R^{14}$ and $R^2$ are exemplified by azetidine, pyrrolidine or piperidine. The rings formed by combination of $R^9$ or $R^{11}$ with $R^{13}$ or $R^{14}$, respectively are exemplified by $C_{3-8}$ cycloalkanes including cyclopropane, cyclobutane, cyclopentane and cyclohexane.

Preferable examples of $R^9$ to $R^{14}$ include a hydrogen atom or $C_{1-4}$ alkyl groups (e.g. methyl, ethyl, propyl and isopropyl), and, especially, a hydrogen atom or methyl group is preferably used.

Preferable examples of B include $C_{2-10}$ alkylene groups (e.g. ethylene, propylene, butylene, pentamethylene, hexamethylene, heptamethylene and octamethylene), and, among them, especially $C_{3-8}$ alkylene groups (e.g. ethylene, propylene, butylene, pentamethylene, hexamethylene and heptamethylene) are commonly employed.

In the above-mentioned formulae, X stands for a bond, an oxygen atom or a sulfur atom. Preferable example of X is a bond.

In the above-mentioned formulae, $R^2$ stands for a hydrogen atom or an optionally substituted hydrocarbon group, and, $R^2$ and B may optionally form a ring together with the adjacent nitrogen atom.

Preferable examples of $R^2$ include a hydrogen atom, optionally substituted alkyl groups or optionally substituted alkenyl groups, especially a hydrogen atom is commonly used.

In the above-mentioned formulae, $R^3$ and $R^{3a}$ stand for an electron-withdrawing group, or $R^2$, $R^3$ and $R^{3a}$ may form a ring together with the adjacent nitrogen atom. Examples of the electron-withdrawing group include (i) —$SO_2R^4$ ($R^4$ stands for an optionally substituted hydrocarbon group), (ii) —CO—$R^5$ ($R^5$ stands for a hydrogen atom or an optionally substituted hydrocarbon group), (iii) —$COOR^6$ ($R^6$ stands for an optionally substituted hydrocarbon group), (iv) —$CON(R^7)R^8$ ($R^7$ and $R^8$ each stand for a hydrogen atom or an optionally substituted hydrocarbon group, or $R^7$ and $R^8$ may form a ring together with the adjacent nitrogen atom), (v) a nitro group and (vi) a cyano group.

Examples of the electron-withdrawing group include —$SO_2R^{4a}$, —CO—$R^{5a}$ and —$COOR^{6a}$ ($R^{4a}$, $R^{5a}$ and $R^{6a}$ each stand for an optionally substituted alkyl group, an optionally substituted alkenyl group, an optionally substituted aralkyl group or an optionally substituted aryl group), especially —$SO_2R^{4a}$ ($R^{4a}$ stands for an optionally substituted alkyl group, an optionally substituted alkenyl group, an optionally substituted aralkyl group or an optionally substituted aryl group) is commonly used among others.

Preferable examples of $R^4$ include an optionally substituted alkyl group, especially a halogeno- $C_{1-6}$ alkyl group (e.g. chloromethyl, trifluoromethyl, 2,2,2-trifluoroethyl and 3,3,3-trifluoropropyl).

Preferable examples of $R^5$ include an optionally substituted alkyl group, especially a halogeno- $C_{1-6}$ alkyl group (e.g. chloromethyl, trifluoromethyl, 2,2,2-trifluoroethyl and 3,3,3-trifluoropropyl).

Preferable examples of $R^6$ include an optionally substituted alkyl group, especially a halogeno- $C_{1-6}$ alkyl group (e.g. chloromethyl, trifluoromethyl, 2,2,2-trifluoroethyl and 3,3,3-trifluoropropyl).

Preferable examples of $R^7$ and $R^8$ include a hydrogen atom or an optionally substituted alkyl group, especially a hydrogen atom or a halogeno- $C_{1-6}$ alkyl group (e.g. chloromethyl, trifluoromethyl, 2,2,2-trifluoroethyl and 3,3,3-trifluoropropyl).

Examples of the ring, which $R^2$, $R^3$ and $R^{3a}$ form together with the adjacent nitrogen atom, include pyrrolidin-2-one, piperidin-2-one, indolin-2-one, isoindolin-1-one, isoindoline-1,3-dione, oxazolidin-2-one, oxazolidine-2,4-dione, thiazolidin-2-one, thiazolidine-2,4-dione and 1,2-benzisothiazol-3(2H)-one. These rings optionally have substituents such as electron-withdrawing groups. As the said "electron-withdrawing group", use is made of, for example, the above-mentioned "electron-withdrawing groups".

Preferable examples of the compounds (I') are shown as follows:

Compounds of the following formula or salts thereof.

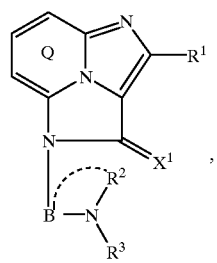

(II)

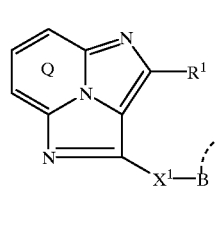

(III)

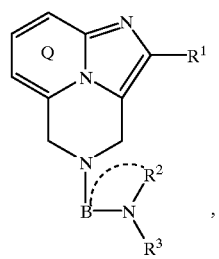

(IV)

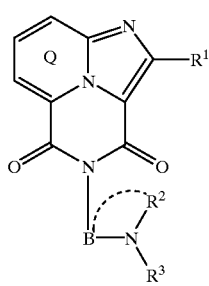

(V)

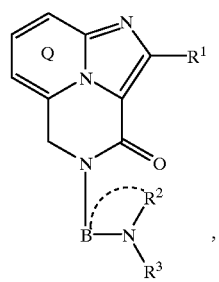

(VI)

-continued

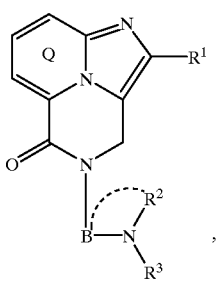

(VII)

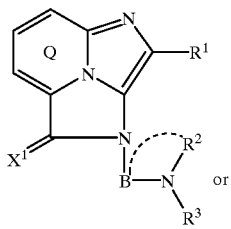

or (VII')

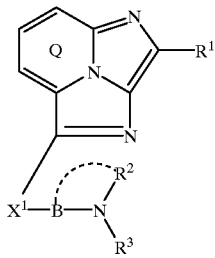

(VII")

wherein X¹ stands for an oxygen atom or a sulfur atom, and the other symbols are of the same meaning as defined above, especially the compound (II) or (VI).

In these compounds (II) to (VII"),
(1) a compound, wherein ring Q is unsubstituted, is preferable;
(2) a compound, wherein $R^1$ stands for a hydrogen atom, an optionally substituted alkyl group or an optionally substituted alkenyl group, is preferable, and, especially those, wherein $R^1$ stands for a hydrogen atom or a $C_{1-6}$ alkyl group (e.g. methyl, ethyl, propyl, isopropyl and butyl), are preferably used;
(3) a compound, wherein $R^2$ stands for a hydrogen atom or a $C_{1-6}$ alkyl group (e.g. methyl, ethyl, propyl, isopropyl and butyl), is preferable, and, especially those, wherein $R^2$ stands for a hydrogen atom, are preferably used;
(4) a compound, wherein $X^1$ stands for an oxygen atom, is preferable;
(5) a compound, wherein $X^1$ stands for a sulfur atom, is preferable;
(6) a compound, wherein B stands for a $C_{2-10}$ alkylene group (e.g. ethylene, propylene, butylene, pentamethylene, hexamethylene and octamethylene), is preferable, and, especially those, wherein B stands for a $C_{3-8}$ alkylene group (e.g. propylene, butylene, pentamethylene, hexamethylene and heptamethylene), are preferable;
(7) a compound, wherein the electron-withdrawing group shown by $R^3$ is $-SO_2R^{4a}$ ($R^{4a}$ stands for an optionally substituted alkyl group, an optionally substituted alkenyl group, an optionally substituted aralkyl group or an optionally substituted aryl group), is preferable; and
(8) a compound, wherein $R^4$ stands for a halogeno- $C_{1-6}$ alkyl group (e.g. chloromethyl, trifluoromethyl, 2,2,2-trifluoroethyl and 3,3,3-trifluoropropyl), is preferable.

More preferable example of the compound (I) is a compound represented by the formula:

(A)

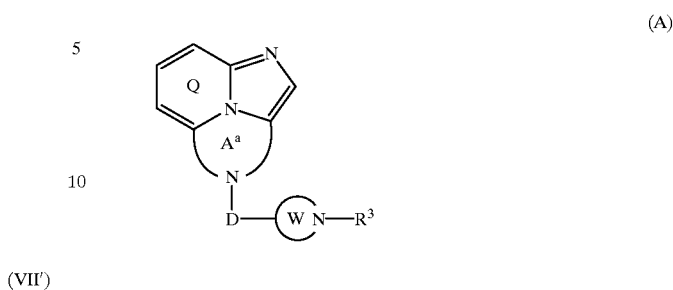

wherein the all symbols are of the same meanings as defined above.

In the compound (A), ring Q is of the same meaning as defined above, and preferably unsubstituted ring.

In the compound (A), ring $A^a$ is a nitrogen-containing heterocyclic ring which may have one oxo group. The "nitrogen-containing heterocyclic ring" have two nitrogen atoms other than carbon atoms. Preferable examples of the nitrogen-containing heterocyclic ring represented by $A^a$ are a 5- to 10-membered nitrogen-containing heterocyclic ring, and more preferably 5- or 6-membered nitrogen-containing heterocyclic ring.

In the compound (A), examples of the moiety:

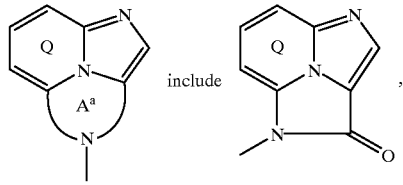 include

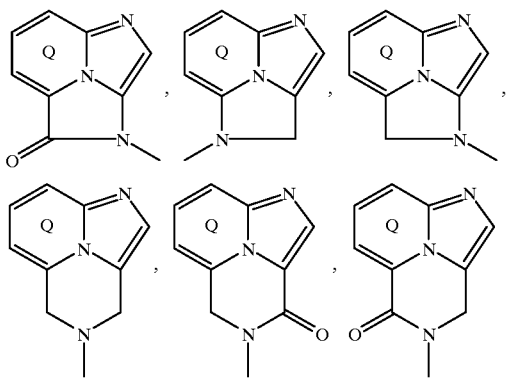

wherein ring Q is of the same meaning as defined above, and preferably the moiety:

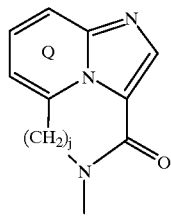

wherein j is 0 or 1, and preferably 0, and ring Q is of the same meaning as defined above.

In the compound (A), D is a bond or an optionally substituted divalent hydrocarbon. D is preferably an optionally substituted divalent hydrocarbon. The "optionally substituted divalent hydrocarbon" is of the same meaning as defined in above. The "divalent hydrocarbon" is preferably, for example, $C_{1-15}$ alkylene group (e.g. methylene, ethylene, propylene, butylene, pentamethylene, hexamethylene, heptamethylene, octamethylene), $C_{2-16}$ alkenylene group (e.g. vinylene, propenylene, 1-butenylene, 2-butenylene, 1-pentenylene, 2-pentenylene, 3-pentenylene), $C_{2-16}$ alkynylene group (e.g. ethynylene, propynylene, 1-butynylene, 2-butynylene, 1-pentynylene, 2-pentynylene, 3-pentynylene), phenylene group, and a combination of them. And more preferable example of the "divalent hydrocarbon group" is $C_{1-15}$ alkylene group (e.g. methylene, ethylene, propylene, butylene, pentamethylene, hexamethylene, heptamethylene, octamethylene).

The substituent of the "divalent hydrocarbon group" is exemplified by the same substituents as those of the "divalent hydrocarbon group" as mentioned above.

In the compound (A), ring W is an optionally substituted nitrogen-containing heterocyclic ring, and preferably an optionally substituted 5- or 6-membered nitrogen-containing heterocyclic ring.

Preferable examples of the "nitrogen-containing heterocyclic ring" are the moiety:

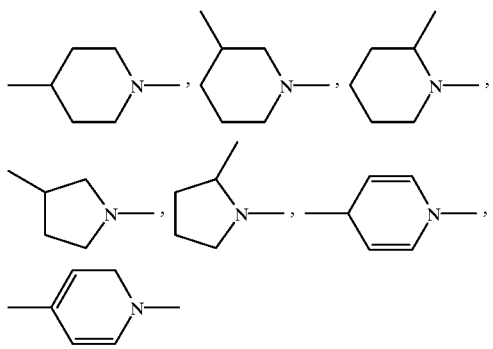

and more preferably the moiety:

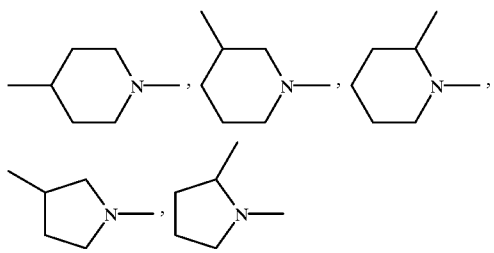

and most preferably the moiety:

The substituent of the "nitrogen-containing heterocyclic group" is exemplified by the same one as the substituent of ring Q.

Preferable example of the compound (A) is a compound represented by the formula:

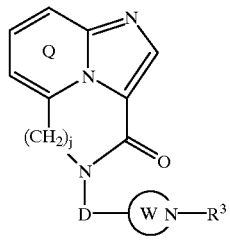

(A-a)

wherein all symbols are of the same meanings as defined above.

In the compound (A-a), ring Q is preferably unsubstituted pyridine ring.

In the compound (A-a), $R^3$ is preferably —$SO_2R^4$ ($R^4$ is an optionally substituted hydrocarbon group), —$COR^5$ ($R^5$ is a hydrogen atom is an optionally substituted hydrocarbon group) or —$COOR^6$ ($R^6$ is an optionally substituted hydrocarbon group). And, preferable examples of $R^4$, $R^5$ and $R^6$ are an optionally halogenated hydrocarbon group (e.g. $C_{1-6}$ alkyl group which may have 1 to 5 halogen atoms such as methyl, ethyl, propyl, isopropyl, butyl, chloromethyl, trifluoromethyl, 2,2,2-trifluoroethyl, 3,3,3-trifluoropropyl, or pentafluoroethyl).

In the compound (A-a), D is preferably a $C_{1-6}$ alkylene (e.g. methylene, ethylene, propylene, butylene, pentamethylene), and more preferably ethylene.

In the compound (A-a), ring W is preferably a moiety:

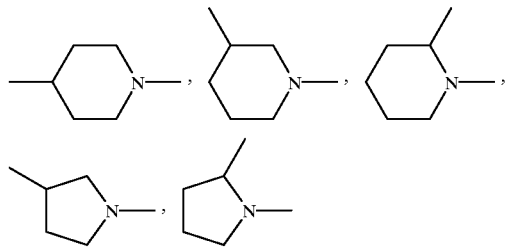

and more preferably a moiety:

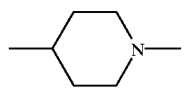

In the compound (A-a), j is preferably 0.

In the compound (A-a), $R^3$ is more preferably —$SO_2R^4$ ($R^4$ is an optionally substituted hydrocarbon group). And, $R^4$ is preferably a $C_{1-6}$ alkyl group which may have 1 to 5 halogen atoms such as methyl, ethyl, propyl, isopropyl, butyl, chloromethyl, trifluoromethyl, 2,2,2-trifluoroethyl, 3,3,3-trifluoropropyl, or pentafluoroethyl).

As preferable salts of the compound (I') (hereinafter referred to as "compound (I')" including the compound (I)), mention is especially made of pharmaceutically acceptable salts and physiologically acceptable acid addition salts. These salts are exemplified by those with inorganic acids (e.g. hydrochloric acid, phosphoric acid, hydrobromic acid and sulfuric acid) or with organic acids (e.g. acetic acid, formic acid, propionic acid, fumaric acid, maleic acid, succinic acid, tartaric acid, citric acid, malic acid, oxalic acid, benzoic acid, methansulfonic acid and benzenesulfonic acid). Further, when the compound (I') of the present invention has an acid group such as carboxylic group, it may optionally form a salt with, for example, an inorganic base (e.g. an alkali metal or an alkaline earth metal such as sodium, potassium, calcium and magnesium, or ammonia) or an organic base (e.g. a tri- $C_{1-3}$ alkylamine such as triethylamine).

As the starting compounds for producing the desired compound (I') of the present invention, similar salts to those mentioned above are employed, and they are not specifically limited unless they exert undesirable influence upon the reaction.

The compound (I') or a salt thereof has, in some instances, asymmetric carbons in the molecule. When two kinds of stereoisomers of R-configuration and S-configurated isomers, are present, each of them and a mixture of them are all included in the scope of the present invention.

Preferable practical examples of the compound (I') and salts thereof are set forth as follows:

1,2-dihydro-3-methyl-1-[4-(trifluoromethanesulfonamido) butan-1-yl]-1,4,7b-triazacyclopent[cd]inden-2-one,
1,2-dihydro-3-methyl-1-[5-(trifluoromethanesulfonamido) pentan-1-yl]-1,4,7b-triazacyclopent[cd]inden-2-one,
1,2-dihydro-3-methyl-1-[3,3-dimethyl-5-(trifluoromethanesulfonamido)pentan-1-yl]-1,4,7b-triazacyclopent[cd]inden-2-one,
1,2-dihydro-3-methyl-1-[4-[(2,2,2-trifluoro)ethanesulfonamido]butan-1-yl]-1,4,7b-triazacyclopent[cd]inden-2-one,
3-methyl-2-[4-(trifluoromethanesulfonamido)butan-1-ylthio]-1,4,7b-triazacyclopent[cd]inden,
4,5-dihydro-4-[4-(trifluoromethanesulfonamido)butan-1-yl]-3H-1,4,8b-triazaacenaphthylene,
4,5-dihydro-2-methyl-4-[4-(trifluoromethanesulfonamido)butan-1-yl]-3H-1,4,8b-triazaacenaphthylene,
4,5-dihydro-4-[4-(trifluoromethanesulfonamido)butan-1-yl]-3H-1,4,8b-triazaacenaphthylene-3,5-dione,
4,5-dihydro-4-[4-(trifluoromethanesulfonamido)butan-1-yl]-3H-1,4,8b-triazaacenaphthylen-3-one,
4,5-dihydro-5-[5-(trifluoromethanesulfonamido)pentan-1-yl]-3H-1,4,8b-triazaacenaphthylen-3-one,
4,5-dihydro-4-[4-(trifluoromethanesulfonamido)butan-1-yl]-3H-1,4,8b-triazaacenaphthylen-5-one,
1,2-dihydro-1-(1-trifluoromethanesulfonylpiperidine-4-ylmethyl)-1,4,7b-triazacyclopento[cd]inden-2-one,
1,2-dihydro-1-[2-(1-trifluoromethanesulfonylpiperidin-4-yl)ethane-1-yl]-1,4,7b-triazacyclopent[cd]inden-2-one,
1,2-dihydro-1-[3-(1-trifluoromethanesulfonylpiperidin-4-yl)propane-1-yl]-1,4,7b-triazacyclopent[cd]indene-2-one,
4,5-dihydro-4-(1-trifluoromethanesulfonylpiperidin-4-ylmethyl)-3H-1,4,8b-triazaacenaphthylen-3-one,
4,5-dihydro-4-[2-(1-trifluoromethanesulfonylpiperidine-4-yl)ethane-1-yl]-3H-1,4,8b-triazaacenaphthylen-3-one, and their salts (preferable example of the salts is hydrochloride). Especially preferable practical examples of the compound (I') and salts thereof are set forth as follows;
1,2-dihydro-3-methyl-1-[5-(trifluoromethanesulfonamido) pentan-1-yl]-1,4,7b-triazacyclopent[cd]inden-2-one,
4,5-dihydro-4-[4-(trifluoromethanesulfonamido)butan-1-yl]-3H-1,4,8b-triazaacenaphthylen-3-one,
1,2-dihydro-1-[2-(1-trifluoromethanesulfonylpiperidin-4-yl)ethane-1-yl]-1,4,7b-triazacyclopent[cd]inden-2-one and their salts (preferable example of the salts is hydrochloride).

The compound (I') or a salt thereof of the present invention can be synthesized by the following method.

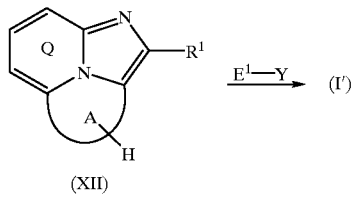

wherein $E^1$ stands for a leaving group such as halogen (e.g. chlorine, bromine, iodine), methanesulfonyloxy and p-toluenesulfonyloxy;

the other symbols are of the same meaning as defined above.

The compound (XII) include novel compounds represented by the formula

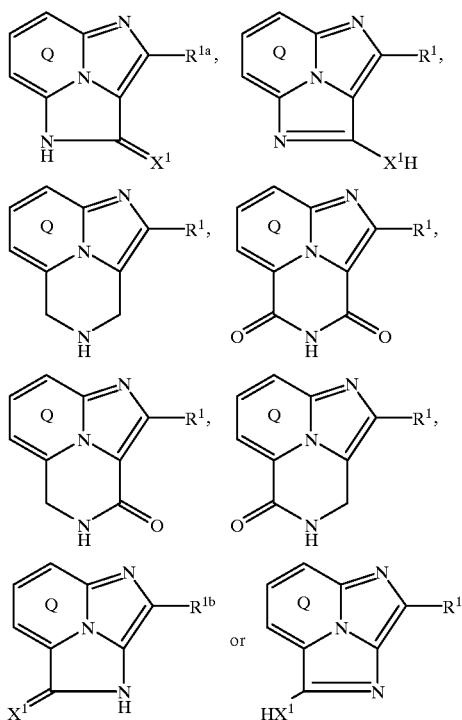

wherein $R^{1a}$ stands for a halogen atom, an optionally substituted hydrocarbon group or an acyl group, except for methyl group as $R^{1a}$;

$R^{1b}$ stands for a halogen atom, an optionally substituted hydrocarbon group or an acyl group; and the other symbols are of the same meaning as defined above, or a salt thereof.

Practically the compound (I') or a salt thereof of the present invention can be synthesized by, for example, a process for producing the compound (I') or a salt thereof which comprises reacting a compound of the formula

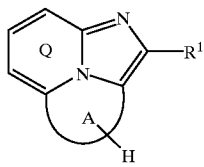

(XII)

wherein the symbols are of the same meanings as defined above, or a salt thereof, with a compound of the formula

$E^1$—Y wherein the symbols are of the same meanings as defined above, or a salt thereof. Hereinafter, in the formula containing the symbols "B" and "$R^2$", the symbols "B" and "$R^2$" include the definition "$R^2$ and B may form a ring together with the adjacent nitrogen atom", without a broken line between "B" and "$R^2$" being indicated. More, specifically, the compound (I) or a salt thereof of the present invention can be synthesized by, for example, the following methods.

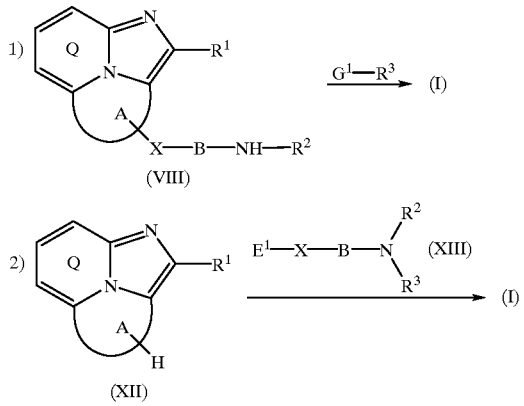

wherein $G^1$ stands for a halogen (e.g. chloro, bromo or iodo) or —$OR^3$; $E^1$ stands for a leaving group such as halogen (e.g. chlorine, bromine or iodine), methanesulfonyloxy and p-toluenesulfonyloxy; and the other symbols are of the same meanings as defined above.

And, by subjecting such compounds as shown below to ring-closure reaction (e.g. Mannich reaction or dehydrative ring-closure), the compound (I) or a salt thereof can also be synthesized.

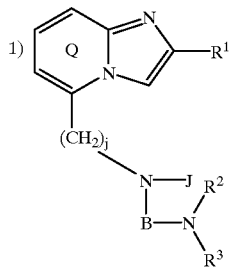

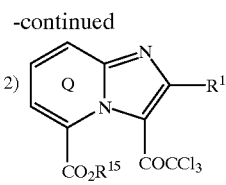

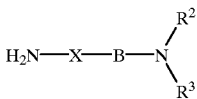

wherein j denotes 0 or 1, J stands for a hydrogen atom or a protecting group (e.g. benzyloxycarbonyl, tert-butoxycarbonyl, trifluoroacetyl, trityl and benzyl), $R^{15}$ stands for an optionally substituted alkyl group, and the other symbols are of the same meanings as defined above.

In more detail, for example, the synthesis can be carried out by the following methods.

(1) A method of producing the compound (I) or a salt thereof by allowing a compound represented by the general formula

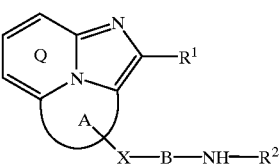

wherein the symbols are of the same meanings as defined above or a salt thereof to react with a compound represented by the general formula $G^1$—$SO_2$—$R^4$ ($G^1$ stands for a halogen such as chlorine, bromine and iodine, or $R^4SO_2$—O—, and $R^4$ is of the same meaning as defined above) or a salt thereof.

(2) A method of producing the compound (I) or a salt thereof by allowing a compound represented by the general formula

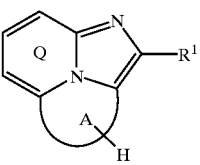

wherein the symbols are of the same meanings as defined above or a salt thereof to react with a compound represented by the general formula

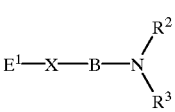

wherein $E^1$ stands for a leaving group such as a halogen (e.g. chlorine, bromine and iodine), methanesulfonyloxy and p-toluenesulfonyloxy, and the other symbols are of the same meaning as defined above, or a salt thereof.

(3) A method of producing the compound (II), (VI) or salts of them, which comprises subjecting a compound represented by the general formula

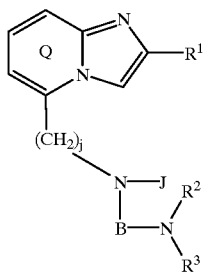

wherein j denotes 0 or 1, J stands for a hydrogen atom or a protecting group (e.g. benzyloxycarbonyl, tert-butoxycarbonyl, trifluoroacetyl, trityl and benzyl), and the other symbols are of the same meanings as defined above or a salt thereof to trichloroacetylation, then, upon necessity, deprotection of the protecting group J, and, further subjecting the resultant compound to ring-closure reaction.

(4) A method of producing the compound (IV) or a salt thereof by subjecting a compound represented by the general formula

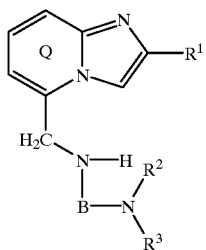

wherein the symbols are of the same meanings as defined above or a salt thereof to Mannich reaction to cause ring closure.

(5) A method of producing the compound (V) or a salt thereof by allowing a compound represented by the general formula

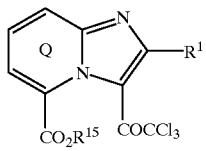

wherein $R^{15}$ stands for a $C_{1-4}$ alkyl group, and the other symbols are of the same meanings as defined above or a salt thereof to react with a compound represented by the general formula

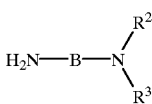

wherein the symbols are of the same meanings as defined above or a salt thereof.

These methods of producing the target compounds and those of producing the starting compounds are described as follows in further detail.

(A) method: In the case where $R^3$ of the compound (I) is —$SO_2R^4$,

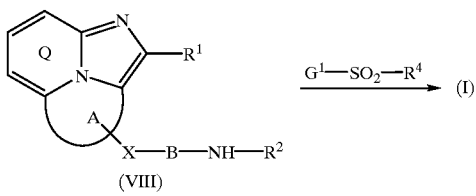

wherein $G^1$ stands for a halogen (e.g. chlorine) or $R^4SO_2$—O—, and the other symbols are of the same meanings as defined above.

(B) method: In the case where $R^3$ of the compound (I) is —CO—$R^5$,

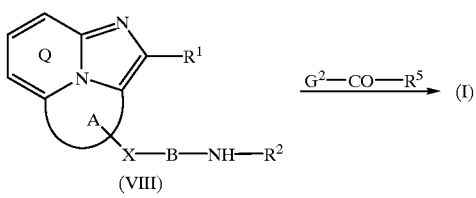

wherein $G^2$ stands for a halogen (e.g. chlorine) or $R^5CO$—O—, and the other symbols are of the same meanings as defined above.

(C) method: In the case where $R^3$ of the compound (I) is —$COOR^6$,

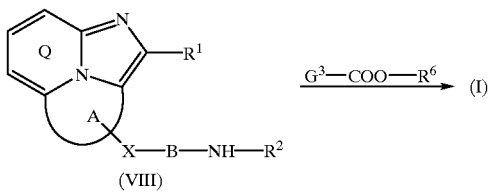

wherein $G^3$ stands for a halogen (e.g. chlorine) or $R^6CO_2$—O—, and the other symbols are of the same meanings as defined above.

(D) method: In the case where $R^3$ of the compound (I) is —$CON(R^7)R^8$,

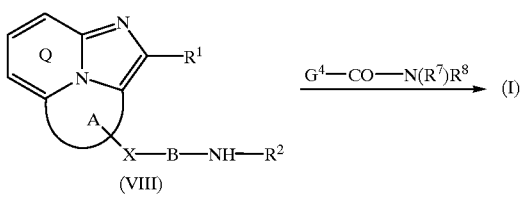

wherein $G^4$ stands for a phenoxy or halogen (e.g. chlorine), and the other symbols are of the same meanings as defined above.

(E) method:

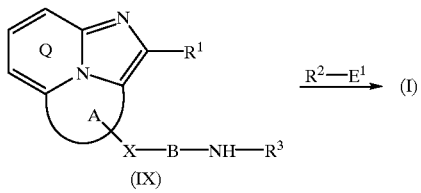

wherein $E^1$ stands for a halogen (e.g. chlorine, bromine and iodine) or a leaving group such as methanesulfonyloxy and p-toluenesulfonyloxy, and the other symbols are of the same meanings as defined above.

(F) method:

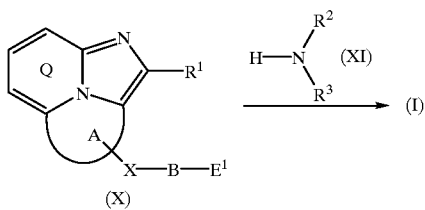

wherein the symbols are of the same meanings as defined above.

(G) method:

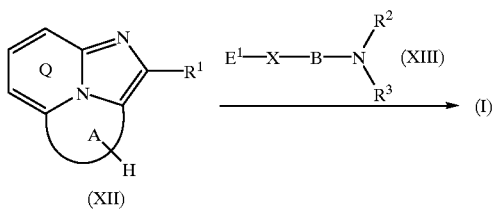

wherein the symbols are of the same meanings as defined above.

(H) method:

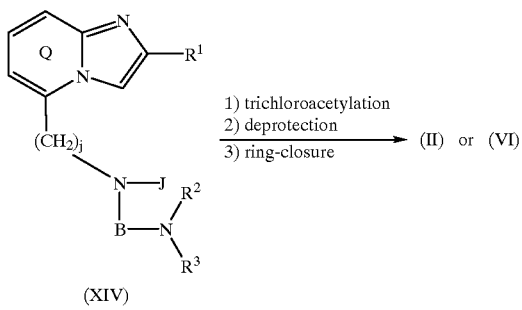

wherein j denotes 0 or 1, J stands for a hydrogen atom or a protective group of secondary amino group (e.g. benzyloxycarbonyl, tert-butoxycarbonyl, trifluoroacetyl, trityl and benzyl), and the other symbols are of the same meanings as defined above.

(I) method:

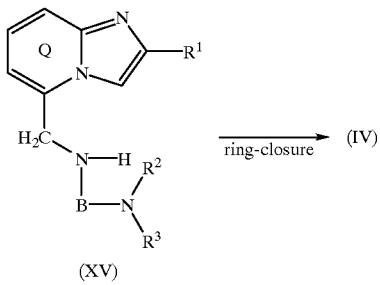

wherein the symbols are of the same meanings as defined above.

(J) method:

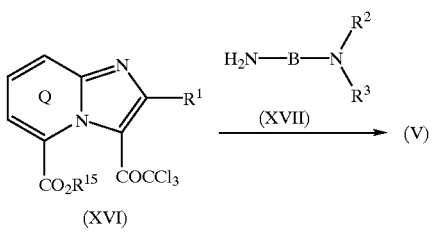

wherein $R^{15}$ stands for an alkyl group, and the other symbols are of the same meanings as defined above.

(K) method: In the case where $X^1$ of the compound (II) is a sulfur atom,

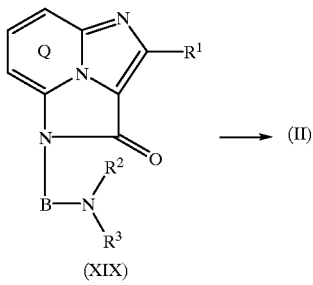

wherein $X^1$ stands for a sulfur atom, and the other symbols are of the same meanings as defined above.

(L) method: In the case where $R^2$ of the compound (I) is a hydrogen atom,

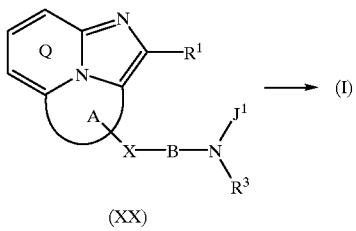

wherein $J^1$ stands for a protecting group of an amino group, and the other symbols are of the same meanings as defined above.

In the above-mentioned methods A to L, a compound, which can form a salt, may be used in the form of salt. Examples of such a salt include those as described in the above-mentioned compound (I'). In the following description of the respective methods, of a salt of each compound may also be included.

In the reaction between the compound (XII) and the compound $E^1$—Y in the method of producing the compound (I'), one equivalent to a large excess amount (1 to 10 equivalents) of the compound $E^1$—Y is employed relative to the compound (XII). In this case, a basic compound such as sodium hydroxide, potassium hydroxide, potassium hydroxide, triethylamine, diisopropylethylamine and 1,8-diazabicyclo[5,4,0]-7-undecene may be used in an amount of 1 to 10 equivalents. The reaction temperature ranges from −20 to 200° C. Examples of the solvents to be employed include water, lower alcohols (e.g. methanol, ethanol and propanol), ketones (e.g. acetone and methyl ethyl ketone), ethers (e.g. tetrahydrofuran) and aprotic polar solvents (e.g. N,N-dimethylformamide and dimethylsulfoxide). For the said reaction, as a reaction promoter, sodium iodide may be added in an amount ranging from 1 equivalent to a large excess (1 to 10 equivalents). The reaction time ranges usually from 10 minutes to 24 hours, preferably from 0.5 to 6 hours.

In the reaction between the compound (VIII) and the compound $G^1$—$SO_2$—$R^4$ in the method A, one equivalent to a large excess amount (1 to 10 equivalents) of the compound $G^1$—$SO_2$—$R^4$ is employed relative to the compound (VIII). In this case, an inorganic base such as potassium carbonate and sodium hydrogencarbonate, or an organic base such as triethylamine, pyridine, dimethylaniline and 1,4-diazabicyclo[2.2.2]octane (DABCO) may be used in an amount of 1 to 10 equivalents. The reaction temperature ranges from −30 to 100° C. Examples of the solvents to be employed include halogenated hydrocarbons (e.g. methylene chloride, chloroform and dichloroethane), ethers (e.g. diethylether and tetrahydrofuran), esters (e.g. methyl acetate and ethyl acetate), and aprotic polar solvents (e.g. N,N-dimethylformamide, dimethyl sulfoxide and acetonitrile). The reaction time ranges usually from 10 minutes to 24 hours, preferably from 0.5 to 6 hours.

The reaction between the compound (VIII) and the compound of $G^2$—CO—$R^5$ in the method B is conducted, for example, under conditions similar to those of the reaction between the compound (VIII) and the compound $G^1$—$SO_2$—$R^4$ in the method A.

The reaction between the compound (VIII) and the compound $G^3$—COO—$R^6$ in the method C is conducted, for example, under conditions similar to those of the reaction between the compound (VIII) and the compound $G^1$—$SO_2$—$R^4$ in the method A.

The reaction between the compound (VIII) and the compound of $G^4$—CO—$N(R^7)R^8$ in the method D is conducted, for example, under conditions similar to those of the reaction between the compound (VIII) and the compound $G^1$—$SO_2$—$R^4$ in the method A.

In the reaction between the compound (IX) and the compound $R^2$—$E^1$ in the method E, the compound $R^2$—$E^1$ is used in an amount ranging from one equivalent to a large excess (1 to 10 equivalents) relative to the compound (IX). And, a basic compound such as sodium hydroxide, potassium hydroxide, sodium hydride, potassium carbonate, triethylamine, diisopropylethylamine and 1,8-diazabicyclo[5.4.0]-7-undecene may optionally be used in an amount of 1 to 10 equivalents. The reaction temperature ranges from −20 to 200° C. Examples of the solvent to be employed include water, lower alcohols (e.g. methanol, ethanol and propanol), ketones (e.g. acetone and methyl ethyl ketone), ethers (e.g. tetrahydrofuran) and aprotic polar solvents (e.g. N,N-dimethylformamide and dimethyl sulfoxide). For the said reaction, as a reaction promoter, sodium iodide may be added in an amount ranging from 1 equivalent to a large excess (1 to 10 equivalents). The reaction time ranges usually from 10 minutes to 24 hours, preferably from 0.5 to 6 hours.

The reaction between the compound (X) and the compound (XI) in the method F is conducted, for example, under conditions similar to those of the reaction between the compound (IX) and the compound $R^2$—$E^1$ in the method E.

The reaction between the compound (XII) and the compound (XIII) in the method G is conducted, for example, under conditions similar to those of the reaction between the compound (IX) and the compound $R^2$—$E^1$ in the method E.

For the trichloroacetylation of the compound (XIV) in the method H, trichloroacetyl chloride or anhydrous trichloroacetate is used in an amount ranging from one equivalent to a large excess (1 to 10 equivalents) relative to the compound (XIV). In this case, 1 to 10 equivalents of an inorganic base (e.g. potassium carbonate and sodium hydrogencarbonate) or an organic base (e.g. 4-N,N-dimethylaminopyridine, triethylamine, pyridine, dimethylaniline and 1,4-diazabicyclo[2.2.2]octane) may optionally be employed. The reaction temperature ranges from 0 to 100° C. Examples of the solvent then employed include halogenated hydrocarbons (e.g. methylene chloride, chloroform and dichloroethane), ethers (e.g. diethyl ether and tetrahydrofuran), esters (e.g. methyl acetate and ethyl acetate) and aprotic polar solvents (e.g. N,N-dimethylformamide, dimethyl sulfoxide and acetonitrile). The reaction time ranges usually from 10 minutes to 100 hours, preferably from 3 to 24 hours. The above-mentioned deprotection reactions of the protective group of secondary amino group are all per se known reactions, which can be conducted in according to known conditions. For example, the benzyloxycarbonyl group or the benzyl group as the amino-protecting group can be removed by catalytic reduction (reaction temperatures ranging from room temperature to 100° C.) in a solvent (e.g. alcohol, acetic acid, water, tetrahydrofuran and an appropriate mixture of them) in the presence of a catalyst (e.g. palladium carbon or platinum oxide). In the case of trityl group or tert-butoxycarbonyl group, it can be removed by the reaction in a solvent (e.g. water, alcohol, tetrahydrofuran and dioxane) in the presence of an acid (e.g. a mineral acid such as hydrochloric acid, phosphoric acid and sulfuric acid or an organic acid such as toluenesulfonic acid, methansulfonic acid and acetic acid), at temperatures ranging from 0 to 150° C. And, in the case of tert-butoxycarbonyl group, it can be removed by processing with, for example, iodotrimethylsilane in a solvent such as chloroform. Further, trifluoroacetyl group can be easily removed by treating with alkali (e.g. an aqueous solution of sodium hydroxide or sodium hydrogencarbonate). The ring-closure reaction can be conducted concurrently with the reaction of removing the protecting group. Or, after removing the protecting group, the ring-closure reaction can be conducted by using 1 to 10 equivalents of an inorganic base (e.g. potassium carbonate and sodium hydrogencarbonate) or an organic base (e.g. 4-N,N-dimethylaminopyridine, triethylamine, pyridine, dimethylaniline and 1,4-diazabicyclo[2.2.2]octane. The reaction temperatures ranges from 0 to 100° C. Examples of the solvent then employed include halogenated hydrocarbons (e.g. methylene chloride, chloroform and dichloroethane), ethers (e.g. diethyl ether and tetrahydrofuran), esters (e.g. methyl acetate and ethyl acetate) and aprotic polar solvents (e.g. N,N-dimethylformamide, dimethyl sulfoxide and acetonitrile).

The reaction time ranges usually from 10 minutes to 24 hours, preferably from 10 minutes to 6 hours.

For the ring-closure reaction by Mannich reaction using the compound (XV) and formalin in the method I, formalin is used in an amount of large excess (2 to 20 equivalents) relative to the compound (XV). The reaction temperature ranges from −20 to 150° C. Examples of the solvent then used include water, lower alcohols (e.g. methanol, ethanol, propanol and isopropanol) and lower fatty acids (e.g. acetic acid and propionic acid). The reaction time ranges usually from 10 minutes to 24 hours, preferably from 10 minutes to 3 hours.

The reaction between the compound (XVI) and the compound (XVII) in the method J is conducted, for example, under conditions similar to those of the reaction between the compound (VIII) and the compound $G^1$—$SO_2$—$R^4$ in the method A.

The conversion of the compound (XIX) to the thiolactam in the method K can be conducted with, for example, one equivalent to a large excess (1 to 10 equivalents) of phosphorus pentachloride relative to the compound (XIX). The reaction temperature ranges from 0 to 200° C. Examples of the solvent then employed include aromatic hydrocarbons (e.g. benzene, toluene and xylene) and pyridine. The reaction time ranges usually from 30 minutes to 24 hours, preferably from 1 to 12 hours.

The reaction for removing the amino-protective group of the compound (XX) in the method L can be conducted, for example, under conditions similar to removing the amino-protecting group in the method H.

The compound (VIII) can be synthesized by, for example, the following methods.

(i)

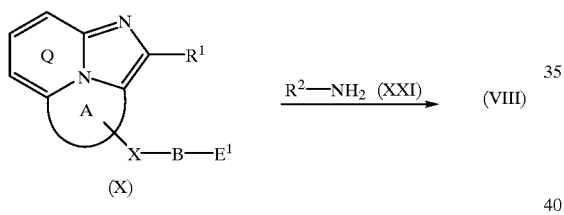

wherein the symbols are of the same meanings as defined above.

The reaction between the compound (X) and the compound (XXI) is conducted under conditions similar to those of the reaction between the compound (X) and the compound (XI) in the method F.

(ii)

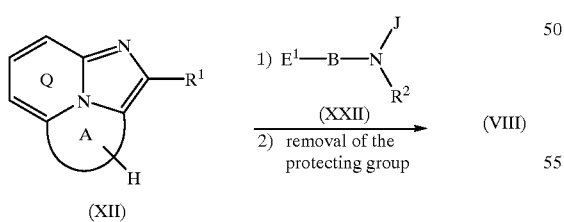

wherein the symbols are of the same meanings as defined above.

The reaction between the compound (XII) and the compound (XXII) is conducted under conditions similar to those of the reaction between the compound (XII) and the compound (XIII) in the method G. And, the reaction for removing the amino-protective group is conducted under conditions similar to those of removing the protective group in the method H.

The compound (IX) can be synthesized by, for example, the following method.

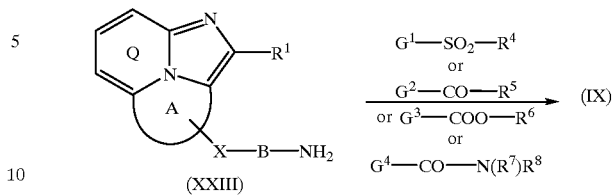

wherein the symbols are of the same meanings as defined above.

The reaction between the compound (XXIII) and $G^1$—$SO_2$—$R^4$ is conducted, for example, under conditions similar to those of the reaction between the compound (VIII) and $G^1$—$SO_2$—$R^4$ in the method A. The reaction between the compound (XXIII) and $G^2$—CO—$R^5$ is conducted, for example, under conditions similar to those of the reaction between the compound (VIII) and $G^2$—CO—$R^5$ in the method B. The reaction between the compound (XXIII) and $G^3$—COO—$R^6$ is conducted, for example, under conditions similar to those of the reaction between the compound (VIII) and $G^3$—COO—$R^6$ in the method C. The reaction between the compound (XXIII) and $G^4$—CO—N($R^7$)$R^8$ is conducted, for example, under conditions similar to those of the reaction between the compound (VIII) and $G^4$—CO—N($R^7$)$R^8$ in the method D.

The compound (X) can be synthesized by, for example, the following method.

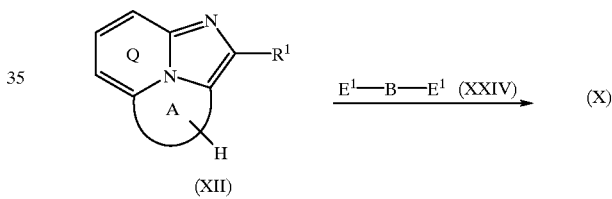

wherein the symbols are of the same meanings as defined above.

The reaction between the compound (XII) and the compound (XXIV) is conducted, for example, under conditions similar to those of the reaction between the compound (XII) and the compound (XIII) in the method G.

The compound (XII) can be synthesized by, for example, the following method.

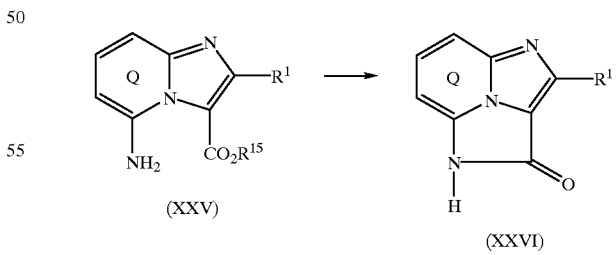

wherein the symbols are of the same meanings as defined above.

The cyclization of the compound (XXV), can be conducted with one equivalent to a large excess (1 to 10 equivalents) of a base such as sodium hydride, potassium hydride or lithium diisopropyl amide relative to one equivalent of the compound (XXV). The reaction temperature ranges from −20 to 150° C. The solvent then employed is exemplified by ethers (e.g. tetrahydrofuran and dioxane) and aprotic polar solvents (e.g. N,N-dimethylformamide and dimethyl sulfoxide). The reaction time ranges usually from 10 minutes to 6 hours, preferably from 0.5 to 3 hours.

(ii)

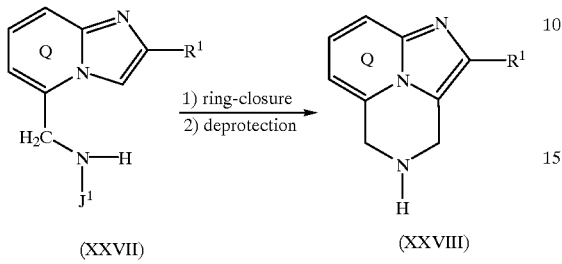

(XXVII)   (XXVIII)

wherein the symbols are of the same meanings as defined above.

The ring-closure reaction of the compound (XXVII) is conducted, for example, under conditions similar to those of the ring-closure reaction of the compound (XV) in the method I. And, the reaction for removing the amino-protecting group is conducted, for example, under conditions similar to those of the reaction of removing the protective group in the method H.

(iii)

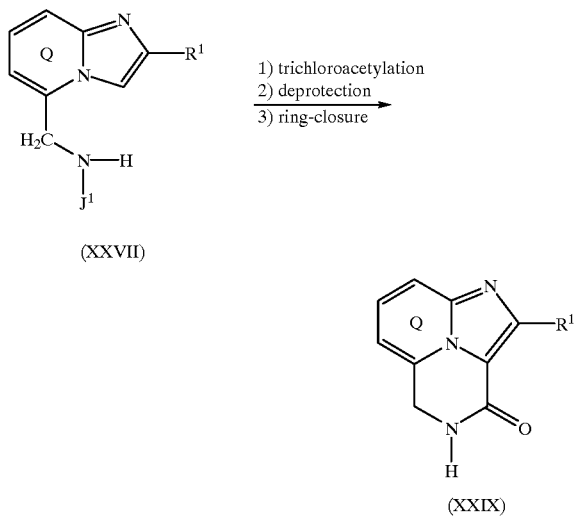

(XXVII)

(XXIX)

wherein the symbols are of the same meanings as defined above.

The trichloroacetylation, removal of the protective group and ring-closure reaction of the compound (XXVII) are conducted, for example, under conditions similar to those for the trichloroacetylation, removal of the protective group and ring-closure reaction of the compound (XIV) in the method H.

(iv)

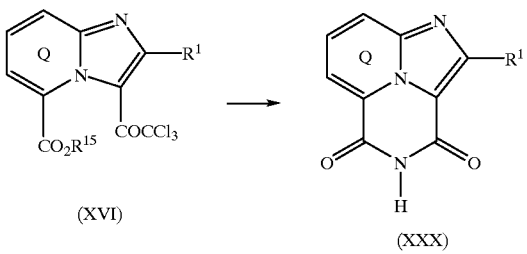

(XVI)   (XXX)

wherein the symbols are of the same meanings as defined above.

The ring-closure reaction of the compound (XVI), can be conducted with, for example, one equivalent to a large excess amount (1 to 100 equivalents) of aqueous ammonia relative to one equivalent of the compound (XVI). The reaction temperature ranges from 0 to 150° C. The solvent then employed is exemplified by water, lower alcohols (e.g. methanol, ethanol, propanol and isopropanol), halogenated hydrocarbons (e.g. methylene chloride, chloroform and dichloroethane), ethers (e.g. tetrahydrofuran and dioxane), esters (e.g. methyl acetate and ethyl acetate), and aprotic polar solvents (e.g. N,N-dimethylformamide and dimethyl sulfoxide). The reaction temperature ranges usually from 10 minutes to 24 hours, preferably from 3 to 12 hours.

The compound (XIV) can be synthesized by, for example, the following method.

(i) When j is 1;

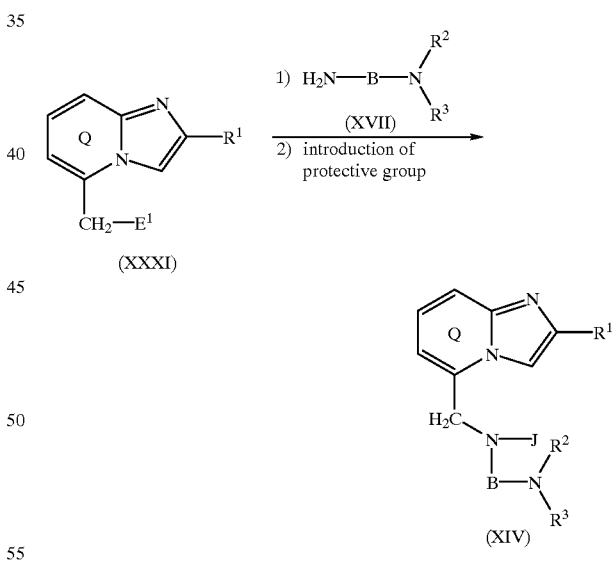

(XXXI)

(XIV)

wherein the symbols are of the same meanings as defined above.

The reaction between the compound (XXXI) and the compound (XVII) is conducted, for example, under conditions similar to those of the reaction between the compound (X) and the compound (XI) in the method F. The reaction for introducing the amino-protecting group is a per se known reaction such as the above-mentioned deprotection of the amino group, which can be conducted according to known conditions.

(ii) When j is 0 and J is a hydrogen atom;

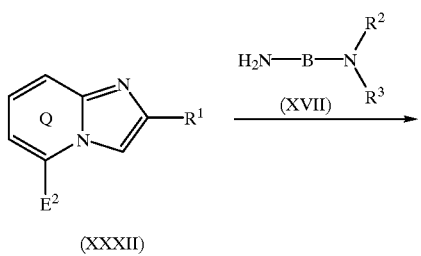

(XXXII)

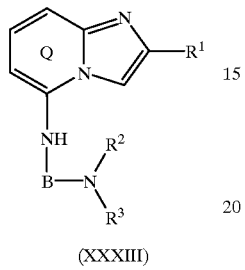

(XXXIII)

wherein $E^2$ stands for, for example, a halogen (e.g. chlorine, bromine and iodine), and the other symbols are of the same meanings as defined above.

The reaction between the compound (XXXII) and the compound (XVII) is conducted, for example, under conditions similar to those of the reaction between the compound (X) and the compound (XI) in the method F.

(iii) When j is 0, and, J and $R^2$ are both a hydrogen atom;

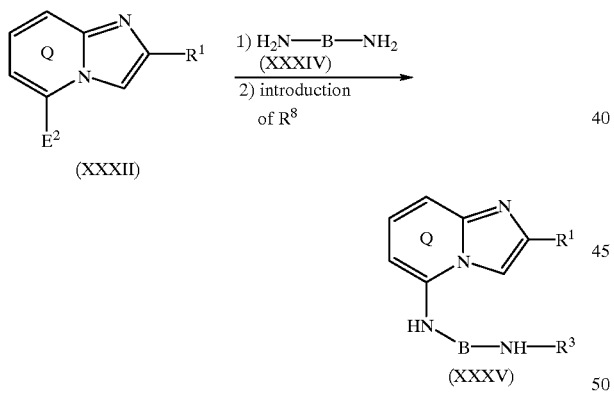

wherein the symbols are of the same meanings as defined above.

The reaction between the compound (XXXII) and the compound (XXXIV) is conducted, for example, under conditions similar to those of the reaction between the compound (X) and the compound (XI) in the method F. Introduction of $R^3$ is conducted, for example, under conditions similar to those of the reaction between the compound (VIII) and $G^1—SO_2—R^4$ in the method A, those of the reaction between the compound (VIII) and $G^2—CO—R^5$ in the method B, those for the reaction between the compound (VIII) and $G^3—COO—R^6$ in the method C and those for the reaction between the compound (VIII) and $G^4—CO—N(R^7)R^8$ in the method D.

(iv) When j is 1 and $R^2$ is a hydrogen atom;

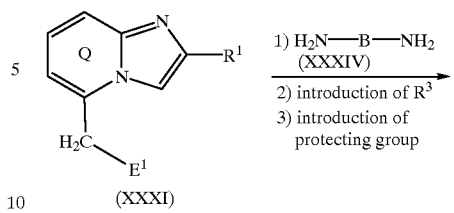

(XXXI)

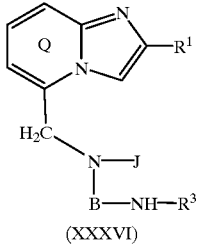

(XXXVI)

The reaction between the compound (XXXI) and the compound (XXXIV) and the introduction of $R^3$ are conducted under conditions similar to those of the reaction between the compound (XXXII) and the compound (XXXIV) and for the introduction of $R^3$ described in (iii) above.

The reactions for introducing the amino-protecting group are all per se known ones as described above, for example, and they can be conducted according to the conditions of them.

The compound (XV) can be synthesized by, for example, the following methods.

(i)

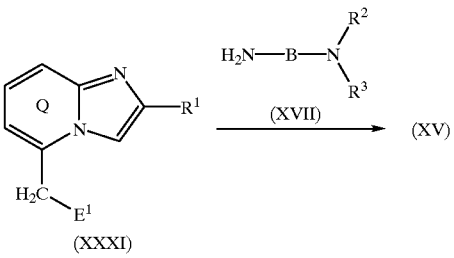

(XXXI)

wherein the symbols are of the same meanings as defined above.

The reaction between the compound (XXXI) and the compound (XVII) is conducted, for example, under conditions similar to those of the reaction between the compound (X) and the compound (XI) in the method F.

(ii)
When $R^2$ is a hydrogen atom;

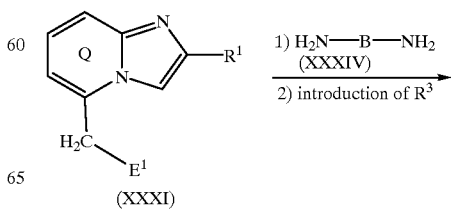

(XXXI)

(i)

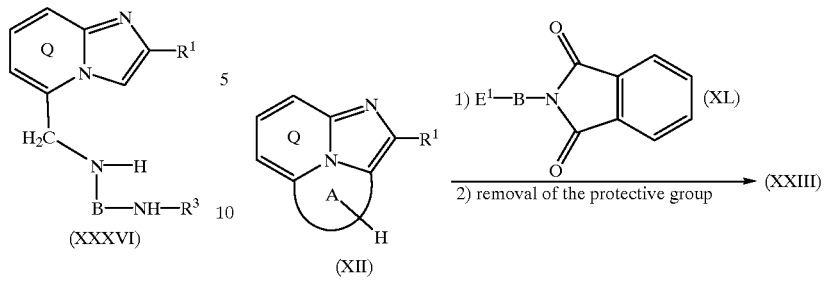

(XXIII)

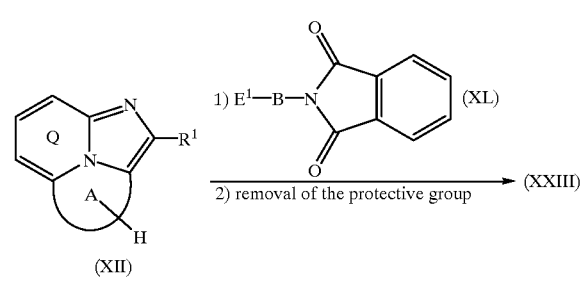

wherein the symbols are of the same meanings as defined above.

The reaction between the compound (XII) and the compound (XL) is conducted, for example, under conditions similar to those of the reaction between the compound (XII) and the compound (XIII) in the method G. The removal of phthalimido group, which is the amino-protecting group, can be conducted by the reaction with hydrazine hydrate in a solvent (e.g. methanol and ethanol).

(ii)

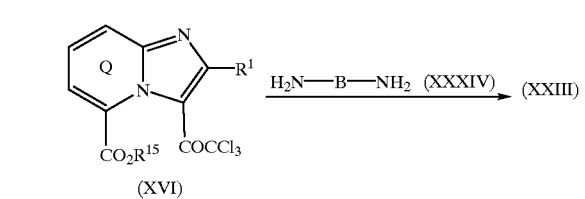 (XXIII)

wherein the symbols are of the same meanings as defined above.

The reaction between the compound (XVI) and the compound (XXXIV) is conducted, for example, under conditions similar to those of the reaction between the compound (XVI) and the compound (XVII) in the method J.

The compound (XXV) can be synthesized by, for example, the following method.

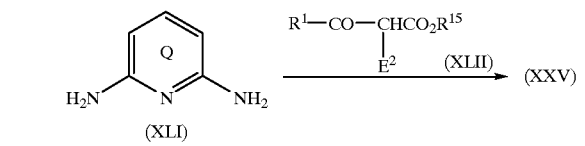 (XXV)

wherein the symbols are of the same meanings as defined above.

For the reaction between the compound (XLI) and the compound (XLII), the compound (XLII) is used in an amount ranging from one equivalent to a large excess (1 to 10 equivalents) relative to one equivalent of the compound (XLI). The reaction temperature ranges from 0 to 200° C. Examples of the solvent then employed include water, lower alcohols (e.g. methanol, ethanol and propanol), ethers (e.g. tetrahydrofuran, dimethoxyethane and dioxane), nitrites (e.g. acetonitrile and propionitrile) and aprotic polar solvents (e.g. N,N-dimethylformamide and dimethyl sulfoxide). To the reaction system, may optionally be added, as the agent for removing acid 1 to 10 equivalents of an inorganic base such as potassium carbonate and sodium hydrogencarbonate, or an organic base such as triethylamine, pyridine and dimethylaniline. The reaction wherein the symbols are of the same meanings as defined above.

The reaction between the compound (XXXI) and the compound (XXXIV) is conducted, for example, under conditions similar to those of the reaction between the compound (X) and the compound (XI) in the method F. Introduction of $R^3$ is conducted, for example, under conditions similar to those of the reaction between the compound (VIII) and $G^1$—$SO_2$—$R^4$ in the method A, those of the reaction between the compound (VIII) and $G^2$—$CO_2$—$R^5$ in the method B, those of the reaction between the compound (VIII) and $G^3$—COO—$R^6$ in the method C and those of the reaction between the compound (VIII) and $G^4$—CO—N($R^7$) $R^8$ in the method D.

The compound (XVI) can be synthesized by, for example, the following method.

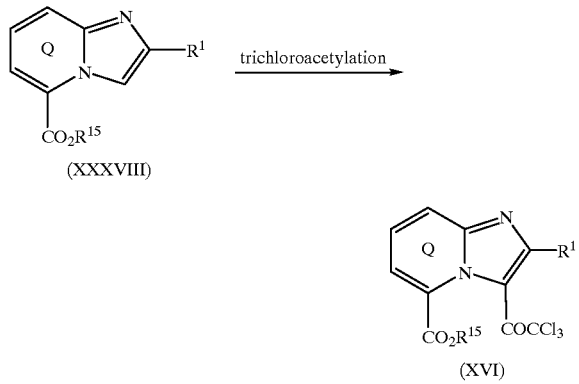

wherein the symbols are of the same meanings as defined above.

Trichloroacetylation of the compound (XXXVIII) is conducted, for example, under conditions similar to those of trichloroacetylation of the compound (XIV) in the method H.

The compound (XXIII) can be synthesized by the following methods.

time ranges usually from 10 minutes to 7 days, preferably from one hour to two days.

The compound (XXVII) can be synthesized by, for example, the following method.

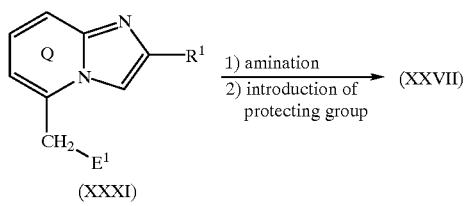

(XXXI)

wherein the symbols are of the same meanings as defined above.

The reactions for introducing primary amino group into the compound (XXXI) are all per se known ones, which can be conducted according to known reaction conditions. For example, hexamethylene tetramine in an amount of one equivalent to a large excess (1 to 10 equivalents) is used relative to one equivalent of the compound (XXXI). Examples of the solvent for this reaction include water, lower alcohols (e.g. methanol, ethanol and propanol), ethers (e.g. tetrahydrofuran, dimethoxyethane and dioxane), nitriles (e.g. acetonitrile and propionitrile) and aprotic polar solvents (e.g. N,N-dimethylformamide and dimethyl sulfoxide). The reaction temperature ranges from 0 to 200° C. The quaternary ammonium salt then formed can be hydrolyzed with an acid, such as hydrochloric acid (1 to 20 equivalents). The reaction temperature ranges from 0 to 100° C. The reaction time ranges usually from 10 minutes to 24 hours, preferably from 1 to 3 hours. Further, the reactions for introducing a protective group into primary amino group are all per se known ones, which can be conducted according to known reaction conditions.

The compound (XXXI) can be synthesized by, for example, the following method.

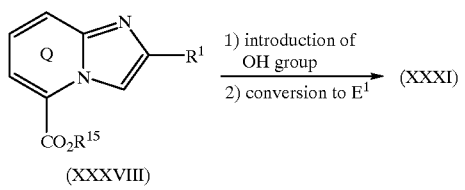

(XXXVIII)

wherein the symbols are of the same meanings as defined above.

The reduction of the compound (XXXVIII) is conducted by using a reducing agent, for example, a metal hydride complex compound such as sodium borohydride, lithium borohydride and aluminum lithium hydride or borane complex compounds in an amount ranging from one equivalent to a large excess (1 to 10 equivalents) relative to one equivalent of the compound (XXXVIII). The reaction temperature ranges from −20 to 100° C. Examples of the solvent employed for this reaction include alcohols (e.g. methanol and ethanol) and ethers (e.g. ethyl alcohol, tetrahydrofuran and dioxane). The reaction time ranges usually from 10 minutes to 24 hours, preferably from 0.5 to 6 hours. The conversion of hydroxyl group to $E^1$ is conducted, when $E^1$ is halogen atom, by allowing 1 to 5 equivalents of a halogenating agent, for example, phosphorus halogenide such as phosphorus trichloride, phosphorus oxychloride, phosphorus pentachloride and phosphorus tribromide, a mixture of red phosphorus and halogen, or thionyl chloride to react with one equivalent of an alcohol compound. When $E^1$ is toluenesulfonyloxy group or methanesulfonyloxy group, 1 to 5 equivalents of toluenesulfonyl chloride or methanesulfonyl chloride is allowed to react with one equivalent of an alcohol compound. In this case, 1 to 10 equivalents of, for example, an inorganic base such as potassium carbonate and sodium hydrogencarbonate or an organic base such as 4-N,N-dimethylaminopyridine, triethylamine, pyridine, dimethyl aniline and 1,4-diazabicyclo[2.2.2]octane may optionally be used. The reaction temperature ranges from 0 to 100° C. Examples of the solvent used in this case include halogenated hydrocarbons (e.g. methylene chloride, chloroform and dichloroethane), water, ethers (e.g. diethyl ether and tetrahydrofuran), esters (e.g. methyl acetate and ethyl acetate) and aprotic polar solvents (e.g. N,N-dimethylformamide, dimethyl sulfoxide and acetonitrile). The reaction time ranges usually from 10 minutes to 100 hours, preferably from 3 to 24 hours.

The compound (XXXII) can be synthesized by, for example, the following method.

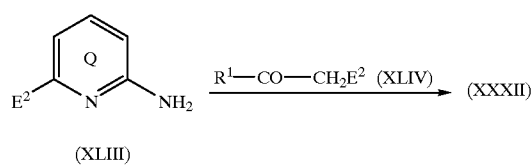

(XLIII)

wherein the symbols are of the same meanings as defined above.

The reaction between the compound (XLIII) and the compound (XLIV) can be conducted under conditions similar to those of the reaction between the compound (XLI) and the compound (XLII) in the above-mentioned method of synthesizing the compound (XXV).

The compound (XXXVIII) can be synthesized by, for example, the following method.

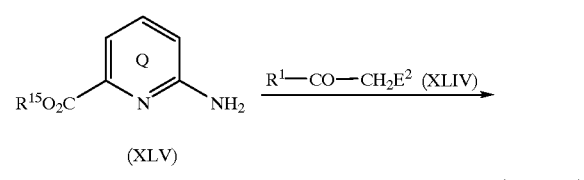

(XLV)

(XXXVIII)

wherein the symbols are of the same meanings as defined above.

The reaction between the compound (XLV) and the compound (XLIV) can be conducted under conditions similar to those of the reaction between the compound (XLI) and the compound (XLII) in the above-mentioned method for synthesizing the compound (XXV).

The compound (A) or a salt thereof of the present invention can be synthesized by, for example, (1) a process for producing the compound (A) or a salt thereof which comprises reacting a compound of the formula:

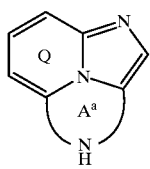
(B)

wherein all symbols are of the same meanings as defined above, or a salt thereof, with a compound of the formula:

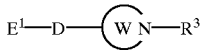
(C)

wherein all symbols are of the same meanings as defined above, or a salt thereof, (2) a process for producing the compound (A) or a salt thereof which comprises reacting a compound of the formula:

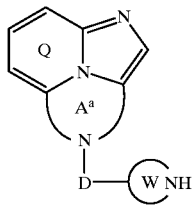
(D)

wherein all symbols are of the same meanings as defined above, or a salt thereof, with a compound of the formula:
G$^1$—R$^3$ wherein all symbols are of the same meanings as defined above, or a salt thereof, (3) a process for producing the compound (A) or a salt thereof (J is 0) which comprises reacting a compound of the formula:

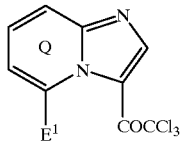
(E)

wherein all symbols are of the same meanings ad defined above, or a salt thereof, with a compound of the formula:

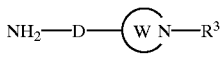
(F)

wherein all symbols are of the same meanings as defined above, or a salt thereof, (4) a process for producing the compound (A) or a salt thereof (J is 1) which comprises reacting a compound of the formula:

(G)

wherein R$^a$ is C$_{1-6}$ alkyl group (e.g. methyl, ethyl, propyl, isopropyl), and the other symbols are of the same meanings as defined above, or a salt thereof, with a compound of the formula:

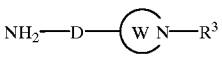
(F)

wherein all symbols are of the same meanings as defined above, or a salt thereof, (5) a process for producing the compound (A) or a salt thereof which comprises subjecting a compound of the formula:

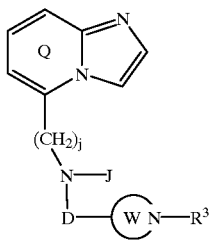
(H)

wherein all symbols are of the same meanings as defined above, or a salt thereof to trichloroacetylation, and then in case of need, deprotection of the protecting group J, and further subjecting the resultant compound to ring-closure reaction, (6) a process for producing the compound (A) or a salt thereof which comprises subjecting a compound of the formula:

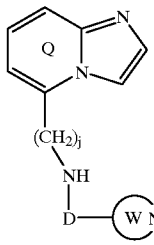
(J)

wherein all symbols are of the same meanings as defined above, or a salt thereof to ring-closure reaction by using Mannich reaction, and (7) a process for producing the compound (A) or a salt thereof (J is 0) which comprises reacting a compound of the formula:

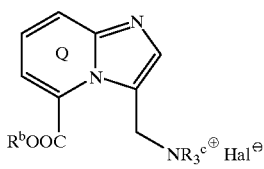

(K)

wherein $R^b$ and $R^c$ are respectively $C_{1-6}$ alkyl group (e.g. methyl, ethyl, propyl, isopropyl), Hal is a halogen atom (e.g. chlorine, bromine, iodine), ring Q is of the same meaning as defined above, or a salt thereof, with a compound of the formula:

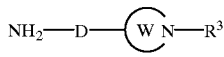

(F)

wherein all symbols are of the same meanings as defined above, or a salt thereof.

A method of producing the compound (A) or a salt thereof, or the satarting compound for producing it is as follow.

Method M

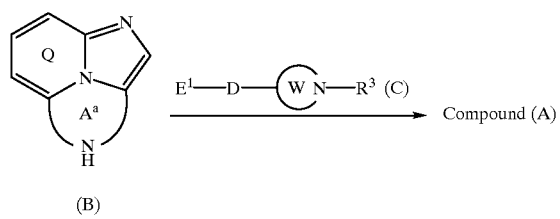

(wherein all symbols are of the same meanings as defined above)

Method N

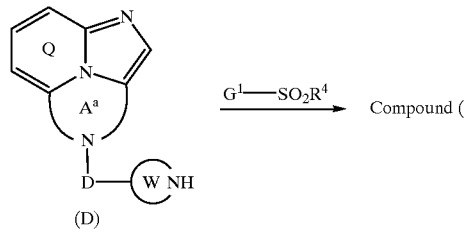

(wherein all symbols are of the same meanings as defined above)

Method O

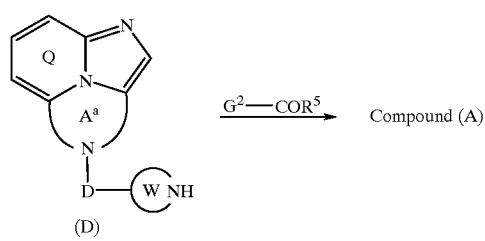

(wherein all symbols are of the same meanings as defined above)

Method P

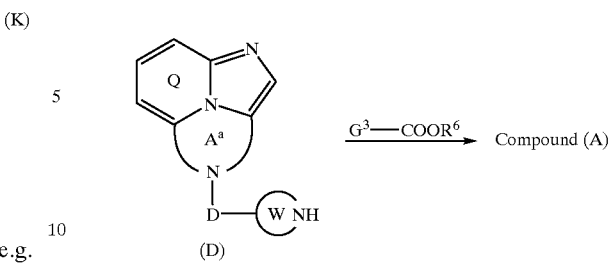

(wherein all symbols are of the same meanings as defined above)

Method Q

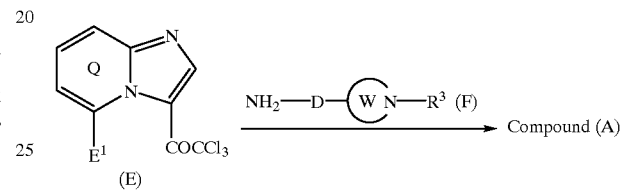

(wherein all symbols are of the same meanings as defined above)

Method R

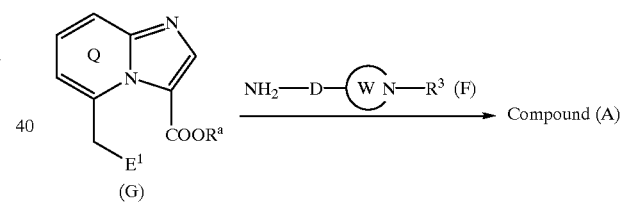

(wherein all symbols are of the same meanings as defined above)

Method S

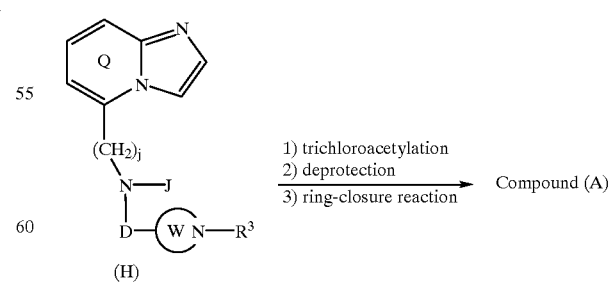

(wherein all symbols are of the same meanings as defined above)

Method T

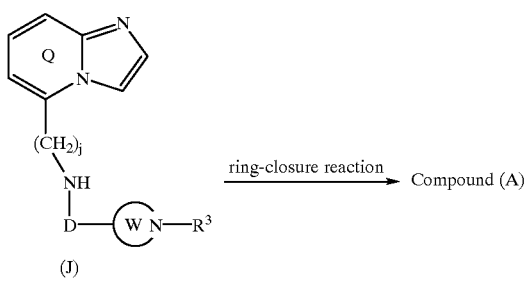

(wherein all symbols are of the same meanings as defined above)

Method U

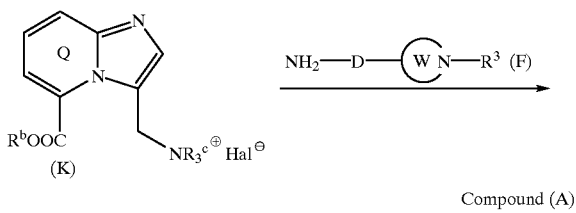

(wherein all symbols are of the same meanings as defined above)

In the reaction between the compound (B) and the compound (C) in the method M for producing the compound (A), one equivalent to a large excess amount (1 to 10 equivalents) of the compound (C) is employed relative to the compound (B). In this case, a basic compound such as sodium hydroxide, potassium hydroxide, sodium hydride, potassium carbonate, triethylamine, diisopropylethylamine 1,4-diazabicyclo[2.2.2]octane and 1,8-diazabicyclo[5.4.0]-7-undecene may be used in an amount of 1 to 10 equivalents. The reaction temperature ranges from −20 to 200° C. Examples of the solvents to be employed include water, lower alcohols (e.g. methanol, ethanol and propanol), ketones (e.g. acetone and methyl ethyl ketone), ethers (e.g. tetrahydrofuran) and aprotic polar solvents (e.g. N,N-dimethylformamide and dimethylsulfoxide). For the said reaction, as a reaction-promoting agent, sodium iodide may be added in an amount ranging from one equivalent to a large excess (1 to 10 equivalents). The reaction time ranges usually from 10 minutes to 24 hours, preferably from 0.5 to 6 hours.

In the reaction between the compound (D) and the compound: $G^1$—$SO_2$—$R^4$ in the method N, one equivalent to a large excess amount (1 to 10 equivalents) of the compound: $G^1$—$SO_2$—$R^4$ is employed relative to the compound (D). In this case, an inorganic base such as potassium carbonate and sodium hydrogencarbonate, or an organic base such as triethylamine, pyridine, dimethylaniline, 1,4-diazabicyclo[2.2.2]octane (DABCO), or 1,8-diazabicyclo[5.4.0]-7-undecene may be used in an amount of 1 to 10 equivalents. The reaction temperature ranges from −30 to 100° C. Examples of the solvents to be employed include halogenated hydrocarbons (e.g. methylene chloride, chloroform and dichloroethane), ethers (e.g. diethylether and tetrahydrofuran), esters (e.g. methyl acetate and ethyl acetate) and aprotic polar solvents (e.g. N,N-dimethylformamide, dimethyl sulfoxide and acetonitrile). The reaction time ranges usually from 10 minutes to 24 hours, preferably from 0.5 to 6 hours.

The reaction between the compound (D) and the compound: $G^2$—CO—$R^5$ in the method O is conducted, for example, under conditions similar to those of the reaction between the compound (D) and the compound: $G^1$—$SO_2$—$R^4$ in the method N.

The reaction between the compound (D) and the compound: $G^3$—COO—$R^6$ in the method P is conducted, for example, under conditions similar to those of the reaction between the compound (D) and the compound: $G^1$—$SO_2$—$R^4$ in the method N.

The reaction between the compound (E) and the compound (F) in the method Q is conducted, for example, under conditions similar to those of the reaction between the compound (B) and the compound (C) in the method M.

The reaction between the compound (G) and the compound (F) in the method R is conducted, for example, under conditions similar to those of the reaction between the compound (B) and the compound (C) in the method M.

For the trichloroacetylation of the compound (H) in the method S, trichloroacetyl chloride or anhydrous trichloroacetate is used in an amount ranging from one equivalent to a large excess (1 to 10 equivalents) relative to the compound (H). In this case, 1 to 10 equivalents of an inorganic base (e.g. potassium carbonate and sodium hydrogencarbonate) or an organic base (e.g. 4-N,N-dimethylaminopyridine, triethylamine, pyridine, dimethylaniline and 1,4-diazabicyclo[2.2.2]octane, 1,8-diazacyclo[5.4.0]-7-undene) may optionally be employed. The reaction temperature ranges from 0 to 100° C. Examples of the solvent then employed include halogenated hydrocarbons (e.g. methylene chloride, chloroform and dichloroethane), ethers (e.g. diethyl ether and tetrahydrofuran), esters (e.g. methyl acetate and ethyl acetate) and aprotic polar solvents (e.g. N,N-dimethylformamide, dimethyl sulfoxide and acetonitrile). The reaction time ranges usually from 10 minutes to 100 hours, preferably from 3 to 24 hours. The above-mentioned deprotection reactions of the protective group of secondary amino group represented by J, are all per se known reactions, which can be conducted in according to known conditions. For example, the benzyloxycarbonyl group or the benzyl group as the amino-protecting group can be removed by catalytic reduction (reaction temperatures ranging from room temperature to 100° C.) in a solvent (e.g. alcohol, acetic acid, water, tetrahydrofuran and an appropriate mixture of them) in the presence of a catalyst (e.g. palladium carbon or platinum oxide). In the case of trityl group or tert-butoxycarbonyl group, it can be removed by the reaction in a solvent (e.g. water, alcohol, tetrahydrofuran and dioxane) in the presence of an acid (e.g. a mineral acid such as hydrochloric acid, phosphoric acid and sulfuric acid or an organic acid such as toluenesulfonic acid, methansulfonic acid and acetic acid), at temperatures ranging from 0 to 150° C. And, in the case of tert-butoxycarbonyl group, it can be removed by processing with, for example, iodotrimethylsilane in a solvent such as chloroform. Further, trifluoroacetyl group can be easily removed by treating with an alkali (e.g. an aqueous solution of sodium hydroxide or sodium hydrogencarbonate). The ring-closure reaction can be conducted concurrently with the reaction of removing the protecting group. Or, after removing the protecting group, the ring-closure reaction can be conducted by using 1 to 10 equivalents of an inorganic base (e.g. potassium carbonate and sodium hydrogencarbonate) or an organic base (e.g. 4-N,N-dimethylaminopyridine, triethylamine, pyridine, dimethylaniline, 1,4-diazabicyclo[2.2.2]octane and 1,8-diazacyclo[5.4.0]-7-undene). The reaction temperatures ranges from 0 to 100° C. Examples of the solvent then employed include halogenated hydrocarbons (e.g. methylene chloride, chloroform and dichloroethane), ethers (e.g. diethyl ether and tetrahydrofuran), esters (e.g. methyl acetate and ethyl acetate) and aprotic polar solvents (e.g. N,N-dimethylformamide, dimethyl sulfoxide and acetonitrile). The reaction time ranges usually from 10 minutes to 24 hours, preferably from 10 minutes to 6 hours.

For the ring-closure reaction by Mannich reaction using the compound (J) and formalin in the method T, formalin is used in an amount of large excess (2 to 20 equivalents) relative to the compound (J). The reaction temperature ranges from −20 to 150° C. Examples of the solvent used include water, lower alcohols (e.g. methanol, ethanol, propanol and isopropanol) and lower fatty acids (e.g. acetic acid and propionic acid). The reaction time ranges usually from 10 minutes to 24 hours, preferably from 10 minutes to 3 hours.

In the reaction between the compound (K) and the compound (F) in the method U of producing the compound (A), one equivalent to a large excess amount (1 to 10 equivalents) of the compound (F) is employed relative to the compound (K). In this case, sodium hydroxide, potassium hydroxide, sodium hydride, potassium carbonate, triethylamine, diisopropylethylamine, 1,4-diazabicyclo[2.2.2]octane or 1,8-diazabicyclo[5.4.0]-7-undene may be used in an amount of 1 to 10 equivalents. The reaction temperature ranges from −20 to 200° C. Examples of the solvents to be employed include water, lower alcohols (e.g. methanol, ethanol, propanol, isopropanol), ethers (e.g. diethylether, tetrahydrofuran), estels (e.g. methyl acetate, ethyl acetate) and aprotic polar solvents (e.g. N,N-dimethylformamide, dimethylsulfoxide). The reaction time ranges usually from 0.5 to 96 hours, preferably from 6 to 24 hours.

The compound (B) can be synthesized by using the similar method of producing the compound (II).

The oxo group on ring $A^a$ of the compound (B) can be reduced as follow.

(i)

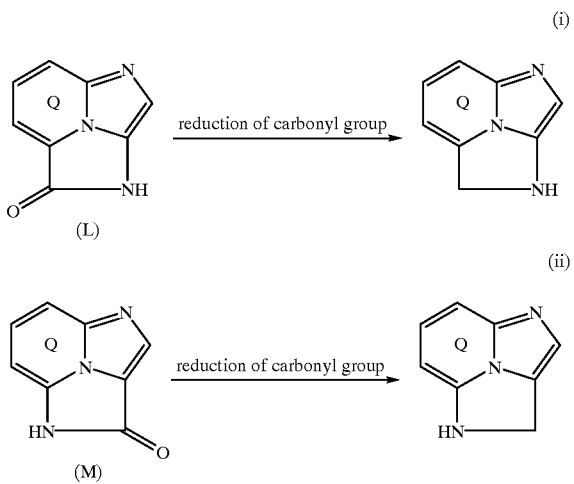

(wherein ring Q is of the same meaning as defined above)

In the reduction of the compounds (L) and (M), one equivalent to a large excess amount (1 to 10 equivalents) of metal hydride complex compound (e.g. sodium boron hydride, lithium boron hydride, lithium aluminum hydride) or borane complex compound is employed relative to the compounds (L) or (M). In this case, alcohols (e.g. methanol, ethanol) and ethers (e.g. ethylether, tetrahydrofuran, dioxane) may be used as the solvent.

The reaction temperature ranges from −10 to 100° C. The reaction time ranges usually from 10 minutes to 24 hours, preferably from 0.5 to 6 hours.

The compound (D) can be synthesized by following methods and so on.

(i)

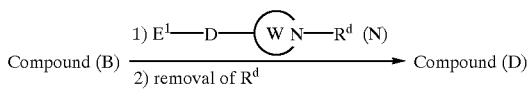

(wherein $R^d$ is a hydrogen atom or a protective group of amino group (e.g. benzyloxycarbonyl, tert-butoxycarbonyl, trifluoroacetyl, trityl, benzyl), and the other symboles are of the same meanings as defined above)

The reaction between the compound (B) and the compound (N) is conducted, for example, under conditions similar to those of the reaction between the compound (B) and the compound (C) in the method M. Removal of protective group $R^d$ of secondary amino group is a per se known reaction and so on.

(ii)

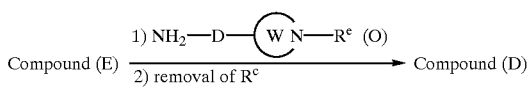

(wherein $R^e$ is a hydrogen atom or a protective group of amino group (e.g. benzyloxycarbonyl, tert-butoxycarbonyl, trifluoroacetyl, trityl, benzyl), and the other symboles are of the same meanings as defined above)

The reaction between the compound (E) and the compound (O) is conducted, for example, under conditions similar to those of the reaction between the compound (B) and the compound (C) in the method M. Removal of protective group $R^e$ of secondary amino group is a per se known reaction and so on.

(iii)

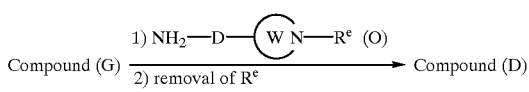

(wherein all symbols are of the same meanings as defined above)

The reaction between the compound (G) and the compound (O) is conducted, for example, under conditions similar to those of the reaction between the compound (B) and the compound (C) in the method M.

Removal of protective group $R^e$ of secondary amino group is a per se known reaction and so on.

(iv)

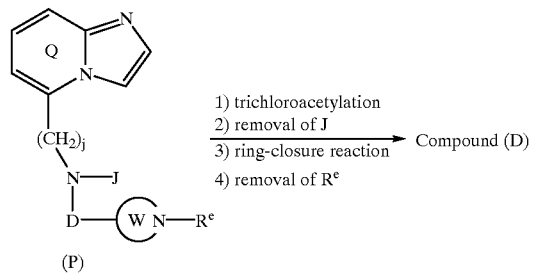

(wherein all symbols are of the same meanings as defined above)

The trichloroacetylation of the compound (P) is conducted, for example, under conditions similar to those of the trichloroacetylation of the compound (H) in the method S. Removal of protective group J of secondary amino group is conducted, for example, under conditions similar to those of the removal of protective group of amino group in the method S.

The ring-closure reaction is conducted, for example, under conditions similar to those of the ring-closure reaction in the method S. Removal of $R^e$ is a per se known reaction and so on.

(v)

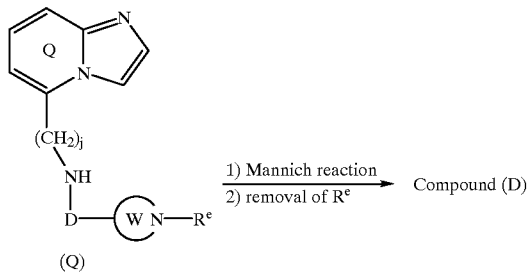

(wherein all symbols are of the same meanings as defined above)

The Mannich reaction of the compound (Q) is conducted, for example, under conditions similar to those of the Mannich reaction of the compound (J) in the method T. Removal of protective group $R^e$ of secondary amino group is a per se known reaction and so on.

(vi)

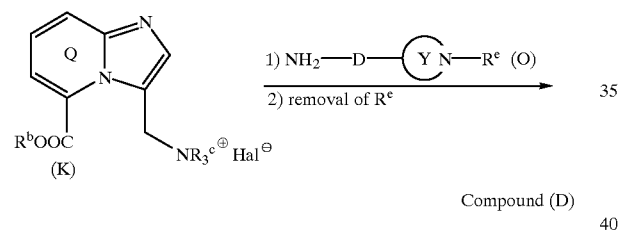

(wherein all symbols are of the same meanings as defined above)

The reaction between the compound (K) and the compound (O) is conducted, for example, under conditions similar to those of the reaction between the compound (K) and the compound (F) in the method U. Removal of protective group $R^b$ of secondary amino group is a per se known reaction and so on.

The compounds (L) and (M) can be synthesized by the similar methods for producing the compound (XII) such as the compounds (XXVI), (XXVIII) and (XXIX) as described above.

The compound (G) can be synthesized be the following method.

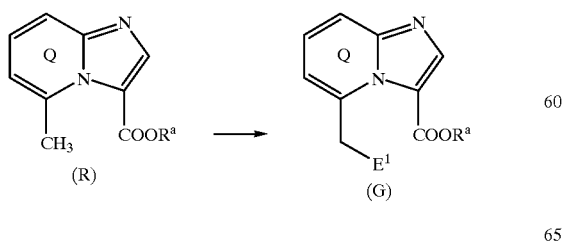

(wherein all symbols are of the same meanings as defined above)

The reaction for introducing $E^1$ into the compound (R) is a per se known reaction and so on. For example, chlorine, bromine, tert-butyl hypohalogerite, N-halogenosuccinimido (e.g. N-bromosuccinimido), N-bromocaprolactam, N-bromophthalimido, 1,3-dibromo-5,5-dimethylhydantoin, trichloromethanesulfonyl halide (e.g. trichloromethanesulfonylchloride), tribromomethane and phosphorus pentachloride are used in the halogenation reaction. For the reaction, addition of a peroxide (e.g. benzoyl peroxide) or an optical irradiate for promoting the reaction promotor may be used. The reaction temperature ranges from −20 to 200° C., and the reaction time ranges usually from 0.5 to 6 hours. In this case, solvents, such as aromatic hydrocarbons (e.g. benzene), halogenated hydrocarbons (e.g. methylene chloride, chloroform, dichloroethane), saturated hydrocarbons (e.g. hexane, heptane, cyclohexane), esters (e.g. methyl acetate, ethyl acetate) may be used.

The compound (H) can be synthesized by the following method.

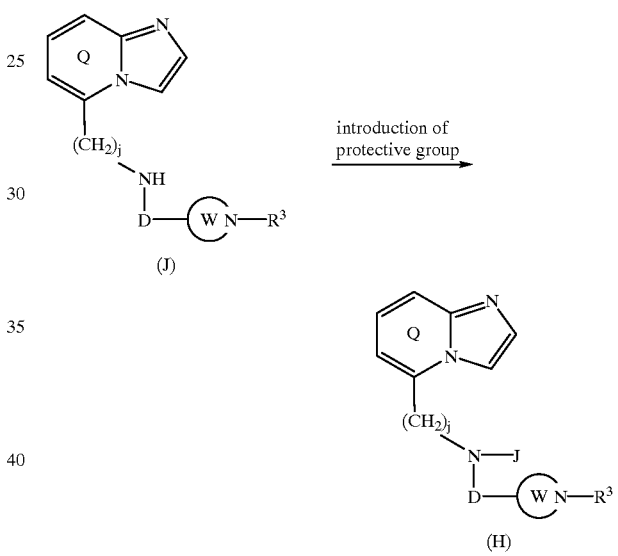

(wherein all symbols are of the same meanings as defined above)

The reaction for introducing protective group J into amino group on the compound (J) is a per se known reaction and so on.

The compound (P) can be synthesized by the following method.

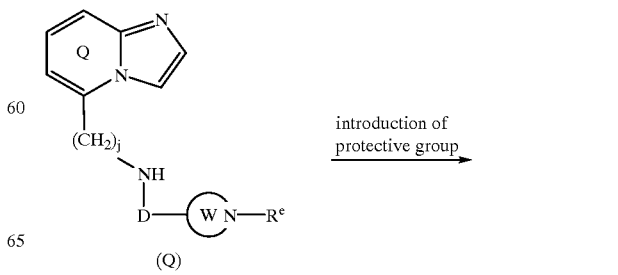

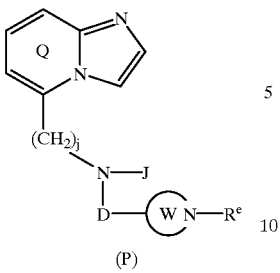

(P)

(wherein all symbols are of the same meanings as defined above)

The reaction for introducing protective group J into amino group on the compound (Q) is a per se known reaction and so on.

The compound (J) can be synthesized by the following method.

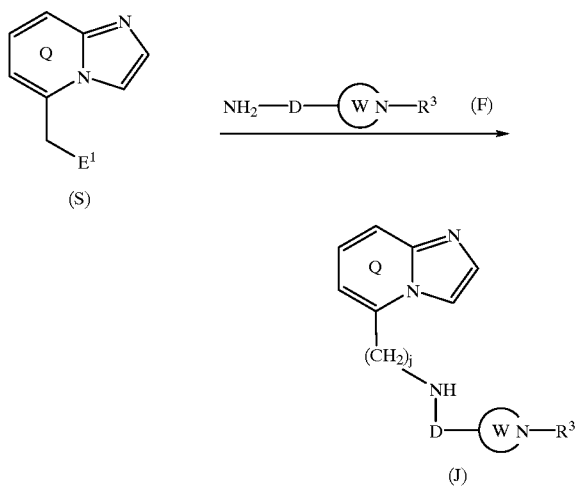

(wherein all symbols are of the same meanings as defined above)

The reaction between the compound (S) and the compound (F) is conducted, for example, under conditions similar to those of the reaction between the compound (B) and the compound (C) in the method M.

The compound (Q) can be synthesized by the following method.

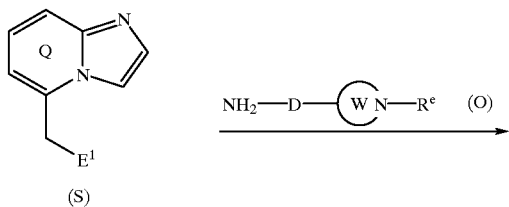

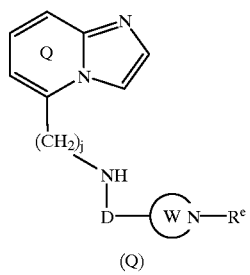

(Q)

(wherein all symbols are of the same meanings as defined above)

The reaction betwen the compound (S) and the compound (O) is conducted, for example, under conditions similar to those of the reaction betwen the compound (B) and the compound (C) in the method M.

The compound (K) can be synthesized by the following method.

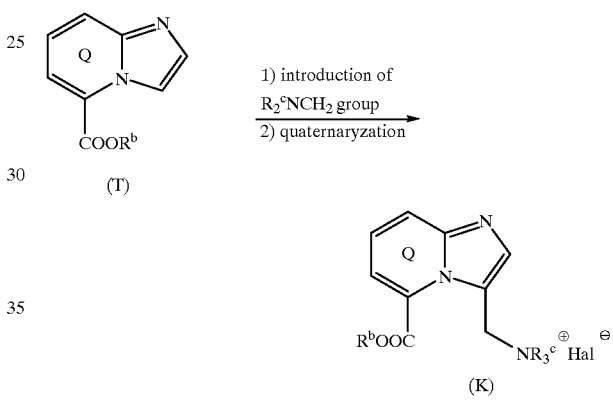

In the dialkylaminomethylation of the compound (T), one equivalent to a large excess amount (1 to 10 equivalents) of N,N-dimethyleneammonium iodide is employed relative to the compound (T). The reaction temperature ranges from 0 to 100° C., and the reaction time ranges usually from 0.5 hour to 24 hours, preferably from 1 to 6 hours. Examples of the solvents to be employed include, for example, halogenated hydrocarbons (e.g. methylene chloride, chloroform, carbon tetrachloride, dichloroethane), ethers (e.g. diethylether, tetrahydrofuran), esters (e.g. methyl acetate, ethyl acetate) and aprotic polar solvents (e.g. N,N-dimethylformamide, dimethylsulfoxide, acetonitrile).

In the quaternarization, one equivalent to a large excess amount (1 to 10 equivalents) of $C_{1-6}$ alkyl halide such as methyl iodide is employed relative to the dialkylaminomethyl compound. The reaction temperature ranges from 0 to 100° C., and the reaction time ranges usually from 1 to 100 hours, preferably 6 to 24 hours. Examples of the solvents to be employed include, for example, halogenated hydrocarbons (e.g. methylene chloride, chloroform, carbon tetrachloride, dichloroethane), ethers (e.g. diethylether, tetrahydrofuran), estes (e.g. methyl acetate, ethyl acetate) and aprotic polar solvents (e.g. N,N-dimethylformamide, dimethylsulfoxide, acetonitrile).

The compound (S) can be synthesized by the following method.

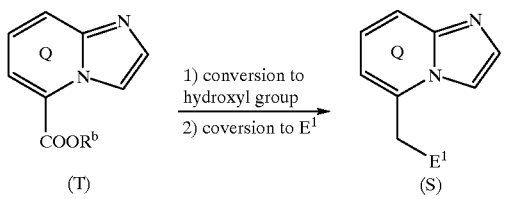

(wherein all symbols are of the same meanings as defined above)

In the reduction of the compound (T), one equivalent to a large excess amount (1 to 10 equivalents) of metal hydride complex compound (e.g. sodium boron hydride, lithium boron hydride, lithium alminum hydride) or borane complex compound is employed relative to the compound (T). The reaction temperature ranges from −20 to 100° C., and the reaction time ranges usually from 10 minutes to 24 hours, preferably 0.5 to 6 hours. Examples of the solvents to be employed include, for example, alcohols (e.g. methanol, ethanol), ethers (e.g. diethylether, tetrahydrofuran, dioxane).

In the conversion from hydroxyl group to $E^1$ (e.g. halogen), 1 to 5 equivalents of halogenated phosphorus (e.g. phosphorus trichloride, phosphorus oxychloride, phosphorus pentachloride, phosphorus tribromide), halogenation agent (e.g. red phosphorus and halogen, thionyl chloride) are employed relative to the alcohol compound.

In the conversion from hydroxyl group to $E^1$ (e.g. p-toluenesulfonyloxy, methanesulfonyloxy), 1 to 5 equivalents of p-toluensulfonylchloride or methanesulfonyl chloride are employed relative to the alcohol compound. In this case, an inorganic base such as potassium carbonate, sodium hydrogencarbonate, an organic base such as 4-N,N-dimethylaminopyridine, triethylamine, pyridine, dimethylamiline, 1,4-diazabicyclo[2.2.2]octane, 1,8-diazabicyclo[5.4.0]-7-undecene may be used in an amount of 1 to 10 equivalents. The reaction temperature ranges from 0 to 100° C., and the reaction time ranges usually from 10 minutes to 100 hours, preferably from 3 to 24 hours. Examples of the solvents to be employed include, for example, halogenated hydrocarbons (e.g. methylene chloride, chloroform, dichloroethane), water, ethers (e.g. diethylether, tetrahydrofuran), esters (e.g. methyl acetate, ethyl acetate) and aprotic polar solvents (e.g. N,N-dimethylformamide, dimethylsulfoxide, acetonitrile).

The compound (T) can be synthesized by the following method.

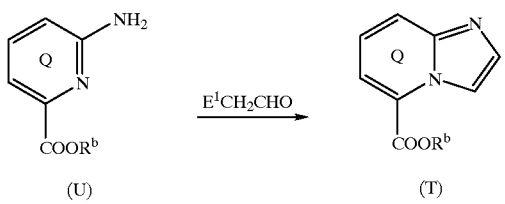

(wherein all symbols are of the same meanings as defined above)

In the reaction between the compound (U) and the compound: $E^1CH_2CHO$, one equivalent to a large excess amount (1 to 10 equivalents) of the compound of the compound (Y) is employed relative to the compound (U). The reaction temperature ranges from 0 to 200° C., and the reaction time ranges usually from 10 minutes t 24 hours, preferably 0.5 to 6 hours. Examples of the solvents to be employed include, for example, halogenated hydrocarbons (e.g. methylene chloride, chloroform, dichloroethane), water, alcohols (e.g. methanol, ethanol), ethers (e.g. diethylether, tetrahydrofuran, dioxane), esters (e.g. methyl acetate, ethyl acetate) and aprotic polar solvents (e.g. N,N-dimethylformamide, dimethylsulfoxide, acetonitrile).

The compound (E) can be synthesized by the following method.

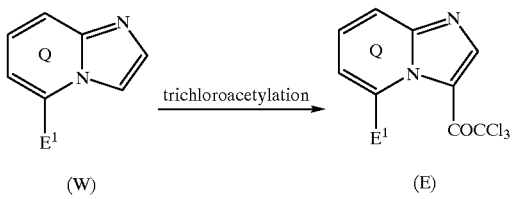

(wherein all symbols are of the same meanings as defined above)

The trichloroacetylation of the compound (W) is conducted, for example, under conditions similar to those of the trichloroacetylation of the compound (H).

The compound (W) can be synthesized by the following method.

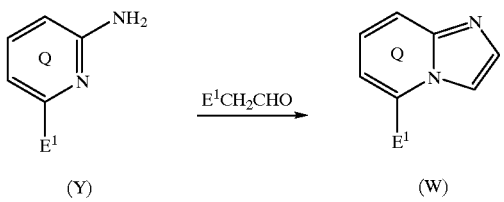

(wherein all symbols are of the same meanings as defined above)

The reaction between the compound (Y) and the compound: $E^1CH_2CHO$ is conducted, for example, under conditions similar to those of the reaction between the compound (U) and the compound: $E^1CH_2CHO$.

The starting materials for producing the compound (I') may form a salt. The salt may be employed as similar as the salt of the compound (I').

The intermediate compounds for synthesizing the desired compound (I') or a salt obtained by the above-mentioned methods can be isolated by the following conventional separation means, or reaction mixture per se may optionally be used, as the starting materials for the subsequent step without isolation.

The isolation and purification of the compound (I') from the reaction mixture is conducted according to conventional separation means (for example, extraction, concentration, filtration, recrystallization, column chromatography and thin-layer chromatography).

And, in each of the above-mentioned reactions, when the starting compounds and intermediate compounds has amino group, carboxyl group or hydroxyl group as the substituent, they may have a protective group generally used in the peptide chemistry. After completion of the reaction, the desired compound can be obtained by removing the protective group upon necessity.

Examples of the amino-protecting group include optionally substituted $C_{1-6}$ alkyl carbonyl (e.g. formyl, methyl carbonyl and ethyl carbonyl), phenyl carbonyl, $C_{1-6}$ alkyl-oxycarbonyl (e.g. methoxycarbonyl and ethoxycarbonyl), phenyloxycarbonyl (e.g. benzoxycarbonyl), $C_{7-10}$ aralkyloxy-carbonyl (e.g. benzyloxycarbonyl), trityl and phthaloyl. Examples of substituents of them include halogen atoms (e.g. fluoro, chloro, bromo and iodo), $C_{1-6}$ alkylcarbonyl (e.g. methylcarbonyl, ethylcarbonyl and butylcarbonyl) and nitro group, and the number of the substituents ranges from about 1 to 3.

Examples of the carboxyl-protecting group include $C_{1-6}$ alkyl (e.g. methyl, ethyl, n-propyl, i-propyl, n-butyl and tert-butyl), phenyl, trityl and silyl. Examples of substituents of them include halogen atoms (e.g. fluorine, chlorine, bromine and iodine), $C_{1-6}$ alkylcarbonyl (formyl, methylcarbonyl, ethylcarbonyl and butylcarbonyl) and nitro group, and the number of the substituents ranges from about 1 to 3.

Examples of the hydroxyl-protecting group include for example, optionally substituted $C_{1-6}$ alkyl (e.g. methyl, ethyl, n-propyl, i-propyl, n-butyl and tert-butyl), phenyl, $C_{7-10}$ aralkyl (e.g. benzyl), $C_{1-6}$ alkylcarbonyl (e.g. formyl, methylcarbonyl and ethylcarbonyl), phenyloxycarbonyl, $C_{7-10}$ aralkyloxy-carbonyl (e.g. benzyloxycarbonyl), pyranyl, furanyl and silyl. As the substituents mentioned above, halogen atoms (e.g. fluoro, chloro, bromo and iodo), $C_{1-6}$ alkyl, phenyl, $C_{7-10}$ aralkyl and nitro group were used. The number of substituents ranges from about 1 to 4.

And, the protecting groups can be introduced and removed by per se known means or those analogous thereto (for example, I.F.W. McOmie et al., PROTECTIVE GROUPS IN ORGANIC CHEMISTRY, Plenum Press). More specifically, those protecting groups are removed by, for example, acid, base, reduction, ultraviolet ray, hydrazine, phenylhydrazine, sodium N-methyldithiocarbamate, tetrabutylammonium fluoride or palladium acetate.

The compound (I') produced by the above-mentioned methods can be isolated and purified by a conventional separating means such as recrystallization, distillation and chromatography. When the compound (I') thus obtained is in the free form, it can be converted to a salt by per se known means or analogous means thereto (e.g. neutralization). Conversely, when the compound (I') is obtained in the form of a salt, it can be converted to the free form or any other salt by per se known means or analogous means thereto.

Further, when the compound (I') is an optically active compound, it can be resolved into d-isomer and l-isomer by a conventional means for optical resolution.

The compound (I') and the pharmaceutically acceptable salt of the present invention have an excellent inhibiting activity of PDGF action, antihypertensive activity, ameliorating activity of renal diseases and activity of lowering lipid level, and are relatively less toxic. Therefore, these compounds or their salts can be safely used, in mammals (e.g. mouse, rat, hamster, rabbit, cat, dog, cow, horse, sheep, monkey and human), as therapeutic agents of, for used as hypertension, renal diseases (e.g. acute renal failure, diabetic nephropathy, nephritis, mesangial proliferative glomerulonephritis, endocapillary proliferative glomerulonephritis, membranoproliferative glomerulonephritis type I–III, crescentic glomerulonephritis, diffuse sclerosing glomerulonephritis), arteriosclerotic diseases, the other cardiovasular diseases, chronic rheumatoid arthritis, restenosis after PTCA, cancers and hyperlipemia.

While the compound (I') or a salt thereof can be administered as it is, it is usually administered in the form of preparation formulated by a conventional method using carriers or diluents for pharmaceutical preparations adequately selected from excipients (e.g. calcium carbonate, kaolin, sodium hydrogencarbonate, lactose, starch, crystalline cellulose, talc, fine granulated sugar and porous substance), binders (e.g. dextrin, gum, alcoholated starch, gelatin, hydroxypropyl cellulose, hydroxypropyl methyl cellulose and furfuran), disintegrants (e.g. carboxymethyl cellulose calcium, closcarmellose sodium, clospovidone, low-substituted hydroxypropyl cellulose and partial α-starch), lubricants (e.g. magnesium stearate, calcium stearate, talc, starch and sodium benzoate), colorants (e.g. tar pigment, caramel, iron sesquioxide, titanium oxide and riboflavins), flavoring agents (e.g. sweeteners and perfume), stabilizers (e.g. sodium sulfite) and preservatives (e.g. parabens and sorbic acid) in adequate amounts respectively. The therapeutic agent of the present invention containing the above-mentioned pharmaceutical preparation contains the compound (I') or a salt thereof in a amount effective for the therapy and prophylaxis. The content of the compound (I') or a salt thereof in the pharmaceutical preparation of the present invention ranges usually from 0.1 to 100 weight % relative to the whole weight of the pharmaceutical preparation. And, the pharmaceutical preparation of the present invention may contain, as active components, medicinal components other than the compound (I') or a salt thereof. These medicinal components are not specifically restricted so long as the object of this invention is attained, and can be used in adequate ratios. As the said "medicinal components", use is made of, for example, diuretic, angiotensin II receptor antagonist, calcium blocker, ACE inhibitor, kimase inhibitor, HMG-CoA reductase inhibitor and squalene synthetase inhibitor. Specific examples of the formulation include tablets (including sugar-coated tablets and film-coated tablets), pills, capsules, granules, powdery preparations, syrups, emulsions, suspensions, injections, inhalants and ointments. These formulations are prepared by a conventional method (e.g. the method described in the Japanese Pharmacopeia).

More specifically, tablets can be prepared by, for example, the following processes:

1) the pharmaceutical preparation as it is, or a homogeneous mixture of the pharmaceutical preparation with an excipient, a binder, a disintegrant or any other suitable additive, is granulated by an adequate means, to which is added, for example, a lubricant, and the whole mixture is subjected to compression molding;
2) the pharmaceutical preparation as it is, or a homogeneous mixture of the pharmaceutical preparation with an excipient, a binder, a disintegrant or any other suitable additive, is directly subjected to compression molding; or
3) the granules prepared in advance as they are, or a homogeneous mixture of the granules with a suitable additive, is subjected to compression molding. And, to this pharmaceutical preparation, a colorant or a flavoring agent may optionally be supplemented upon necessity. Furthermore, this pharmaceutical preparation may optionally be coated with a coating agent.

Injectable preparations can be provided by dissolving, suspending or emulsifying a given amount of the pharmaceutical preparation in, when using an aqueous solvent, e.g. water for injection, physiological saline or Ringer's solution, and, when using a water-insoluble solvent, usually e.g. vegetable oil, or by filling a given amount of the pharmaceutical preparation into a vessel, followed by sealing the vessel.

As the carriers for orally administrable preparations, use is made of substances commonly employed in the field of pharmaceutical preparations, for example, starch, mannitol, crystalline cellulose and sodium carboxymethyl cellulose. As the carriers for injectable preparations, use is made of, for example, distilled water, physiological saline solution, glucose solution and an agent of infusion. Besides, additives generally employed for pharmaceutical preparations can be adequately supplemented.

The pharmaceutical preparations of this invention are relatively less toxic and useful as medicinal preparations, which have PDGF-inhibiting activity, antihypertensive activity, ameliorating activity of renal diseases and lipid lowering activity. Therefore, the pharmaceutical preparations of this invention are useful as medicines for diseases due to these pharmacological actions. The pharmaceutical preparations of this invention can thus be used as the therapy or prophylaxis of, among others, hypertension, acute renal failure, diabetic nephropathy, nephritis, arteriosclerosis, chronic rheumatoid arthritis, cancers and hyperlipemia.

The dose of the pharmaceutical preparations of this invention varies with administration routes, symptoms, the age and body weight of patients and it is preferable that for treating hypertension, renal diseases or arteriosceotic diseases a daily dose of 0.01 to 300 mg/kg, preferably 0.2 to 50 mg/kg, more preferably 5 to 30 mg/kg for oral administration is given once or divided into several times. The administration route may be either oral or non-oral.

The experimental results showing the pharmacological effects of the compound (I') or a salt thereof of this invention are described as follows:

Test Example 1

Inhibitory Effects on the Contraction due to PDGF

Method: The thoracic aorta of stroke prone spontaneously hypertensive rats at ages ranging from 16 to 36 weeks were isolated, and strip (2 mm in width, 2 cm in length) were prepared from the aorta. Each strip was mounted in 10 ml of an organ bath, which was loaded at 2 g and allowed to stabilized for 2 to 3 hours. As the nutrient, a Krebs-Henseleit solution, bubbled with a mixture gas (95% O2, 5% $CO_2$), was used. At the time when the contraction response against 60 mM KCl becomes constant, each strip was applied by 1.7 nM of PDGF-AB (Cosmobio Inc.) for contraction. Observation was continued until the contraction become maximum and stable (30 to 40 minutes after application of PDGF-AB). Then, the strips were washed, and, in about one hour later (after the tone of the vaso-contraction was recovered to the original level), 10 $\mu$l of the drug (DMSO solution) was added. Thirty minutes after drug, 1.7 nM of PDGF-AB was added again and subjected to observation until the contraction became maximum. The PDGF-AB-induced contraction was isometrically recorded on a polygraph (Nihon Denki San-ei). From the contractile response of the strips to PDGF-AB in the absence or presence of drugs, % inhibition of each drug was calculated. $IC_{50}$ value for the inhibitory effects was calculated in accordance with the Filler's theorem using the least squares method. The results are shown in Table 1.

TABLE 1

| Inhibitory effects on PDGF-induced contraction | |
|---|---|
| Compound (No. of Ex.) | $IC_{50}$ ($\mu$M) |
| 1 | 2.13 |
| 3 | 0.29 |
| 6 | 1.27 |
| 8 | 0.31 |
| 26 | 0.37 |
| 30 | 2.26 |

From the Table 1, it is demonstrated that the compound (I') or a its salt of the present invention has an excellent action of inhibiting PDGF-induced contraction.

Test Example 2

Antihypertensive Action in Spontaneously Hypertensive Rats (SHRs)

Method: Male SHR at ages ranging from 20 to 24 weeks were anesthetized with pentobarbital.sodium (50 mg/kg, i.p.) and, from the femoral artery of each animal, a polyethylene tube was inserted. The polyethylene tube was connected to a pressure transducer and blood pressure after oral administration of drugs was recorded continuously under non-anesthesia. The animals, after the operation, were allowed to freely access to drinking water and eating, until administration of the drugs. The compounds were all orally administered as a suspension in gum arabic (2 ml/kg). The results are shown in Table 2.

TABLE 2

| Antihypertensive action | | |
|---|---|---|
| Compound (No. of Ex.) | dose (mg/kg) | blood-pressure change (mmHg) |
| 1 | 10 | −21 [after 5 hrs.] |
| 6 | 10 | −19 [after 4 hrs.] |
| 11 | 30 | −31 [after 7 hrs.] |
| 26 | 10 | −22 [after 7 hrs.] |
| 27 | 30 | −17 [after 7 hrs.] |
| 28 | 30 | −13 [after 3 hrs.] |
| 30 | 30 | −17 [after 7 hrs.] |
| 35 | 30 | −14 [after 2 hrs.] |
| 37 | 30 | −14 [after 5 hrs.] |
| 38 | 30 | −19 [after 4 hrs.] |
| 40 | 30 | −20 [after 7 hrs.] |

From Table 2, in the test groups, an antihypertensive effect of about 20 mmHg as compared with the control group was observed at 2 to 7 hours after administration of the compound (I') or a salt thereof of the present invention. Therefore, the compound (I') or a salt thereof of the present invention was considered to have an excellent antihypertensive action.

Test Example 3

Antiproteinuric Effect in 5/6 Nephrectomized Rats

Method: Male Sprague Dawley rats of five-week old (Japan Clea) were anesthetized with pentobarbital.sodium (50 mg/kg, i.p.), and the right kidney was excised by dorsal incision, and its two-thirds were cut. Two weeks later, the whole of left kidney was removed. In the Sham group, only the second operation was performed. In two weeks after the second operation, urine was collected for 24 hours under drinking water ad libitum. Urinary albumin and total protein were quantitatively determined by the use of A/G B-test (Wako). On the following day of collecting urine, the blood pressure was measured by the tail cuff method. Test animals showing more proteinuria than that of Sham group were selected. Based on the amount of the proteinuria and the blood pressure level, the animals were grouped so that, the average and distribution of urinary protein and blood pressure same in each group. The drug was suspended in gumarabic/water or dissolved in water, and orally administered once a day for 6–8 weeks in a volume of 2 ml/kg. The administration was consecutively performed, and, at 2, 4, 6 and 8th weeks of treatment, urine was collected and blood pressure was measured. The vehicle group was orally administered with only water at a dose of 2 ml/kg. The results are shown in Table 3.

TABLE 3

Antiproteinurea action
(Urinary protein excretion)

| Compound | | Urinary protein excretion (mg/day) | | | | |
|---|---|---|---|---|---|---|
| (No. of Ex.) | Dose (mg/kg) | 0 | 2 | 4 | 6 | 8 (weeks) |
| Control group | | 114.4 | 123.1 | 102.5 | 256.9 | 220.4 |
| 1 | 3 | 114.5 | 117.0 | 98.2 | 156.3 | 102.8 |
| 6 | 10 | 114.1 | 103.0 | 93.9 | 167.2 | 117.3 |
| 11 | 10 | 115.1 | 69.1 | 62.5 | 170.3 | 125.4 |
| 30 | 3 | 114.1 | 98.2 | 69.7 | 180.5 | 156.5 |

TABLE 4

Antiproteinuric action
(Urinary albumin excretion)

| Compound | | Urinary protein excretion (mg/day) | | | | |
|---|---|---|---|---|---|---|
| (No. of Ex.) | Dose (mg/kg) | 0 | 2 | 4 | 6 | 8 (weeks) |
| Control group | | 10.0 | 29.2 | 30.6 | 54.2 | 69.7 |
| 1 | 3 | 11.2 | 16.9 | 18.4 | 13.0 | 25.1 |
| 6 | 10 | 6.8 | 13.5 | 17.2 | 13.1 | 24.8 |
| 11 | 10 | 10.2 | 19.8 | 30.3 | 26.0 | 38.3 |
| 30 | 3 | 8.6 | 13.9 | 13.2 | 13.5 | 21.0 |

From Table 3, it is apparent that, from 4 weeks after renal ablation, urinary protein and urinary albumin in urea were remarkably increased. In contrast, in the test groups, no increase was observed in urinary total protein and urinary albumin. At 4th to 8th week of consecutive administration, the levels of urinary protein and albumin were significantly lower than those of the control group. Therefore, the compound (I') or a salt thereof present the leakage of protein into urine, and its efficacy on the therapy of renal diseases such as glomerulosclerosis is expected.

Test Example 4

Cholesterol Lowering Effects in Hamsters

Method: Syrian hamsters of 10 weeks old were stabilized with common feed for two weeks. The animals were grouped based on the total cholesterol in blood. The vehicle (water) or drug was orally administered in a volume of 2 ml/kg for two weeks. During the period of the administration, blood was collected from retinal vessels with passage of time and the total cholesterol and triglyceride in blood were determined. On the other hand, blood was collected from abdominal aorta on the second week after the consecutive administration of the test compounds to determine the total cholesterol, triglyceride and HDL (high density lipid)-cholesterol in blood. Cholesterol C-test, triglyceride G-test and HDL-cholesterol E test (all manufactured by Wako Pure Chemical Industries, Ltd.) were used for the determination of these parameters, respectively. The results are shown in Table 5.

TABLE 5

Cholesterol-lowering action

| Compound | Dose | % of Vehicle | |
|---|---|---|---|
| (No. of Ex.) | (mg/kg) | TC | TC-HDL |
| 1 | 30 | 64.1 | 68.9 |
| 3 | 10 | 82.2 | 79.0 |
| 6 | 10 | 89.5 | 84.6 |
| 8 | 10 | 81.5 | 77.1 |
| 26 | 30 | 74.5 | 72.1 |
| 28 | 30 | 65.1 | 61.6 |
| 30 | 30 | 81.9 | 77.4 |

From Table 5, it is apparent that, in the control group, the total cholesterol (TC) in blood increased with the passage of time. On the contrary, in the test groups, the increase of cholesterol in blood was suppressed by about 20 to 30%. On the other hand, no difference was observed HDL-cholesterol level at the second week of the consecutive administration between the vehicle group and test groups. From these results, it is apparent that the values, [total cholesterol value]—[HDL-cholesterol value]; were lower in the test groups than that of the control group. Therefore, the compound (I') or a salt thereof act to decrease LDL (low density lipid) and VLDL (very low density lipid) in blood, and are useful against cardivascular diseases, for example, arteriosclerosis.

Test Example 5

Experiments of Urinary Protein Excretion in SHC Rats

Method: Spontaneously hypercholesterolemic rats (male, 7 weeks old) were given a drug suspended in 0.5% methylcellulose (100 cP) by oral administration once daily for 6 weeks. A control group was given 0.5% methylcellulose (100 cP) by the same route once daily. As a normal control group, Sprague-Dawley rats (SD rats) (male, 7 weeks old, CLEA Japan, Inc.) were given 0.5% methylcellulose (100 cP) orally once daily. Before the start of medication and at 2-weeks intervals after the first administration of drugs, urine was collected for twenty four hours and the total protein and albumin excreted in the urine were determined. The assay of total protein and albumin was carried out using the A/GB Test Wako (Wako Pure Chemical Ind.).

The results are shown in Table 6 and Table 7.

TABLE 6

Effect on urinary total protein excretion

| | | Urinary total protein (mg/day) | | | |
|---|---|---|---|---|---|
| | | Duration of administration (weeks) | | | |
| Group | Dose (mg/kg/day) | 0 | 2 | 4 | 6 |
| Control | — | 39.5 | 125.7 | 235.3 | 275.2 |
| Example 83(ii) | 1 | 39.2 | 50.4 | 91.3 | 199.4 |
| SD rat | — | 19.1 | 45.4 | 53.8 | 36.4 |

TABLE 7

Effect on urinary albumin excretion

Urinary albumin (mg/day)

| Group | Dose (mg/kg/day) | Duration of administration (weeks) | | | |
|---|---|---|---|---|---|
| | | 0 | 2 | 4 | 6 |
| Control | — | 12.1 | 67.1 | 154.7 | 174.4 |
| Example 83(ii) | 1 | 12.0 | 10.9 | 46.2 | 129.9 |
| SD rat | — | 4.2 | 10.1 | 8.2 | 9.7 |

Test Example 6
Experiments of PDGF-induced Proliferation in Hs68 Cells
Method: Human skin fibroblasts (Hs68, Institute for Fermentation, Osaka) were seeded in 48-well plates pre-coated with collagen type I (Falcon) (25000 cells/well), and cultured for one day. Then, the cells were cultured in Dulbecco's modified Eagle's medium (high glucose) containing 0.1% bovine serum albumin for 48 hours. Fifteen (15) minutes after the addition of the drug, the cells were stimulated with 5 ng/ml of PDGF-BB (Becton Dickinson Labware) containing $^3$H-thymidine (final concentration 0.4 mCi/ml) (Amersham). After 24 hours, the reaction was stopped with 7.5% trichloroacetic acid at 4° C. and the plate was allowed to stand at 4° C. for 30 minutes. The cells were washed with $Ca^{2+}$- and $Mg^{2+}$-free phosphate-buffered saline (PBS), after then 0.1% sodium dodecyl sulfate (SDS)/0.4N NaOH was added and the plate was allowed to stand at 37° C. for 1 hour to lyze the cells. The whole content of each well was taken in a vial and neutralized with 1N HCl, and then toluene scintillator (Wako Pure Chemical Ind.) was added to each vial. After stirring, the amount of $^3$H-thymidine incorporated in the cells was determined with a liquid scintillation counter. The cellular uptake of $^3$H-thymidine was used as an indicator of cell proliferation. The effect of the drug on the PDGF-BB (5 ng/ml) uptake of $^3$H-thymidine was expressed as % inhibition. The results are shown in Table B.

TABLE 8

Inhibitory effect on cell proliferation

| Compound (Example No.) | Concentration (M) | % Inhibition |
|---|---|---|
| 83(ii) | $3 \times 10^{-7}$ | 94.9 |
| 85(iii) | $3 \times 10^{-6}$ | 59.2 |
| 86(ii) | $1 \times 10^{-6}$ | 96.6 |

The present invention provides a novel tricyclic compound and a salt thereof which have excellent PDGF-inhibiting activity, antihypertensive activity, activity of ameliorating renal diseases, and activity of lowering lipid level, and therefore, can be safely used as, therapeutic agents of, for example, hypertension, renal diseases (e.g. acute renal failure, renal diabetes and nephritis), diseases due to arteriosclerosis, the other cardiovascular diseases, chronic articular rhematism, cancers and hyperlipemia.

The present invention will be explained in more detail by the following working examples and reference examples. These are mere examples and are not intended to restrict the present invention in any manner, and may be modified within the range of not deviating the scope of this invention.

In Examples and Reference Examples, abbreviations mean as follows.

NMR: Nuclear magnetic resonance spectrum DMF: dimethylformamide, DMSO: dimethyl sulfoxide, Hz: herz, J: coupling constant, m: multiplet, q: quartet, t: triplet, d: doublet, s: singlet, b: broad, like: approximate Room temperature means 10 to 30° C.

EXAMPLE 1

4,5-Dihydro-4-[4-(trifluoromethanesulfonamido) butan-1-yl]-3H-1,4,8b-triazaacenaphthylene.dihydrochloride i) Synthesis of 5-chloromethylimidazo[1,2-a] pyridine.hydrochloride To a solution consisting of 58.4 ml (800 mmol) of thionyl chloride and 100 ml of methylene chloride was added 23.68 g (160 mmol) of 5-hydroxymethylimidazo[1,2-a]pyridine with small portions. The reaction mixture was stirred for one hour at room temperature. Then, the solvent and excess amount of thionyl chloride were distilled off under reduced pressure. To the resulting white solid residue was added 100 ml of toluene. The mixture was shaken sufficiently, then the solvent was distilled off under reduced pressure. This process was repeated twice to give 31.85 g (98.0%, white solid) of a crude product.

NMR(200 MHz,$D_2O$) δ: 5.09(2H,s), 7.49(1H,t,J=4.8 Hz), 7.85(2H,d,J=4.8 Hz), 7.95(1H,d,J=2.4 Hz), 8.16(1H,d,J=2.4 Hz).

IR(KBr): 1657, 1543, 1157 $cm^{-1}$.

ii) Synthesis of 5-[N-[4-(trifluoromethanesulfonamido)butan-1-yl] aminomethyl]imidazo[1,2-a]pyridine To a suspension formed by adding 36.93 g (181.85 mmol) of 5-chloromethylimidazo[1,2-a]pyridine hydrochloride to 200 ml of acetonitrile was added 32.06 g (363.72 mmol) of 1,4-diaminobutane, then the mixture was heated for 30 minutes under reflux. After completion of the reaction, the reaction mixture was cooled to allow 1,4-diaminobutane.dichloride to precipitate, which was collected by filtration and washed twice with 25 ml of acetonitrile. The filtrate and washings were combined, to which was added 50.68 ml (363.72 mmol) of triethylamine. The mixture was stirred sufficiently, to which was added 64.97 g (181.85 mmol) of N-phenyltrifluoromethanesulfonimide. The mixture was stirred for two hours at room temperature. After completion of the reaction, the solvent was distilled off under reduced pressure. The residue was extracted with 500 ml of chloroform. The organic layer was washed with 500 ml of a saturated aqueous saline solution, which was dried over magnesium sulfate, then the solvent was distilled off under reduced pressure. The residue was purified by silica-gel column chromatography (eluent: chloroform/methanol=20:1) to give 41.60 g (65.3%, a colorless solid) as the desired compound.

NMR(200 MHz,$CDCl_3$) δ: 1.48(13H,m), 3.24(2H,br), 4.67(2H,br), 6.69(1H,d,J=6.2 Hz), 7.19(1H,t,J=6.2 Hz), 7.50–7.80(3H,m).

IR(KBr): 3320, 1641, 1514, 1367 $cm^{-1}$.

(iii) Synthesis of 4,5-dihydro-4-[4-(trifluoromethanesulfonamido)butan-1-yl]-3H-1,4,8b-triazaacenaphthylene To a solution of 6.91 g (19.72 mmol) of 5-[N-[4-(trifluoromethanesulfonamido)butan-1-yl]aminomethyl]

imidazo[1,2-a]pyridine in 20 ml of acetic acid was added 22.1 ml (295.8 mmol) of a 37% aqueous solution of formaldehyde. The mixture was heated at 100° C. for 30 minutes. The solvent was then distilled off under reduced pressure, and the residue was dissolved in 100 ml of a saturated aqueous solution of potassium hydrogencarbonate. This solution was neutralized, under ice-cooling, with 1N HCl, which was subjected to extracted twice with 100 ml of chloroform. The organic layer was dried over magnesium sulfate, then the solvent was distilled off under reduced pressure. The residue was purified by silicagel chromatography (eluent: chloroform/methanol=20:1) to give 4.86 g (68.0%, pale yellow liquid product).

NMR(200 MHz,CDCl$_3$) δ: 1.76(4H,m), 2.55(2H,t,J=6.0 Hz), 3.33(2H,t,J=6.0 Hz), 3.97(2H,s), 4.00(2H,s), 6.55(1H, d,J=6.8 Hz), 7.10(1H,dd,J=9.2,6.8 Hz), 7.25(1H,s), 7.44 (1H,d,J=9.2 Hz).

IR(neat): 1636, 1483, 1370 cm$^{-1}$.

iv) Synthesis of 4,5-dihydro-4-[4-(trifluoromethanesulfonamido)butan-1-yl]-3H-1,4,8b-triazaacenaphthylene.dihydrochloride To a solution of 3.21 g (8.87 mmol) of 4,5-dihydro-4-[4-(trifluoromethanesulfonamido)butan-1-yl]-3H-1,4,8b-triazaacenaphthylene in 10 ml of ethanol was added 2.0 ml of 12N HCl. The mixture was sufficiently blended. The solvent was distilled off under reduced pressure to leave 3.86 g of the desired compound (100%, colorless amorphous).

NMR(200 MHz,DMSO) δ: 1.60(2H,m), 1.85(2H,m), 3.19 (4H,m), 4.83(2H,s), 4.91(2H,s), 7.54(1H,m), 7.99–8.01(2H, m), 8.20(1H,s), 9.55(1H,t,J=6.0 Hz).

IR(KBr): 3463, 1662, 1459, 1440, 1373, 1190 c$^{-1}$.

EXAMPLE 2

4,5-Dihydro-4-[5-(trifluoromethanesulfonamido) pentan-1-yl]-3H-1,4,8b-triazaacenaphthylene.dihydrochloride i) Synthesis of 5-[N-[5-(trifluoromethanesulfonamido)-pentan-1-yl] aminomethyl imidazo[1,2-a]pyridine To a suspension of 10.2 g (50.0 mmol) of 5-chloromethylimidazo[1,2-a]pyridine hydrochloride in 100 ml of acetonitrile was added 10.2 g (100 mmol) of 1,5-diaminopentane. The mixture was heated for 30 minutes under reflux. The reaction mixture was cooled to separate 1,5-diaminopentane.dihydrochloride as precipitates, which was collected by filtration and washed 10 ml of acetonitrile twice. The filtrate and the washing were combined, to which was added 14.0 ml (100 mmol) of triethylamine. The mixture was stirred sufficiently, to which was added 17.86 g (50.0 mmol) of N-phenyltrifluoromethanesulfonimide. The mixture was stirred for two hours at room temperatures. After completion of the reaction, the solvent was distilled off under reduced pressure. The residue was extracted with 250 ml of chloroform. The organic layer was washed with 200 ml of a saturated aqueous saline solution, dried over magnesium sulfate, then the solvent was removed under reduced pressure. The residue was purified by means of a silicagel column chromatography (eluent: chloroform/methanol= 20:1) to give 12.9 g of the object compound (71.0%, colorless solid substance).

NMR(200 MHz,CDCl$_3$) δ: 1.45(2H,m), 1.60(4H,m), 2.47 (2H,t,J=6.6 Hz), 3.28(2H,t,J=6.6 Hz), 4.02(2H,s), 6.78(1H, d,J=7.0 Hz), 7.17(1H,dd,J=7.0,9.2 Hz), 7.57(1H,s), 7.58 (1H,d,J=9.2 Hz), 7.63(1H,s).

IR(KBr): 1637, 1481, 1637, 1295, 1188 cm$^{-1}$.

ii) Synthesis of 4,5-dihydro-4-[5-(trifluoromethanesulfonamido)pentan-1-yl]-3H-1,4,8b-triazaacenaphthylene To a solution of 2.52 g (6.91 mmol) of 5-[N-[5-(trifluoromethanesulfonamido)pentan-1-yl]aminomethyl] imidazo[1,2-a]pyridine in 8 ml of acetic acid was added 7.8 ml (103.7 mmol) of a 37% aqueous solution of formalin. The mixture was heated at 100° C. for 30 minutes. The solvent was then distilled off under reduced pressure. The residue was dissolved in 50 ml of a saturated aqueous solution of potassium carbonate. This solution was neutralized, under ice-cooling, with 1N HCl, which was extracted twice with 100 ml of chloroform. The organic layer was dried over magnesium sulfate, then the solvent was distilled off under reduced pressure. The residue was purified by silicagel column chromatography to give 1.79 g of the desired compound (69.0%, colorless liquid).

NMR(200 MHz,CDCl$_3$) δ: 1.44(2H,m), 1.60(4H,m), 2.47 (2H,t,J=6.6 Hz), 3.28(1H,t,J=6.6 Hz), 3.91(2H,s), 4.01(2H, s), 6.53(1H,d,J=6.8 Hz), 7.10(1H,dd,J=9.2,6.8 Hz), 7.27 (1H,s), 7.39(1H,d,J=9.2 Hz), 8.25(1H,br).

IR(neat): 1637, 1522, 1450, 1366, 1221 cm$^{-1}$.

iii) Synthesis of 4,5-dihydro-4-[5-(trifluoromethanesulfonamido)pentan-1-yl]-3H-1,4,8b-triazaacenaphthylene.dihydrochloride In a solution consisting of 10 ml of ethanol and 0.5 ml of 12N HCl was dissolved 0.88 g (2.34 mmol) of 4,5-dihydro-4-[5-(trifluoromethanesulfonamido)pentan-1-yl]-3H-1,4,8b-triazaacenaphthylene. The solvent was distilled off under reduced pressure to leave 1.05 g of the desired compound (100%, white amorphous).

NMR(200 MHz,DMSO) δ: 1.39(2H,m), 1.55(2H,m), 1.83 (2H,m), 3.16(4H,m), 4.85(2H,s), 4.93(2H,s), 7.54(1H,m), 8.01(2H,m), 8.19(1H,s), 9.40(1H,t,J=5.8 Hz).

IR(KBr): 3431, 1662, 1549, 1440 cm$^{-1}$.

EXAMPLE 3

4,5-Dihydro-2-methyl-4-[4-(trifluoromethanesulfonamido) butan-1-yl]-3H-1,4,8b-triazaacenaphthylene.dihydrochloride i) Synthesis of 2-methyl-5-hydroxymethylimidazo [1,2-1]pyridine

To a solution of 8.31 g (40 mmol) of 2-methyl-imidazo [1,2-a]pyridine-5-carboxylic acid ethyl ester in 200 ml of methanol was added, under ice-cooling, 4.54 g (120 mmol) of sodium borohydride. The mixture was stirred for 3 hours under ice-cooling. The reaction mixture was poured into 300 ml of ice-water, and the mixture was blended sufficiently, to which was then added 12N HCl until the pH of the solution reached 2. This solution was stirred for two hours at room temperature, which was then neutralized with a 6N aqueous solution of sodium hydroxide, followed by distilling off the solvent completely under reduced pressure. To the residue was added 300 ml of methanol. The mixture was blended sufficiently, and insolubles were filtered off, followed by distilling off the solvent under reduced pressure to leave 5.71 g of a crude product (88%, white solid substance). The crude product was used in the subsequent reaction without purification.

NMR(200 MHz,D$_2$O) δ: 2.48(3H,s), 4.83(2H,s), 6.12(1H, br), 7.87(1H,d,J=3.0 Hz), 7.71(1H,d,J=3.0 Hz), 7.73(1H,s), 8.01(1H,s).

IR(KBr): 3350, 1653, 1643, 1390 cm$^{-1}$.

ii) Synthesis of 2-methyl-5-chloromethylimidazo[1,2-a]pyridine.hydrochloride

To a mixture solution consisting of 12.0 ml (150.0 mmol) of thionyl chloride and 25 ml of methylene chloride was added, 4.87 g (30.0 mmol) of 2-methyl-5-hydroxymethylimidazo[1,2-a]pyridine with small portions. The reaction mixture was stirred for one hour at room temperature, then the solvent and excess volume of thionyl chloride were distilled off under reduced pressure to leave a white solid matter. To the solid was added 50 ml of toluene, and the mixture was stirred sufficiently, followed by distilling off the solvent under reduced pressure. This process was repeated twice to give 6.46 g (99.0%, white solid) of a crude product.

NMR(200 MHz,D$_2$O) δ: 2.50(3H,s), 5.05(2H,s), 7.44(1H, d,J=2.8 Hz), 7.75(1H,s), 7.78(1H,d,J=2.8 Hz), 7.92(1H,s).

IR(KBr): 3222, 1657, 1547, 1429 cm$^{-1}$. iii) Synthesis of 2-methyl-5-[N-[4-(trifluoromethanesulfonamido)butan-1-yl]aminomethyl]imidazo[1,2-1]pyridine To a suspension of 6.52 g (30.0 mmol) of 2-methyl-5-chloromethylimidazo[1,2-a]pyridine chloride in 60 ml of acetonitrile was added 5.30 g (60.1 mmol) of 1,4-diaminobutane. The mixture was heated for 30 minutes under reflux. After completion of the reaction, the reaction mixture was cooled. Precipitates of 1,4-diaminobutane.dihydrochloride then formed were separated by filtration. The precipitates were washed with 10 ml of acetonitrile twice. The filtrate and the washings were combined, to which was added 8.4 ml (60.1 mmol) of triethylamine, and the mixture was stirred sufficiently. To this solution was added 10.73 g (30.0 mmol) of N-phenyltrifluoromethanesulfonimide, and the mixture was stirred for two hours at room temperature. After completion of the reaction, the solvent was distilled off under reduced pressure. The residue was extracted with 150 ml of chloroform. The organic layer was washed with 150 ml of a saturated aqueous saline solution, which was dried over magnesium sulfate, followed by distilling off the solvent under reduced pressure. The residue was purified by silicagel column chromatography (eluent: chloroform/methanol= 20:1) to give 7.44 g of the desired compound (68.0%, colorless solid).

NMR(200 MHz,CDCl$_3$) δ: 1.69(4H,m), 2.44(3H,s), 2.74 (2H,t,J=6.0 Hz), 3.30(2H,t,J=6.0 Hz), 3.97(2H,s), 6.71(1H, d,J=7.0 Hz), 7.12(1H,dd,J=7.0,9.0 Hz), 7.35(1H,s), 7.47 (1H,d,J=9.0 Hz).

IR(KBr): 1639, 1483, 1371 cm$^{-1}$.

iv) Synthesis of 4,5-dihydro-2-methyl-4-[4-(trifluoromethanesulfonamido)butan-1-yl]-3H-1,4,8b-triazaacenaphthylene In 6 ml of acetic acid was dissolved 2.02 g (5.54 mmol) of 2-methyl-5-[N-[4-(trifluoromethanesulfonamido) butan-1-yl]aminomethyl]imidazo(1,2-a]pyridine. To the solution was added 6.2 ml (83.15 mmol) of a 37% aqueous solution of formalin, and the mixture was heated for 30 minutes at 100° C. After completion of the reaction, the solvent was distilled off under reduced pressure. The residue was dissolved in 100 ml of a saturated aqueous solution of potassium carbonate. This solution was neutralized by the addition of 1N HCl under ice-cooling, which was extracted twice with 100 ml of chloroform. The extract was dried over magnesium sulfate, then the solvent was distilled off under reduced pressure. The residue was purified by silicagel column chromatography (eluent: chloroform/methanol= 20:1) to afford 1.45 g of the desired compound (72.0%, colorless liquid).

NMR(200 MHz,CDCl$_3$) δ: 1.73(4H,m), 2.31(3H,s), 2.51 (2H,m), 3.31(2H,m), 3.94(2H,s), 4.01(2H,s), 6.50(1H,d,J= 6.8 Hz), 7.07(1H,dd,J=9.0,6.8 Hz), 7.36(1H,d,J=9.0 Hz).

IR(neat): 1643, 1506, 1454, 1367 cm$^{-1}$.

v) Synthesis of 4,5-dihydro-2-methyl-4-[4-(trifluoromethanesulfonamido)butan-1-yl]-3H-1,4,8b-triazaacenaphthylene.dihydrochloride In a solution consisting of 10 ml of ethanol and 1 ml of 12N HCl was dissolved 1.41 g (3.74 mmol) of 4,5-dihydro-2-methyl-4-[4-(trifluoromethanesulfonamido) butan-1-yl]-3H-1,4,8b-triazaacenaphthylene. The solvent was distilled off under reduced pressure to give the desired compound (100%, white amorphous).

NMR(200 MHz,DMSO) δ: 1.60(2H,m), 1.86(2H,m), 2.54 (3H,s), 3.40(4H,m), 4.84(2H,s), 4.92(2H,s), 7.51(1H,d,J= 6.2 Hz), 7.93(2H,m), 9.53(1H,t,J=5.2 Hz),

IR(KBr): 3428, 1672, 1552, 1450, 1369 cm$^{-1}$.

EXAMPLE 4

4,5-Dihydro-2-ethyl-4-[5-(trifluoromethanesulfonamido) pentan-1-yl]-3H-1,4,8b-triazaacenaphthylene.dihydrochloride i) Synthesis of 2-ethyl-5-hydroxymethylimidazo[1,2-a]pyridine To a solution of 5.29 g (24.24 mmol) of ethyl ester of 2-ethylimidazo[1,2-a]pyridine-5-carboxylic acid was added 2.75 g (72.72 mmol) of sodium borohydride under ice-cooling. The reaction mixture was stirred for 3 hours under ice-cooling. The reaction mixture was then poured into 150 ml of ice-water. The reaction mixture was mixed well, to which was added 12N HCl until the pH of the solution reached 2. This solution was stirred for two hours at room temperature, which was neutralized with a 6N aqueous solution of sodium hydroxide. The solvent was completely distilled off under reduced pressure. To the residue was added 200 ml of methanol. The mixture was mixed well, then insolubles were filtered off. The solvent was distilled off under reduced pressure to give 2.99 g of a crude product (70%, white solid). This crude product was used, without purification, in the subsequent reaction.

NMR(200 MHz,D$_2$O) δ: 1.32(3H,t,J=7.6 Hz), 2.78(2H,q, J=7.6 Hz), 4.83(2H,s), 6.15(1H,br), 7.86(1H,d,J=3.0 Hz), 7.74(1H,d,3.0 Hz), 7.75(1H,s), 8.00(1H,s).

IR(KBr): 3348, 1652, 1644, 1390 cm$^{-1}$.

ii) Synthesis of 2-ethyl-5-chloromethylimidazo[1,2-a]pyridine.hydrochloride

To a mixture solution consisting of 8.8 ml (120.0 mmol) of thionyl chloride and 10 ml of methylene chloride was added, 4.23 g (24.0 mmol) of 2-ethyl-5-hydroxymethylimidazo[1,2-a]pyridine with small portions. The reaction mixture was stirred for one hour at room temperature. Then, the solvent and excess volume of thionyl chloride were distilled off under reduced pressure. To the residual white solid was added 30 ml of toluene. The mixture was stirred well, and the solvent was distilled off under reduced pressure. This process repeated twice to give 5.44 g of a crude product (99.0%, white solid), which was used for the subsequent reaction without purification.

NMR(200 Hz,D$_2$O) δ: 1.35(3H,t,J=7.6 Hz), 2.85(2H,q,J=7.6 Hz), 5.02(2H,s), 7.42(1H,d,J=2.9 Hz), 7.75(1H,s), 7.77(1H,d,J=2.8 Hz), 7.90(1H,s).

IR(KBr): 3225, 1659, 1550, 1430 cm$^{-1}$.

iii) Synthesis of 2-ethyl-5-[N-[5-(trifluoromethanesulfonamido)pentan-1-yl]aminomethyl]imidazo[1,2-a]pyridine To a suspension of 5.50 g (24.0 mmol) of 2-ethyl-5-chloromethylimidazo[1,2-a]pyridine-hydrochloride in 60 ml of acetonitrile was added 4.90 g (48.0 mmol) of 1,5-diaminopentane. The mixture was heated for 30 minutes under reflux. After completion of the reaction, the reaction mixture was cooled, and then, the resulting precipitate of 1.5-diaminopentane.dihydrochloride was separated by filtration and then, washed with 10 ml of acetonitrile twice. The filtrate and the washings were combined, to which was added 6.7 ml (48.0 mmol) of triethylamine. The mixture was stirred sufficiently. To this solution was added 10.29 g (28.8 mmol) of N-phenyl trifluoromethanesulfonimide, and the mixture was stirred for two hours at room temperature. After completion of the reaction, the solvent was distilled off under reduced pressure. The residue was extracted with 150 ml of chloroform. The organic layer was washed with 150 ml of a saturated aqueous saline solution, which was dried over magnesium sulfate, followed by distilling off the solvent under reduced pressure. The residue was purified by silicagel column chromatography (eluent: chloroform/methanol=20:1) to give 6.03 g of the desired compound (64.0%, colorless solid).

NMR(200 MHz,CDCl$_3$) δ: 1.33(3H,t,J=7.6 Hz), 1.29–1.63(6H,m), 2.64(2H,t,J=6.6 Hz), 2.81(2H,q,J=7.6 Hz), 3.29(2H,t,J=7.0 Hz), 3.94(2H,s), 4.85(1H,br,NH), 6.70(1H,d,J=7.0 Hz), 7.11(1H,dd,J=9.0,7.0 Hz), 7.39(1H,s), 7.47(1H,d,J=9.0 Hz).

IR(KBr): 1645, 1480, 1361 cm$^{-1}$.

iv) Synthesis of 4,5-dihydro-2-ethyl-4-[5-(trifluoromethanesulfonamido)pentan-1-yl]-3H-1,4,8b-triazaacenaphthylene To a solution of 785 mg (2.00 mmol) of 2-ethyl-5-[N-[5-(trifluoromethanesulfonamido)pentan-1-yl]aminomethyl]imidazo[1,2-a]pyridine in 5 ml of acetic acid was added 2.25 ml (30.00 mmol) of a 37% aqueous solution of formalin. The mixture was heated for 30 minutes at 100° C. The solvent was then distilled off under reduced pressure. The residue was dissolved in 100 ml of a saturated aqueous solution of potassium carbonate. This solution was neutralized, under ice-cooling, with 1N HCl, which was extracted twice with 100 ml of chloroform. The organic layer was dried over magnesium sulfate, then the solvent was distilled off under reduced pressure. The residue was purified by silicagel column chromatography (eluent: chloroform/methanol=20:1) to give 527 mg of the desired compound (65.2%, colorless liquid).

NMR(200 MHz,CDCl$_3$) δ: 1.29(3H,t,J=7.6 Hz), 1.43(2H,m), 1.60(4H,m), 2.48(2H,t,J=7.0 Hz), 2.72(2H,q,J=7.6 Hz), 3.28(2H,t,J=6.8 Hz), 3.91(2H,s), 4.02(2H,s), 6.50(1H,d,J=7.0 Hz), 7.07(1H,dd,J=9.2,7.0 Hz), 7.36(1H,d,J=9.2 Hz).

IR(neat): 1645, 1508, 1455, 1365 cm$^{-1}$.

v) Synthesis of 4,5-dihydro-2-ethyl-4-[5-(trifluoromethanesulfonamido)pentan-1-yl]-3H-1,4,8b-triazaacenaphthylene.dihydrochloride In a mixture of 10 ml of ethanol and 1 ml of 12N HCl was dissolved 542 mg (1.34 mmol) of 4,5-dihydro-2-ethyl-4-(5-trifluoromethanesulfonamidopentan-1-yl)-3H-1,4,8b-triazaacenaphthylene. The solvent was distilled off under reduced pressure to leave 640 mg of the desired compound (100%, white amorphous substance).

NMR(200 MHz,DMSO) δ: 1.37(5H,m), 1.57(2H,m), 1.85(2H,m), 2.92(2H,q,J=7.6 Hz), 3.15(4H,m), 4.85(2H,s), 4.92(2H,s), 7.68(1H,d,J=6.2 Hz), 7.94(2H,m), 9.43(1H,t,J=5.4 Hz).

IR(KBr): 3427, 1666, 1550, 1458, 1365 cm$^{-1}$.

EXAMPLE 5

4,5-Dihydro-2-phenyl-4-[5-(trifluoromethanesulfonamido)pentan-1-yl]-3H-1,4,8b-triazaacenaphthylene.dihydrochloride i) Synthesis of 2-phenyl-5-hydroxymethylimidazo[1,2-a]pyridine

To a solution of 3.14 g (11.79 mmol) of ethyl ester of 2-phenylimidazo[1,2-a]pyridine-5-carboxylic acid was added, under ice-cooling, 1.34 g (35.37 mmol) of sodium borohydride. The mixture was stirred for 3 hours under ice-cooling. The reaction mixture was poured into 150 ml of ice-water, which was sufficiently blended. To the mixture was added 12N HCl until the pH reached 2. This solution was stirred for two hours at room temperature, which was neutralized with a 6N aqueous solution of NaOH. The solvent was then completely distilled off under reduced pressure. To the residue was added 200 ml of methanol. The mixture was sufficiently blended, then insolubles were filtered off. The solvent was distilled off under reduced pressure to leave 1.37 g of a crude product (52.0%, white solid). This crude product was used in the subsequent reaction without purification.

NMR(200 MHz,DMSO-d$_6$) δ: 4.95(2H,s), 6.15(1H,br), 6.90(1H,d,J=6.0 Hz), 7.21–7.54(6H,m), 8.03(1H,d,J=7.0 Hz), 8.45(1H,s).

IR(KBr): 3360, 1663, 1653, 1395 cm$^{-1}$.

ii) Synthesis of 2-phenyl-5-chloromethylimidazo[1,2-a]pyridine.hydrochloride To a mixture solution consisting of 3.7 ml (50.0 mmol) of thionyl chloride and 5.0 ml of methylene chloride was added, 2.24 g (10.0 mmol) of 2-phenyl-5-hydroxymethylimidazo[1,2-a]pyridine with small portion. The reaction mixture was stirred for one hour at room temperature, then the solvent and excess volume of thionyl chloride were distilled off under reduced pressure to leave a white solid. Toluene (20 ml) was added to the white solid, and the mixture was sufficiently blended, followed by distilling off the solvent under reduced pressure. This process was repeated twice to give 2.76 g a crude product (99.0%, white solid).

NMR(200 MHz,DMSO-d$_6$) δ: 5.10(2H,s), 6.95(1H,d,J=6.0 Hz), 7.25–7.60(6H,m), 8.09(1H,d,J=7.0 Hz), 8.51(1H,s).

IR(KBr): 3222, 1665, 1546, 1431 cm$^{-1}$.

iii) Synthesis of 2-phenyl-5-[N-[5-(trifluoromethanesulfonamido)pentan-1-yl]aminomethyl]imidazo[1,2-a]pyridine To a suspension of 2.79 g (10.0 mmol) of 2-phenyl-5-chloromethylimidazo[1,2-a]pyridine.hydrochloride in 35 ml of acetonitrile was added 2.04 g (20.0 mmol) of 1,5-diaminopentane. The mixture was heated for 30 minutes under reflux. After completion of the reaction, the reaction mixture was cooled. The resulting precipitate of 1,5-diaminopentane.dihydrochloride was separated by filtration and washed twice with 10 ml of acetonitrile. The filtrate and washings were combined, to which was added 2.8 ml (20.0 mmol) of triethylamine. The mixture was stirred sufficiently, to which was added 4.29 g (12.0 mmol) of N-phenyltrifluoromethanesulfonimide, and the mixture was stirred for two hours at room temperature. After completion of the reaction, the solvent was distilled off under reduced pressure. The residue was subjected to extraction with 100 ml of chloroform. The organic layer was washed with 100 ml of a saturated aqueous saline solution and dried over magnesium sulfate. Then, the solvent was distilled off under reduced pressure. The residue was purified by silicagel column chromatography (eluent: chloroform/methanol=20:1) to give 2.66 g of the desired compound (60.3%, colorless solid).

NMR(200 MHz,DMSO-$d_6$) δ: 1.51(6H,m), 2.62(2H,t,J=6.8 Hz), 3.12(2H,t,J=6.8 Hz), 4.07(2H,s), 6.91(1H,d,J=6.0 Hz), 7.21–7.54(6H,m), 8.02(1H,d,J=1.0 Hz), 8.42(1H,s).

IR(KBr): 1640, 1480, 1370 $cm^{-1}$.

iv) Synthesis of 4,5-dihydro-2-phenyl-4-[5-(trifluoromethanesulfonamido)pentan-1-yl]-3H-1,4,8b-triazaacenaphthylene To a solution of 440 mg (1.00 mmol) of 2-phenyl-5-[N-[5-(trifluoromethanesulfonamido)pentan-1-yl] aminomethyl]imidazo[1,2-1]pyridine in 5 ml of acetic acid was added 1.12 ml (15.00 mmol) of a 37% aqueous solution of formalin. The mixture was heated for 30 minutes at 100° C. After completion of the reaction, the solvent was distilled off under reduced pressure. The residue was dissolved in 100 ml of a saturated aqueous solution of potassium carbonate. This solution was neutralized, under ice-cooling, with 1N HCl, which was extracted twice with 100 ml of chloroform. The organic layer was dried over magnesium sulfate, then the solvent was distilled off under reduced pressure. The residue was purified by silicagel column chromatography (eluent: chloroform/methanol=20:1) to give 354 mg of the object compound (78.3%, colorless liquid).

NMR(200 MHz,CDCl$_3$) δ: 1.24(2H,m), 1.44(4H,m), 2.39 (2H,t,J=7.0 Hz), 3.14(2H,t,J=7.0 Hz), 3.90(2H,s), 4.21(2H, s), 6.52(1H,d,J=6.8 Hz), 7.12(1H,dd,J=9.2,6.8 Hz), 7.33 (1H,d,J=7.2 Hz), 7.40–7.72(5H,m).

IR(neat): 1645, 1508, 1455, 1366 $cm^{-1}$.

v) Synthesis of 4,5-dihydro-2-phenyl-4-[5-(trifluoromethanesulfonamido)pentan-1-yl]-3H-1,4,8b-triazaacenaphthylene.dihydrochloride In a solution consisting of 5 ml of ethanol and 0.1 ml of 12N HCl was dissolved 254 mg (0.56 mmol) of 4,5-dihydro-2-phenyl-4-[5-(trifluoromethanesulfonamido)pentan-1-yl]-3H-1,4,8b-triazaacenaphthylene. The solvent was distilled under reduced pressure to give 295 mg of the desired compound (100%, white amorphous).

NMR(200 MHz,DMSO-$d_6$) δ: 1.48(2H,m), 1.59(2H,m), 1.85(2H,m), 3.16(4H,m), 4.87(2H,s), 4.98(2H,s), 7.45(1H, t,J=3.6 Hz), 7.61–7.70(3H,s), 7.84–7.94(4H,m), 9.38(1H,t, J=5.8 Hz).

IR(KBr): 3423, 1662, 1441, 1369, 1192 $cm^{-1}$.

EXAMPLE 6

4,5-Dihydro-4-[4-(trifluoromethanesulfonamido) butan-1-yl]-3H-1,4,8b-triazaacenaphthylen-3-one.hydrochloride i) Synthesis of 5-[N-tert-butoxycarbonyl-N-[4-trifluoromethanesulfonamido)butan-1-yl] aminomethyl]imidazo[1,2-a]pyridine To a solution of 29.10 g (83.05 mmol) of 5-[N-[4-(trifluoromethanesulfonamido)butan-1-yl]aminomethyl] imidazo[1,2-a]pyridine in 100 ml of ethanol was added dropwise, taking 10 minute, 18.13 g (83.13 mmol) of di-tert-butyl dicarbonate. The reaction mixture was stirred for one hour at room temperature, then the solvent was distilled off under reduced pressure. The residue was purified by silicagel column chromatography (eluent: chloroform/methanol=20:1) to give 26.33 g of the desired compound(70.4%, pale yellow solid).

NMR(200 MHz,CDCl$_3$) δ: 1.48(13H,m), 3.24(4H,br), 4.67(2H,br), 6.69(1H,d,J=6.2 Hz), 7.19(1H,t,J=6.2 Hz), 7.50–7.80(3H,m).

IR(KBr): 2978, 1691, 1516, 1379, 1228 $cm^{-1}$.

ii) Synthesis of 3-trichloroacetyl-5-[N-tert-butoxycarbonyl-N-[4-(trifluoromethanesulfonamido)butan-1-yl]aminomethyl]imidazo[1,2-a]pyridine To a solution of 7.86 g (17.44 mmol) of 5-[N-tert-butoxycarbonyl-N-[4-(trifluoromethanesulfonamido)butan-1-yl]aminomethyl]imidazo[1,2-a]pyridine and 6.39 g (52.31 mmol) of 4-dimethylaminopyridine in 100 ml of chloroform was added dropwise, taking 5 minutes, 5.84 ml (52.31 mmol) of trichloroacetyl chloride. The reaction mixture was heated for 16 hours under reflux. The reaction mixture was poured into ice-water, which was neutralized with a saturated aqueous solution of sodium hydrogencarbonate, followed by extraction with 100 ml of chloroform. The organic layer was washed with 200 ml of a saturated aqueous saline solution and dried over magnesium sulfate, then the solvent was distilled off under reduced pressure. The residue was purified by silicagel column chromatography (eluent: chloroform/methanol=100:1) to give 5.72 g of the desired compound (55.0%, pale yellow liquid).

NMR(200 MHz,CDCl$_3$) δ: 1.55–1.85(4H,m), 3.38(2H,t, J=7.4 Hz), 3.77(2H,t,J=6.6 Hz), 4.50(2H,s), 7.11(1H,d,J=6.6 Hz), 7.69(1H,dd,J=8.6,7.2 Hz), 7.81(1H,d,J=8.6 Hz), 8.95 (1H,s).

IR(neat): 2978, 1755, 1705, 1768, 1404 $cm^{-1}$.

iii) Synthesis of 4,5-dihydro-4-[4-(trifluoromethanesulfonamido)butan-1-yl]-3H-1,4,8b-triazaacenaphthylen-3-one To a solution of 5.25 g (8.81 mmol) of 3-trichloroacetyl-5-[N-tert-butoxycarbonyl-N-[4-(trifluoromethanesulfonamido)butan-1-yl]aminomethyl] imidazo[1,2-a]pyridine in 25 ml of chloroform was added dropwise 2.5 ml (17.62 mmol) of iodotrimethylsilane at room temperature. The reaction mixture was stirred for 10 minutes, which was poured into ice-water, followed by neutralization with a saturated aqueous solution of sodium hydrogencarbonate. This solution was extracted with 250 ml of ethyl acetate. The organic layer was washed with 100 ml of a 1.0N aqueous solution of sodium thiosulfate, then with 100 ml of a saturated aqueous saline solution. The organic layer was dried over magnesium sulfate, then the solvent was distilled off under reduced pressure. The residue was purified by silicagel column chromatography (eluent: chloroform/methanol=20:1) to give 2.16 g (65.0%) of the desired compound.

NMR(200 MHz,CDCl$_3$) δ: 1.41–1.88(4H,m), 3.42(2H,t, J=6.0 Hz), 3.64(2H,t,J=6.6 Hz), 5.02(2H,s), 6.77(1H,d,J=7.0 Hz), 7.35(1H,dd,J=9.2,7.0 Hz), 7.54(1H,d,J=9.2 Hz), 8.15 (1H,s).

IR(KBr): 1641, 1542, 1369, 1189 $cm^{-1}$.

iv) Synthesis of 4,5-dihydro-4-[4-(trifluoromethanesulfonamido)butan-1-yl]-3H-1,4,8b-triazaacenaphthylen-3-one.hydrochloride In a mixture of 50 ml of ethanol and 1 ml of 12N HCl was dissolved 2.87 g (7.63 mmol) of 4,5-dihydro-4-[4-

(trifluoromethanesulfonamido)butan-1-yl]-3H-1,4,8b-triazaacenaphthylen-3-one, and the solvent was distilled off under reduced pressure to leave 3.15 g of the desired compound (100%, pale yellow solid matter).

NMR(200 MHz,DMSO) δ: 1.45–1.78(4H,m), 3.20(2H, dd,J=9.6,5.6 Hz), 3.55(2H,t,J=6.6 Hz), 5.25(2H,s), 7.43(1H, d,J=8.0 Hz), 7.85(1H,d,J=8.2 Hz), 7.99(1H,dd,J=8.2,8.0 Hz), 8.63(1H,s), 9.44(1H,t,J=5.6 Hz).

IR(KBr): 1649, 1560, 1479, 1369 cm$^{-1}$.

EXAMPLE 7

4,5-Dihydro-4-[3-(trifluoromethanesulfonamido)propan-1-yl]-3H-1,4,8b-triazaacenaphthylen-3-one.hydrochloride i) Synthesis of 5-[N-[3-(trifluoromethanesulfonamido)propan-1-yl]aminomethyl]imidazo[1,2-a]pyridine To a suspension of 6.89 g (33.9 mmol) of 5-chloromethylimidazo[1,2-a]pyridine hydrochloride in 100 ml of acetonitrile was added 5.03 g (67.9 mmol) of 1,3-diaminopropane. The mixture was heated for 30 minutes under reflux. After completion of the reaction, the reaction mixture was cooled to cause precipitation of 1,3-diaminopropane.dihydrochloride. The precipitate was separated by filtration and washed twice with 10 ml of acetonitrile. The filtrate and the washings were combined, to which was added 9.46 ml (67.9 mmol) of triethylamine, and the mixture was stirred sufficiently. To the solution was added 24.26 g (67.9 mmol) of N-phenyltrifluoromethanesulfonimide, and the mixture was stirred for two hours at room temperature. After completion of the reaction, the solvent was distilled off under reduced pressure. The residue was extracted with 250 ml of chloroform. The organic layer was washed with 200 ml of a saturated aqueous saline solution, which was dried over magnesium sulfate, followed by distilling off the solvent under reduced pressure. The residue was purified by silicagel column chromatography (eluent: chloroform/methanol=20:1) to give 7.18 g of the desired compound (63.0%, colorless solid matter).

NMR(200 MHz,CDCl$_3$) δ: 1.82(2H,m), 2.88(2H,t,J=5.8 Hz), 3.43(2H,t,J=5.8 Hz), 4.00(2H,s), 4.85(1H,br), 6.73(1H, d,J=6.6 Hz), 7.12(1H,dd,J=9.2,6.6 Hz), 7.54(1H,d,J=9.2 Hz), 7.57(2H,s).

IR(KBr): 1620, 1464, 1367, 1225, 1184 cm$^{-1}$.

ii) Synthesis of 5-[N-tert-butoxycarbonyl-N-[3-(trifluoromethanesulfonamido)propan-1-yl]aminomethyl]imidazo[1,2-a]pyridine To a solution of 3.03 g (9.01 mmol) of 5-[N-[3-(trifluoromethanesulfonamido)propan-1-yl]aminomethyl]imidazo[1,2-a]pyridine in 20 ml of ethanol was added dropwise, taking 5 minutes, 1.97 g (9.01 mmol) of di-tert-butyl dicarbonate. The reaction mixture was stirred for one hour at room temperature, then the solvent was distilled off under reduced pressure. The residue was purified by means of a silicagel column chromatography (eluent: chloroform/methanol=20:1) to give 3.38 g of the desired compound (86.1%, colorless liquid).

NMR(200 MHz,CDCl$_3$) δ: 1.51(9H,s), 1.60(2H,m), 3.21 (2H,t,J=6.2 Hz), 3.41(2H,br), 4.66(2H,s), 6.88(1H,d,J=7.0 Hz), 7.18(1H,m), 7.53(3H,m).

IR(KBr): 1691, 1469, 1416, 1371, 1186 cm$^{-1}$.

iii) Synthesis of 3-trichloroacetyl-5-[N-tert-butoxycarbonyl-N-[3-(trifluoromethanesulfonamido)propan-1-yl]aminomethyl]imidazo[1,2-a]pyridine To a solution of 3.15 g (7.22 mmol) of 5-[N-tert-butoxycarbonyl-N-[3-(trifluoromethanesulfonamido)propan-1-yl]aminomethyl]imidazo[1,2-a]pyridine and 2.65 g (21.65 mmol) of 4-dimethylaminopyridine in 30 ml of chloroform was added dropwise, while stirring at room temperature for 3 minutes, 2.4 ml (21.65 mmol) of trichloroacetyl chloride. The reaction mixture was heated for 15 hours under reflux. After completion of the reaction, the reaction mixture was poured into ice-water, which was neutralized with a saturated aqueous solution of sodium hydrogencarbonate. The solution was extracted with 150 ml of chloroform. The organic layer was washed with 250 ml of a saturated aqueous saline solution and dried over magnesium sulfate. The solvent was then distilled off under reduced pressure. The residue was purified by silicagel column chromatography (eluent: chloroform/methanol=100:1) to give 2.31 g of the desired compound (54.8%, pale yellow liquid).

NMR(200 MHz,CDCl$_3$) δ: 1.21(9H,s), 1.84(2H,m), 3.35 (2H,m), 3.53(2H,t,J=5.8 Hz), 4.46(2H,s), 7.09(1H,d,J=7.2 Hz), 7.73(1H,dd,J=8.8,7.4 Hz), 7.85(1H,dd,J=7.6 Hz), 8.98 (1H,s).

IR(KBr): 1680, 1471, 1373, 1296, 1188 cm$^{-1}$.

iv) Synthesis of 4,5-dihydro-4[3-(trifluoromethanesulfonamido)propan-1-yl]-3H-1,4,8b-triazaacenaphthylene-3-one To a solution of 1.16 g (2.00 mmol) of 3-trichloroacetyl-5-[N-tert-butoxycarbonyl-N-[3-(trifluoromethanesulfonamido)propan-1-yl]aminomethyl]imidazo[1,2-a]pyridine in 25 ml of chloroform was added dropwise 0.57 ml (4.00 mmol) of iodotrimethylsilane at room temperature. The reaction mixture was stirred for 15 minutes, which was then poured into ice-water, followed by neutralization with a saturated aqueous solution of sodium hydrogencarbonate. This solution was extractedith 150 ml of ethyl acetate. The organic layer was washed with 100 ml of a 1.0N aqueous solution of sodium thiosulfate, then with 100 ml of a saturated aqueous saline solution. The organic layer was dried over magnesium sulfate, followed by distilling off the solvent under reduced pressure. The residue was purified by silicagel column chromatography (eluent: chloroform/methanol=20:1) to give 397 mg of the desired compound (54.8%, pale yellow solid).

NMR(200 MHz,CDCl$_3$) δ: 1.95(2H,m), 3.34(2H,t,J=5.8 Hz), 3.73(2H,t,J=6.0 Hz), 5.04(2H,s), 6.79(1H,d,J=7.0 Hz), 7.68(1H,br,NH), 8.13(1H,s).

IR(KBr): 1637, 1545, 1367, 1184 cm$^{-1}$.

v) Synthesis of 4,5-dihydro-4-[3-(trifluoromethanesulfonamido)propan-1-yl]-3H-1,4,8b-triazaacenaphthylene-3-one.hydrochloride In a mixture solution consisting of 5 ml of ethanol and 0.1 ml of 12N HCl was dissolved 145 mg (0.40 mmol) of 4,5-dihydro-4-[3-(trifluoromethanesulfonamido)propan-1-yl]-3H-1,4,8b-triazaacenaphthylen-3-one. The solvent was distilled off under reduced pressure to leave 160 mg of the desired compound (100%, pale yellow solid substance).

NMR(200 MHz,DMSO) δ: 1.91(2H,m), 3.26(2H,q,J=6.0 Hz), 3.60(2H,t,J=7.6 Hz), 5.28(2H,s), 7.46(1H,d,J=6.8 Hz), 7.88(1H,d,J=8.8 Hz), 8.02(1H,dd,J=8.8,6.8 Hz), 8.66(1H,s), 9.52(1H,t,J=5.8 Hz).

IR(KBr): 3455, 1659, 1444, 1371, 1182 cm$^{-1}$.

EXAMPLE 8

4,5-Dihydro-4-[5-(trifluoromethanesulfonamido)
pentan-1-yl]-3H-1,4,8b-triazaacenaphthylen-3-
one.hydrochloride i) Synthesis of 5-[N-tert-butoxycarbonyl-N-[5-
(trifluoromethanesulfonamido)pentan-1-yl]
aminomethyl]imidazo[1,2-a]pyridine To a solution of 5.00 g (13.72 mmol) of 5-[N-[5-(trifluoromethanesulfonamido)pentan-1-yl]aminomethyl] imidazo[1,2-a]pyridine in 25 ml of ethanol was added dropwise, taking 5 minutes, 2.99 g (13.72 mmol) of di-tert-butyl dicarbonate. The reaction mixture was stirred for one hour at room temperature, then the solvent was distilled off under reduced pressure. The residue was purified by silica-gel column chromatography (eluent: chloroform/methanol= 20:1) to give 5.73 g of the desired compound (90.2%, colorless liquid).

NMR(200 MHz,CDCl$_3$) δ: 1.28(6H,m), 1.48(9H,s), 3.10–3.25(4H,m), 4.68(2H,s), 6.68(1H,d,J=6.8 Hz), 7.19 (1H,t,J=6.8 Hz), 7.57(1H,s), 7.61(1H,s), 7.75(1H,br).

IR(neat): 1699, 1512, 1471, 1419 cm$^{-1}$.

ii) Synthesis of 3-trichloroacetyl-5-[N-tert-
butoxycarbonyl-N-[5-(trifluoromethanesulfonamido)
pentan-1-yl]aminomethyl]imidazo[1,2-a]pyridine To a solution of 3.55 g (7.64 mmol) of 5-[N-tert-butoxycarbonyl-N-[5-(trifluoromethanesulfonamido) pentan-1-yl]aminomethyl]imidazo[1,2-a]pyridine and 2.80 g (22.92 mmol) of 4-dimethylaminopyridine in 35 ml of chloroform was added dropwise 2.6 ml (22.92 mmol) of trichloroacetyl chloride, while stirring at room temperature for 3 minutes. The reaction mixture was heated for 15 hours under reflux. The reaction mixture was poured into ice-water, which was neutralized with a saturated aqueous solution of sodium hydrogencarbonate, which was extracted with 150 ml of chloroform. The organic layer was washed with 250 ml of a saturated aqueous saline solution, which was dried over magnesium sulfate, followed by distilling off the solvent under reduced pressure. The residue was purified by silicagel column chromatography (eluent: chloroform/methanol=100:1) to give 2.70 g of the desired compound (58.2%, pale yellow liquid).

NMR(200 MHz,CDCl$_3$) δ: 1.23(9H,s), 1.48(2H,m), 1.69 (4H,m), 3.35(4H,m), 4.49(2H,s), 6.31(1H,br), 7.13(1H,d,J= 7.0 Hz), 7.72(1H,dd,J=8.8,7.0 Hz), 7.84(1H,d,J=8.8 Hz), 8.96(1H,s).

IR(neat): 1695, 1670, 1497, 1470 cm$^{-1}$.

iii) Synthesis of 4,5-dihydro-4-[5-
(trifluoromethanesulfonamido)pentan-1-yl]-3H-1,4,
8b-triazaacenaphthylene-3-one To a solution of 1.75 g (2.87 mmol) of 3-trichloroacetyl-5-[N-tert-butoxycarbonyl-N-[5-(trifluoromethanesulfonamido)pentan-1-yl]aminomethyl] imidazo[1,2-a]pyridine in 25 ml of chloroform was added dropwise 0.82 ml (5.74 mmol) of iodotrimethylsilane at room temperature. The reaction mixture was stirred for 15 minutes, which was poured into ice-water, followed by neutralization with a saturated aqueous solution of sodium hydrogencarbonate. This solution was extracted with 150 ml of ethyl acetate. The organic layer was washed with a 1.0N aqueous solution of sodium thiosulfate, then with 100 ml of a saturated aqueous saline solution. The organic layer was dried over magnesium sulfate, followed by distilling off the solvent under reduced pressure. The residue was purified by silicagel column chromatography (eluent: chloroform/methanol=20:1) to give 706 mg of the object product (63.1%, pale yellow solid substance).

NMR(200 MHz,CDCl$_3$) δ: 1.48(2H,m), 1.71(4H,m), 3.32 (2H,t,J=6.6 Hz), 3.57(2H,t,J=6.8 Hz), 4.99(2H,s), 6.74(1H, d,J=7.0 Hz), 7.30(1H,dd,J=9.2,7.0 Hz), 7.48(1H,d,J=9.2 Hz), 8.07(1H,s), 8.11(1H,br).

IR(KBr): 1707, 1610, 1544, 1332, 1219 cm$^{-1}$.

iv) Synthesis of 4,5-dihydro-4-[5-
(trifluoromethanesulfonamido)pentan-1-yl]-3H-1,4,
8b-triazaacenaphthylen-3-one.hydrochloride In a mixture solvent consisting of 5 ml of ethanol and 0.1 ml of 12N HCl was dissolved 593 mg (1.52 mmol) of 4,5-dihydro-4-[5-(trifluoromethanesulfonamido)pentan-1-yl]-3H-1,4,8b-triazaacenaphthylene-3-one. The solvent was distilled off under reduced pressure to leave 650 mg of the desired compound (100%, pale yellow solid).

NMR(200 MHz,DMSO) δ: 1.40(2H,m), 1.60(4H,m), 3.15 (4H,m), 5.27(2H,s), 1.47(1H,d,J=7.2 Hz), 7.55(1H,d,J=9.0 Hz), 8.03(1H,dd,J=9.0,7.2 Hz), 8.64(1H,s), 9.45(1H,t,J=5.4 Hz).

IR(KBr): 1720, 1655, 1442, 1365, 1188 cm$^{-1}$.

EXAMPLE 9

4,5-Dihydro-2-methyl-4-[4-
(trifluoromethanesulfonamido) butan-1-yl]-3H-1,4,
8b-triazaacenaphthylen-3-one.hydrochloride i) Synthesis of 2-methyl-5-[N-tert-butoxycarbonyl-
N-[4-(trifluoromethanesulfonamido)butan-1-yl]
aminomethyl]imidazo[1,2-a]pyridine To a solution of 2.41 g (6.61 mmol) of 2-methyl-5-[N-[4-(trifluoromethanesulfonamido)butan-1-yl]aminomethyl] imidazo[1,2-a]pyridine in 15 ml of ethanol was added dropwise, for 5 minutes, 1.44 g (6.61 mmol of di-tert-butyl dicarbonate. The reaction mixture was stirred for one hour at room temperature, then the solvent was distilled off under reduced pressure. The residue was purified by silicagel column chromatography (eluent: chloroform/methanol= 20:1) to give 2.21 g of the desired compound (72.1%, colorless liquid).

NMR(200 MHz,CDCl$_3$) δ: 1.49(9H,s), 2.44(3H,s), 3.23 (4H,m), 4.62(2H,s), 6.61(1H,d,J=6.8 Hz), 7.14(1H,t,J=8.6 Hz), 7.35(1H,br), 7.48(1H,d,J=8.6 Hz).

IR(neat): 1686, 1510, 1467, 1367 cm$^{-1}$.

ii) Synthesis of 2-methyl-3-trichloroacetyl-5-[N-
tert-butoxycarbonyl-N-[4-
(trifluoromethanesulfonamido)butan-1-yl]
aminomethyl]imidazo[1,2-a]pyridine To a solution of 2.90 g (6.24 mmol) of 2-methyl-5-[N-tert-butoxycarbonyl-N-[4-(trifluoromethanesulfonamido) butan-1-yl]aminomethyl]imidazo[1,2-a]pyridine and 2.29 g (18.73 mmol) of 4-dimethylaminopyridine in 25 ml of chloroform was added dropwise, for 3 minutes, 2.1 ml (18.73 mmol) of trichloroacetyl chloride. The reaction mixture was heated for 20 hours under reflux. The reaction mixture was then poured into ice-water, which was neutralized with a saturated aqueous solution of sodium hydrogencarbonate, followed by extraction with 100 ml of chloroform. The organic layer was washed with 200 ml of a saturated aqueous saline solution and dried over magnesium sulfate, followed by distilling off the solvent under reduced pressure. The residue was purified by silicagel column chromatography (eluent: chloroform/methanol=100:1) to give 2.47 g of the desired compound (65.2%, pale yellow liquid).

NMR(200 MHz,CDCl$_3$) δ: 1.23(9H,br), 1.66(4H,m), 2.83 (3H,s), 3.38(4H,m), 4.07(2H,s), 6.96(1H,d,J=7.0 Hz), 7.60 (1H,dd,J=8.8,7.0 Hz), 7.75(1H,d,J=8.8 Hz).

IR(neat): 1693, 1672, 1465, 1365 cm$^{-1}$.

iii) Synthesis of 4,5-dihydro-2-methyl-4-[4-(trifluoromethanesulfonamido)-1-yl]-3H-1,4,8b-triazaacenaphthylen-3-one To a solution of 781 mg (1.28 mmol) of 2-methyl-3-trichloroacetyl-5-[N-tert-butoxycarbonyl-N-[4-(trifluoromethanesulfonamido)butan-1-yl]aminomethyl] imidazo[1,2-a]pyridine in 10 ml of chloroform was added dropwise, at room temperature, 0.36 ml (2.56 mmol) of iodotrimethylsilane. The reaction mixture was stirred for 10 minutes, which was poured into ice-water, followed by neutralization with a saturated aqueous solution of sodium hydrogencarbonate. This solution was extracted with 100 ml of ethyl acetate. The organic layer was washed with 50 ml of a 1.0N aqueous solution of sodium thiosulfate, then with 50 ml of a saturated aqueous saline solution. The organic layer was dried over magnesium sulfate, then the solvent was distilled off under reduced pressure. The residue was purified by silicagel column chromatography (eluent: chloroform/methanol=20:1) to give 290 mg of the desired compound (58.0%, pale yellow solid).

NMR(200 MHz,CDCl$_3$) δ: 1.86(4H,m), 2.73(3H,s), 3.61 (4H,m), 4.97(2H,s), 6.68(1H,d,J=6.8 Hz), 7.28(1H,dd,J=9.2, 6.8 Hz), 7.41(1H,d,J=9.2 Hz).

IR(KBr): 1697, 1660, 1535, 1448 cm$^{-1}$.

iv) Synthesis of 4,5-dihydro-2-methyl-4-(4-trifluoromethanesulfonamidobutan-1-yl)-3H-1,4,8b-triazaacenaphthylen-3-one.hydrochloride 234 mg (0.6 mmol) of 4,5-dihydro-2-methyl-4-[4-(trifluoromethanesulfonamido)butan-1-yl]-3H-1,4,8b-triazaacenaphthylen-3-one was dissolved in a mixture solvent consisting of 2 ml of ethanol and 0.05 ml of 12N HCl. The solvent was distilled off under reduced pressure to leave 256 mg of the desired compound (100%, pale yellow solid substance).

NMR(200 MHz,CDCl$_3$) δ: 1.65(2H,m), 1.81(2H,m), 2.56 (3H,s), 3.15(4H,m), 5.27(1H,s), 7.47(1H,d,J=7.2 Hz), 7.87 (1H,d,J=9.0 Hz), 8.03(1H,dd,J=9.0,7.2 Hz), 8.67(1H,s), 9.31(1H,br).

IR(KBr): 3428, 1716, 1664, 1444 cm$^{-1}$.

EXAMPLE 10

4,5-Dihydro-2-ethyl-4-[5-(trifluoromethanesulfonamido)pentan-1-yl]-3H-1,4, 8b-triazaacenaphthylene.hydrochloride i) Synthesis of 2-ethyl-5-tert-butoxycarbonyl-N-[5-(trifluoromethanesulfonamido)pentan-1-yl] aminomethyl]imidazo[1,2-a]pyridine To a solution of 3.00 g (7.64 mmol) of 2-ethyl-5-[N-[5-(trifluoromethanesulfonamido)pentan-1-yl]aminomethyl] imidazo[1,2-a]pyridine in 20 ml of ethanol was added dropwise, for 5 minutes, 1.67 g (7.64 mmol) of di-tert-butyl dicarbonate. The mixture was stirred for one hour at room temperature, then the solvent was distilled off under reduced pressure. The residue was purified by silicagel column chromatography (eluent: chloroform/methanol=20:1) to give 3.09 g of the desired compound (82.1%, colorless liquid).

NMR(200 MHz,CDCl$_3$) δ: 1.21–1.45(9H,m), 1.49(9H,s), 2.82(2H,q,J=7.6 Hz), 3.06(2H,br), 3.22(2H,br), 4.65(2H,br), 6.60(1H,d,J=6.0 Hz), 7.13(2H,m), 7.51(1H,d,J=9.2 Hz).

IR(neat): 1684, 1512, 1462, 1365 cm$^{-1}$.

ii) Synthesis of 2-ethyl-3-trichloroacetyl-5-[N-tert-butoxycarbonyl-N-[5-(trifluoromethanesulfonamido) pentan-1-yl]aminomethyl]imidazo[1,2-a]pyridine To a solution of 2.85 g (5.79 mmol) of 2-methyl-5-[N-tert-butoxycarbonyl-N-[5-(trifluoromethanesulfonamido) pentan-1-yl]aminomethyl]imidazo[1,2-a]pyridine and 3.53 g (28.93 mmol) of 4-dimethylaminopyridine in 35 ml of chloroform was added dropwise, for 3 minutes under stirring at room temperature, 3.2 ml (28.93 mmol) of trichloroacetyl chloride. The reaction mixture was heated for 20 hours under reflux. After completion of the reaction, the reaction mixture was poured into ice-water, which was neutralized with a saturated aqueous solution of sodium hydrogencarbonate, followed by extraction with 100 ml of chloroform. The organic layer was washed with 200 ml of a saturated aqueous saline solution, which was dried over magnesium sulfate, followed by distilling off the solvent under reduced pressure. The residue was purified by silica-gel column chromatography (eluent: chloroform/methanol= 100:1) to give 2.04 g of the desired compound (55.2%, pale yellow liquid).

NMR(200 MHz,CDCl$_3$) δ: 1.23(9H,br), 1.43(3H,t,J=7.6 Hz), 1.65(6H,m), 3.15(2H,q,J=7.6 Hz), 3.34(4H,m), 4.11 (2H,s), 6.94(1H,d,J=7.0 Hz), 7.57(1H,dd,J=8.8,7.0 Hz), 7.71(1H,d,J=8.8 Hz).

IR(neat): 1690, 1670, 1470, 1363 cm$^{-1}$.

iii) Synthesis of 4,5-dihydro-2-ethyl-4-[5-(trifluoromethanesulfonamido)pentan-1-yl]-3H-1,4, 8b-triazaacenaphthylen-3-one To a solution of 1.73 g (2.71 mmol) of 2-ethyl-3-trichloroacetyl-5-[N-tert-butoxycarbonyl-N-[5-(trifluoromethanesulfonamido)pentan-1-yl]aminomethyl] imidazo[1,2-a]pyridine in 15 ml of chloroform was added dropwise 0.80 ml (5.42 mmol) of iodotrimethylsilane at room temperature. The reaction mixture was stirred for 10 minutes, which was poured into ice-water, followed by neutralization with a saturated aqueous solution of sodium hydrogencarbonate. This solution was extracted with 100 ml of ethyl acetate. The organic layer was washed with 50 ml of 1.0N aqueous solution of sodium thiosulfate, then with 50 ml of a saturated aqueous saline solution. The organic layer was dried over magnesium sulfate, then the solvent was distilled off under reduced pressure. The residue was purified by silicagel column chromatography (eluent: chloroform/methanol=20:1) to give 603 mg of the desired compound (52.3%, pale yellow solid).

NMR(200 MHz,CDCl$_3$) δ: 1.35(3H,t,J=7.6 Hz), 1.48(2H, m), 1.70(4H,m), 3.13(2H,q,J=7.6 Hz), 3.33(2H,t,J=6.2 Hz), 3.58(2H,t,J=6.6 Hz), 4.96(2H,s), 6.68(1H,d,J=7.0 Hz), 7.00 (1H,br), 7.28(1H,dd,J=8.8,7.0 Hz), 7.44(1H,d,J=8.8 Hz).

IR(KBr): 1700, 1650, 1537, 1446 cm$^{-1}$.

iv) Synthesis of 4,5-dihydro-2-ethyl-4-[5-(trifluoromethanesulfonamido)pentan-1-yl]-3H-1,4,8b-triazaacenaphthylen-3-one.hydrochloride In a mixture solvent consisting of 2 ml of ethanol and 0.05 ml of 12N HCl was dissolved 110 mg (0.26 mmol) of 4,5-dihydro-2-ethyl-4-[5-(trifluoromethanesulfonamido)pentan-1-yl]-3H-1,4,8b-triazaacenaphthylen-3-one. The solvent was distilled off under reduced pressure to leave 120 mg of the desired compound (100%, pale yellow solid).

NMR(200 MHz,DMSO) δ: 1.18(3H,t,J=7.6 Hz), 1.32(2H, m), 1.53(4H,m), 3.01(t,2H,J=6.2 Hz), 3.42(2H,t,J=6.6 Hz), 5.26(2H,s), 7.45(1H,d,J=7.2 Hz), 7.86(1H,d,J=9.0 Hz), 8.01 (1H,dd,J=9.0,7.2 Hz), 8.65(1H,s), 9.32(1H,br).

IR(KBr): 3425, 1720, 1665, 1442 $cm^{-1}$.

EXAMPLE 11

4,5-Dihydro-4-[4-(trifluoromethanesulfonamido)butan-1-yl]-3H-1,4,8b-triazaacenaphthylene-3,5-dione.hydrochloride i) Synthesis of 4,5-dihydro-4-[4-(trifluoromthanesulfonamido)butan-1-yl]-3H-1,4,8b-triazaacenaphthylene-3,5-dione To a solution of 5.05 g (57.3 mmol) of 1,4-diaminobutane and 14.81 g (114.6 mmol) of N,N-diisopropylethylamine in 200 ml of acetonitrile was added a solution of 19.22 g (57.3 mmol) of 5-ethoxycarbonyl-3-trichloroacetylimidazo[1,2-a]pyridine in 100 ml of acetonitrile. The mixture was heated for 0.5 hour under reflux. The reaction mixture was left standing for cooling. Insolubles were then filtered off. To the filtrate was added 24.56 g (68.7 mmol) of N-phenyltrifluoromethanesulfonimide. The mixture was stirred for 0.5 hour at room temperature. The solvent was distilled off. To the residue was added chloroform, and the mixture was washed with an aqueous solution of sodium hydrogencarbonate, which was dried over anhydrous magnesium sulfate. The solvent was distilled off, and the residue was purified by means of a column chromatography (eluent: ethyl acetate). The purified product was recrystallized from ethyl acetate. The crystalline product was collected by filtration, washed with ethyl acetate and dried to give 9.06 g of the desired compound (40.5%, colorless crystals), m.p.205.0–207.0° C.

Elemental Analysis for $C_{14}H_{13}N_4O_4SF_3$:

Calcd.: C, 43.08; H, 3.36; N, 14.35. Found: C, 43.32; H, 3.43; N, 14.30.

NMR(200 MHz,CDCl$_3$-DMSO-d$_6$) δ: 1.60–1.92(4H,m), 3.26(2H,t,J=6.6 Hz), 4.19(2H,t,J=7.0 Hz), 7.83(1H,dd,J=8.8,7.6 Hz), 8.18(1H,d,J=7.6 Hz), 8.20(1H,d,J=8.8 Hz), 8.60 (1H,br), 8.62(1H,s).

ii) Synthesis of 4,5-dihydro-4-[4-(trifluoromethanesulfonamido)butan-1-yl]-3H-1,4,8b-triazaacenaphthylene-3,5-dione.hydrochloride To a suspension of 204 mg (0.52 mmol) of 4,5-dihydro-4-[4-(trifluoromethanesulfonamido)butan-1-yl]-3H-1,4,8b-triazacenaphthylene-3,5-dione in 10 ml of methanol was added 0.12 ml of conc. HCl, then the solvent was distilled off. To the residue was added acetone, and the resulting solid substance was washed with acetone and dried to give 170 mg of the desired compound (76.2%, colorless solid substance), m.p.206.0–207.0° C.

Elemental Analysis for $C_{14}H_{13}N_4O_4SF_3$.HCl:

Calcd.: C, 39.40; H, 3.31; N, 13.13. Found: C, 39.42; H, 3.38; N, 12.95.

NMR(200 MHz,DMSO-d$_6$) δ: 1.50–1.80(4H,m), 3.18 (2H,m), 4.04(2H,t,J=6.6 Hz), 7.92(1H,dd,J=8.8,7.4 Hz), 8.14(1H,dd,J=7.4,1.0 Hz), 8.31(1H,dd,J=8.8,1.0 Hz), 8.69 (1H,s), 9.35(1H,br).

EXAMPLE 12

4,5-Dihydro-4-[3-(trifluoromethanesulfonamido)propan-1-yl]-3H-1,4,8b-triazaacenaphthylene-3,5-dione.hydrochloride i) Synthesis of 4,5-dihydro-4-[3-(trifluoromethanesulfonamido)propan-1-yl]-3H-1,4,8b-triazaacenaphthylene-3,5-dione To a solution of 273 mg (3.68 mmol) of 1,3-diaminopropane and 951 mg (7.36 mmol) of N,N-diisopropylethylamine in 15 ml of acetonitrile was added a solution of 1.235 g (3.68 mmol) of 5-ethoxycarbonyl-3-trichloroacetylimidazo[1,2-a]pyridine in 15 ml of acetonitrile. The mixture was heated for 45 minutes under reflux. After cooling, the resulting insolubles were filtered off. To the filtrate was added 1.578 g (4.42 mmol) of N-phenyltrifluoromethanesulfonimide. The mixture was stirred for one hour at room temperature. The solvent was distilled off. To the residue was added chloroform. The mixture was washed with an aqueous solution of sodium hydrogencarbonate, dried over anhydrous magnesium sulfate. The solvent was distilled off, and the residue was purified by column chromatography (eluent: ethyl acetate), which was crystallized from ethyl acetate. The crystalline product was collected by filtration, washed with ether, and dried to give 607 mg of the desired compound (43.8%, colorless solid), m.p.169.0–170.0° C.

Elemental Analysis for $C_{13}H_{11}N_4O_4SF_3$:

Calcd.: C, 41.19; H, 2.95; N, 14.89. Found: C, 41.19; H, 2.98; N, 14.63.

NMR(200 MHz,CDCl$_3$-DMSO-d$_6$) δ: 2.02(2H,m), 3.34 (2H,t,J=6.8 Hz), 4.25(2H,m), 7.85(1H,m), 8.15–8.22(2H, m), 8.62(1H,s).

ii) Synthesis of 4,5-dihydro-4-[3-(trifluoromethanesulfonamido)propan-1-yl]-3H-1,4,8b-triazaacenaphthylene-3,5-dione.hydrochloride To a suspension of 186 mg (0.49 mmol) of 4,5-dihydro-4-[3-(trifluoromethanesulfonamido)propan-1-yl]-3H-1,4,8b-triazacenaphthylene-3,5-dione in 10 ml of methanol was added 0.09 ml of conc. HCl. The solvent was distilled off. To the residue was added acetone, and the resulting solid was washed with acetone and dried to give 177 mg of the desired compound (86.8%, colorless solid), m.p.124.0–125.0° C.

Elemental Analysis for $C_{13}H_{11}N_4O_4SF_3$.HCl:

Calcd.: C, 37.83; H, 2.93; N, 13.57. Found: C, 37.63; H, 3.00; N, 13.23.

NMR(200 MHz,DMSO-d$_6$) δ: 1.89(2H,m), 3.28(2H,m), 4.06(2H,m), 7.92(1H,dd,J=8.8,7.4 Hz), 8.14(1H,dd,J=7.4, 1.0 Hz), 8.30(1H,dd,J=8.8,1.0 Hz), 8.69(1H,s), 9.46(1H,br).

EXAMPLE 13

4,5-Dihydro-4-[5-(trifluoromethanesulfonamido)pentan-1-yl]-3H-1,4,8b-triazaacenaphthylene-3,5-dione.hydrochloride i) Synthesis of 4,5-dihydro-4-[5-(trifluoromethanesulfonamido)pentan-1-yl]-3H-1,4,8b-triazaacenaphthylene-3,5-dione To a solution of 1.44 g (14.1 mmol) of 1,5-diaminopentane and 3.64 g (28.2 mmol) of N,N- diisopropylethylamine in 50 ml of acetonitrile was added 4.73 g (14.1 mmol) of 5-ethoxycarbonyl-3-trichloroacetylimidazo[1,2-a]pyridine in 50 ml of acetonitrile. The mixture was heated for 45 minutes under reflux. After cooling, the resulting insolubles were filtered off. To the filtrate was added 6.04 g (16.9 mmol) of N-phenyltrifluoromethanesulfonimide. The mixture was stirred for one hour at room temperature. The solvent was distilled off. To the residue was added chloroform, and the mixture was washed with an aqueous solution of sodium hydrogencarbonate, dried over anhydrous magnesium sulfate. The solvent was distilled off, and the residue was purified by means of a column chromatography (eluent: ethyl acetate), followed by crystallization from ethyl acetate. The crystalline product was collected by filtration, washed with ether and dried to give 2.05 g of the desired compound (36.0%, colorless solid), m.p.166.0–167.0° C.

Elemental Analysis for $C_{15}H_{15}N_4O_4SF_3$:

Calcd.: C, 44.55; H, 3.74; N, 13.86. Found: C, 44.37; H, 3.79; N, 13.81.

NMR(200 MHz,CDCl$_3$-DMSO-d$_6$) δ: 1.47–1.83(6H,m), 3.20(2H,t,J=6.6 Hz), 4.17(2H,m), 7.84(1H,dd,J=8.4,7.6 Hz), 8.18(1H,d,J=7.6 Hz), 8.18(1H,d,J=8.4 Hz), 8.61(1H,s), 8.61(1H,br).

ii) Synthesis of 4,5-dihydro-4-[5-(trifluoromethanesulfonamido)pentan-1-yl]-3H-1,4,8b-triazaacenaphthylene-3,5-dione.hydrochloride To a suspension of 469 mg (1.16 mmol) of 4,5-dihydro-4-[5-(trifluoromethanesulfonamido)pentan-1-yl]-3H-1,4,8b-triazaacenathylene-3,5-dione in 20 ml of methanol was added 0.19 ml of conc. HCl, then the solvent was distilled off. To the residue was added acetone, and the resulting solid substance was washed with acetone and ether, which was dried to give 461 mg of the desired compound (90.2%, colorless solid), m.p.165.0–166.0° C.

Elemental Analysis for $C_{15}H_{15}N_4O_4SF_3$.HCl:

Calcd.: C, 40.87; H, 3.66; N, 12.71. Found: C, 40.67; H, 3.69; N, 12.61.

NMR(200 MHz,DMSO-d$_6$) δ: 1.26–1.74(6H,m), 3.14(2H,m), 4.01(2H,m), 7.92(1H,dd,J=8.8,7.2 Hz), 8.14(1H,d,J=7.2 Hz), 8.31(1H,d,J=8.8 Hz), 8.69(1H,s), 9.35(1H,br).

EXAMPLE 14

4,5-Dihydro-4-[2,2-dimethyl-3-(trifluoromethanesulfonamido)propan-1-yl]-3H-1,4,8b-triazaacenaphthylene-3,5-dione.hydrochloride i) Synthesis of 4,5-dihydro-4-[2,2-dimethyl-3-(trifluoromethanesulfonamido)propan-1-yl]-3H-1,4,8b-triazaacenaphthylene-3,5-dione To a solution of 0.51 g (5.0 mmol) of 1,3-diamino-2,2-dimethylpropane and 1.29 g (10.0 mmol) of N,N-diisopropylethylamine in 30 ml of acetonitrile was added a solution of 1.74 g (5.0 mmol) of 5-ethoxycarbonyl-3-trichloroacetylimidazo[1,2-a]pyridine in 15 ml of acetonitrile. The mixture was stirred for two hours. To the reaction mixture was added 2.68 g (7.50 mmol) of N-phenyltrifluoromethanesulfonimide. The mixture was stirred for one hour at room temperature. The solvent was distilled off. To the residue was added chloroform, which was washed with an aqueous solution of sodium hydrogencarbonate, dried over anhydrous magnesium sulfate. The solvent was distilled off. The residue was purified by a column chromatography (eluent: ethyl acetate) to give 1.70 g of the desired compound (84.5%, pale yellow solid).

NMR(200 MHz,CDCl$_3$) δ: 1.10(6H,s), 2.94(2H,d,J=6.0 Hz), 4.10(2H,s), 6.97(1H,br), 7.85(1H,dd,J=8.6,7.6 Hz), 8.22(1H,d,J=7.6 Hz), 8.23(1H,d,J=8.6 Hz), 8.69(1H,s).

ii) Synthesis of 4,5-dihydro-4-[2,2-dimethyl-3-(trifluoromethanesulfonamido)propan-1-yl]-3H,1,4,8b-triazaacenaphthylene-3,5-dione.hydrochloride To a suspension of 1.465 g (3.62 mmol) of 4,5-dihydro-4-[2,2-dimethyl-3-(trifluoromethanesulfonamido)propan-1-yl]-3H-1,4,8b-triazaacenaphthylene-3,5-dione in 25 ml of methanol was added 0.67 ml of conc. HCl, then the solvent was distilled off. To the residue was added acetone, and the resulting solid was washed with acetone and ether, dried to give 1.315 g of the desired compound (82.3%, colorless solid), m.p.196.0–198.0° C.

Elemental Analysis for $C_{15}H_{15}N_4O_4SF_3$.HCl:

Calcd.: C, 40.87; H, 3.66; N, 12.71. Found: C, 40.92; H, 3.73; N, 12.87.

NMR(200 MHz,DMSO-d$_6$) δ: 0.95(6H,s), 3.12(2H,d,J=5.6 Hz), 4.01(2H,s), 7.92(1H,dd,J=8.8,7.4 Hz), 8.14(1H,dd,J=7.4,1.0 Hz), 8.30(1H,dd,J=8.8,1.0 Hz), 8.70(1H,s), 9.26(1H,br).

EXAMPLE 15

4,5-Dihydro-2-methyl-4-[4-(trifluoromethanesulfonamido)butan-1-yl]-3H-1,4,8b-triazaacenaphthylene-3,5-dione.hydrochloride i) Synthesis of 4,5-dihydro-2-methyl-4-[4-(trifluoromethanesulfonamido)butan-1-yl]-3H-1,4,8b-triazaacenaphthylene-3,5-dione To a solution of 529 mg (6.00 mmol) of 1,4-diaminobutane and 1.55 g (12.0 mmol) of diisopropylethylamine in 20 ml of acetonitrile was added a solution of 2.10 g (60.0 mmol) of 5-ethoxycarbonyl-2-methyl-trichloroacetylimidazo[1,2-a]pyridine in 10 ml of acetonitrile. The mixture was heated for one hour under reflux. After cooling, to which was added 2.58 g (7.22 mmol) of N-phenyltrifluoromethanesulfonimide. The mixture was then stirred for two hours at room temperature. Insolubles were filtered off, and the filtrate was concentrated. To the concentrate was added chloroform, and the mixture was washed with an aqueous solution of sodium hydrogencarbonate, followed by drying over anhydrous magnesium sulfate. The solvent was distilled off, and the residue was purified by column chromatography (eluent: ethyl acetate), treated with ether to give 1.04 g of the desired compound (42.8%, colorless solid), m.p.183.0–184.0° C.

Elemental Analysis for $C_{15}H_{15}N_4O_4SF_3$:

Calcd.: C, 44.55; H, 3.74; N, 13.86. Found: C, 44.45; H, 3.79; N, 13.86.

NMR(200 MHz,CDCl$_3$-DMSO-d$_6$) δ: 1.60–1.90(4H,m), 2.88(3H,s), 3.26(2H,m), 4.18(2H,t,J=7.0), 7.77(1H,dd,J=9.0, 7.4 Hz), 8.03(1H,dd,J=9.0, 1.0 Hz), 8.09(1H,J=7.4, 1.0 Hz), 8.56(1H,br).

ii) Synthesis of 4,5-dihydro-2-methyl-4-[4-(trifluoromethanesulfonamido)butan-1-yl]-3H-1,4,8b-triazaacenaphthylene-3,5-dione.hydrochloride To a suspension of 816 mg (2.02 mmol) of 4,5-dihydro-2-methyl-4-[4-(trifluoromethanesulfonamido)butan-1-yl]-3H-1,4,8b-triazaacenaphthylene-3,5-dione in 10 ml of methanol was added 0.34 ml of conc. HCl, and the solvent was distilled off. To the residue was added acetone, and the resulting solid was washed with acetone, dried to give 790 mg of the desired compound (88.8%, colorless solid), m.p.181.0–182.0° C.

Elemental Analysis for $C_{15}H_{15}N_4O_4SF_3 \cdot HCl$:

Calcd.: C, 40.87; H, 3.66; N, 12.71. Found: C, 40.93; H, 3.66; N, 12.88.

NMR(200 MHz,DMSO-$d_6$) δ: 1.46–1.80(4H,m), 2.76 (3H,s), 3.19(2H,m), 4.03(2H,t,J=7.0 Hz), 7.90(1H,dd,J=8.8, 7.4 Hz), 8.08(1H,dd,J=7.4,1.0 Hz), 8.18(1H,dd,J=8.8,1.0 Hz), 9.36(1H,br).

EXAMPLE 16

4,5-Dihydro-4-[4-(tert-butoxycarbonylamino)butan-1-yl]-3H-1,4,8b-triazaacenaphthylene-3,5-dione To a solution of 4.07 g (54.9 mmol) of 1,3-diaminopropane and 5.32 g (41.2 mmol) of N,N-diisopropylethylamine in 70 ml of acetonitrile was added a solution of 9.21 g (27.4 mmol) of 5-ethoxycarbonyl-3-trichloroacetylimidazo[1,2-a]pyridine in 70 ml of acetonitrile. The mixture was heated for 0.5 hour under reflux. After cooling, to which was added 23.96 g (110 mmol) of di-tert-butyl dicarbonate, stirred for one hour at room temperature. The solvent was distilled off. To the residue was added chloroform. The mixture was washed with water, then dried over anhydrous magnesium sulfate. The solvent was distilled off, and the residue was purified by a column chromatography (eluent: ethyl acetate), treated with ethyl acetate and n-hexane to give 7.66 g of the desired compound (81.1%, pale yellow solid), m.p.150.0–151.0° C.

Elemental Analysis for $C_{17}H_{20}N_4O_4$:

Calcd.: C, 59.29; H, 5.85; N, 16.27. Found: C, 59.20; H, 5.97; N, 16.32.

NMR(200 MHz,CDCl$_3$) δ: 1.44(9H,s), 1.93(2H,m), 3.17 (2H,m), 4.26(2H,t,J=6.6 Hz), 5.14(1H,br), 7.80(1H,dd,J=8.0,6.8 Hz), 8.17(1H,d,J=8.0 Hz), 8.17(1H,d,J=6.8 Hz), 8.65 (1H,s).

EXAMPLE 17

4,5-Dihydro-4-[4-(tert-butoxycarbonylamino)butan-1-yl]-3H-1,4,8b-triazaacenaphthylene-3,5-dione To a solution of 13.56 g (153.8 mmol) of 1,4-diaminobutane and 15.00 g (116.1 mmol) of N,N-diisopropylethylamine was added a solution of 25.96 g (76.9 mmol) of 5-ethoxycarbonyl-3-trichloroacetylimidazo [1,2-a]pyridine in 150 ml of acetonitrile. The mixture was heated for 0.5 hour under reflux. After cooling, the resulting insolubles were filtered off. To the filtrate was added 67.54 g (309.5 mmol) of di-tert-butyl dicarbonate. The mixture was stirred for 0.5 hour at room temperature. The solvent was distilled off. To the residue was added chloroform, and the mixture was washed with water, dried over anhydrous magnesium sulfate. The solvent was distilled off, and the residue was purified by column chromatography (eluent: ethyl acetate), followed by crystallization from ethyl acetate and n-hexane. The crystalline product was collected by filtration, washed with n-hexane and dried to give 21.72 g of the object product (78.3%, colorless solid), m.p.118.0–119 0° C.

Elemental Analysis for $C_{18}H_{22}N_4O_4$:

Calcd.: C, 60.32; H, 6.19; N, 15.63. Found: C, 60.50; H, 6.16; N, 15.68.

NMR(200 MHz,CDCl$_3$) δ: 1.43(9H,s), 1.50–1.85(4H,m), 3.19(2H,m), 4.20(2H,t,J=7.2 Hz), 4.63(1H,br), 7.80(1H,dd, J=8.0,6.8 Hz), 8.17(1H,d,J=6.8 Hz), 8.17(1H,d,J=8.0 Hz), 8.65(1H,s).

EXAMPLE 18

4,5-Dihydro-4-[5-(tert-butoxycarbonylamino)pentan-1-yl]-3H-1,4,8b-triazaacenaphthylene-3,5-dione To a solution of 5.11 g (50.0 mmol) of 1,5-diaminopentane and 4.85 g (37.5 mmol) of N,N-diisopropylethylamine in 70 ml of acetonitrile was added a solution of 8.39 g (25.0 mmol) of 5-ethoxycarbonyl-3-trichloroacetylimidazo[1,2-a]pyridine in 70 ml of acetonitrile. The mixture was heated for 0.5 hour under reflux. After cooling, the insolubles were filtered off. To the filtrate was added 21.83 g (100 mmol) of di-tert-butyl dicarbonate, and the mixture was stirred for one hour at room temperature. The solvent was distilled off. To the residue was added chloroform. The mixture was washed with water and dried over anhydrous magnesium sulfate. The solvent was distilled off, and the residue was purified by column chromatography to give 7.06 g of the desired compound (75.8%, pale brown solid), m.p.82.0–83.0° C.

Elemental Analysis for $C_{19}H_{24}N_4O_4$:

Calcd.: C, 61.28; H, 6.50; N, 15.04. Found: C, 60.96; H, 6.41; N, 15.06.

NMR(200 MHz,CDCl$_3$) δ: 1.43(9H,s), 1.32–1.65(4H,m), 1.75(2H,m), 3.13(2H,m), 4.18(2H,m), 4.60(1H,br), 7.79 (1H,dd,J=8.8,7.2 Hz), 8.16(1H,d,J=8.8 Hz), 8.16(1H,d,J=7.2 Hz), 8.64(1H,s).

EXAMPLE 19

4,5-Dihydro-4-[4-[(2,2,2-trifluoro)ethanesulfonamido]butane-1-yl]-3H-1,4,8b-triazaacenaphthylene-3,5-dione.hydrochloride i) Synthesis of 4,5-dihydro-4-[4-(amino)butan-1-yl]-3H-1,4,8b-triazaacenaphthylene-3,5-dione.dihydrochloride To a solution of 3.58 g (10.0 mmol) of 4,5-dihydro-4-[4-(tert-butoxycarbonylamino)butan-1-yl]-3H-1,4,8b-triazaacenaphthylene-3,5-dione in 30 ml of methanol was added 15 ml of conc. HCl. The mixture was stirred for one hour at room temperature. The solvent was distilled off. To the residue were added ethanol and ether. The resulting precipitate was collected by filtration and dried to give 3.28 g of the desired compound (99.1%, white solid), m.p.250.0–252.0° C.

Elemental Analysis for $C_{13}H_{14}N_4O_2 \cdot 2HCl \cdot 0.3H_2O$

Calcd.: C, 46.39; H, 4.97; N, 16.64. Found: C, 46.37; H, 5.02; N, 16.51.

NMR(200 MHz,D$_2$O) δ: 1.75(4H,m), 3.04(2H,m), 4.15 (2H,m), 8.22(1H,dd,J=9.0,7.4 Hz), 8.36(1H,d,J=9.0 Hz), 8.41(1H,d,J=7.4 Hz), 8.85(1H,s).

ii) Synthesis of 4,5-dihydro-4-[4-[(2,2,2-trifluoro]ethanesulfonamido]butan-1-yl]-3H-1,4,8b-triazaacenaphthylene-3,5-dione To a suspension of 994 mg (3.0 mmol) of 4,5-dihydro-4-[4-(amino)butan-1-yl]-3H-1,4,8b-triazaacenaphthylene-3,5-dione.dihydrochloride in 50 ml of methylene chloride was added, while stirring under ice-cooling, 1.47 ml (10.5 mmol)

of triethylamine. The mixture was stirred for 5 minutes, to which was added dropwise 0.66 g (3.6 mmol) of 2,2,2-trifluoroethanesulfonyl chloride. The reaction mixture was cooled with ice for one hour, which was stirred for 19 hours at room temperature. The reaction mixture was washed with an aqueous solution of sodium hydrogencarbonate, which was dried over anhydrous magnesium sulfate. The solvent was distilled off, and the residue was purified by column chromatography (eluent: ethyl acetate), followed by washing with ether and dried to give 470 mg of the desired compound (38.7%, colorless solid), m.p.154.0–155.0° C.

NMR(200 MHz,CDCl$_3$-DMSO-d$_6$) δ: 1.58–1.90(4H,m), 3.17(2H,m), 3.84(2H,q,J=9.2 Hz), 4.19(2H,t,J=7.0 Hz), 7.45 (1H,br), 7.83(1H,dd,J=8.6,7.6 Hz), 8.17(1H,d,J=7.6 Hz), 8.18(1H,d,J=8.6 Hz), 8.61(1H,s).

iii) Synthesis of 4,5-dihydro-4-[4-[(2,2,2-trifluoro) ethanesulfonamido]butan-1-yl]-3H-1,4,8b-triazaacenaphthylene-3,5-dione hydrochloride To a suspension of 440 mg (1.09 mmol) of 4,5-dihydro-4-[4-[(2,2,2-trifluoro)ethanesulfonamido]butan-1-yl]-3H-1,4,8b-triazaacenaphthylene-3,5-dione in 20 ml of methanol was added 0.15 ml of conc. HCl, and the solvent was distilled off. To the residue was added acetone, and the resulting solid product was collected by filtration, followed by washing with acetone and drying to give 435 mg of the desired compound (90.6%, colorless solid), m.p.154.0–155.0° C.

Elemental Analysis for $C_{15}H_{15}N_4O_4SF_3 \cdot HCl \cdot 0.5H_2O$

Calcd.: C, 40.05; H, 3.81; N, 12.45. Found: C, 40.17; H, 3.62; N, 12.47.

NMR(200 MHz,DMSO-d$_6$) δ: 1.43–1.78(4H,m), 3.03 (2H,m), 4.03(2H,m), 4.35(2H,q,J=9.8 Hz), 7.74(1H,br), 7.96(1H,dd,J=8.8,7.4 Hz), 8.15(1H,d,J=7.4 Hz), 8.31(1H,d, J=8.8 Hz), 8.71(1H,s).

EXAMPLE 20

4-[4-[2-(trifluoromethanesulfonamido)ethan-1-yl] phenyl]-4,5-dihydro-3H-1,4,8b-triazaacenaphthylene-3,5-dione.hydrochloride i) Synthesis of 4-[4-[2-(trifluoromethanesulfonamido)-ethan-1-yl]phenyl]-4,5-dihydro-3H-1,4,8b-triazaace-naphthylene-3,5-dione To a solution of 1.18 g (4.4 mmol) of 4-[2-(trifluoromethanesulfonamido)ethan-1-yl]aniline and 0.68 g (5.3 mmol) of N,N-diisopropylethylamine in 20 ml of acetonitrile was added a solution of 1.53 g (4.4 mmol) of 5-ethoxycarbonyl-3-trichloroacetylimidazo[1,2-a]pyridine. The mixture was heated for 38 hours under reflux. After cooling, and the solvent was distilled off. To the residue was added chloroform. The mixture was washed with water and dried over anhydrous magnesium sulfate. The solvent was distilled off. The residue was purified by column chromatography (eluent: ethyl acetate) to give 130 mg of the desired compound (6.8%, brown solid).

NMR(200 MHz,CDCl$_3$) δ: 2.98(2H,t,J=6.6 Hz), 3.62(2H, t,J=6.6 Hz), 6.15(1H,br), 7.25(2H,m), 7.42(2H,m), 7.83(1H, dd,J=8.8,7.6 Hz), 8.20(1H,dd,J=7.6,1.0 Hz), 8.21(1H,dd,J= 8.8,1.0 Hz), 8.58(1H,s).

ii) Synthesis of 4-[4-[2-(trifluoromethanesulfonamido)ethan-1-yl]phenyl-4,5-dihydro-3H-1,4,8b-triazaacenaphthylene-3,5-dione.hydrochloride To a suspension of 130 mg (0.30 mmol) of 4-[4-[2-(trifluoromethanesulfonamido)ethan-1-yl]phenyl]-4,5-dihydro-3H-1,4,8b-triazacenaphthylene-3,5-dione in 10 ml of methanol was added 0.1 ml of conc. HCl. The solvent was then distilled off. To the residue was added acetone. The resulting solid matter was collected by filtration, washed with acetone and dried to give 82 mg of the desired compound (58.2%, pale brown solid).

NMR(200 MHz,DMSO-d$_6$) δ: 2.93(2H,t,J=7.2 Hz), 3.48 (2H,m), 7.29(2H,d,J=8.4 Hz), 7.42(2H,d,J=8.4 Hz), 7.95 (1H,dd,J=8.8,7.4 Hz), 8.14(1H,d,J=7.4 Hz), 8.34(1H,d,J= 8.8 Hz), 8.73(1H,s), 9.63(1H,br).

EXAMPLE 21

4,5-Dihydro-4[5-(tert-butoxycarbonylamino)pentan-1-yl]-3H-1,4,8b-triazaacenaphthylen-5-one A solution of 7.78 g (20 mmol) of 3-[(trimethylammonio) methyl]-5-ethoxycarbonylimidazo[1,2-a]pyridine iodide, 6.07 g (30 mmol) of 5-tert-butoxycarbonylamino-1-pentylamine and 5.58 ml (40 mmol) of triethylamine was heated for 64 hours under reflux. The solvent was distilled off. To the residue was added methylene chloride, washed with water, and dried over anhydrous magnesium sulfate. The solvent was distilled off, and the residue was purified by column chromatography (eluent: ethyl acetate/ethanol= 10:1) to afford 3.93 g of the desired compound (54.9%, a pale yellow solid).

NMR(200 MHz,CDCl$_3$) δ: 1.42(9H,s), 1.27–1.85(6H,m), 3.13(2H,m), 3.61(2H,t,J=7.2 Hz), 4.64(1H,br), 5.11(2H,s), 7.21(1H,dd,J=9.0, 7.0 Hz), 7.43(1H,s), 7.53(1H,dd,J=7.0, 1.0 Hz), 7.61(1H,dd,J=9.0, 7.0 Hz).

EXAMPLE 22

4,5-Dihydro-4[5-(trifluoromethanesulfonamido) pentan-1-yl]-3H-1,4,8b-triazaacenaphthylen-5-one i) Synthesis of 4,5-dihydro-4[5-(amino)pentan-1-yl]-3H-1,4,8b-triazaacenaphthylen-5-one.dihydrochloride To a solution of 2.24 g (6.25 mmol) of 4,5-dihydro-4[5-(tert-butoxycarbonylamino)pentan-1-yl]-3H-1,4,8b-triazaacenaphthylen-5-one in 20 ml of ethanol was added 20 ml of conc. HCl. The mixture was stirred for 1.5 hour at room temperature. The solvent was distilled off to leave 2.05 g of the desired compound (quant. a pale brown solid). This product was used in the subsequent reaction without further purification.

NMR(200 MHz,D$_2$O) δ: 1.28–1.90(6H,m), 2.94(2H,t,J= 7.2 Hz), 3.60(2H,t,J=7.2 Hz), 5.16(2H,s), 7.75(1H,s), 7.82–7.95(3H,m).

ii) 4,5-Dihydro-4[5-(trifluoromethanesulfonamido) pentan-1-yl]-3H-1,4,8b-triazaacenaphthylen-5-one To a suspension of 2.05 g (6.19 mmol) of 4,5-dihydro-4 [5-(amino)pentan-1-yl]-3H-1,4,8b-triazaacenaphthylen-5-one.dihydrochloride and 4.31 ml (30.9 mmol) of triethylamine in 10 ml of methylene chloride-N,N-dimethylformamide was added 4.42 g (12.4 mmol) of N-phenyltrifluoromethanesulfonimide. The mixture was stirred for 4 hour at room temperature. The reaction mixture was washed with water, and dried over anhydrous magnesium sulfate. The solvent was distilled off, and the residue was purified by column chromatography (eluent: ethyl acetate/ethanol=10:1), followed by recrystallization from ethyl acetate to afford 964 mg of the desired compound (39.9%, a pale yellow crystals).

NMR(200 MHz,DMSO-D$_6$): 1.38(2H,m), 1.45–1.75(4H, m), 3.15(2H,t,J=6.8 Hz), 3.51(2H,t,J=6.8 Hz), 5.13(2H,s), 7.26(1H,dd,J=9.0, 7.0 Hz), 7.39(1H,dd,J=7.0, 1.0 Hz), 7.47(1H,s), 7.66(1H,dd,J=9.0, 1.0 Hz), 9.33(1H,br).

EXAMPLE 23

4,5-Dihydro-4[4-(trifluoromethanesulfonamido)butan-1-yl]-3H-1,4,8b-triazaacenaphthylen-5-one A solution of 778 mg (2.0 mmol) of 5-ethoxycarbonylimidazo[1,2-a]pyridin-8-ylmethyl trimethylammonium iodide, 616 mg (2.4 mmol) of 4-trifluoromethanesulfonamido-1-butylamine and 1.12 ml (8.0 mmol) of triethylamine in 40 ml of acetonitrile was heated for 14 hours under reflux. The solvent was distilled off. To the residue was added chloroform, and washed with water. The aqueous layer was further extracted with chloroform. The chloroform layers were combined, and dried over anhydrous magnesium sulfate. The solvent was distilled off. The residue was crystallized from chloroform. The crystalline product was collected by filtration, washed with chloroform and dried to afford 141 mg (18.8%, colorless crystals) of the desired compound.

Elemental Analysis Calcd for C$_{14}$H$_{15}$N$_4$O$_3$SF$_3$:

Calcd.: C, 44.68; H, 4.02; N, 14.89. Found: C, 44.93; H, 3.89; N, 15.13.

NMR(200 MHz,CDCl$_3$-DMSO-d$_6$) δ: 1.58–1.90(4H,m), 3.27(2H,m), 3.64(2H,m), 5.15(2H,s), 7.22(1H,dd,J=9.0,7.0 Hz), 7.46(1H,s), 7.51(1H,dd,J=7.0, 1.0 Hz), 7.62(1H,dd,J=9.0, 1.0 Hz).

EXAMPLE 24

1,2-Dihydro-3-methyl-1-[3-(trifluoromethanesulfonamido)propan-1-yl]-1,4,7b-triazacyclopento[cd]inden-2-one.hydrochloride i) Synthesis of 1,2-dihydro-3-methyl-1-[3-(trifluoromethanesulfonamido)propan-1-yl]-1,4,7b-triazacyclopent[cd]inden-2-one To a solution of 1.16 g (5.04 mmol) of 1-[3-(amino)propan-1-yl]-1,2-dihydro-3-methyl-1,4,7b-triazacyclopento[cd]inden-2-one and 1.05 ml (7.53 mmol) of triethylamine in 60 ml of methylene chloride was added, while stirring under ice-cooling, 1.71 g (6.06 mmol) of trifluoromethane sulfonic acid anhydride. The mixture was stirred for 30 minutes at the same temperature. The reaction mixture was washed with an aqueous solution of sodium hydrogencarbonate, dried over anhydrous magnesium sulfate. The solvent was distilled off, and the residue was purified by means of a column chromatography (eluent: ethyl acetate) to give 1.15 g of the desired compound (63.0%, pale brown solid), m.p.168.0–169° C.

NMR(200 MHz,CDCl$_3$) δ: 2.08(2H,m), 2.85(3H,s), 3.33(2H,m), 4.26(2H,m), 6.88(1H,d,J=7.4 Hz), 6.97(1H,br), 7.58(1H,d,J=8.6 Hz), 7.78(1H,dd,J=8.6,7.4 Hz).

ii) Synthesis of 1,2-dihydro-3-methyl-1-[3-(trifluoromethanesulfonamido)propan-1-yl]-1,4,7b-triazacyclopent[cd]inden-2-one.hydrochloride To a suspension of 866 mg (2.39 mmol) of 1,2-dihydro-3-methyl-1-[3-(trifluoromethanesulfonamido)propan-1-yl]-1,4,7b-triazacyclopent[cd]inden-2-one in 20 ml of methanol was added 0.24 ml of conc. HCl. The solvent was then distilled off. To the residue were added ethanol, acetone and ether. The resulting solid was washed with ether and, then dried to give 844 mg of the desired compound (88.6%, pale yellow solid), m.p.145.0–146° C.

Elemental Analysis for C$_{13}$H$_{13}$N$_4$O$_3$SF$_3$.HCl:

Calcd.: C, 39.15; H, 3.54; N, 14.05. Found: C, 39.13; H, 3.47; N, 14.05.

NMR(200 MHz,DMSO-d$_6$) δ: 2.02(2H,m), 2.78(3H,s), 3.30(2H,m), 4.14(2H,t,J=7.0 Hz), 7.52(1H,d,J=7.8 Hz), 7.74(1H,d,J=8.6 Hz), 8.12(1H,dd,J=8.6,7.8 Hz), 9.55(1H,br).

EXAMPLE 25

1,2-Dihydro-3-methyl-1-[3-[(2,2,2-trifluoro)ethanesulfonamido]propan-1-yl]-1,4,7b-triazacyclopent[cd]inden-2-one.hydrochloride i) Synthesis of 1,2-dihydro-3-methyl-1-[3-[(2,2,2-trifluoro)ethanesulfonamido]propan-1-yl]-1,4,7b-triazacyclopent[cd]inden-2-one To a solution of 0.43 g (1.87 mmol) of 1-[3-(amino)propan-1-yl]-1,2-dihydro-3-methyl-1,4,7b-triazacyclopent[cd]inden-2-one and 0.39 ml (2.80 mmol) of triethylamine in 30 ml of methylene chloride was added, while stirring under ice-cooling, 0.41 g (2.26 mmol) of 2,2,2-trifluoroethanesulfonyl chloride. The mixture was stirred for 30 minutes at the same temperature. The reaction mixture was washed with an aqueous solution of sodium hydrogencarbonate, which was then dried over anhydrous magnesium sulfate. The solvent was distilled off, and the residue was purified by column chromatography (eluent: ethyl acetate) to give 412 mg of the desired compound (58.6%, white powdery).

NMR(200 MHz,CDCl$_3$) δ: 2.09(2H,m), 2.84(3H,s), 3.25(2H,m), 3.85(2H,q,J=9.0 Hz), 4.25(2H,m), 6.28(1H,brt,J=6.0 Hz), 6.88(1H,d,J=7.4 Hz), 7.56(1H,d,J=8.6 Hz), 7.77(1H,dd,J=8.6,7.4 Hz).

ii) Synthesis of 1,2-dihydro-3-methyl-1-[3-[(2,2,2-trifluoro)ethanesulfonamido]propan-1-yl]-1,4,7b-triazacyclopento[cd]inden-2-one.hydrochloride To a solution of 405 mg (1.08 mmol) of 1,2-dihydro-3-methyl-1-[3-[(2,2,2-trifluoro)ethanesulfonamido]propan-1-yl]-1,4,7b-triazacyclopent[cd]inden-2-one in 10 ml of methanol was added 0.11 ml of conc. HCl, then the solvent was distilled off. To the residue were added ethanol, acetone and ether. The resulting solid was washed with ether and dried to give 436 mg of the desired compound (98.2%, white solid), m.p.157.0–158.0° C.

Elemental Analysis for C$_{14}$H$_{15}$N$_4$O$_3$SF$_3$.HCl:

Calcd.: C, 40.73; H, 3.91; N, 13.57. Found: C, 40.85; H, 3.97; N, 13.38.

NMR(200 MHz,DMSO-d$_6$) δ: 199(2H,m), 2.79(3H,s), 3.14(2H,m), 4.12(t,J=7.0 Hz), 4.41(2H,q,J=10.0 Hz), 7.55(1H,d,J=7.6 Hz), 7.76(1H,d,J=8.6 Hz), 7.92(1H,br), 8.15(1H,dd,J=8.6,7.6 Hz).

EXAMPLE 26

1,2-Dihydro-3-methyl-1-[5-(trifluoromethanesulfonamido)pentan-1-yl]-1,4,7b-triazacyclopent[cd]inden-2-one.hydrochloride i) Synthesis of 1,2-dihydro-3-methyl-1-[5-(trifluoromethanesulfonamido)pentan-1-yl]-1,4,7b-triazacyclopent[cd]inden-2-one To a solution of 1.512 g (5.85 mmol) of 1-[5-(amino)pentan]-1,2-dihydro-3-methyl-1,4,7b-triazacyclopent[cd]

inden-2-one and 1.23 ml (8.82 mmol) of triethylamine in 35 ml of methylene chloride was added, while stirring at room temperature, 2.51 g (7.03 mmol) of N-phenyltrifluoromethanesulfonimide. The mixture was stirred for 14 hours at the same temperature. The reaction mixture was washed with water, dried over anhydrous magnesium sulfate. The solvent was distilled off, and the residue was purified by column chromatography (eluent: ethyl acetate) to give 1.236 g of the desired compound (54.1%, pale yellow solid substance).

Elemental Analysis for $C_{15}H_{17}N_4O_3SF_3$:

Calcd.: C, 46.15; H, 4.39; N, 14.35. Found: C, 46.29; H, 4.38; N, 14.41.

NMR(200 MHz,CDCl$_3$) δ: 1.50(2H,m), 1.74(2H,m), 1.90 (2H,m), 2.77(3H,s), 3.33(2H,t,J=6.4 Hz), 4.10(2H,t,J=6.6 Hz), 6.82(1H,d,J=7.6 Hz), 7.45(1H,d,J=8.6 Hz), 7.71(1H, dd,J=8.6,7.6 Hz)

ii) Synthesis of 1,2-dihydro-3-methyl-1-[5-(trifluoromethanesulfonamido)pentan-1-yl]-1,4,7b-triazacyclopento[cd]inden-2-one.hydrochloride To a suspension of 1.195 g (3.06 mmol) of 1,2-dihydro-3-methyl-1-[5-(trifluoromethanesulfonamido)pentan-1-yl]-1,4,7b-triazacyclopent[cd]inden-2-one in 15 ml of methanol was added 0.31 ml of conc. HCl, the solvent was distilled off. To the residue was added acetone and ether. And the resulting solid was washed with ether, dried to give 1.190 g of the desired compound (91.0%, white solid), m.p.149.0–150.0° C.

Elemental Analysis for $C_{15}H_{17}N_4O_3SF_3.HCl$:

Calcd.: C, 42.21; H, 4.25; N, 13.13. Found: C, 42.03; H, 4.14; N, 13.22.

NMR(200 MHz,DMSO-d$_6$) δ: 1.37(2H,m), 1.55(2H,m), 1.78(2H,m), 2.78(3H,s), 3.11(2H,m), 4.07(2H,t,J=7.0 Hz), 7.52(1H,d,J=7.8 Hz), 7.74(1H,d,J=8.6 Hz), 8.11(1H,dd,J=8.6,7.8 Hz), 9.33(1H,br).

EXAMPLE 27

1,2-Dihydro-3-methyl-1-[5-[(2,2,2-trifluoro)ethanesulfonamido]pentan-1-yl]-1,4,7b-triazacyclopent[cd]inden-2-one.hydrochloride i) Synthesis of 1,2-dihydro-3-methyl-1-[5-[(2,2,2-trifluoro)ethanesulfonamido]pentan-1-yl]-1,4,7b-triazacyclopent[cd]inden-2-one To a solution of 1.630 g (6.31 mmol) of 1-[5-(amino)pentyl]-1,2-dihydro-3-methyl-1,4,7b-triazacyclopent[cd]inden-2-one and 1.32 ml (9.47 mmol) of triethylamine in 30 ml of methylene chloride was added, while stirring under ice-cooling, 1.38 g (7.56 mmol) of 2,2,2-trifluoroethanesulfonylchloride. The mixture was stirred for 30 minutes at the same temperature. The reaction mixture was washed with an aqueous solution of sodium hydrogencarbonate, which was then dried over anhydrous magnesium sulfate. The solvent was distilled off, and the residue was purified by column chromatography (eluent: ethyl acetate) to give 1.669 g of the desired compound (65.4%, pale brown solid substance).

NMR(200 MHz,CDCl$_3$) δ: 1.49(2H,m), 1.70(3H,s), 1.88 (2H,m), 2.80(3H,s), 3.19(2H,m), 3.80(2H,q,J=9.0 Hz), 4.07 (2H,t,J=6.4 Hz), 5.87(1H,br t, J=6.0 Hz), 6.82(1H,d,J=7.6 Hz), 7.47(1H,d,J=8.6 Hz), 7.71(1H,dd,J=8.6,7.6 Hz).

ii) Synthesis of 1,2-dihydro-3-methyl-1-[5-[(2,2,2-trifluoro)ethanesulfonamido]pentan-1-yl]-1,4,7b-triazacyclopent[cd]inden-2-one.hydrochloride To a solution of 1.485 g (3.67 mmol) of 1,2-dihydro-3-methyl-1-[5-[(2,2,2-trifluoro)ethanesulfonamido]pentan-1-yl]-1,4,7b-triazacyclopento[cd]inden-2-one in 30 ml of methanol was added 0.37 ml of conc. HCl, was the solvent was distilled off. To the residue was added ethanol, acetone and ether, and, the resulting crystals were washed with ether, followed by drying to give 1.632 g of the desired compound (quantitative, colorless crystals), m.p.143.0–145.0° C.

Elemental Analysis for $C_{16}H_{19}N_4O_3SF_3.HCl.H_2O$:

Calcd.: C, 41.88; H, 4.83; N, 12.21. Found: C, 41.73; H, 4.79; N, 12.18.

NMR(200 MHz,DMSO-d$_6$) δ: 1.25–1.60(4H,m), 1.77 (2H,m), 2.77(3H,s), 2.96(2H,m), 4.07(2H,t,J=6.8 Hz), 4.33 (2H,q,J=10.0 Hz), 7.49(1H,d,J=7.4 Hz), 7.72(1H,br), 7.73 (1H,d), J=8.8 Hz), 8.08(1H,dd,J=8.8, 7.4 Hz).

EXAMPLE 28

1,2-Dihydro-3-methyl-1-[6-(trifluoromethanesulfonamido)hexan-1-yl]-1,4,7b-triazacyclopent[cd]inden-2-one.hydrochloride i) Synthesis of 1,2-dihydro-3-methyl-1-[6-(trifluoromethanesulfonamido)hexane-1-yl]-1,4,7b-triazacyclopent[cd]inden-2-one To a solution of 770 mg (2.83 mmol) of 1-[6-(amino)hexane-1-yl]-1,2-dihydro-3-methyl-1,4,7b-triazacyclopent[cd]inden-2-one and 0.59 ml (4.23 mmol) of triethylamine in 25 ml of methylene chloride was added, while stirring at room temperature, 1.21 g (3.39 mmol) of N-phenyltrifluoromethanesulfonimide. The mixture was stirred for 14 hours at the same temperature. The reaction mixture was washed with water, dried over anhydrous magnesium sulfate. The solvent was distilled off, and the residue was purified by column chromatography (eluent: ethyl acetate) to give 633 mg of the desired compound (55.4%, pale yellow solid).

NMR(200 MHz,CDCl$_3$) δ: 1.31–1.73(6H,m), 1.87(2H, m), 2.81(3H,s), 3.31(2H,t,J=6.4 Hz), 4.09(2H,t,J=7.2 Hz), 6.82(1H,d,J=7.6 Hz), 7.50(1H,d,J=8.6 Hz), 7.73(1H,dd,J=8.6,7.6 Hz).

ii) Synthesis of 1,2-dihydro-3-methyl-1-[6-(trifluoromethanesulfonamido)hexan-1-yl]-1,4,7b-triazacyclopent[cd]inden-2-one.hydrochloride To a suspension of 623 mg (1.54 mmol) of 1,2-dihydro-3-methyl-1-[6-(trifluoromethanesulfonamido)hexan-1-yl]-1,4,7b-triazacyclopent[cd]inden-2-one in 10 ml of methanol was added 0.16 ml of conc. HCl and, then, the solvent was distilled off. To the residue were added acetone and ether. The resulting solid was washed with ether, dried to give 570 mg of the desired compound (83.9%, pale yellow solid).

NMR(200 MHz,DMSO-d$_6$) δ: 1.25–1.56(6H,m), 1.75 (2H,m), 2.75(3H,s), 3.11(2H,m), 7.46(1H,d,J=7.8 Hz), 7.70 (1H,d,J=8.6 Hz), 8.05(1H,dd,J=8.6,7.8 Hz), 9.31(1H,br).

EXAMPLE 29

1,2-Dihydro-3-methyl-1-[6-[(2,2,2-trifluoro)ethanesulfonamido]hexan-1-yl]-1,4,7b-triazacyclopent[cd]inden-2-one.hydrochloride i) Synthesis of 1,2-dihydro-3-methyl-1-[6-[(2,2,2-trifluoro)ethanesulfonamido]hexan-1-yl]-1,4,7b-triazacyclopent[cd]inden-2-one To a solution of 676 mg (2.48 mmol) of 1-[6-(amino)hexyl]-1,2-dihydro-3-methyl-1,4,7b-triazacyclopent[cd]

inden-2-one and 0.52 ml (3.73 mmol) of triethylamine in 30 ml of methylene chloride was added, while stirring under ice-cooling, 0.55 g (3.01 mmol) of 2,2,2-trifluoroethanesulfonylchloride, and the mixture was stirred for 30 minutes at the same temperature range. The reaction mixture was washed with an aqueous solution of sodium hydrogencarbonate, dried over anhydrous magnesium sulfate. The solvent was distilled off, and the residue was purified by column chromatography (eluent: ethyl acetate) to give 802 mg of the desired compound (77.2%, pale brown solid).

NMR(200 MHz,CDCl$_3$) δ: 1.30–1.68(6H,m), 1.86(2H, m), 2.82(3H,s), 3.18(2H,m), 3.81(2H,q,J=9.0 Hz), 4.07(2H, t,J=6.8 Hz), 5.48(1H,br t,J=6.0 Hz), 6.81(1H,d,J=7.4 Hz), 7.50(1H,d,J=8.6 Hz), 7.71(1H,dd,J=8.6,7.6 Hz).

ii) Synthesis of 1,2-dihydro-3-methyl-1-[6-[(2,2,2-trifluoro)ethanesulfonamido]hexan-1-yl]-1,4,7b-triazacyclopent[cd]inden-2-one.hydrochloride To a solution of 702 mg (1.68 mmol) of 1,2-dihydro-3-methyl-1-[6-[(2,2,2-trifluoro)ethanesulfonamido]hexan-1-yl]-1,4,7b-triazacyclopent[cd]inden-2-one in 15 ml of methanol was added 0.17 ml of conc. HCl, then the solvent was distilled off. To the residue were added acetone and ether. The resulting crystals were washed with ether and dried to give 718 mg of the desired compound (94.1%, colorless crystals), m.p.141.0–143.0° C.

Elemental Analysis for C$_{17}$H$_{21}$N$_4$O$_3$SF$_3$.HCl:

Calcd.: C, 44.89; H, 4.87; N, 12.32. Found: C, 44.79; H, 4,83; N, 12.41.

NMR(200 MHz,DMSO-d$_6$) δ: 1.22–1.50(6H,m), 1.76 (2H,m), 2.78(3H,s), 2.96(2H,m), 4.07(2H,t,J=7.0 Hz), 4.33 (2H,q,J=10.0 Hz), 7.53(1H,d,J=7.8 Hz), 7.71(1H,br), 7.75 (1H,d,J=8.6 Hz), 8.12(1H,dd,J=8.6,7.8 Hz).

EXAMPLE 30

1,2-Dihydro-3-methyl-1-[4-(trifluoromethanesulfonamido)butan-1-yl]-1,4,7b-triazacyclopent[cd]inden-2-one.hydrochloride To a solution of 7.05 g (28.9 mmol) of 1-[4-(amino)butan-1-yl]-1,2-dihydro-3-methyl-1,4,7b-triazacyclopent[cd] inden-2-one and 8.04 ml (57.7 mmol) of triethylamine in 300 ml of methylene chloride was added, while stirring at room temperature, 20.62 g (57.7 mmol) of N-phenyltrifluoromethanesulfonimide. The mixture was stirred for 8 hours at the same temperature. The reaction mixture was washed with water, dried over anhydrous magnesium sulfate. The solvent was distilled off, and the residue was purified by column chromatography (eluent: ethyl acetate) to give a solid, washed with ether to afford 6.17 g of the desired compound (56.8%, pale yellow solid substance), m.p.195.0–196.0° C.

Elemental Analysis for C$_{14}$H$_{15}$N$_4$O$_3$SF$_3$:

Calcd.: C, 44.68; H, 4.02; N, 14.89. Found: C, 44.68; H, 3.95; N, 15.02.

NMR(200 MHz,CDCl$_3$) δ: 1.78(2H,m), 2.02(2H,m), 2.77 (3H,s), 3.44(2H,t,J=6.2 Hz), 4.14(2H,t,J=6.6 Hz), 6.82(1H, d,J=7.6 Hz), 7.41(1H,d,J=8.8 Hz), 7.70(1H,dd,J=8.8,7.6 Hz).

ii) Synthesis of 1,2-dihydro-3-methyl-1-[4-(trifluoromethanesulfonamido)butan-1-yl]-1,4,7b-triazacyclopent[cd]inden-2-one.hydrochloride To a suspension of 5.00 g (13.3 mmol) of 1,2-dihydro-3-methyl-1-[4-(trifluoromethanesulfonamido)butan-1-yl]-1,4, 7b-triazacyclopento[cd]inden-2-one in 100 ml of methanol was added 1.33 ml of conc. HCl, then the solvent was distilled off. To the residue were added methanol and ether, and the resulting solid was collected by filtration, washed with ether and dried to give 5.38 g of the desired compound (98.2%, colorless solid).

NMR(200 MHz,DMSO-d$_6$) δ: 1.58(2H,m), 1.83(2H,m), 2.80(3H,s), 3.19(2H,m), 4.11(2H,t,J=6.8 Hz), 7.57(1H,d,J= 7.8 Hz), 7.77(1H,d,J=8.6 Hz), 8.16(1H,dd,J=8.6,7.8 Hz), 9.40(1H,br).

EXAMPLE 31

1,2-Dihydro-3-methyl-1-[4-(methanesulfonamido) butan-1-yl]-1,4,7b-triazacyclopent[cd]inden-2-one.hydrochloride i) Synthesis of 1,2-dihydro-3-methyl-1-[4-(methanesulfonamido)butan-1-yl]-1,4,7b-triazacyclopento[cd]inden-2-one To a solution of 977 mg (4.0 mmol) of 1-[4-(amino)butan-1-yl]-1,2-dihydro-3-methyl-1,4,7b-triazacyclopent[cd] inden-2-one and 607 mg (6.0 mmol) of triethylamine in 40 ml of methylene chloride was added, while stirring under ice-cooling, 836 mg (4.8 mmol) of methanesulfonic acid anhydride. The mixture was stirred for one hour at room temperature. The reaction mixture was washed with an aqueous solution of sodium hydrogencarbonate, dried over anhydrous sodium hydrogencarbonate. The solvent was distilled off, and the residue was recrystallized from methylene chloride-ethanol to give 827 mg of the desired compound (64.2%, colorless crystals), m.p.183.0–184.0° C.

ii) Synthesis of 1,2-dihydro-3-methyl-1-[4-(methanesulfonamido)butan-1-yl]-1,4,7b-triazacyclopent[cd]inden-2-one.hydrochloride To a suspension of 500 mg (1.55 mmol) of 1,2-dihydro-3-methyl-1-[4-(methanesulfonamido)butan-1-yl]-1,4,7b-triazacyclopent[cd]inden-2-one in 20 ml of methanol was added 0.17 ml of conc. HCl. The solvent was then distilled off. The residue was washed with ether to give 555 mg of the desired compound (99.6%, colorless solid), m.p.166.0–167.0° C.

NMR(200 MHz,DMSO-d$_6$) δ: 1.53(2H,m), 1.82(2H,m), 2.79(3H,s), 2.86(3H,s), 2.96(2H,m), 4.09(2H,t,J=6.8 Hz), 7.00(1H,br), 7.56(1H,d,J=7.6 Hz), 7.76(1H,d,J=8.6 Hz), 8.15(1H,dd,J=8.6,7.6 Hz).

EXAMPLE 32

1,2-Dihydro-3-methyl-1-[4-(benzamido)butan-1-yl]-1,4,7b-triazacyclopent[cd]inden-2-one.hydrochloride i) Synthesis of 1,2-dihydro-3-methyl-1-[4-(benzamido)butan-1-yl]-1,4,7b-triazacyclopent[cd]inden-2-one To a solution of 2.44 g (10.0 mmol) of 1-[4-(amino)butan-1-yl]-1,2-dihydro-3-methyl-1,4,7b-triazacyclopent[cd] inden-2-one and 2.09 ml (15.0 mmol) of triethylamine in 80 ml of methylene chloride was added, while stirring under ice-cooling, 1.39 ml (12.0 mmol) of benzoyl chloride. The mixture was stirred for 0.5 hour at the same temperature. The reaction mixture was washed with an aqueous solution of sodium hydrogencarbonate, dried over anhydrous magnesium sulfate. The solvent was distilled off, and the residue was purified by column chromatography (eluent: ethyl acetate/ethanol=10:1).

NMR(200 MHz,CDCl₃) δ: 1.74(2H,m), 1.95(2H,m), 2.80 (3H,s), 3.55(2H,m), 4.12(2H,t,J=6.8 Hz), 6.75(1H,br), 6.87 (1H,d,J=7.4 Hz), 7.33–7.54(4H,m), 7.69(1H,dd,J=8.6,7.4 Hz), 7.75–7.85(2H,m).

ii) Synthesis of 1,2-dihydro-3-methyl-1-[4-(benzamido)butan-1-yl]-1,4,7b-triazacyclopent[cd]inden-2-one.hydrochloride To a solution of 3.06 g (8.78 mmol) of 1,2-dihydro-3-methyl-1-[4-(benzamido)butan-1-yl]-1,4,7b-triazacyclopent[cd]inden-2-one in 50 ml of methanol was added 0.88 ml of conc. HCl, then the solvent was distilled off. The residue was crystallized from methanol-acetone. The crystals were collected by filtration and washed with acetone to give 2.90 g of the object product (85.8%, colorless solid), m.p.173.0–175.5° C.

Elemental Analysis for $C_{20}H_{20}N_4O_2 \cdot HCl \cdot 0.2H_2O$:

Calcd.: C, 61.84; H, 5.55; N, 14.42. Found: C, 61.82; H, 5.48; N, 14.34.

NMR(200 MHz,DMSO-d₆) δ: 1.60(2H,m), 1.82(2H,m), 2.77(3H,s), 3.31(2H,m), 4.12(2H,t,J=6.8 Hz), 7.37–7.50 (3H,m), 7.54(1H,d,J=7.6 Hz), 7.73(1H,d,J=8.8 Hz), 7.81 (2H,m), 8.10(1H,dd,J=8.8,7.6 Hz), 8.48(1H,br).

EXAMPLE 33

1,2-Dihydro-3-methyl-1-[4-(trifluoroacetamido)butan-1-yl]-1,4,7b-triazacyclopent[cd]inden-2-one.hydrochloride i) Synthesis of 1,2-dihydro-3-methyl-1-[4-(trifluoroacetamido)butan-1-yl]-1,4,7b-triazacyclopent[cd]inden-2-one To a solution of 1.71 g (7.0 mmol) of 1-[4-(amino)butan-1-yl]-1,2-dihydro-3-methyl-1,4,7b-triazacyclopent[cd]inden-2-one and 1.46 ml (10.5 mmol) of triethylamine in 50 ml of methylene chloride was added, while stirring under ice-cooling, 1.76 g (8.4 mmol) of trifluoroacetic acid anhydride. The mixture was stirred for 3 hours at room temperature. The reaction mixture was washed with an aqueous solution of sodium hydrogencarbonate, dried over anhydrous magnesium sulfate. The solvent was distilled off, and the residue was crystallized from chloroform-ethanol-ether. The crystals were collected by filtration and washed with ether to give 0.986 g of the desired compound (41.4%, pale yellow crystals).

NMR(200 MHz,CDCl₃) δ: 1.73(2H,m), 1.93(2H,m), 2.82 (3H,s), 3.48(2H,m), 4.12(2H,t,J=6.8 Hz), 6.83(1H,d,J=7.4 Hz), 6.91(1H,br), 7.50(1H,d,J=8.6 Hz), 7.73(1H,dd,J=8.6, 7.4 Hz).

ii) Synthesis of 1,2-dihydro-3-methyl-1-[4-(trifluoroacetamido)butan-1-yl]-1,4,7b-triazacyclopento[cd]inden-2-one.hydrochloride To a solution of 978 mg (2.87 mmol) of 1,2-dihydro-3-methyl-1-[4-(trifluoroacetamido)butan-1-yl]-1,4,7b-triazacyclopent[cd]inden-2-one in 15 ml of methanol was added 0.29 ml of conc. HCl. The solvent was then distilled off to give 1.084 g of the desired compound (100%, pale yellow solid).

NMR(200 MHz,DMSO-d₆) δ: 1.56(2H,m), 1.77(2H,m), 2.78(3H,s), 3.22(2H,m), 4.10(2H,t,J=6.8 Hz), 7.54(1H,d,J= 7.8 Hz), 7.75(1H,d,J=8.6 Hz), 8.13(1H,dd,J=8.6,7.8 Hz), 9.44(1H,br).

EXAMPLE 34

1,2-Dihydro-3-methyl-1-[4-(benzenesulfonamido)butan-1-yl]-1,4,7b-triazacyclopento[cd]inden-2-one.hydrochloride i) Synthesis of 1,2-dihydro-3-methyl-1-[4-(benzenesulfonamido)butan-1-yl]-1,4,7b-triazacyclopent[cd]inden-2-one To a solution of 1.22 g (5.0 mmol) of 1-[4-(amino)butan-1-yl]-1,2-dihydro-3-methyl-1,4,7b-triazacyclopento[cd]inden-2-one and 0.77 ml (6.0 mmol) of triethylamine in 40 ml of methylene chloride was added, while stirring under ice-cooling, 1.07 g (6.0 mmol) of benzenesulfonyl chloride. The mixture was stirred for 0.5 hour at room temperature. The reaction mixture was washed with an aqueous solution of sodium hydrogencarbonate, dried over anhydrous magnesium sulfate. The solvent was distilled off, and the residue was crystallized from methylene chloride-ether. The crystals were collected by filtration, which was washed with ether to give 1.09 g (56.8%, grayish white solid) of the desired compound.

NMR(200 MHz,CDCl₃) δ: 1.60(2H,m), 1.92(2H,m), 2.81 (3H,s), 3.05(2H,m), 4.07(2H,t,J=7.0 Hz), 4.94(1H,br), 6.82 (1H,d,J=7.4 Hz), 7.39–7.69(4H,m), 7.71(1H,dd,J=8.8,7.4 Hz), 7.80–7.90(2H,m).

ii) Synthesis of 1,2-dihydro-3-methyl-1-[4-(benzenesulfonamido)butan-1-yl]-1,4,7b-triazacyclopento[cd]inden-2-one.hydrochloride To a suspension of 961 mg (2.50 mmol) of 1,2-dihydro-3-methyl-1-[4-(benzenesulfonamido)butan-1-yl]-1,4,7b-triazacyclopent[cd]inden-2-one in 30 ml of methanol was added 0.42 ml of conc. HCl, and the solvent was distilled off. The residue was washed with acetone to give 1.013 g of the desired compound (96.3%, colorless solid), m.p.163.0–164.0° C.

Elemental Analysis for $C_{19}H_{20}N_4O_3S \cdot HCl$:

Calcd.: C, 54.22; H, 5.03; N, 13.31. Found: C, 53.86; H, 5.04; N, 13.15.

NMR(200 MHz,DMSO-d₆) δ: 1.43(2H,m), 1.75(2H,m), 2.77(2H,m), 2.79(3H,s), 4.03(2H,t,J=6.8 Hz), 7.46–7.60 (4H,m), 7.64(1H,br), 7.70–7.81(3H,m), 8.13(1H,dd,J=8.6, 7.6 Hz).

EXAMPLE 35

1,2-Dihydro-3-methyl-1-[4-(ethanesulfonamido)butan-1-yl]-1,4,7b-triazacyclopent[cd]inden-2-one.hydrochloride i) Synthesis of 1,2-dihydro-3-methyl-1-[4-(ethanesulfonamido)butan-1-yl]-1,4,7b-triazacyclopento[cd]inden-2-one To a solution of 1.22 g (5.0 mmol) of 1-[4-(amino)butan-1-yl]-1,2-dihydro-3-methyl-1,4,7b-triazacyclopento[cd]inden-2-one and 1.1 ml (7.9 mmol) of triethylamine in 40 ml of methylene chloride was added, while stirring under ice-cooling, 0.62 ml (6.5 mmol) of ethanesulfonyl chloride. The mixture was stirred for 0.5 hour at room temperature. The reaction mixture was washed with an aqueous solution of sodium hydrogencarbonate, dried over anhydrous magnesium sulfate. The solvent was distilled off, and the residue was recrystallized from methylene chloride-ether to give 1.32 g of the desired compound (78.6%, pale brown crystals).

NMR(200 MHz,CDCl₃) δ: 1.36(3H,t,J=7.4 Hz), 1.69(2H, m), 1.97(2H,m), 2.82(3H,s), 3.03(2H,q,J=7.4 Hz), 3.22(2H, m), 4.12(2H,t,J=7.0 Hz), 4.57(1H,br), 6.86(1H,d,J=7.6 Hz), 7.50(1H,d,J=8.8 Hz), 7.72(1H,dd,J=8.8,7.6 Hz).

ii) Synthesis of 1,2-dihydro-3-methyl-1-[4-(ethanesulfonamido)butan-1-yl]-1,4,7b-triazacyclopento[cd]inden-2-one.hydrochloride To a suspension of 1.166 g (3.47 mmol) of 1,2-dihydro-3-methyl-1-[4-(ethanesulfonamido)butan-1-yl]-1,4,7b- triazacyclopent[cd]inden-2-one in 20 ml of methanol was added 0.4 ml of conc. HCl. The solvent was then distilled off. and the residue was washed with ether to give 1.275 g of the desired compound (98.7%, pale brown solid), m.p.144.0–145.0° C.

Elemental Analysis for $C_{15}H_{20}N_4O_3S \cdot HCl$:

Calcd.: C, 48.32; H, 5.68; N, 15.03. Found : C, 47.94; H, 5.62; N, 14.84.

NMR(200 MHz,DMSO-$d_6$) δ: 1.17(3H,t,J=7.2 Hz), 1.52 (2H,m,), 1.82(2H,m), 2.80(3H,s), 2.96(2H,q,J=7.2 Hz), 4.09 (2H,t,J=6.8 Hz), 7.04(1H,br), 7.57(1H,d,J=7.8 Hz), 7.77 (1H,d,J=8.8 Hz), 8.16(1H,dd,J=8.8,7.8 Hz).

EXAMPLE 36

1,2-Dihydro-3-methyl-1-[4-(propan-1-ylsulfonamido)butan-1-yl]-1,4,7b-triazacyclopent[cd]inden-2-one.hydrochloride i) Synthesis of 1,2-dihydro-3-methyl-1-[4-(propan-1-ylsulfonamido)butan-1-yl]-1,4,7b-triazacyclopent[cd]inden-2-one To a solution of 1.22 g (5.0 mmol) of 1-[4-(amino)butan-1-yl]-1,2-dihydro-3-methyl-1,4,7b-triazacyclopent[cd]inden-2-one and 1.1 ml (7.9 mmol) of triethylamine in 40 ml of methylene chloride was added, while stirring under ice-cooling, 0.73 ml (6.5 mmol) of propan-1-ylsulfonyl chloride. The mixture was stirred for 0.5 hour at room temperature. The reaction mixture was washed with an aqueous solution of sodium hydrogencarbonate, which was then dried over anhydrous magnesium sulfate. The solvent was distilled off, and the residue was recrystallized from methylene chloride—methanol—ether to give 1.313 g of the desired compound (75.0%, pale brown crystals), m.p.150.0–151.0° C.

NMR(200 MHz,CDCl$_3$) δ: 1.06(3H,t,J=7.4 Hz), 1.60–2.05(6H,m), 2.82(3H,s), 2.98(2H,m), 3.22(2H,m), 4.12(2H,t,J=7.0 Hz), 4.48(1H,br), 6.86(1H,d,J=7.4 Hz), 7.50 (1H,d,J=8.6 Hz), 7.73(1H,dd,J=8.6,7.4 Hz).

ii) Synthesis of 1,2-dihydro-3-methyl-1-[4-(propan-1-ylsulfonamido)butan-1-yl]-1,4,7b-triazacyclopento-[cd]inden-2-one.hydrochloride To a suspension of 1.16 g (3.31 mmol) of 1,2-dihydro-3-methyl-1-[4-(propan-1-ylsulfonamido)-1-yl]-1,4,7b-triazacyclopent[cd]inden-2-one in 30 ml of methanol was added 0.4 ml of conc. HCl. The solvent was distilled off to give 1.28 g of the desired compound (100%, pale brown solid).

NMR(200 MHz,DMSO-$d_6$) δ: 0.95(3H,t,J=7.4 Hz), 1.43–1.90(6H,m), 2.79(3H,s), 2.93(2H,m), 4.09(2H,t,J=6.8 Hz), 7.02(1H,br), 7.56(1H,d,J=7.8 Hz), 7.76(1H,d,J=8.6 Hz), 8.15(1H,dd,J=8.6,7.8 Hz).

EXAMPLE 37

1,2-Dihydro-3-methyl-1-[4-(methoxycarbonylamino)butan-1-yl]-1,4,7b-triazacyclopento[cd]inden-2-one.hydrochloride i) Synthesis of 1,2-dihydro-3-methyl-1-[4-(methoxycarbonylamino)butan-1-yl]-1,4,7b-triazacyclopent[cd]inden-2-one To a solution of 1.22 g (5.0 mmol) of 1-[4-(amino)butan-1-yl]-1,2-dihydro-3-methyl-1,4,7b-triazacyclopent[cd]inden-2-one and 1.1 ml (7.9 mmol) of triethylamine in 40 ml of methylene chloride was added, while stirring under ice-cooling, 0.50 ml (6.5 mmol) of methyl chlorocarbonate. The mixture was stirred for 0.5 hour at room temperature. The reaction mixture was washed with an aqueous solution of sodium hydrogencarbonate, which was dried over anhydrous magnesium sulfate. The solvent was distilled off, and the residue was recrystallized from methylene chloride—methanol—ether to give 1.192 g of the desired compound (78.9%, colorless crystals), m.p.175–176° C.

NMR(200 MHz,CDCl$_3$) δ: 1.62(2H,m), 1.90(2H,m), 2.83 (3H,s), 3.26(2H,m), 3.66(3H,s), 4.10(2H,t,J=7.0 Hz), 4.85 (1H,br), 6.84(1H,d,J=7.4 Hz), 7.50(1H,d,J=8.6 Hz), 7.22 (1H,dd,J=8.6,7.4 Hz).

ii) Synthesis of 1,2-dihydro-3-methyl-1-[4-(methoxycarbonylamino)butan-1-yl]-1,4,7b-triazacyclopento-[cd]inden-2-one.hydrochloride To a suspension of 1.069 g (3.54 mmol) of 1,2-dihydro-3-methyl-1-[4-(methoxycarbonylamino)butan-1-yl]-1,4,7b-triazacyclopent[cd]inden-2-one in 30 ml of methanol was added 0.4 ml of conc. HCl. The solvent was distilled off to give 1.19 g of the desired compound (99.4%, colorless crystals), m.p.160.0–163.0° C.

EXAMPLE 38

1,2-Dihydro-3-methyl-1-[4-[(2,2,2-trifluoro)ethanesulfonamido]butan-1-yl]-1,4,7b-triazacyclopent[cd]inden-2-one.hydrochloride i) Synthesis of 1,2-dihydro-3-methyl-1-[4-[(2,2,2-trifluoro)ethanesulfonamido]butan-1-yl]-1,4,7b-triazacyclopent[cd]inden-2-one To a solution of 5.58 g (22.8 mmol) of 1-[4-(amino)propan-1-yl]-1,2-dihydro-3-methyl-1,4,7b-triazacyclopent[cd]inden-2-one and 4.78 ml (34.3 mmol) of triethylamine in 200 ml of methylene chloride was added, while stirring under ice-cooling, 5.0 g (27.4 mmol) of 2,2,2-trifluoroethanesulfonyl chloride. The mixture was stirred for one hour at the same temperature. The reaction mixture was washed with an aqueous solution of sodium hydrogencarbonate, dried over anhydrous magnesium sulfate. The solvent was distilled off, and the residue was purified by means of a column chromatography (eluent: ethyl acetate/ethanol=10:1), followed by crystallization from ethyl acetate-n-hexane. The crystals were collected by filtration, washed with n-hexane to give 3.89 g of the desired compound (43.6%, colorless crystals), m.p.165.0–166.0° C.

Elemental Analysis for $C_{15}H_{17}N_4O_3SF_3$:

Calcd.: C, 46.15; H, 4.39; N, 14.35. Found: C, 46.15; H, 4.39; N, 14.52.

ii) Synthesis of 1,2-dihydro-3-methyl-1-[3-[(2,2,2-trifluoro)ethanesulfonamido]butan-1-yl]-1,4,7b-triazacyclopent[cd]inden-2-one.hydrochloride To a solution of 840 mg (2.15 mmol) of 1,2-dihydro-3-methyl-1-[3-[(2,2,2-trifluoro)ethanesulfonamido]butan-1-yl]-1,4,7b-triazacyclopent[cd]inden-2-one in 10 ml of methanol was added 0.22 ml of conc. HCl. The solvent was distilled off, and the residue was washed with acetone-ether to give 915 mg of the desired compound (99.7%, colorless solid), m.p.116.0–118° C.

EXAMPLE 39

1,2-Dihydro-3-methyl-1-[3-(methanesulfonamido)propan-1-yl]-1,4,7b-triazacyclopent[cd]inden-2-one.hydrochloride i) Synthesis of 1,2-dihydro-3-methyl-1-[3-(methanesulfonamido)propan-1-yl]-1,4,7b-triazacyclopent[cd]inden-2-one To a solution of 800 mg (3.47 mmol) of 1-[3-(amino)propan-1-yl]-1,2-dihydro-3-methyl-1,4,7b-triazacyclopent

[cd]inden-2-one and 0.73 ml (5.24 mmol) of triethylamine in 20 ml of methylene chloride was added, while stirring under ice-cooling, 726 mg (4.17 mmol) of methanesulfonic acid anhydride. The mixture was stirred for 0.5 hour at room temperature. The reaction mixture was washed with an aqueous solution of sodium hydrogencarbonate, dried over anhydrous magnesium sulfate. The solvent was distilled off, and the residue was recrystallized from methylene chloride—ethanol—ether to give 634 mg of the desired compound (59.2%, pale yellow crystals).

ii) Synthesis of 1,2-dihydro-3-methyl-[3-(methanesulfonamido)propan-1-yl]-1,4,7b-triazacyclopent[cd]inden-2-one.hydrochloride To a suspension of 500 mg (1.62 mmol) of 1,2-dihydro-3-methyl-1-[3-(methanesulfonamido)propan-1-yl]-1,4,7b-triazacyclopent[cd]inden-2-one in 30 ml of methanol was added 0.18 ml of conc. HCl. The solvent was distilled off to give 557 mg of the desired compound (99.6%, pale yellow crystals), m.p.184.0–185.0° C.

Elemental Analysis for $C_{13}H_{16}N_4O_3S \cdot HCl$:

Calcd.: C, 45.28; H, 4.97; N, 16.25. Found: C, 44.99; H, 4.95; N, 16.16.

NMR(200 MHz,DMSO-$d_6$) δ: 1.98(2H,m), 2.78(3H,s), 2.89(3H,s), 3.06(2H,m), 4.13(2H,t,J=7.0 Hz), 7.12(1H,br), 7.54(1H,d,J=7.8 Hz), 7.75(1H,d,J=8.6 Hz), 8.14(1H,dd,J=8.6,7.8 Hz).

EXAMPLE 40

1,2-Dihydro-3-methyl-1-[3,3-dimethyl-5-(trifluoromethanesulfonamido)pentan-1-yl]-1,4,7b-triazacyclopent[cd]inden-2-one.hydrochloride i) Synthesis of 3,3-dimethyl-1,5-pentanediol To a solution of 13.38 g (83.5 mmol) of 3,3-dimethylglutaric acid and 90 ml (60 mmol) of methanol in 200 ml of 1,2-dichloroethane was added 4.18 ml of conc. sulfuric acid at room temperature. The mixture was heated for 16 hours under reflux. The reaction mixture was cooled, to which was added water. The organic layer was separated, washed with an aqueous solution of sodium hydrogencarbonate and dried. The solvent was distilled off, and the residue was purified by column chromatography (eluent: n-hexane/ethyl acetate=2:1) to give ethyl 3,3-dimethyl glutarate. This product was added, at room temperature, to a suspension of 3.80 g (100 mmol) of lithium aluminum hydride in 250 ml of tetrahydrofuran. The mixture was stirred for 16 hours. Water was added to this mixture until excess amount of lithium aluminum hydride was decomposed. The organic layer was dried, and the resulting precipitate was filtered off. The solvent was then distilled off to give 10.62 g of the desired compound (96.2%, white crystals).

NMR(200 MHz,CDCl$_3$) δ: 0.95(6H,s), 1.58(4H,t,J=7.0 Hz), 3.74(4H,t,J=7.0 Hz).

ii) Synthesis of 1-benzyloxymethoxy-3,3-dimethyl-5-pentanol

To a solution of 7.93 g (60 mmol) of 3,3-dimethyl-1,5-pentandiol and 10.45 ml of diisopropylethylamine in 120 ml of dichloromethane was added, at room temperature, 8.35 ml (60 mmol) of benzylchloromethylether. The mixture was stirred for 3 hours, to which was added a saturated aqueous solution of sodium hydrogencarbonate. The mixture was extracted with dichloromethane. The extract was dried, and then the solvent was distilled off. The residue was purified by column chromatography (eluent: n-hexane/ethyl acetate= 2:1) to give 5.50 g of the desired compound (36.3%, colorless oil).

NMR(200 MHz,CDCl$_3$) δ: 0.95(6H,s), 1.53–1.63(4H,m), 3.61–3.76(4H,m), 4.61(2H,s), 4.75(2H,s), 7.35–7.37(5H,m).

IR(neat): 3425, 2933, 1454, 1380, 1110, 1043, 787, 698 cm$^{-1}$.

iii) Synthesis of 1-(3,3-dimethyl-5-benzyloxymethoxypentyl)phthalimide

To a solution of 5.50 g (21.8 mmol) of 3,3-dimethyl-5-benzyloxymethoxy-1-pentanol and 3.14 ml (22.5 mmol) of triethylamine in 100 ml of dichloromethane was added, at 0° C., 1.74 ml (22.5 mmol) of methanesulfonyl chloride. The mixture was stirred for 30 minutes at room temperature, to which was added a saturated aqueous solution of sodium hydrogencarbonate. The mixture was extracted with dichloromethane. The extract was dried, followed by distilling off the solvent to give 3,3-dimethyl-5-benzyloxymethoxy-1-methanesulfonyl -oxypentane.

NMR(200 MHz,CDCl$_3$) δ: 0.97(6H,s), 1.61–1.78(4H,m), 2.98(3H,s), 3.58–3.66(2H,m), 4.29(2H,t,J=8.0 Hz), 4.59 (2H,s), 4.74(2H,s), 7.32–7.42(5H,m).

IR(neat): 2933, 1479, 1356, 1174, 951, 737, 699 cm$^{-1}$.

To a solution of the above-mentioned product in 80 ml of N,N-dimethylformamide was added, at room temperature, 3.70 g (20 mmol) of phthalimide potassium salt. The mixture was stirred for 4 hours at 80° C. The reaction mixture was cooled and, then, the solvent was distilled off. The residue was dissolved in a mixture of dichloromethane and a saturated aqueous solution of sodium hydrogencarbonate. The organic layer was separated, washed with water and dried, followed by distilling off the solvent. The residue was purified by column chromatography (eluent: n-hexane/ethyl acetate=5:1→2:1) to give 5.85 g of the desired compound (70.3%, colorless oily).

NMR(200 MHz,CDCl$_3$) δ: 1.02(6H,s), 1.58–1.68(4H,m), 3.64–3.75(4H,m), 4.61(2H,s), 4.76(2H,s), 7.30–7.37(5H,m), 7.68–7.72(2H,m), 7.81–7.85(2H,m).

IR(neat): 2954, 1770, 1714, 1400, 1369, 1045, 719, 698 cm$^{-1}$.

iv) Synthesis of 1-(3,3-dimethyl-5-hydroxypentyl) phthalimide

To a solution of 5.70 g (14.9 mmol) of 1-(3,3-dimethyl-5-benzyloxymethoxypentyl)phthalimide in 70 ml of methanol was added 3.75 ml (45 mmol) of conc. HCl. The mixture was stirred for 3 hours at 60° C. The reaction mixture was cooled, and the solvent was distilled off. The residue was dissolved in 100 ml of water, to which was added 30 ml of 1N aqueous solution of sodium hydroxide. The mixture was extracted with dichloromethane. The extract solution was dried, and the solvent was distilled off. The residue was purified by column chromatography (eluent: n-hexane/ethyl acetate=2:1→1:2) to give 3.63 g of the desired compound (93.2%, white solid).

NMR(200 MHz,CDCl$_3$) δ: 1.02(6H,s), 1.56–1.67(4H,m), 3.67–3.78(4H,m), 7.69–7.73(2H,m), 7.82–7.86(2H,m).

IR(KBr): 2954, 1772, 1713, 1400, 1365, 719 cm$^{-1}$.

v) Synthesis of 1,2-dihydro-3-methyl-1-[3,3-dimethyl-5-(phthalimido)pentan-1-yl]-1,4,7b-triazacyclopento-[cd]inden-2-one To a solution of 1.57 g (6.0 mmol) of 1-(3,3-dimethyl-5-hydroxypentyl)phthalimide and 0.92 ml (6.6. mmol) of triethylamine in 30 ml of dichloromethane was added, at 0° C., 0.51 ml (6.6 mmol) of methanesulfonyl chloride. The mixture was stirred for 30 minutes at room temperature, to which was added a saturated aqueous solution of sodium hydrogencarbonate. The mixture was extracted with dichloromethane. The extract was dried, followed by distilling off the solvent to give 1-(3,3-dimethyl-5-methanesulfonyloxypentyl)phthalimide.

NMR(200 MHz,CDCl$_3$) δ: 1.05(6H,s), 1.56–1.65(2H,m), 1.81(2H,t,J=7.8 Hz), 3.70(3H,s), 3.65–3.74(2H,m), 4.36 (2H,t,J=7.8 Hz), 7.69–7.73(2H,m), 7.82–7.86(2H,m).

IR(neat): 2962, 1770, 1714, 1344, 1171, 947, 716, 527 cm$^{-1}$.

To a suspension of 0.24 g (6.0 mmol) of sodium hydride (60% despersion in oil) in 30 ml of N,N-dimethylformamide was added, at room temperature, 1.04 g (6.0 mmol) of 1,2-dihydro-3-methyl-1,4,7b-triazacyclopento[cd]indene. The mixture was stirred for 10 minutes. To this mixture was added the above-mentioned product. The mixture was stirred for 2 hours at 100° C. The reaction mixture was cooled, which was then poured into water, extracted with ethyl acetate. The organic layer was washed with water, dried, distilled off the solvent. The residue was purified by column chromatography (eluent: ethyl acetate→ethyl acetate/ethanol=9:1) to give 1.32 g of the desired compound (52.8%, pale yellow oil).

NMR(200 MHz,CDCl$_3$) δ: 1.41(6H,s), 1.67–1.89(4H,m), 2.82(3H,s), 3.73–3.82(2H,m), 4.11–4.20(2H,m), 7.02(1H,d, J=7.4 Hz), 7.49(1H,d,J=8.8 Hz), 7.70–7.78(3H,m), 7.84–7.88(2H,m).

IR(KBr): 2966, 1709, 1626, 1406, 1371, 775, 752, 717 cm$^{-1}$.

vi) Synthesis of 1,2-dihydro-3-methyl-1-[3,3-dimethyl-5-(trifluoromethanesulfonamido)pentan-1-yl]-1,4,7b-triazacyclopent[cd]inden-2-one To a suspension of 1.25 g (3.0 mmol) of 1,2-dihydro-3-methyl-[3,3-dimethyl-5-(phthalimido)pentan-1-yl]-1,4,7b-triazacyclopent[cd]inden-2-one in 30 ml of ethanol was added, at room temperature, 0.44 ml (9.0 mmol) of hydrazinemonohydrate. The mixture was heated under reflux. The reaction mixture was cooled, and the resulting precipitates were filtered off. The solvent was distilled off. The residue was dissolved in chloroform. The solution was washed with a saturated aqueous solution of sodium hydrogencarbonate, dried, distilled off the solvent to give 1,2-dihydro-3-methyl-1-[3,3-dimethyl-5-(amino)pentan-1-yl]-1,4,7b-triazacyclopent[cd]inden-2-one.

NMR(200 MHz,CDCl$_3$) δ: 1.05(6H,s), 1.49–1.58(2H,m), 1.69–1.78(2H,m), 2.75–2.83(4H,m), 4.02–4.11(2H,m), 6.78 (1H,d,J=7.4 Hz), 7.48(1H,d,J=8.6 Hz), 7.04(1H,d,J=7.4,8.8 Hz).

To a solution of the above-mentioned product and 0.56 ml (4.0 mmol) of triethylamine in 25 ml of acetonitrile was added, at 0° C., 1.43 g (4.0 mmol) of N-phenyltrifluoromethanesulfonimide. The mixture was stirred for 12 hours at room temperature. To the reaction mixture was added water, to extracted with chloroform. The extract solution was dried, the solvent was distilled off. The residue was purified by column chromatography to give 1.03 g of the desired compound (82.1%, pale yellow foam).

NMR(200 MHz,CDCl$_3$) δ: 1.07(6H,s), 1.72–1.81(4H,m), 2.81(3H,s), 3.36–3.44(2H,m), 4.01–4.11(2H,m), 6.83(1H,d, J=7.8 Hz), 7.34–7.38(1H,m), 7.51(1H,d,J=9.2 Hz), 7.73(1H, dd,J=7.6,8.8 Hz);

vii) Synthesis of 1,2-dihydro-3-methyl-1-[3,3-dimethyl-5-(trifluoromethanesulfonamido)pentan-1-yl]-1,4,7b-triazacyclopent[cd]inden-2-one.hydrochloride To a solution of 1.03 g (2.46 mmol) of 1,2-dihydro-3-methyl-1-[3,3-dimethyl-5-(trifluoromethanesulfonamido) pentan-1-yl]-1,4,7b-triazacyclopent[cd]inden-2-one in 30 ml of methanol was added 0.29 ml (3.5 mmol) of conc. HCl. The solvent was distilled off, and the residue was recrystallized (solvent: ethanol/diethylether) to give 0.928 g of the desired compound (82.9%, pale yellow powdery substance), m.p.162.0–165.0° C.

Elemental Analysis for C$_{17}$H$_{21}$N$_4$O$_3$S.HCl:

Calcd.: C, 44.89; H, 4.87; N, 12.32. Found: C, 44.86; H, 4.89; N, 12.43.

NMR(200 MHz,CD$_3$OD) δ: 1.10(6H,s), 1.62–1.84(4H, m), 2.92(3H,s), 3.22–3.32(2H,m), 4.14–4.22(2H,m), 7.56 (1H,d,J=7.8 Hz), 7.80(1H,d,J=8.8 Hz), 8.32(1H,t,J=8.0 Hz).

EXAMPLE 41

3-Methyl-2-[4-(trifluoromethanesulfonamido)butan-1-ylthio]-1,4,7b-triazacyclopent[cd] inden.hydrochloride i) Synthesis of 3-methyl-2-[4-(trifluoromethanesulfonamido)butan-1-ylthio]-1,4,7b-triazacyclopento[cd]indene To a solution of 1.30 g (5.0 mmol) of 3-methyl-2-[4-(amino)butan-1-ylthio]-1,4,7b-triazacyclopent[cd]indene and 0.84 ml (6.0 mmol) of triethylamine in 40 ml of methylene chloride was added, while stirring at room temperature, 1.97 g (5.5 mmol) of N-phenyltrifluoromethanesulfonimide. The mixture was stirred for 18 hours at the same temperature. The reaction mixture was washed with an aqueous solution of sodium hydrogencarbonate, dried over anhydrous magnesium sulfate. The solvent was distilled off, and the residue was purified by column chromatography (eluent: ethyl acetate) to give 883 mg (45.1%, pale brown solid).

NMR(200 MHz,CDCl$_3$) δ: 1.85(2H,m), 2.19(2H,m), 2.90 (3H,s), 3.37(2H,m), 3.64(2H,t,J=6.0 Hz), 7.76(1H,d,J=7.8 Hz), 7.89(1H,d,J=7.6 Hz), 7.99(1H,dd,J=7.8,7.6 Hz), 9.01 (1H,br).

ii) Synthesis of 3-methyl-2-[4-(trifluoromethanesulfonamido)butan-1-ylthio]-1,4,7b-triazacyclopent[cd]indene.hydrochloride To a suspension of 873 mg (2.22 mmol) of 3-methyl-2-[4-(trifluoromethanesulfonamido)butan-1-ylthio]-1,4,7b-triazacyclopent[cd]indene in 10 ml of methanol was added 0.23 ml of conc. HCl. The solvent was then distilled off. The residue was recrystallized from ethanol-ether to give 762 mg of the desired compound (79.9%, colorless crystals), m.p.129.0–131.0° C.

Elemental Analysis for C$_{14}$H$_{15}$N$_4$O$_2$S$_2$F$_3$.HCl:

Calcd.: C, 39.21; H, 3.76; N, 13.06. Found: C, 38.92; H, 3.80; N, 13.33.

EXAMPLE 42

4,5-Dihydro-4-[4-(methanesulfonamido) phenylmethyl]-3H-1,4,8b-triazaacenaphthylene-3,5-dione.hydrochloride i) Synthesis of 4,5-dihydro-4-[4-methanesulfonamido) phenylmethyl]-3H-1,4,8b-triazaacenaphthylene-3,5-dione To a suspension of 877 mg (3.0 mmol) of 4-[4-(amino) phenylmethyl]-4,5-dihydro-3H-1,4,8b- triazaacenaphthylene-3,5-dione and 0.63 ml (4.5 mmol) of triethylamine in methylene chloride (60 ml) was added dropwise 0.30 ml (3.9 mmol) of methanesulfonyl chloride while stirring at room temperature. The mixture was stirred for 72 hours at room temperature. The solvent was distilled off. To the residue was added chloroform, washed with 1N-HCl, and dried over anhydrous magnesium sulfate. The solvent was distilled off, and the residue was purified by column chromatography (eluent: chloroform/methanol= 20:1) to afford 274 mg of the desired compound (24.7%, a pale yellow solid).

NMR(200 MHz,CDCl$_3$-DMSO-d$_6$) δ: 2.89(3H,s), 5.30 (2H,s) 7.23(2H,m), 7.51(2H,m), 7.83(1H,dd,J=9.0, 7.2 Hz), 8.17(1H,d,J=9.0 Hz), 8.18(1H,d,J=7.2 Hz), 8.63(1H,s), 9.33 (1H,br).

ii) Synthesis of 4,5-dihydro-4-[4-(methanesulfonamido) phenylmethyl]-3H-1,4,8b-triazaacenaphthylene-3,5-dione.hydrochloride To a suspension of 248 mg (0.67 mmol) of 4,5-dihydro-4-[4-(methanesulfonamido)phenylmethyl]-3H-1,4,8b-triazaacenaphthylene-3,5-dione in 15 ml of methanol was added 0.09 ml of conc. HCl. The solvent was distilled off. To the residue was added acetone. The resulting solid was washed with acetone and dried to afford 273 mg of the desired compound (100%, a colorless solid).

EXAMPLE 43

4,5-Dihydro-4-[4-(trifluoromethanesulfonamido) phenylmethyl]-3H-1,4,8b-triazaacenaphthylene-3,5-dione.hydrochloride i) Synthesis of 4,5-dihydro-4-[4-(trifluoromethane sulfonamido)phenylmethyl]-3H-1,4,8b-triazaacenaphthylene-3,5-dione To a suspension of 1.46 g (5.0 mmol) of 4-[4-(amino) phenylmethyl]-4,5-dihydro-3H-1,4,8b-triazaacenaphthylene-3,5-dione and 1.05 ml (7.5 mmol) of triethylamine in methylene chloride (100 ml) was added dropwise, while stirring under ice-cooling, 1.01 ml (6.0 mmol) of trifluoromethanesulfonic acid anhydride. The mixture was stirred for one hour at room temperature. The reaction mixture was washed with 1N-HCl, and dried over anhydrous magnesium sulfate. The solvent was distilled off, and the residue was eluted by column chromatography (eluent:chloroform/ethyl acetate=1:1) to afford 502 mg of 4,5-dihydro-4-[4-bis(trifluoromethane sulfonyl)imido) phenylmethyl]-3H-1,4,8b-triazaacenaphthylene-3,5-dione (18.1%, a pale reddish brown solid).

NMR(200 MHz,CDCl$_3$) δ: 5.40(2H,s), 7.35(2H,m), 7.74 (2H,m), 7.81(1H,dd,J=9.0, 7.2 Hz), 8.18(1H,d,J=9.0 Hz), 8.19(1H,d,J=7.2 Hz), 8.67(1H,s).
and was further elution (eluent:chloroform/ethyl acetate= 1:1) afforded 137 mg of the desired compound (6.5%, a pale brown solid).

NMR(200 MHz,CDCl$_3$) δ: 5.35(2H,s), 7.24(2H,m), 7.59 (2H,m), 7.81(1H,dd,J=9.2, 7.2 Hz), 8.18(1H,d,J=9.2 Hz), 8.19(1H,d,J=7.2 Hz), 8.66(1H,s).

ii) Synthesis of 4,5-dihydro-4-[4-(trifluoromethane sulfonamido)phenylmethyl]-3H-1,4,8b-triazaacenaphthylene-3,5-dione.hydrochloride To a suspension of 129 mg (0.30 mmol) of 4,5-dihydro-4-[4-(trifluoromethanesulfonamido) phenylmethyl]-3H-1,4, 8b-triazaacenaphthylene-3,5-dione in 10 ml of methanol was added 0.04 ml of conc. HCl. The solvent was distilled off. To the residue was added acetone. The resulting solid was washed with acetone and dried to afford 141 mg of the desired compound (100%, a pale brown solid).

NMR(200 MHz,DMSO-d$_6$) δ: 5.21(2H,s), 7.20(2H,d,J= 8.4 Hz), 7.45(2H,d,J=8.4 Hz), 7.94(1H,dd,J=8.8, 7.2 Hz), 8.17(1H,d,J=7.2 Hz), 8.33(1H,d,J=8.8 Hz), 8.73(1H,s), 11.78(1H,br).

EXAMPLE 44

4,5-Dihydro-4-[1-(tert-butoxycarbonyl)piperidin-4-ylmethyl]-3H-1,4,8b-triazaacenaphthylene-3,5-dione To a suspension of 10.59 g (30.3 mmol) of 5-ethoxycarbonyl-3-trichloroacetylimidazo[1,2-a]pyridine and 5.09 g (39.4 mmol) of diisopropylethylamine in 200 ml of acetonitrile was added 4.15 g (36.3 mmol) of 4-aminomethylpiperidine. The mixture was stirred for 20 hours at room temperature. To the reaction mixture was added dropwise 15.87 g (72.7 mmol) of di-tert-butyl dicarbonate, and the mixture was stirred for one hour at room temperature. The solvent was distilled off. To the residue was added methylene chloride. The mixture was washed with water and dried over anhydrous magnesium sulfate. The solvent was distilled off, and the residue was purified by column chromatography (eluent: ethyl acetate/ ethanol=20:1), and treated with ethyl acetate and n-hexane to afford 9.10 g (78.1%, a pale yellow solid) of the desired compound.

NMR(200 MHz,CDCl$_3$) δ: 1.22–1.48(2H,m), 1.45(9H,s), 1.57–1.73(2H,m), 2.05(1H,m), 2.55–2.75(2H,m), 3.98–4.22 (2H,m), 4.12(2H,d,J=7.0 Hz), 7.81(1H,m), 8.13–8.21(2H, m), 8.65(1H,s).

EXAMPLE 45

4,5-Dihydro-4-[1-(trifluoroacetyl)piperidin-4-ylmethyl]-3H-1,4,8b-triazaacenaphthylene-3,5-dione i) Synthesis of 4,5-dihydro-4-(piperidin-4-ylmethyl)-3H-1,4,8b-triazaacenaphthylene-3,5-dione.dihydrochloride To a suspension of 7.99 g (20.8 mmol) of 4,5-dihydro-4-[1-(tert-butoxycarbonyl)piperidin-4-ylmethyl]-3H-1,4,8b-triazaacenaphthylene-3,5-dione in 50 ml of ethanol was added dropwise 25 ml of conc. HCl. The mixture was stirred for two hours at room temperature. The resulting crystalline precipitates were collected by filtration, washed with ethanol and then with ether to afford 7.07 g (87.4%, a colorless solid substance) of the desired compound Elemental Analysis Calcd for $C_{15}H_{16}N_4O_4$.2HCl.2H$_2$O:
Calcd.: C, 47.75; H, 5.88; N; 14.85. Found: C, 47.91; H, 5.49; N, 14.84.

NMR(200 MHz,D$_2$O) δ: 1.47–1.72(2H,m), 1.89–2.06 (2H,m), 2.21(1H,m), 2.96(2H,m), 3.44(2H,m), 4.12(2H,d, J=7.2 Hz), 8.26(1H,dd,J=9.0, 7.2 Hz), 8.40(1H,d,J=9.0 Hz), 8.44(1H,d,J=7.2 Hz), 8.89(1H,s).

ii) Synthesis of 4,5-dihydro-4-[1-(trifluoroacetyl) piperidin-4-ylmethyl]-3H-1,4,8b-triazaacenaphthylene-3,5-dione To a suspension of 1.08 g (2.77 mmol) of 4,5-dihydro-4-(piperidin-4-ylmethyl)-3H-1,4,8b-triazaacenaphthylene-3,5-dione.dihydrochloride in 100 ml of acetonitrile were added 1.93 ml (13.9 mmol) of triethylamine, 2.0 g (16.4 mmol) of 4-dimethylaminopyridine and 5.25 g (25.0 mmol) of trifluoroacetic acid anhydride. The mixture was stirred for one hour at room temperature. The solvent was distilled off. To the residue was added ethyl acetate—tetrahydrofuran. The mixture was washed with an aqueous solution of sodium hydrogencarbonate, and dried over anhydrous magnesium sulfate. The solvent was distilled off. The residue was purified by column chromatography (eluent: ethyl acetate), which was then recrystallized from ethyl acetate to afford 862 mg (81.7%, a colorless crystals) of the desired compound.

Elemental Analysis Calcd for $C_{17}H_{15}N_4O_3F_3$:

Calcd.: C, 53.69; H, 3.98; N; 14.73. Found: C, 53.62; H, 3.96; N, 14.69.

NMR(200 MHz,CDCl$_3$) δ: 1.50(2H,m), 1.84(2H,m), 2.24 (1H,m), 2.77(1H,m), 3.09(1H,m), 4.03(1H,m), 4.15(2H,d, J=7.2 Hz), 4.54(1H,m), 7.82(1H,dd,J=9.0, 7.4 Hz), 8.19(1H, d,J=7.4 Hz), 8.20(1H,d,J=9.0 Hz), 8.67(1H,s).

EXAMPLE 46

4,5-Dihydro-4-[1-(trifluoromethanesulfonyl) piperidin-4-ylmethyl]-3H-1,4,8b-triazaacenaphthylene-3,5-dione To a suspension of 1.95 g (5.0 mmol) of 4,5-dihydro-4-(piperidin-4-ylmethyl)-3H-1,4,8b-triazaacenaphthylene-3,5-dione.dihydrochloride in 50 ml of acetonitrile were added 3.5 ml (25.0 mmol) of triethylamine and 8.93 g (25.0 mmol) of N-phenyltrifluoromethanesulfonimide. The mixture was stirred for 66 hours at room temperature. The solvent was distilled off. To the residue was added methylene chloride. The mixture was washed with water and dried over anhydrous magnesium sulfate. The solvent was distilled off, and the residue was purified by column chromatography (eluent: ethyl acetate), which was recrystallized from ethyl acetate—ethanol to afford 1.32 g (63.2%, a colorless crystals) of desired compound.

NMR(200 MHz,CDCl$_3$) δ: 1.56(2H,m), 1.83(2H,m), 2.13 (1H,m), 3.01(2H,m), 3.97(2H,m). 4.16(2H,d,J=7.2 Hz), 7.82 (2H,dd,J=8.8, 7.2=Hz), 8.19(1H,d,J=7.2 Hz), 8.20(1H,d,J= 8.8 Hz), 8.67(1H,s).

EXAMPLE 47

3-Methyl-1-[5-(trifluoroacetamido)pentyl]-1,4,7b-triazacyclopent[cd]inden-2-one

To a solution of 2.58 g (10.0 mmol) of 3-methyl-1-[5-(amino)pentyl]-1,4,7b-triazacyclopent[cd]inden-2-one and 1.81 ml (13.0 mmol) of triethylamine in 100 ml of acetonitrile was added, while stirring under ice-cooling, 1.43 ml (12.0 mmol) of trifluoroacetic acid ethyl ester. The mixture was stirred for one hour at the same temperature. The solvent was distilled off. To the residue was added ethyl acetate—tetrahydrofuran. The mixture was washed with an aqueous saline solution, and dried over anhydrous magnesium sulfate. The solvent was distilled off. The residue was purified by column chromatography (eluent: ethyl acetate), which was recrystallized from ethyl acetate—n-hexane to afford 2.57 g (72.6%, a pale yellow crystals) of the desired compound.

NMR(200 MHz,CDCl$_3$) δ: 1.44(2H,m), 1.75(2H,m), 1.92 (2H,m), 2.82(3H,s), 3.39(2H,m), 4.11(2H,t,J=6.6 Hz), 6.83 (1H,d,J=7.4 Hz), 6.92(1H,br), 7.51(1H,d,J=8.6 Hz), 7.74 (1H,dd,J=8.6, 7.4 Hz).

EXAMPLE 48

3-Methyl-1-[4-(pentafluoropropanoylamino)butan-1-yl]-1,4,7b-triazacyclopent[cd]inden-2-one To a solution of 2.44 g (10.0 mmol) of 3-methyl-1-[4-(amino)butan-1-yl]-1,4,7b-triazacyclopent[cd]inden-2-one and 1.81 ml (13.0 mmol) of triethylamine in 100 ml of acetonitrile was added, while stirring at room temperature, 2.31 g (12.0 mmol) of ethyl ester of pentafluoropropionic acid. The mixture was stirred for 14 hours at the same temperature. The solvent was distilled off. To the residue was added methylene chloride. The mixture was washed with water, which was dried over anhydrous magnesium sulfate. The solvent was distilled off, and the residue was purified by column chromatography (eluent:ethyl acetate), and recrystallized from ethyl acetate—hexane to afford 1.53 g (39.1%, a colorless crystals) of the desired compound.

Elemental Analysis Calcd for $C_{16}H_{15}N_4O_2F_5$:

Calcd.: C, 49.25; H, 3.87; N; 14.35. Found: C, 49.15; H, 3.91; N, 14.21.

NMR(200 MHz,CDCl$_3$) δ: 1.73(2H,m), 1.92(2H,m), 2.82 (3H,s), 3.50(2H,m), 4.13(2H,t,J=6.8 Hz), 6.84(1H,d,J=7.4 Hz), 7.05(1H,br), 7.50(1H,d,J=8.6 Hz), 7.73(1H,dd,J=8.6, 7.4 Hz).

EXAMPLE 49

3-Methyl-1-[5-(pentafluoropropanoylamino)pentan-1-yl]-1,4,7b-triazacyclopent[cd]inden-2-one To a solution of 2.58 g (10.0 mmol) of 3-methyl-1-[5-(amino)pentan-1-yl]-1,4,7b-triazacyclopent[cd]inden-2-one and 1.81 ml (13.0 mmol) of triethylamine in 100 ml of acetonitrile was added, while stirring at room temperature, 2.31 g (12.0 mmol) of pentafluoropropionic acid ethyl ester. The mixture was stirred for 4 hours at the same temperature. The solvent was distilled off. To the residue was added methylene chloride, and the mixture was washed with water, and dried over anhydrous magnesium sulfate. The solvent was distilled off, and the residue was purified by column chromatography (eluent: ethyl acetate) to afford 2.04 g of the desired compound (50.4%, a pale yellow solid).

NMR(200 MHz,CDCl$_3$) δ: 1.43(2H,m), 1.75(2H,m), 1.90 (2H,m), 2.82(3H,s), 3.41(2H,m), 4.10(2H,t,J=6.6 Hz), 6.83 (1H,d,J=7.4 Hz), 7.11(1H,br), 7.51(1H,d,J=8.6 Hz), 7.74 (1H,dd,J=8.6, 7.4 Hz).

EXAMPLE 50

3-Methyl-2-[5-(trifluoromethanesulfonamido) pentan-1-ylthio]-1,4,7b-triazacyclopent[cd]indene To a solution of 500 mg (1.82 mmol) of 3-methyl-2-[5-(amino)pentan-1-ylthio]-1,4,7b-triazacyclopent[cd]indene in 30 ml of acetonitrile were added 0.51 ml (3.66 mmol) of triethylamine and 1.302 g (3.66 mmol) of N-phenyltrifluoromethanesulfonamide. The mixture was stirred for two hours at room temperature. The solvent was distilled off. To the residue was added methylene chloride, which was washed with water, and dried over anhydrous magnesium sulfate. The solvent was distilled off, and the residue was purified by column chromatography (eluent: ethyl acetate) to afford 608 mg (82.1%, a pale yellow solid) of the desired compound.

NMR(200 MHz,CDCl$_3$) δ: 1.55–1.85(4H,m), 1.97(2H, m), 2.90(3H,s), 3.39(2H,m), 3.50(2H,t,J=7.0 Hz), 7.69(1H, d,J=7.8 Hz), 7.73(1H,d,J=8.0 Hz), 7.95(1H,dd,J=8.0, 7.8 Hz).

EXAMPLE 51

3-Methyl-2-[5-(trifluoroacetamido)pentan-1-ylthio]-1,4,7b-triazacyclopent[cd]indene To a solution of 275 mg (1.00 mmol) of 3-methyl-2-[5-(amino)pentan-1-ylthio]-1,4,7b-triazacyclopent[cd]indene in 30 ml of acetonitrile were added 0.19 ml (1.36 mmol) of triethylamine and 171 mg (1.20 mmol) of ethyl ester of trifluoroacetic acid. The mixture was stirred for 15 hours at room temperature. The solvent was distilled off. To the residue was added ethyl acetate, which was washed with water, and dried over anhydrous magnesium sulfate. The solvent was distilled off, and the residue was purified by column chromatography (eluent: ethyl acetate) to afford 267 mg (72.0%, a pale yellow solid) of the desired compound.

NMR(200 MHz,CDCl$_3$) δ: 1.50–2.10(6H,m), 2.90(3H,s), 3.42(2H,m), 3.52(2H,t,J=7.0 Hz), 6.56(1H,br), 7.67(1H,d,J=7.8 Hz), 7.73(1H,d,J=8.0 Hz), 7.95(1H,dd,J=8.0, 7.8 Hz).

EXAMPLE 52

3-Methyl-2-[5-(pentafluoropropanoylamino)pentan-1-ylthio]-1,4,7b-triazacyclopent[cd]indene To a solution of 275 mg (1.00 mmol) of 3-methyl-2-[5-(amino)pentan-1-ylthio]-1,4,7b-triazacyclopent[cd]indene in 30 ml of acetonitrile were added 0.19 ml (1.36 mmol) of triethylamine and 231 mg (1.20 mmol) of pentafluoropropionic acid ethyl ester. The mixture was stirred for 15 hours at room temperature, and the the solvent was distilled off. To the residue was added ethyl acetate, washed with water, and dried over anhydrous magnesium sulfate. The solvent was distilled off, and the residue was purified by column chromatography (eluent: ethyl acetate) to afford 245 mg (58.1%, a pale brown solid) of the desired compound.

NMR(200 MHz,CDCl$_3$) δ: 1.50–1.80(4H,m), 1.96(2H,m), 2.90(3H,s), 3.44(2H,m), 3.52(2H,t,J=7.0 Hz), 6.68(1H,br), 7.67(1H,d,J=7.8 Hz), 7.73(1H,d,J=8.0 Hz), 7.95(1H,dd,J=8.0,7.8 Hz).

EXAMPLE 53

3,4-Dihydro-3-[5-(tert-butoxycarbonylamino)pentan-1-yl]-1,3,7b-triazacyclopent[cd]inden-4-one To a suspension of 29 mg (0.077 mmol) of 3,4-dihydro-3-[5-(phthalimido)pentan-1-yl]-1,3,7b-triazacyclopent[cd]inden-4-one in 5 ml of ethanol was added 24 mg (0.048 mmol) of hydrazinemonohydrate. The mixture was stirred for three hours under reflux. After cooling, the solvent was distilled off. To the residue was added 2 ml of chloroform. To the mixture were added 80 mg (0.37 mmol) of di-tert-butyl dicarbonate and 100 mg (0.99 mmol) of triethylamine, and stirred for 14 hours at room temperature. The reaction mixture was washed with water, and dried over anhydrous magnesium sulfate. The solvent was distilled off. The residue was purified by column chromatography (eluent: ethyl acetate/ethanol=10:1) to afford 18 mg (67.4%, a colorless solid) the desired compound.

NMR(200 MHz,CDCl$_3$) δ: 1.30–1.82(6H,m), 1.44(9H,s), 2.98(1H,m), 3.13(2H,m), 4.46(1H,m), 4.58(1H,br), 6.90 (1H,dd,J=7.0, 1.2 Hz), 7.15(1H,s), 7.17(1H,dd,J=9.2,7.0 Hz), 7.40(1H,dd,J=9.2, 1.2 Hz).

EXAMPLE 54

3,4-Dihydro-3-[5-(trifluoromethanesulfonamido)pentan-1-yl]-1,3,7b-triazacyclopent[cd]inden-4-one To a solution of 18 mg (0.052 mmol) of 3,4-dihydro-3-[5-(tert-butoxycarbonylamino)pentan-1-yl]-1,3,7b-triazacyclopent[cd]inden-4-one in 1 ml of methanol was added 1 ml of conc.HCl, and the mixture was stirred for 15 minutes at room temperature. The solvent was distilled off. To the residue was added toluene. The solvent was further distilled off. To the residue were added 3 ml of acetonitrile, 0.2 ml (1.43 mmol) of triethylamine and 100 mg (0.28 mmol) of N-phenyltrifluoromethanesulfonimide. The mixture was stirred for 14 hours at room temperature. The solvent was distilled off. To the residue was added chloroform, washed with water, and dried over anhydrous magnesium sulfate. The solvent was distilled off, and the residue was purified by column chromatography (eluent: ethyl acetate/ethanol=10:1) to afford 13 mg (66.0%, a colorless solid) of the desired compound.

NMR(200 MHz,CDCl$_3$) δ: 1.35–1.85(6H,m), 3.05(1H,m), 3.33(2H,m), 4.43(1H,m), 6.53(1H,br), 6.97(1H,dd,J=7.0,1.0 Hz), 7.16(1H,s), 7.23(1H,dd,J=9.0, 7.0 Hz), 7.43 (1H,dd,J=9.0, 1.0 Hz).

EXAMPLE 55

4,5-Dihydro-4-(4-trifluoroacetamidobutan-1-yl)-3H-1,4,8b-triazaacenaphthylene.dihydrochloride i) Synthesis of 5-[N-(4-trifluoroacetamidobutan-1-yl) aminomethyl]imidazo[1,2-a]pyridine A suspension of 38.94 g (179.36 mmol) of 5-chloromethylimidazo[1,2-a]pyridine.hydrochloride and 31.62 g (358.73 mmol) of 1,4-diaminobutane in 500 ml of acetonitrile was heated for one hour under reflux with stirring. The reaction mixture was cooled to room temperature, and 1,4-diaminobutane.dihydrochloride formed as precipitate was filtered off. To the filtrate were added 21.34 ml (179.36 mmol) of trifluoroacetic acid ethyl ester and 30 ml (215.23 mmol) of triethylamine. The mixture was stirred for one hour at room temperature. The solvent was then distilled off under reduced pressure. The residue was extracted with 500 ml of dichloromethane. The organic layer was washed with 350 ml of a saturated aqueous saline solution, dried over magnesium sulfate, and distilled off the solvent under reduced pressure. The residue was purified by silica gel column chromatography (eluent;dichloromethane:methanol=20:1) to afford 29.38 g (52.1%, a pale yellow liquid) of the disired compound.

NMR(200 MHz,CDCl$_3$) δ: 1.65(4H,m), 2.73(2H,t,J=6.2 Hz), 3.37(2H,m), 4.04(2H,s), 6.78(1H,d,J=7.0 Hz), 7.18(1H,dd,J=9.2 Hz,7.0 Hz), 7.57(1H,d,J=9.2 Hz), 7.67(1H,s), 7.69 (1H,s), 7.88(1H,brs,NH).

IR(Neat): 1714, 1558, 1207, 1153 cm$^{-1}$ ii) Synthesis of 4,5-dihydro-4-(4-trifluoroacetamido butan-1-yl)-3H-1,4,8b-triazaacenaphthylene To a solution of 3860 mg (12.28 mmol) of 5-[N-(4-trifluoroacetamidobutan-1-yl)aminomethyl]imidazo[1,2-a] pyridine in 15 ml of acetic acid was added 13.8 ml (184.21 mmol) of a 37% aqueous solution of formalin. The mixture was heated for 30 minutes at 100° C. The solvent was distilled off under reduced pressure, and the residue was dissolved in 100 ml of purified water. To this solution was added 2N sodium hydroxide to adjust the pH to 8, and extracted with 150 ml of dichloromethane. The organic layer was washed with 200 ml of a saturated aqueous saline solution, and dried over magnesium sulfate. The solvent was then distilled off under reduced pressure. The residue was purified by silica gel column chromatography (eluent; dichloromethane:methanol=20:1) to afford 2890 mg of the desired compound (72.0%, a white solid).

NMR(200 MHz,CDCl$_3$) δ: 1.69(4H,m), 2.53(2H,m), 3.40 (2H,m), 3.99(2H,s), 4.14(2H,s), 6.55(1H,d,J=6.8 Hz), 7.12 (1H,dd,J=9.2 Hz, 6.8 Hz), 7.39(1H,s), 7.45(1H,d,J=9.2 Hz), 8.14(1H,brs,NH).

IR(KBr): 1707, 1562, 1260, 1140 cm$^{-1}$.

iii) Synthesis of 4,5-dihydro-4-(4-trifluoroacetamido
butan-1-yl)-3H-1,4,8b-
triazaacenaphthylene.dihydrochloride To a solution of 1100 mg (3.37 mmol) of 4,5-dihydro-4-(4-trifluoroacetamidobutan-1-yl)-3H,1,4,8b-triazaacenaphthylene in 20 ml of ethanol was added 0.70 ml (8.43 mmol) of 12N hydrochloric acid. The mixture was stirred for one hour at room temperature. The resulting precipitates were collected by filtration, washed with a small volume of ethanol and ether, and dried to afford 1160 mg of the desired compound (86.2%, a white crystals).

NMR(200 MHz,DMSO-d$_6$) δ: 1.50–1.82(4H,m), 3.04 (2H,m), 3.23(2H,m), 4.64(2H,s), 4.70(2H,s), 7.48(1H,d,J=7.4 Hz), 7.95–7.99(2H,m), 8.12(1H,s), 9.05(1H,t,J=5.2 Hz).

IR(KBr): 1716, 1549, 1224, 1186, 1149 cm$^{-1}$.

EXAMPLE 56

4,5-Dihydro-4-(4-trifluoroacetamidobutan-1-yl)-3H-1,4,8b-triazaacenaphthylene-3-one.hydrochloride i) 5-[N-tert-butoxycarbonyl-N-(4-trifluoroacetamido
butan-1-yl)aminomethyl]imidazo[1,2-a]pyridine To a solution of 29.38 g (93.47 mmol) of 5-[N-(4-trifluoroacetamidobutan-yl)aminomethyl]imidazo[1,2-a]pyridine in 200 ml of ethanol was added 20.40 g (93.47 mmol) of di-tert-butyl dicarbonate. The mixture was stirred for one hour at room temperature. The solvent was then distilled off under reduced pressure. The residue was purified by silica gel column chromatography (eluent; dichloromethane:methanol=20:1) to afford 30.12 g of the desired compound (77.8%, a colorless liquid).

NMR(200 MHz,CDCl$_3$)δ: 1.35–1.50(13H,m), 3.26(4H, m), 4.71(2H,s), 6.69(1H,d,J=6.6 Hz), 7.20(1H,t,J=8.8 Hz), 7.59–7.80(3H,m).

IR(Neat): 1713, 1686, 1556, 1147 cm$^{-1}$.

ii) Synthesis of 3-trichloroacetyl-5-[N-tert-butoxy
carbonyl-N-(4-trifluoroacetamidobutan-1-yl)
aminomethyl]imidazo[1,2-a]pyridine To a solution of 7.69 g (18.56 mmol) of 5-[N-tert-butoxycarbonyl-N-(4-trifluoroacetamidobutan-1-yl)amino methyl]imidazo[1,2-a]pyridine and 10.20 g (83.52 mmol) of 4-(N,N-dimethylamino)pyridine in 100 ml of THF was added 6.21 ml (55.67 mmol) of trichloroacetyl chloride. The reaction mixture was heated for 16 hours under reflux. The reaction mixture was poured into ice-water, and extracted with 100 ml of ethyl acetate. The organic layer was washed with 150 ml of a saturated aqueous saline solution, dried over magnesium sulfate, and distilled off the solvent under reduced pressure. The residue was purified by silica gel column chromatography (eluent; chloroform) to afford 4.98 g of the desired compound (48.0%, a pale yellow amorphous).

NMR(200 MHz,CDCl$_3$)δ: 1.26(9H,s), 1.68(4H,m), 3.43 (4H,m), 4.51(1H,s), 4.68(1H,s), 6.95(1H,brs,NH), 7.11(1H, d,J=7.0 Hz), 7.65–7.78(2H,m), 8.69(0.5H,s), 8.97(0.5H,s).

IR(KBr): 1701, 1514, 1178, 1153 cm$^{-1}$.

iii) Synthesis of 4,5-dihydro-4-(4-trifluoroacetamido
butan-1-yl)-3H-1,4,8b-triazaacenaphthylen-3-one To a solution of 2.60 g (4.64 mmol) of 3-trichloro acetyl-5-[N-tert-butoxycarbonyl-N-(4-trifluoroacetamidobutan-1-yl)aminomethyl]imidazo[1,2-a] pyridine in 20 ml of ethanol was added 1.90 ml (23.22 mmol) of 12N HCl. The mixture was stirred for one hour at room temperature. The solvent and excess volume of hydrochloric acid were distilled off under reduced pressure. The residue was dissolved in a mixture of 20 ml of purified water and 20 ml of ethanol. To this solution was added a 2N aqueous solution of sodium hydroxide to neutralize. This solution was extracted with 100 ml of dichloromethane. The organic layer was washed with 100 ml of a saturated aqueous saline solution, dried over magnesium sulfate, and distilled off the solvent under reduced pressure. The residue was purified by silica gel column chromatography (eluent; dichloromethane:methanol=20:1) to afford 1.26 g of the desired compound (75.9%, pale yellow amorphous).

NMR(200 MHz,CDCl$_3$)δ: 1.74(4H,m), 3.48(2H,m), 3.63 (2H,m), 5.03(2H,s), 6.77(1H,d,J=7.0 Hz), 7.28(1H,brs,NH), 7.34(1H,dd,J=9.2 Hz, 7.0 Hz), 8.15(1H,s).

IR(KBr): 1702, 1643, 1207, 1159 cm$^{-1}$ iv) Synthesis of 4,5-dihydro-4-(4-
trifluoroacetamidobutan-1-yl)-3H-1,4,8b-
trifluoroacetamidobutan-3-one.hydrochloride To a solution of 1.13 g (3.32 mmol) of 4,5-dihydro-4-(4-trifluoroacetamidobutan-1-yl)-3H-1,4,8b-triazaacenaphthylen-3-one in 20 ml of ethanol was added 0.42 ml (4.98 mmol) of 12N hydrochloric acid. The mixture was concentrated under reduced pressure. The resulting crystals was collected by filtration, which was washed with a small volume of ethanol and ether to afford 560 mg of the desired compound (44.8%, a white crystals.

NMR(200 MHz,DMSO-d$_6$)δ: 1.63(4H,m), 3.27(2H,m), 3.53(2H,m), 5.25(2H,s), 7.43(1H,d,J=7.4 Hz), 7.85(1H,d,J= 8.2 Hz), 8.02(1H,dd,J=8.2,7.4 Hz), 8.61(1H,s), 9.06(1H,t, NH,J=5.4 Hz).

IR(KBr): 1709, 1653, 1255 cm$^{-1}$.

EXAMPLE 57

4,5-Dihydro-4-(4-pentafluoropropionamidobutan-1-yl)-3H-1,4,8b-triazaacenaphthylene.dihydrochloride i) Synthesis of 5-[N-(4-
pentafluoropropionamidobutan-1-yl)aminomethyl]
imidazo[1,2-a]pyridine A suspension of 15.13 g (69.69 mmol) of 5-chloromethylimidazo[1,2-a]pyridine.hydrochloride and 12.29 g (139.38 mmol) of 1,4-diaminobutane in 150 ml of acetonitrile was heated for one hour under reflux while stirring. The reaction mixture was cooled to room temperature. The resulting precipitates of 1,4-diaminobutane.dihydrochloride were filtered off. To the filtrate were added 20.61 ml (139.38 mmol) of ethyl ester of pentafluoropropionic acid and 19.43 ml (139.38 mmol) of triethylamine. The mixture was stirred for one hour at room temperature. The solvent was then distilled off under reduced pressure, and the residue was extracted with 200 ml of dichloromethane. The organic layer was washed with 150 ml of a saturated aqueous saline solution, dried over magnesium sulfate, and distilled off the solvent. The residue was purified by silica gel column chromatography (eluent; dichloromethane:methanol=20:1) to afford 13.61 g of the desired compound (53.6%, a pale yellow liquid).

NMR(200 MHz,CDCl$_3$)δ: 1.54–1.75(4H,m), 2.72(2H,t, J=6.6 Hz), 3.39(2H,q,J=6.6 Hz), 4.03(2H,s), 6.78(1H,d,J= 6.8 Hz), 7.17(1H,dd,J=9.0 Hz, 6.8 Hz), 7.54(1H,d,J=9.0 Hz), 7.64(1H,s), 7.69(1H,s), 8.32(1H,brs,NH).

IR(Neat): 1710, 1550, 1221, 1161 cm$^{-1}$.

ii) Synthesis of 4,5-dihydro-4-(4-pentafluoropropionamidobutan-1-yl)-3H-1,4,8b-triazaacenaphthylene To a solution of 2620 mg (7.19 mmol) of 5-[N-(4-pentafluoropropionamidobutan-1-yl)aminomethyl]imidazo[1,2-a]pyridine in 10 ml of acetic acid was added 8.1 ml (107.88 mmol) of a 37% aqueous solution of formalin. The mixture was heated for 30 minutes at 100° C. The solvent was distilled off under reduced pressure, and the residue was dissolved in 100 ml of purified water. To this solution was added 2N sodium hydroxide to adjust the pH to 8, and extracted with 100 ml of dichloromethane. The organic layer was washed with 100 ml of a saturated aqueous saline solution, dried over magnesium sulfate, and distilled off the solvent under reduced pressure. The residue was purified by silica gel column chromatography to afford 2250 mg of the desired compound (83.2%, a pale yellow liquid).

NMR(200 MHz,CDCl$_3$)δ: 1.64–1.74(4H,m), 2.53(2H,m), 3.42(2H,m), 3.97(2H,s), 4.10(2H,s), 6.54(1H,d,J=6.8 Hz), 7.11(1H,dd,J=9.2,6.8 Hz), 7.34(1H,s), 7.41(1H,d,J=9.2 Hz), 8.63(1H,brs,NH).

IR(Neat): 1718, 1545, 1221, 1169 cm$^{-1}$.

iii) Synthesis of 4,5-dihydro-4-(4-pentafluoropropionamidobytan-1-yl)-3H-1,4,8b-triazaacenaphthylene.dihydrochloride To a solution of 2230 mg (5.93 mmol) of 4,5-dihydro-4-(4-pentafluoropropionamidobutan-1-yl)-3H-1,4,8b-triazaacenaphthylene in 35 ml of ethanol was added 1.22 ml (14.31 mmol) of 12N hydrochloric acid. The mixture was stirred for one hour at room temperature. The resulting precipitates was collected by filtration, washed with a small volume of ethanol and ether, and dried to afford 2120 mg of the desired compound (76.9%, white crystals).

NMR(200 MHz,CDCl$_3$)δ: 1.23–1.34(2H,m), 1.36–1.93 (2H,m), 3.20–3.30(4H,m), 4.85(2H,s), 4.94(2H,s), 7.54(1H, m), 8.00(2H,m), 8.21(1H,s), 9.66(1H,t,NH,J=5.4 Hz)

IR(Neat): 1712, 1549, 1223, 1167 cm$^{-1}$.

EXAMPLE 58

Synthesis of 4,5-dihydro-4-(4-pentafluoropropionamidobutan-1-yl)-3H-1,4,8b-triazaacenaphthylen-3-one.hydrochloride i) Synthesis of 5-[N-tert-butoxycarbonyl-N-(4-pentafluoropropionamidobutan-1-yl)aminomethyl]imidazo[1,2-a]pyridine To a solution of 12.41 g (34.06 mmol) of 5-[N-(4-pentafluoropropionamidobutan-1-yl)aminomethyl]imidazo[1,2-a]pyridine in 100 ml of ethanol was added 7.44 g (34.06 mmol) of di-tert-butyl dicarbonate. The mixture was stirred for one hour at room temperature. The solvent was distilled off under reduced pressure. The residue was purified by silica gel column chromatography (eluent;dichloromethane:methanol=20:1) to afford 11.78 g of the desired compound (74.5%, a colorless liquid).

NMR(200 MHz,CDCl$_3$)δ: 1.22–1.72(13H,s), 3.06–3.53 (4H,m), 4.71(2H,s), 6.70(1H,d,J=6.6 Hz), 7.20(1H,t,J=8.6 Hz), 7.45–7.95(4H,m).

IR(Neat): 1712, 1687, 1523, 1221, 1165 cm$^{-1}$.

ii) Synthesis of 3-trichloroacetyl-5-[N-tert-butoxycarbonyl-N-(4-pentafluoropropionamidobutan-1-yl)aminomethyl]imidazo[1,2-a]pyridine To a solution of 11.78 g (25.36 mmol) of 5-[N-tert-butoxycarbonyl-N-(4-pentafluoropropionamidobutan-1-yl)aminomethyl]imidazo[1,2-a]pyridine and 13.94 g (114.36 mmol) of 4-(N,N-dimethylamino)pyridine in 250 ml of chloroform was added 8.50 ml (76.09 mmol) of trichloroacetyl chloride. The mixture was heated for 16 hours under reflux. The reaction mixture was poured into ice-water, and extracted with 100 ml of chloroform. The organic layer was washed with 200 ml of a saturated aqueous saline solution, dried over magnesium sulfate, and the solvent was distilled off under reduced pressure. The residue was purified by silica gel column chromatography (eluent: chloroform) to afford 6.80 g of the desired compound (44.0%, a pale yellow liquid).

NMR(200 MHz,CDCl$_3$)δ: 1.00–1.45(9H,s), 1.55–1.80 (4H,m), 3.25–3.55(4H,m), 4.51(2H,s), 7.10(1H,d,J=7.4 Hz), 7.72(1H,t,J=8.8 Hz), 7.83(1H,d,J=8.6 Hz), 8.97(1H,s).

IR(Neat): 1724, 1678, 1670, 1219, 1157 cm$^{-1}$.

iii) Synthesis of 4,5-dihydro-4-(4-pentafluoropropionamidobutan-1-yl)-3H-1,4,8b-triazaacenaphthylen-3-one To a solution of 5.00 g (8.2 mmol) of 3-trichloroacetyl-5-[N-tert-butoxycarbonyl-N-(4-pentafluoropropionamidobutan-1-yl)aminomethyl]imidazo[1,2-a]pyridine in 100 ml of ethanol was added 3.4 ml (41.0 mmol) of 12N hydrochloric acid. The mixture was stirred for one hour at room temperature. The solvent and an excess volume of hydrochloric acid were distilled off under reduced pressure. The residue was dissolved in a mixture of 50 ml of purified water and 50 ml of ethanol. The solution was neutralized with 2N aqueous solution of sodium hydroxide. This solution was extracted with 150 ml of dichloromethane. The organic layer was washed with 150 ml of a saturated aqueous saline solution, dried over magnesium sulfate, and distilled off the solvent under reduced pressure. The residue was purified by silica gel column chromatography (eluent; dichloromethane:methanol=20:1) to afford 2.11 g of the desired compound (66.1%, a pale yellow solid).

NMR(200 MHz,CDCl$_3$)δ: 1.62–1.85(4H,m), 3.42–3.54 (2H,m), 3.55–3.68(2H,m), 5.02(2H,s), 6.76(1H,d,J=7.0 Hz), 7.27–7.56(1H,m), 7.52(1H,brs,NH), 7.53(1H,d,J=9.2 Hz), 8.15(1H,s).

IR(KBr): 1702, 1646, 1543, 1220, 1161 cm$^{-1}$.

iv) Synthesis of 4,5-dihydro-4-(4-pentafluoropropionamidobutan-1-yl)-3H-1,4,8b-triazaacenaphthylen-3-one.hydrochloride To a solution of 840 mg (2.15 mmol) of 4,5-dihydro-(4-pentafluoropropionamidobutan-1-yl)-3H-1,4,8b-triazaacenaphthylene-3-one in 15 ml of ethanol was added 0.27 ml (3.23 mmol) of 12N hydrochloric acid. The mixture was concentrated under reduced pressure. The resulting crystalline precipitates were collected by filtration, and washed with a small volume of ethanol and ether to afford 662 mg of the desired compound (72.1%, white crystals).

NMR(200 MHz,DMSO-d$_6$)δ: 1.58(4H,m), 3.26(2H,m), 3.55(2H,t,J=6.2 Hz), 5.24(2H,s), 7.42(1H,d,J=7.4 Hz), 7.84 (1H,d,J=9.2 Hz), 7.99(1H,dd,J=7.4,9.2 Hz),

IR(KBr): 1718, 1636, 1548, 1224, 1163 cm$^{-1}$.

EXAMPLE 59

Synthesis of 1-(1-tert-butoxycarbonyl-2-(S)-pyrrolidin-2-ylmethyl)-3-methyl-2H-1,4,7b-triazacyclopent[cd]inden-2-one i) Synthesis of 1-tert-butoxycarbonyl-2-(S)-pyrrolidin-2-ylmethyl p-toluenesulfonate To a solution of 10.18 g (50.58 mmol) of (S)-1-butoxycarbonylprolinol and 8.00 g (101.16 mmol) of pyridine in 100 cc of dichloromethane was added 9.64 g (50.58 mmol) of p-toluenesulfonyl chloride. The reaction mixture was stirred for two hours at room temperature, to which was added 100 cc of dichloromethane. The mixture was washed with 200 cc of purified water, then with 200 cc of a saturated aqueous saline solution. The organic layer was dried over magnesium sulfate. The solvent was distilled off under reduced pressure. The residue was purified by silica gel column chromatography (eluent; hexane:ethyl acetate=1:1) to afford 15.28 g of the desired compound (85.0%, a colorless liquid).

NMR(200 MHz,CDCl$_3$)δ: 1.37(9H,s), 1.78–1.93(4H,m), 2.44(3H,s), 3.25–3.31(2H,m), 3.89–4.09(3H,m), 7.34(2H,d, J=8.0 Hz), 7.77(2H,d,J=8.0 Hz).

IR(Neat): 1722, 1666, 1166 cm$^{-1}$.

ii) Synthesis of 1-(1-tert-butoxycarbonyl-2-(S)-pyrrolidin-2-ylmethyl)-3-methyl-2H-1,4,7b-triazacyclopent[cd]inden-2-one To a solution of 5.85 g (33.81 mmol) of 3-methyl-2H-1,4,7b-triazacyclopent[cd]inden-2-one in 100 cc of DMF was added, while stirring under ice-cooling, 1.35 g (33.81 mmol) of sodium hydride (purity 60%) under the atmosphere of argon. The mixture was stirred for 30 minutes under the atmosphere of argon. To the reaction mixture was added at 0° C., under the atmosphere of argon, a solution of 14.42 g (40.57 mmol) of 1-tert-butoxycarbonyl-2-(S)-pyrrolidin-2-ylmethyl p-toluenesulfonate in 10 cc of DMF. The mixture was heated for 3 hours at 100° C. under the atmosphere of argon. The reaction mixture was poured into ice-water, and extracted with 500 cc of ethyl acetate. The organic layer was washed with water three times, and further with 300 cc of a saturated aqueous saline solution, dried over magnesium sulfate, and the solvent was distilled off under reduced pressure. The residue was purified by silica gel column chromatography (eluent: ethyl acetate) to afford 7.54 g of the desired compound (64.9%, a pale yellow liquid).

NMR(200 MHz,CDCl$_3$)δ: 1.48(9H,s), 1.89(4H,m), 2.83 (3H,s), 4.23(3H,m), 7.10(d,J=7.4 Hz) and 6.79(d,J=7.4 Hz) for 1H, 7.49(1H,d,J=8.8 Hz), 7.70(1H,dd,J=7.4,8.8 Hz).

IR(Neat): 1710, 1679, 1166 cm$^{-1}$.

EXAMPLE 60

1,2-Dihydro-3-methyl-1-(1-trifluoromethanesulfonyl-2-(S)-pyrrolidin-2-ylmethyl)-1,4,7b-triazacyclopent[cd]inden-2-one.hydrochloride i) Synthesis of 1,2-dihydro-3-methyl-1-(2-(S)-pyrrolidin-2-ylmethyl-1,4,7b-triazacyclopent[cd]inden-2-one.dihydrochloride A solution of 3.42 g (10 mmol) of 1-(1-tert-butoxycarbonyl-2-(S)-pyrrolidin-2-ylmethyl)-3-methyl-2H-1,4,7b-triazacyclopent[cd]inden-2-one in a mixture of 25 cc of ethanol and 2 cc of 1N hydrochloric acid was stirred for one hour at room temperature. The solvent was distilled off under reduced pressure. To the residue was added 20 cc of toluene. The solvent was distilled off under reduced pressure. This procedure was repeated twice. The residue was dried sufficiently to afford 4.11 g of a crude product (100%, a while solid). This crude product was used in the subsequent reaction without purification.

NMR(200 MHz,D$_2$O)δ: 1.74–2.38(4H,m), 2.83(3H,s), 3.17–3.40(2H,m), 4.00(1H,m), 4.49(2H,d,J=6.4 Hz), 7.52 (1H,d,J=8.0 Hz), 7.75(1H,d,J=8.8 Hz), 8.23(1H,dd,J=8.0 Hz, 8.8 Hz).

IR(KBr): 3433, 1720, 1646, 1591 cm$^{-1}$.

ii) Synthesis of 1,2-dihydro-3-methyl-1-(1-trifluoromethanesulfonyl-2-(S)-pyrrolidin-2-ylmethyl)-1,4,7b-triazacyclopent[cd]inden-2-one To a suspension of 786 mg (2.5 mmol) of 1,2-dihydro-3-methyl-1-(2-(S)-pyrrolidin-2-ylmethyl)-1,4,7b-triazacyclopent[cd]inden-2-one.dihydrochloride in 15 cc of acetonitrile was added, while stirring under ice-cooling, 1.4 cc (10.0 mmol) of triethylamine, followed by addition of 5.14 g (6.25 mmol) of N-phenyltrifluoromethanesulfonimide. The reaction mixture was stirred for two hours at room temperature. The solvent was distilled off under reduced pressure. The residue was purified by silica gel chromatography (eluent: ethyl acetate) to afford 751 mg of the desired compound (80.2%, a pale yellow liquid).

NMR(200 MHz,CDCl$_3$)δ: 2.09(1H,m), 2.82(3H,s), 3.59 (2H,m), 4.34(3H,m), 7.02(1H,d,J=7.6 Hz), 7.53(1H,d,J=8.6 Hz), 7.78(1H,dd,J=7.6, 8.6 Hz).

IR(Neat): 1729, 1650, 1385 cm$^{-1}$.

iii) Synthesis of 1,2-dihydro-3-methyl-1-(1-trifluoromethanesulfonyl-2-(S)-pyrrolidin-2-ylmethyl)-1,4,7b-triazacyclopent[cd]inden-2-one.hydrochloride In a solvent consisting of 20 cc of ethanol and 0.1 cc of 12N hydrochloric acid was dissolved 800 mg (2.14 mmol) of 1,2-dihydro-3-methyl-1-(1-trifluoromethanesulfonyl-2-(S)-pyrrolidin-2-ylmethyl)-1,4,7b-triazacyclopent[cd] indene. The solvent was distilled off under reduced pressure. The residue was dried to afford 880 mg of the desired compound (100%, a white solid).

NMR(200 MHz,DMSO)δ: 1.98–2.18(5H,m), 2.85(3H,s), 3.50(2H,m), 4.19(2H,m), 7.58(1H,d,J=7.6 Hz), 7.81(1H,d, J=8.4 Hz), 8.25(1H,dd,J=7.6,8.4 Hz).

IR(KBr): 1733, 1651, 1385 cm$^{-1}$.

EXAMPLE 61

1,2-Dihydro-3-methyl-1-[1-(2,2,2-trifluoroethanesulfonyl)-2-(s)-pyrrolidin-2-ylmethyl]-1,4,7b-triazacyclopent[cd]inden-2-one.hydrochloride i) Synthesis of 1,2-dihydro-3-methyl-1-[1-(2,2,2-trifluoroethanesulfonyl)-2-(S)-pyrrolidin-2-ylmethyl]-1,4,7b-triazacyclopent[cd]inden-2-one To a suspension of 786 mg (2.5 mmol) of 1,2-dihydro-3-methyl-1-(2-(S)-pyrrolidin-2-ylmethyl)-1,4,7b-triazacyclopent[cd]inden-2-one.dihydrochloride in 15 cc of dichloromethane was added, while stirring under ice-cooling, 1.4 cc (10.0 mmol) of triethylamine, and added 0.33 cc (3.0 mmol) of 2,2,2-trifluoroethanesulfonyl chloride. The reaction mixture was stirred for one hour at room temperature. The solvent was then distilled off under reduced pressure. The residue was purified by silica gel chromatography (eluent: ethyl acetate) to afford 651 mg of the desired compound (67.1%, a white solid).

NMR(200 MHz,CDCl$_3$)δ: 2.00(3H,m), 2.26(1H,m), 3.21–3.58(2H,m), 3.86(2H,q,J=9.2 Hz), 4.12–4.34(3H,m), 7.10(1H,d,J=7.6 Hz), 7.52(1H,d,J=8.6 Hz), 7.77(1H,dd,J= 7.6,8.6 Hz).

IR(Neat): 1731, 1651, 1358 cm$^{-1}$.

ii) Synthesis of 1,2-dihydro-3-methyl-1-[1-(2,2,2-trifluoroethanesulfonyl)-2-(S)-pyrrolidin-2-ylmethyl]-1,4,7b-triazacyclopent[cd]inden-2-one.hydrochloride In a solvent consisting of 20 cc of ethanol and 0.1 cc of 12N hydrochloric acid was dissolved 626.1 mg (1.61 mmol)

of 1,2-dihydro-3-methyl-1-[1-(2,2,2-trifluoroethanesulfonyl]-2-(S)-pyrrolidin-2-ylmethyl]-1,4,7b-triazacyclopent[cd]inden-2-one. The solvent was distilled off under reduced pressure. The residue was dried to afford 685 mg of the desired compound (100%, a white solid).

NMR(200 MHz,DMSO-$d_6$)δ: 1.89–2.07(4H,m), 2.85(3H,s), 3.44(2H,m), 4.16–4.38(3H,m), 4.48(2H,g,J=10.1 Hz), 7.60(1H,d,J=8.0 Hz), 7.81(1H,d,J=8.0 Hz), 8.26(1H,t,J=8.0 Hz).

IR(KBr): 1738, 1650, 1589, 1358 cm$^{-1}$.

EXAMPLE 62

4,5-Dihydro-4-[2-[4-(trifluoromethanesulfonamido) phenyl]ethan-1-yl]-3H-1,4,8b-triazaacenaphthylene-3,5-dione.hydrochloride i) Synthesis of 4,5-dihydro-4-[2-[4-(trifluoromethanesulfonamide)phenyl]ethan-1-yl]-3H-1,4,8b-triazaacenaphthylene-3,5-dione To a suspension of 1.53 g (5.0 mmol) of 4,5-dihydro-4-[2-[4-(amino)phenyl]ethan-1-yl]-3H-1,4,8b-triazaacenaphthylene-3,5-dione and 1.05 ml (7.5 mmol) in methylene chloride (150 ml) was added dropwise, while stirring under ice-cooling, 1.21 ml (7.2 mmol) of trifluoromethanesulfonic acid anhydride. The mixture was stirred for 14 hours at room temperature. The reaction mixture was washed with 1N-HCl, which was dried over anhydrous magnesium sulfate. The solvent was distilled off, and the residue was eluted by column chromatography (eluent: ethyl acetate/methylene chloride=1:1) to afford 245 mg of 4,5-dihydro-4-[2-[4-[bis(trifluoromethanesulfonyl)imido]phenyl]ethan-1-yl]-3H-1,4,8b-triazaacenaphthylene-3,5-dione (8.6%, a pale yellow solid).

NMR(200 MHz,CDCl$_3$)δ: 3.10(2H,m), 4.43(2H,m), 7.34 (2H,d,J=8.4 Hz), 7.49(2H,d,J=8.4 Hz), 7.80(1H,dd,J=8.8, 7.6 Hz), 8.16(1H,dd,J=7.6, 1.0 Hz), 8.18(1H,dd,J=8.8, 1.0 Hz), 8.67(1H,s).

IR(KBr): 1710, 1666, 1632, 1444, 1340, 1290, 1223, 1163, 1128 cm$^{-1}$

And further elution (eluent: ethyl acetate/methylene chloride=1:1) afforded 77 mg of the desired compound (3.5%, a pale yellow solid).

NMR(200 MHz,DMSO-$d_6$)δ: 2.90(2H,m), 4.22(2H,m), 7.20(2H,d,J=8.4 Hz), 7.33(2H,d,J=8.4 Hz), 7.91(1H,dd,J=8.8, 7.4 Hz), 8.13(1H,dd,J=7.4, 1.0 Hz), 8.31(1H,dd,J=8.8, 1.0 Hz), 8.67(1H,s).

IR(KBr): 1707, 1662, 1633, 1510, 1371, 1340, 1284, 1209, 1167, 1137 cm$^{-1}$ ii) Synthesis of 4,5-dihydro-4-[2-[4-(trifluoromethanesulfonamido)phenyl]ethan-1-yl]-3H-1,4,8b-triazaacenaphthylene-3,5-dione.hydrochloride To a suspension of 59 mg (0.13 mmol) of 4,5-dihydro-4-[2-[4-(trifluoromethanesulfonamido)phenyl]ethan-1-yl]-3H-1,4,8b-triazaacenaphthylene-3,5-dione in 5 ml of methanol was added 0.05 ml of conc. hydrochloric acid. The solvent was distilled off to afford 64 mg of the desired compound (100%, a pale yellow solid).

NMR(200 MHz,DMSO-$d_6$)δ: 2.91(2H,m), 4.22(2H,m), 7.21(2H,d,J=8.4 Hz), 7.34(2H,d,J=8.4 Hz), 7.93(1H,dd,J=8.8, 7.4 Hz), 8.14(1H,dd,J=7.4, 1.0 Hz), 8.32(1H,dd,J=8.8, 1.0 Hz), 8.69(1H,s).

IR(KBr): 3099, 1724, 1681, 1649, 1348, 1209, 1144 cm$^{-1}$

EXAMPLE 63

3,4-Dihydro-3-[5-(tert-butoxycarbonylamino) penten-1-yl]-2-methyl-1,3,7b-triazacyclopent[cd] inden-4-one To a suspension of 355 mg (0.91 mmol) of 3,4-dihydro-3-[5-(phthalimido)pentan-1-yl]-2-methyl-1,3,7b-triazacyclopent[cd]inden-4-one in 15 ml of ethanol was added 229 mg (4.57 mmol) of hydrazinemonohydrate. The mixture was stirred for two hours while heating under reflux. After cooling the resulting precipitates were filtered off, and the filtrate was concentrated. To the concentrate was added 30 ml of chloroform. To the mixture were added 1.00 g (4.58 mmol) of di-tert-butyl dicarbonate and 0.38 ml (2.73 mmol) of triethylamine. The mixture was stirred for one hour at room temperature. The reaction mixture was washed with water and dried over anhydrous magnesium sulfate. The solvent was distilled off. The residue was purified by column chromatography (eluent: ethyl acetate/ethanol=10:1) to afford 244 mg of the desired compound (74.4%, a pale yellow foam).

NMR(200 MHz,CDCl$_3$)δ: 1.20–1.80(6H,m), 1.44(9H,s), 2.07(3H,s), 3.02(1H,m), 3.10(2H,m), 4.34(1H,m), 4.54(1H, br), 6.98(1H,dd,J=6.8, 1.2 Hz), 7.16(1H,dd,J=9.0, 6.8 Hz), 7.32(1H,dd,J=9.0, 1.2 Hz).

EXAMPLE 64

3,4-Dihydro-2-methyl-3-[5-(trifluoromethanesulfonamido) pentan-1-yl]-1,3,7b-triazacyclopent[cd]inden-4-one To a solution of 228 mg (0.64 mmol) of 3,4-dihydro-3-[5-(tert-butoxycarbonylamino)pentan-1-yl]-2-methyl-1,3,7b-triazacyclopent[cd]inden-4-one in 5 ml of methanol was added 5 ml of conc. hydrochloric acid. The mixture was stirred for 30 minute at room temperature. The solvent was distilled off. To the residue was added toluene, and the solvent was distilled off. To the residue were added 20 ml of acetonitrile, 0.89 ml (6.39 mmol) of triethylamine and 1.14 g (3.19 mmol) of N-phenyltrifluoromethanesulfonimide. The mixture was stirred for 20 hours at room temperature. The solvent was distilled off. To the residue was added chloroform. The mixture was washed with water and dried over magnesium sulfate. The solvent was distilled off. The residue was purified by column chromatography (eluent: ethyl acetate/ethanol=10:1) to afford 13 mg of the desired compound (5.2%, a pale yellow solid).

NMR(200 MHz,CDCl$_3$)δ: 1.20–1.80(6H,m), 2.08(3H,s), 3.02(1H,m), 3.18(2H,m), 4.33(1H,m), 7.02(1H,dd,J=6.8,1.2 Hz), 7.19(1H,dd,J=9.0, 6.8 Hz), 7.32(1H,dd,J=9.0,1.2 Hz), 8.64(1H,br)

EXAMPLE 65

4,5-Dihydro-4-(3-trifluoromethanesulfonamidopropan-1-yl)-3H-1,4,8b-triazaacenaphthylene.dihydrochloride i) Synthesis of 3-carbomethoxy-5-[N-tert-butoxycarbonyl-N-(3-trifluoromethanesulfonamidopropan-1-yl) aminomethyl]imidazo[1,2-a]pyridine To a solution of 581 mg (1.00 mmol) of 3-trichloroacetyl-5-[N-tert-butoxycarbonyl-N-(3- trifluoromethanesulfonamidopropan-1-yl)aminomethyl]imidazo[1,2-a]pyridine in 5.0 ml of methanol was added 0.46 ml (2.00 mmol) of a 25% methanol solution of sodium methylate. The mixture was stirred for 10 minutes at room temperature. The reaction mixture was poured into ice-water, which was neutralized with 1N HCl. The mixture was extracted with 50 ml of chloroform. The organic layer was washed with 50 ml of a saturated aqueous saline solution, and dried over magnesium sulfate. The solvent was distilled off under reduced pressure. The residue was purified by silica gel column chromatography (eluent: chloroform) to afford 462 mg of the desired compound (93.4%, a pale yellow liquid).

NMR(200 MHz,CDCl$_3$)δ: 1.32(9H,s), 1.83(2H,m), 3.35 (2H,brs), 3.49(2H,t,J=6.0 Hz), 3.93(3H,s), 4.85(2H,s), 6.84 (1H,d,J=7.2 Hz), 7.49(1H,t,J=7.2 Hz), 7.70(1H,d,J=8.8 Hz), 8.36(1H,s).

IR(Neat): 1699, 1680, 1512, 1471, 1419 cm$^{-1}$ ii) Synthesis of 3-hydroxymethyl-5-[N-tert-butoxycarbonyl-N-(3-trifluoromethanesulfonamidopropan-1-yl)aminomethyl]imidazo[1,2-a]pyridine To a solution of 396 mg (0.80 mmol) of 3-carbomethoxy-5-[N-tert-butoxycarbonyl-N-(3-trifluoromethanesulfonamidopropan-1-yl)aminomethyl]imidazo[1,2-a]pyridine in a mixture of 5.0 ml of THF and 1.0 ml of methanol was added, at room temperature, 87.12 mg (4.00 mmol) of lithium borohydride with small portions. The mixture was heated for 30 minutes under reflux. The reaction mixture was cooled to room temperature, and poured into ice-water. The mixture was neutralized with 1N HCl, and extracted with 50 ml of chloroform. The organic layer was washed with 50 ml of a saturated aqueous saline solution, which was dried over magnesium sulfate. The solvent was then distilled off under reduced pressure. The residue was purified by silica gel column chromatography (eluent; chloroform:methanol=20:1) to afford 269 mg of the desired compound (72%, a pale yellow liquid).

NMR(200 MHz,CDCl$_3$)δ: 1.40(9H,s), 1.83(2H,m), 3.35 (2H,t,J=6.4 Hz), 3.49(2H,t,J=6.4 Hz), 4.90(2H,s), 5.18(2H, s), 6.59(1H,d,J=7.4 Hz), 7.12–7.25(1H,m), 7.42–7.52(2H, m).

IR(Neat): 1695, 1497, 1470 cm$^{-1}$ iii) Synthesis of 4,5-dihydro-4-(3-trifluoromethanesulfonamidopropan-1-yl)-3H-1,4,8b-triazaacenaphthylene To a solution of 233 mg (0.50 mmol) of 3-hydroxymethyl-5-[N-tert-butoxycarbonyl-N-(3-trifluoromethanesulfonamidopropan-1-yl)aminomethyl]imidazo[1,2-a]pyridine in 5.0 ml of chloroform was added 0.36 ml (2.50 mmol) of trimethylsilyl iodide. The mixture was stirred for 18 hours at room temperature. The reaction mixture was poured into ice-water, which was neutralized with a saturated aqueous solution of sodium hydrogencarbonate, and extracted of the desired compound with 50 ml of chloroform. The organic layer was washed with 50 ml of a saturated aqueous saline solution and dried over magnesium sulfate, and the solvent was distilled off under reduced pressure. The residue was purified by silica gel column chromatography (eluent; chloroform:methanol=20:1) to afford 109 mg of the desired compound (62.8%, a pale yellow liquid).

NMR(200 MHz,CDCl$_3$)δ: 1.82(2H,m), 2.68(2H,m), 3.43 (2H,m), 3.91(2H,s), 4.01(2H,s), 6.53(1H,d,J=6.8 Hz), 7.10 (1H,dd,J=9.2,6.8 Hz), 7.27(1H,s), 7.39(1H,d,J=9.2 Hz), 8.27(1H,brs,NH)

IR(Neat): 1637, 1552, 1450, 1363 cm$^{-1}$ iv) Synthesis of 4,5-dihydro-4-(3-trifluoromethanesulfonamidopropan-1-yl)-3H-1,4,8b-triazaacenaphthylene.dihydrochloride To a solution of 248 mg (0.72 mmol) of 4,5-dihydro-4-(3-trifluoromethanesulfonamidopropan-1-yl)-3H-1,4,8b-triazaacenaphthylene in 5.0 ml of ethanol was added 0.18 ml (2.16 mmol) of 12N HCl. The mixture was stirred, and concentrated under reduced pressure. resulting precipitates were washed with a small volume of ethanol and ether to afford 253 mg of the desired compound (84.2%, a white solid).

NMR(200 MHz,DMSO-d$_6$)δ: 2.02(2H,m), 3.17(4H,m), 4.85(2H,s), 4.93(2H,s), 7.54(1H,m), 7.99–8.02(2H,m), 8.19 (1H,s), 9.39(1H,t,NH,J=5.6 Hz)

IR(Neat): 3430, 1660, 1550, 1441 cm$^{-1}$

EXAMPLE 66

4,5-Dihydro-4-[4-(2-trifluoromethanesulfonamidoethan-1-yl)phenyl]-3H-1,4,8b-triazaacenaphthylen-3-one.hydrochloride i) Synthesis of 5-[N-[4-(2-trifluorommethanesulfonamidoethan-yl)phenyl]aminomethyl]imidazo[1,2-a]pyridine A solution of 6.51 g (30.00 mmol) of 5-chloromethylimidazo[1,2-a]pyridine, 8.05 g (30.00 mmol) of 1-amino-4-(2-trifluoromethanesulfonamidoethan-1-yl)benzene and 8.4 ml (60.00 mmol) of triethylamine was heated for 3 hours under reflux. The reaction mixture was cooled to room temperature to cause formation of triethylamine hydrochloride, which was filtered off. The filtrate was concentrated under reduced pressure, and the concentrate was extracted with 150 ml of chloroform. The organic layer was washed with 150 ml of a saturated aqueous saline solution. The organic layer was dried over magnesium sulfate. The solvent was distilled off under reduced pressure. The residue was purified by silica gel column chromatography (eluent; ethyl acetate:ethanol=20:1) to afford 9.11 g of the desired compound (76.2%, a colorless liquid).

NMR(200 MHz,CDCl$_3$)δ: 2.37(2H,brs), 3.45(2H,t,J=8.2 Hz), 4.77(2H,brs), 6.48(2H,d,J=8.4 Hz), 6.64(2H,d,J=8.4 Hz), 6.85(1H,d,J=6.8 Hz), 7.21–7.29(1H,m), 7.74(1H,d,J= 7.6 Hz), 7.77(1H,s), 7.89(1H,s).

IR(Neat): 1628, 1518, 1387 cm$^{-1}$.

ii) Synthesis of 5-[N-tert-butoxycarbonyl-N-[4-(2-trifluoromethansulfonamidoethan-1-yl)phenylaminomethyl]imidazo[1,2-a]pyridine To a solution of 2130 mg (5.35 mmol) of 5-[N-[4-(2-trifluoromethansulfonamidoethan-1-yl)phenyl]aminomethyl]imidazo[1,2-a]pyridine in 30 ml of ethanol was added 1167 mg (5.35 mmol) of di-tert-butyl dicarbonate. The mixture was stirred for 2 hours at room temperature. The solvent was distilled off under reduced pressure. The residue was purified by silica gel column chromatography (eluent; ethyl acetate:ethanol=20:1) to afford 2.0 g of the desired compound (75.0%, colorless amorphous).

NMR(200 MHz,CDCl$_3$)δ: 1.50(9H,s),2.39(2H,brs), 3.48 (2H,t,J=8.0 Hz), 4.78(2H,brs), 6.50(1H,brs,NH), 6.75(2H,d, J=8.4 Hz), 6.84(1H,d,J=7.0 Hz), 7.15(2H,d,J=8.4 Hz), 7.25–7.29(1H,m), 7.75(1H,d,J=8.4 Hz), 7.77(1H,s), 7.92 (1H,s).

IR(Neat): 1710, 1630, 1522, 1390 cm$^{-1}$ iii) Synthesis of 3-trichloroacetyl-5-[N-tert-butoxy carbonyl-N-[4-(2-trifluoromethanesulfonamidoethan-1-yl) phenyl] aminomethyl]imidazo[1,2-a]pyridine To a solution of 2.00 g of 5-[N-tert-butoxycarbonyl-N-[4-(2-trifluoromethanesulfonamidoethan-1-yl)phenyl] aminomethyl]imidazo[1,2-a]pyridine and 1.47 g (12.04 mmol) of 4-(N,N-dimethylamino)pyridine in 20 ml of chloroform was added dropwise 1.34 ml (12.04 mmol) of trichloroacetyl chloride at room temperature. The reaction mixture was heated for 18 hours under reflux. The reaction mixture was poured into ice-water. The mixture was neutralized with a saturated aqueous solution of sodium hydrogencarbonate, and extracted with 100 ml of chloroform. The organic layer was washed with 100 ml of purified water three times and further with 100 ml of a saturated aqueous saline solution, and dried over magnesium sulfate. The solvent was distilled off under reduced pressure. The residue was purified by silica gel column chromatography (eluent: chloroform) to afford 1415 mg of the desired compound (54.8%, a yellow liquid).

NMR(200 MHz,CDCl$_3$)δ: 1.23(9H,s), 2.38(2H,brs), 3.48 (2H,t,J=8.0 Hz), 4.58(2H,brs), 6.52(1H,brs,NH), 6.80(2H,d, J=8.4 Hz), 7.24(1H,d,J=7.0 Hz), 7.19(2H,d,J=8.4 Hz), 7.76–7.80(1H,m), 7.81(1H,d,J=8.4 Hz), 8.96(1H,s)

IR(KBr): 1710, 1690, 1525, 1360 cm$^{-1}$ iv) Synthesis of 4,5-dihydro-4-[4-(2-trifluoromethanesulfonamidoethan-1-yl)phenyl]-3H-1,4,8b-triazaacenaphthylen-3-one To a solution of 644 mg (1.00 mmol) of 3-trichloroacetyl-5-[N-tert-butoxycarbonyl-N-[4-(2-trifluoromethanesulfonamidoethan-1-yl)phenyl] aminomethyl]imidazo[1,2-a]pyridine in 5 ml of chloroform was added dropwise 0.29 ml (2.00 mmol) of trimethylsilyl iodide at room temperature. The reaction mixture was stirred for 30 minutes at room temperature, and poured into ice-water. The mixture was neutralized with a saturated aqueous solution of sodium hydrogencarbonate. To the mixture was added 50 ml of chloroform for extraction of the desired compound. The organic layer was washed with 50 ml of a saturated aqueous saline solution, and dried over magnesium sulfate. The solvent was distilled off under reduced pressure. The residue was purified by silica gel column chromatography (eluent; chloroform:methanol=20:1) to afford 195.7 mg of the desired compound (46.1%, a pale yellow solid).

NMR(200 MHz,CDCl$_3$)δ: 2.36(2H,brs), 3.45(2H,t,J=8.0 Hz), 5.08(2H,s), 6.51(1H,brs,NH), 6.85(2H,d,J=8.4 Hz), 6.89(2H,d,J=7.0 Hz), 7.19(2H,d,J=8.4 Hz), 7.34–7.40(1H, m), 7.75(1H,d,J=8.4 Hz), 8.12(1H,s)

IR(KBr): 1708, 1661, 1535, 1430 cm$^{-1}$ v) Synthesis of 4,5-dihydro-4-[4-(2-trifluoromethanesulfonamidoethan-1-yl)phenyl]-3H-1,4,8b-triazaacenaphthylen-3-one.hydrochloride To a solution of 85 mg (0.2 mmol) of 4,5-dihydro-4-[4-(2-trifluoromethanesulfonamidoethan-1-yl)phenyl]-3H-1,4,8b-triazaacenaphthylen-3-one in 5.0 ml of ethanol was added 0.04 ml (0.5 mmol) of 12N HCl. The mixture was stirred at room temperature, and concentrated under reduced pressure. The resulting precipitates were collected by filtration, and washed with a small volume of ethanol and ether to afford 64 mg of the desired compound (69.4%, a pale yellow solid).

NMR(200 MHz,DMSO-d$_6$)δ: 2.22(2H,brs), 3.38(2H,t,J=6.8 Hz), 5.28(2H,s), 7.25(2H,d,J=8.4 Hz), 7.49(2H,d,J=7.2 Hz), 7.59(2H,d,J=8.4 Hz), 7.94–8.00(1H,m), 8.35(1H,d,J=8.4 Hz), 8.72(1H,s)

IR(KBr): 1720, 1665, 1443, 1385 cm$^{-1}$

EXAMPLE 67

1-[1-(tert-Butoxycarbonyl)piperidin-4-ylmethyl]-1,2-dihydro-3-methyl-1,4,7b-triazacyclopent[cd]inden-2-one To a suspension of 735 mg (4.24 mmol) of 1,2-dihydro-3-methyl-1,4,7b-triazacyclopent[cd]inden-2-one in 15 ml of DMF was added, while stirring under ice-cooling, 187 mg (4.68 mmol) of 60% sodium hydride (dispersion in oil). The mixture was stirred for 20 minutes at the same temperature. To the mixture was added a solution of 1.18 g (4.24 mmol) of 4-bromomethyl-1-tert-butoxycarbonylpiperidine in 5 ml of DMF. The mixture was stirred for one hour at 100° C. After cooling, the reaction mixture was poured into water and extracted with ethyl acetate. The extract was washed with water and brine, dried over anhydrous magnesium sulfate. The solvent was distilled off, and the residue was purified by column chromatography (eluent: ethyl acetate) to give 988 mg of the desired compound (62.8%, pale yellow solid).

NMR(200 MHz,CDCl$_3$)δ: 1.41(2H,m), 1.45(9H,s), 1.71 (2H,m), 2.11(1H,m), 2.68(2H,m), 2.83(3H,s), 3.95(2H,d,J=7.2 Hz), 4.15(2H,m), 6.79(1H,d,J=7.6 Hz), 7.50(1H,d,J=8.6 Hz), 7.72(1H,dd,J=8.6, 7.6 Hz).

EXAMPLE 68

1,2-dihydro-1-[1-(trifluoromethanesulfonyl) piperidin-4-ylmethyl]-3-methyl-1,4,7b-triazacyclopent[cd]inden-2 -one.hydrochloride i) Synthesis of 1,2-dihydro-1-(piperidin-4-ylmethyl)-3-methyl-1,4,7b-triazacyclopent[cd]inden-2-one To a solution of 3.65 g (9.85 mmol) of 1-[1-(tert-butoxycarbonyl)piperidin-4-ylmethyl]-1,2-dihydro-3-methyl-1,4,7b-triazacyclopent[cd]inden-2-one in 30 ml of methanol was added 15 ml of conc. HCl. The mixture was stirred for 1.5 hours at room temperature. The solvent was distilled off. To the residue was added chloroform and 2N agueous solution of sodium hydroxide to make alkaline. The mixture was extracted with chloroform. The extract was dried over anhydrous magnesium sulfate. The solvent was distilled off to give 2.316 g of the desired compound (86.9%, pale yellow solid). This product was used in the subsequent reaction without further purification.

ii) Synthesis of 1,2-dihydro-1-[1-(trifluoromethanesulfonyl)piperidin-4-ylmethyl]-3-methyl-1,4,7b-triazacyclopent[cd]inden-2-one To a solution of 1.09 g (4.03 mmol) of 1,2-dihydro-1-(piperidin-4-ylmethyl)-3-methyl-1,4,7b-triazacyclopent[cd]inden-2-one and 0.84 ml (6.03 mmol) of triethylamine in 30 ml of methylene chloride was added 1.73 g (4.84 mmol) of N-phenyltrifluoromethanesulfonimide. The mixture was stirred for 14 hours at room temperature. The reaction mixture was washed with water, dried over anhydrous magnesium sulfate. The solvent was distilled off, and the residue was purified by column chromatography (eluent: ethyl acetate) to give 522 mg of the desired compound (32.2%, pale yellow solid).

NMR(200 MHz,CDCl$_3$)δ: 1.50(2H,m), 1.87(2H,m), 2.20 (1H,m), 2.83(3H,s), 3.02(2H,m), 3.99(2H,d,J=7.0 Hz), 4.00 (2H,m), 6.77(1H,d,J=7.4 Hz), 7.51(1H,d,J=8.6 Hz), 7.73 (1H,dd,J=8.6, 7.4 Hz).

iii) Synthesis of 1,2-dihydro-1-[1-(trifluoromethanesulfonyl)piperidin-4-ylmethyl]-3-methyl-1,4,7b-triazacyclopent[cd]inden-2-one.hydrochloride To a suspension of 494 mg (1.23 mmol) of 1,2-dihydro-1-[1-(trifluoromethanesulfonyl)piperidin-4-ylmethyl]-3-methyl-1,4,7b-triazacyclopent[cd]inden-2-one in 15 ml of methanol was added 0.13 ml of conc. HCl. The solvent was distilled off. The residue was treated with acetone and diethylether to give 526 mg of the desired compound (97.6%, colorless solid).

m.p. 150–152° C.

Elemental Analysis for C$_{16}$H$_{17}$N$_4$O$_3$SF$_3$.HCl.H$_2$O:

Calcd.: C, 42,06; H, 4.41; N, 12.26. Found : C, 42.07; H, 4.27; N, 12.07.

NMR(200 MHz,DMSO-d$_6$)δ: 1.38(2H,m), 1.84(2H,m), 2.16(1H,m), 2.79(3H,s), 3.14(2H,m), 3.84(4H,m), 7.57(1H, d,J=7.6 Hz), 7.76(1H,d,J=8.4 Hz), 8.14(1H,dd,J=8.4, 7.6 Hz).

EXAMPLE 69

1-[1-(tert-Butoxycarbonyl)piperidin-4-yl]-1,2-dihydro-3-methyl-1,4,7b-triazacyclopent[cd]inden-2-one The title compound was synthesized in the same manner as example 67.

NMR(200 MHz,CDCl$_3$)δ: 1.52(9H,s), 2.00(2H,m), 2.17 (2H,m), 2.83(3H,s), 2.94(2H,m), 4.37(2H,m), 4.72(1H,m), 6.90(1H,d,J=7.8 Hz), 7.50(1H,d,J=8.4 Hz), 7.69(1H,dd,J= 8.4, 7.8 Hz).

EXAMPLE 70

1-[2-[1-(tert-Butoxycarbonyl)piperidin-4-yl]ethan-1-yl]-1,2-dihydro-3-methyl-1,4,7b-triazacyclopent[cd]inden-2-one The title compound was synthesized in the same manner as example 67.

NMR(200 MHz,CDCl$_3$)δ: 1.18(2H,m), 1.46(9H,s), 1.50 (1H,m), 1.70–1.86(4H,m), 2.68(2H,m), 2.83(3H,s), 4.11 (4H,m), 6.78(1H,d,J=7.6 Hz), 7.50(1H,d,J=8.6 Hz), 7.71 (1H,dd,J=8.6, 7.6 Hz).

EXAMPLE 71

1,2-Dihydro-1-[2-[1-(trifluoromethanesulfonyl) piperidin-4-yl]ethan-1-yl]-3-methyl-1,4,7b-triazacyclopent[cd]inden-2-one.hydrochloride The title compound was synthesized in the same manner as Example 68.

m.p. 169–170° C.

Elemental Analysis for C$_{17}$H$_{19}$N$_4$O$_3$SF$_3$.HCl:

Calcd.: C, 45.09; H, 4.45; N, 12.37. Found : C, 44.95; H, 4.42; N, 12.13.

NMR(200 MHz,DMSO-d$_6$)δ: 1.23(2H,m), 1.58(1H,m), 1.76(2H,m), 1.91(2H,m), 2.75(3H,s), 3.11(2H,m), 4.10(2H, t,J=7.2 Hz), 7.46(1H,d,J=7.6 Hz), 7.70(1H,d,J=8.8 Hz), 8.04 (1H,dd,J=8.8, 7.6 Hz).

EXAMPLE 72

1,2-Dihydro-3-methyl-1-[4-(N-methyl-N-trifluromethanesulfoneamide)butan-1-yl]-1,4,7b-triazacyclopent[cd]inden-2-one.hydrochloride i) Synthesis of 1,2-dihydro-3-methyl-1-[4-(N-methyl-N-trifluoromethanesulfonamide)butan-1-yl]-1,4,7b-triazacyclopent[cd]indene-2-one To a solution of 1.129 g (3.0 mmol) of 1,2-dihydro-3-methyl-1-[4-(trifluoromethanesulfonamide)butan-1-yl]-1,4, 7b-triazacyclopent[cd]inden-2-one in 30 ml of DMF was added, while stirring under ice-cooling, 144 mg (3.6 mmol) of 60% sodium hydride (dispersion in oil). The mixture was stirred for 15 minutes at the same temperature. To the mixture was added 0.56 ml of methyl iodide. The mixture was stirred for 14 hours at room temperature. The reaction mixture was poured into water and extracted with ethyl acetate. The mixture was washed with water and dried over anhydrous magnesium sulfate. The solvent was distilled off, and the residue was purified by column chromatography (eluent: ethyl acetate) to give 170 mg of the desired compound (14.5%, pale brown solid).

NMR(200 MHz,CDCl$_3$)δ: 1.65–2.02(4H,m), 2.83(3H,s), 3.01(3H,d,J=1.2 Hz), 3.42(2H,m), 4.13(2H,t,J=6.8 Hz), 6.85 (1H,d,J=7.4 Hz), 7.51(1H,d,J=8.6 Hz), 7.73(1H,dd,J=8.6, 7.6 Hz).

ii) Synthesis of 1,2-dihydro-3-methyl-1-[4-(N-methyl-N-trifluoromethanesulfonamide)butan-1-yl]-1,4,7b-triazacyclopent[cd]indene-2-one.hydrochloride To a solution of 168 mg (0.43 mmol) of 1,2-dihydro-3-methyl-1-[4-(N-methyl-N-trifluoromethene sulfonamide) butan-1-yl]-1,4,7b-triazacyclopent[cd]indene-2-one in 5 ml of methanol was added 0.05 ml of conc. HCl. The solvent was distilled off. The residue was washed with acetone to give 163 mg of the desired compound (88.6%, yellow solid).

m.p. 133–135° C.

Elemental Analysis for C$_{15}$H$_{17}$N$_4$O$_3$SF$_3$.HCl:

Calcd.: C, 42.21; H, 4.25; N, 13.13. Found : C, 42.09; H, 4.26; N, 12.95.

NMR(200 MHz,DMSO-d$_6$)δ: 1.58–1.85(4H,m), 2.78(3H, s), 2.99(3H,d,J=1.2 Hz), 3.40(2H,m), 4.12(2H,t,J=6.4 Hz), 7.53(1H,d,J=7.6 Hz), 7.74(1H,d,J=8.6 Hz), 8.11(1H,dd,J= 8.6, 7.6 Hz).

EXAMPLE 73

1-[4-(tert-Butoxycarbonylamino)butan-1-yl]-1,2-dihydro-1,4,7b-triazacyclopent[cd]inden-2-one To a solution of 1.67 g (8.87 mmol) of 4-tert-butoxycarbonylamino-1-butylamine and 1.53 g (11.8 mmol) of N,N-diisopropylethylamine in 30 ml of acetonitrile was added 1.762 g (5.91 mmol) of 5-chloro-3-trichloroacetylimidazo[1,2-a]pyridine. The mixture was heated for 17 hours under reflux with stirring. The solvent was distilled off. To the residue was added chloroform. The residue was washed with water and dried over anhydrous magnesium sulfate. The solvent was distilled off, and the residue was purified by column chromatography (eluent: ethyl acetate) to give 453 mg of 5-[4-(tert-butoxycarbonylamino)butan-1-ylamino]-3-[4-(tert-butoxycarbonylamino)butan-1-ylcarbamoyl]imidazo[1,2-a] pyridine(14.8%, pale brown solid) as fraction 1, NMR(200 MHz,CDCl$_3$)δ: 1.44(18H,s), 1.40–2.00(8H, m), 3.05–3.32(6H,m), 3.49(2H,m), 4.83(2H,br), 5.90(1H,d), 6.99(1H,d,J=8.6 Hz), 7.03(1H,br), 7.31(1H,dd,J=8.6,7.8 Hz), 8.06(1H,s), 8.87(1H,br). and to give 583 mg of the desired compound (29.8%, pale brown solid) as fraction 2, NMR(200 MHz,CDCl$_3$)δ: 1.43(9H,s), 1.62(2H,m), 1.91 (2H,m), 3.22(2H,m), 4.12(2H,t,J=7.2 Hz), 4.89(1H,br), 6.96 (1H,d,J=7.4 Hz), 7.63(1H,d,J=8.8 Hz), 7.77(1H,dd,J=8.8, 7.4 Hz), 8.33(1H,s).

and was eluted (eluent: ethyl acetate/ethanol=10:1) to give 508 mg of 5-chloro-3-[4-tert-butoxycarbonylamino) butan-1-ylcarbamoyl]imidazo[1,2-a]pyridine(23.4%, pale brown solid).

NMR(200 MHz,CDCl$_3$)δ: 1.43(9H,s), 1.50–1.80(4H,m), 3.19(2H,m), 3.52(2H,m), 4.64(1H,br), 6.52(1H,br), 6.98 (1H,dd,J=7.2, 1.0 Hz), 7.28(1H,dd,J=9.0, 7.2 Hz), 7.63(1H, dd,J=9.0, 1.0 Hz), 7.86(1H,s).

EXAMPLE 74

1,2-Dihydro-1-[4-(trifluoromethanesulfonamide) butan-1-yl)-1,4,7b-triazacyclopent[cd]inden-2-one.hydrochloride i) Synthesis of 1-[4-(amino)butan-1-yl]-1,2-dihydro-1,4,7b-triazacyclopent[cd]inden-2-one.dihydrochloride To a solution of 548 mg (1.66 mmol) of 1-[4-tert-butoxycarbonylamino)butan-1-yl]-1,2-dihydro-1,4,7b-triazacyclopent[cd]inden-2-one in 10 ml of methanol was added dropwise 10 ml of conc. HCl. The mixture was stirred for one hour at room temperature. The solvent was distilled off. To the residue was added acetone. The resulting solid was collected by filtration and washed with acetone to give 400 mg of the desired compound (79.5%, grayish white solid).

Elemental Analysis for C$_{12}$H$_{14}$N$_4$O.2HCl:

Calcd.: C, 44.87; H, 5.65; N, 17.44. Found : C, 45.27; H, 5.48; N, 17.56

NMR(200 MHz,D$_2$O)δ: 1.75(2H,m), 1.95(2H,m), 3.02 (2H,m), 4.22(2H,t,J=6.8 Hz), 7.58(1H,d,J=7.8 Hz), 7.88(1H, d,J=8.8 Hz), 8.32(1H,dd,J=8.8, 7.8 Hz), 8.71(1H,s).

ii) Synthesis of 1,2-dihydro-1-[4-(trifluoromethanesulfonamide)butan-1-yl)-1,4,7b-triazacyclopent[cd]indene-2-one To a suspension of 350 mg (1.15 mmol) of 1-[4-(amino) butan-1-yl]-1,2-dihydro-1,4,7b-triazacyclopent[cd]inden-2-one.dihydrochloride was added 0.64 ml (4.62 mmol) of triethylamine. The mixture was stirred for 10 minutes at room temperature. To the mixture was added 619 mg (1.73 mmol) of N-phenyltrifluoromethanesulfonimide. The mixture was stirred for 66 hours at room temperature. The solvent was distilled off. The residue was purified by column chromatography(eluent: ethyl acetate) to give 97 mg of the desired compound (23.2%, colorless solid).

NMR(200 MHz,CDCl$_3$-DMSO-d$_6$)δ: 1.70(2H,m), 1.97 (2H,m), 3.27(2H,m), 4.12(2H,t,J=7.0 Hz), 6.98(1H,d,J=7.4 Hz), 7.65(1H,d,J=8.6 Hz), 7.81(1H,dd,J=8.6, 7.4 Hz), 8.33 (1H,s), 8.70(1H,br).

iii) Synthesis of 1,2-dihydro-1-[4-(trifluoromethanesulfonamide)butan-1-yl)-1,4,7b-triazacyclopent[cd]inden-2-one.dihydrochloride To a suspension of 89 mg (0.25 mmol) of 1,2-dihydro-1-[4-(trifluoromethanesulfonamide)butan-1-yl)-1,4,7b-triazacyclopent[cd]inden-2-one in 5 ml of methanol was added 0.05 ml of conc. HCl. The solvent was distilled off. To the residue was added acetone, and the solvent was distilled off to give 98 mg of the desired compound (100%, coloress solid).

NMR(200 MHz,DMSO-d$_6$) δ: 1.59(2H,m), 1.84(2H,m), 3.19(2H,m), 4.12(2H,t,J=6.8 Hz), 7.57(1H,d,J=7.6 Hz), 7.84 (1H,d,J=8.6 Hz), 8.15(1H,dd,J=8.6, 7.6 Hz), 8.84(1H,s), 9.39(1H,brt,J=5.6 Hz).

EXAMPLE 75

1,2-Dihydro-1-(1-tert-butoxycarbonylpiperidin-4-ylmethyl)-1,4,7b-triazacyclopento[cd]inden-2-one i) Synthesis of (1-tert-butoxycarbonylpiperidin-4-ylmethyl)methanesulfonate To a solution prepared by dissolving 4.31 g (20.0 mM) of 1-tert-butoxycarbonyl-4-hydroxymethylpiperidine and 5.54 ml (40.0 mM) of triethylamine in 50 ml of THF was added 1.86 ml (24.0 mM) of methanesulfonyl chloride dropwise at 0° C. After completion of dropwise addition, the reaction mixture was stirred at room temperature for 30 minutes. After completion of the reaction, the reaction mixture was poured in 50 ml of iced water and extracted with 50 ml of ethyl acetate. The organic layer was washed with 50 ml of saturated aqueous NaCl solution and dried over anhydrous sodium sulfate (Na$_2$SO$_4$). The solvent was then distilled off under reduced pressure and the residue was dried in vacuo to provide 5.86 g (yield 100%) of the title compound as light-yellow liquid.

$^1$H-NMR(200 MHz,CDCl$_3$) δ: 1.18–2.32(2H,m), 1.46 (9H,s), 1.68–1.82(2H,m), 1.82–2.10(1H,m), 2.61–2.82(2H, m), 3.02(3H,s), 4.07(2H,d,J=6.2 Hz), 4.09–4.24(2H,m).

ii) Synthesis of 1,2-dihydro-1-(1-tert-butoxycarbonylpiperidin-4-ylmethyl)-1,4,7b-triazacyclopent[cd]inden-2-one A mixture containing 5.68 g (20.0 mM) of (1-tert-butoxycarbonylpiperidin-4-ylmethyl) methanesulfonate, 4.35 g (20.0 mM) of 1,2-dihydro-1,4,7b-triazacyclopent[cd] inden-2-one.2NaCl, and 3.58 ml (24.0 mM) of DBU in 50 ml of DMF was heated at 80° C. for 2 hours. After completion of the reaction, the reaction mixture was poured in 50 ml of iced water and extracted with 100 ml of ethyl acetate. The organic layer was washed with 50 ml of purified water twice and, then, with 50 ml of saturated aqueous NaCl solution and dried over Na$_2$SO$_4$. The solvent was then distilled off under reduced pressure and the residue was purified by silica gel column chromatography (eluent: ethyl acetate-ethanol=10:1) to provide 3.00 g (yield 42.1%) of the title compound as a brown amorphous substance.

$^1$H-NMR(200 MHz,CDCl$_3$) δ: 1.16–2.40(2H,m), 1.45 (9H,s), 1.62–1.81(2H,m), 2.01–2.24(1H,m), 2.57–2.79(2H, m), 3.97(2H,d,J=7.4 Hz), 4.05–4.29(2H,m), 6.86(1H,d,J= 7.4 Hz), 7.66(1H,d,J=8.8 Hz), 7.88(1H,dd,J=8.8, 7.4 Hz), 8.37(1H,s).

EXAMPLE 76

1,2-Dihydro-1-[2-(1-tert-butoxycarbonylpiperidin-4-yl)ethan-1-yl]-1,4,7b-triazacyclopent[cd]inden-2-one To a solution prepared by dissolving 8.26 g (36.0 mM) of 2-(1-tert-butoxycarbonylpiperidin-4-yl)ethanol and 10.0 ml (72.0 mM) of triethylamine in 50 ml of ether was added 3.34 ml (43.2 mM) of methanesulfonyl chloride dropwise at 0° C.

After completion of dropwise addition, the reaction mixture was stirred at room temperature for 30 minutes. After completion of the reaction, the reaction mixture was poured in 100 ml of iced water and the mixture was extracted with 100 ml of ethyl acetate. The organic layer was washed with 100 ml of saturated aqueous NaCl solution and dried over anhydrous magnesium sulfate ($MgSO_4$) and the solvent was distilled off under reduced pressure to recover the mesylate as solid. To a solution prepared by dissolving this mesylate and 10.37 g (36.0 mM) of 1,2-dihydro-1,4,7b-triazacyclopent[cd]inden-2-one.2NaCl in 25 ml of DMF was added 6.46 ml (43.2 mM) of DBU and the mixture was heated at 80° C. for 2 hours. After completion of the reaction, the reaction mixture was poured in iced water and the mixture was extracted with 200 ml of ethyl acetate. The organic layer was washed with 200 ml of purified water 3 times and further with 200 ml of saturated aqueous NaCl solution and dried over $MgSO_4$. The solvent was then distilled off under reduced pressure and the residue was purified by silica gel column chromatography (eluent: ethyl acetate) to provide 9.10 g (yield 68.2%) of the title compound as light-yellow solid.

$^1$H-NMR(200 MHz,$CDCl_3$) δ: 1.08–1.34(2H,m), 1.46 (9H,s), 1.42–1.63(1H,m), 1.72–1.91(4H,m), 2.57–2.83(2H, m), 3.98–4.24(4H,m), 6.87(1H,d,J=7.4 Hz), 7.66(1H,d,J= 8.6 Hz), 7.79(1H,dd,J=8.6, 7.4Hz), 8.36(1H,s).

IR(KBr): 1704, 1685, 1624, 1431 $cm^{-1}$.

EXAMPLE 77

1,2-Dihydro-1-[2-(1-(tert-butoxycarbonyl)piperidin-4-yl)ethan-1-yl]-1,4,7b-triazacyclopent[cd]inden-2-one To a solution prepared by dissolving 5.73 g (25.0 mM) of 2-[(1-tert-butoxycarbonyl)piperidin-4-yl]ethanol and 7.0 ml (50.0 mM) of triethylamine in 50 ml of ether was added 2.3 ml (30.0 mM) of methanesulfonyl chloride dropwise at 0° C. After completion of dropwise addition, the reaction mixture was stirred at room temperature for 30 minutes. After completion of the reaction, the reaction mixture was poured in 100 ml of iced water and the mixture was extracted with 100 ml of ethyl acetate. The organic layer was washed with 100 ml of saturated aqueous NaCl solution and dried over $MgSO_4$ and the solvent was distilled off under reduced pressure to recover 6.88 g of the mesylate as solid. To 50 ml of DMF was added 6.88 g (22.38 mM) of this mesylate as well as 4.46 g (24.62 mM) of 1,2-dihydro-1,4,7b-triazacyclopent[cd]inden-2-one sodium salt and the mixture was heated at 100° C. for 1 hour. After completion of this reaction, the reaction mixture was poured in iced water and the mixture was extracted with 200 ml of ethyl acetate. The organic layer was washed with 200 ml of purified water 3 times and further with 200 ml of saturated aqueous NaCl solution and dried over $MgSO_4$. The solvent was then distilled off under reduced pressure and the residue was rinsed with ether to provide 5.10 g (yield 55.9%) of the title compound as white solid.

$^1$H-NMR(200 MHz,$CDCl_3$) δ: 1.08–1.34(2H,m), 1.46 (9H,s), 1.42–1.63(1H,m), 1.72–1.91(4H,m), 2.57–2.83(2H, m), 3.98–4.24(4H,m), 6.87(1H,d,J=7.4 Hz), 7.66(1H,d,J= 8.6 Hz), 7.79(1H,d,J=8.6, 7.4 Hz), 8.36(1H,s).

IR(KBr): 1704, 1685, 1624, 1431 $cm^{-1}$.

EXAMPLE 78

1,2-Dihydro-1-[3-(1-tert-butoxycarbonylpiperidin-4-yl)propan-1-yl]-1,4,7b-triazacyclopent[cd]inden-2-one To a solution prepared by dissolving 4.87 g (20.0 mM) of 1-tert-butoxycarbonyl-4-(3-hydroxypropan-1-yl)-piperidine and 5.54 ml (40.0 mM) of triethylamine in 50 ml of THF was added 1.86 ml (24.0 mM) of methanesulfonyl chloride at 0° C. After completion of dropwise addition, the reaction mixture was stirred at room temperature for 30 minutes. After completion of this reaction, the reaction mixture was poured in 50 ml of iced water and extracted with 50 ml of ethyl acetate. The organic layer was washed with 50 ml of saturated NaCl solution and dried over $Na_2SO_4$. The solvent was then distilled off under reduced pressure and the residue was dried in vacuo to provide 6.42 g of yellow liquid. To 50 ml of DMF was added 6.42 g (20.0 mM) of 3-(1-tert-butoxycarbonylpiperidin-4-yl)propan-1-yl methanesulfonate thus obtained as well as 4.35 g (20.0 mM) of 1,2-dihydro-1,4,7b-triazacyclopent[cd]inden-2-one.2NaCl and 3.58 ml (24.0 mM) of DBU and the mixture was heated at 80° C. for 2 hours. After completion of the reaction, the reaction mixture was poured in 50 ml of iced water and extracted with 100 ml of ethyl acetate. The organic layer was washed with 50 ml of purified water twice and further with 50 ml of saturated aqueous NaCl solution and dried over $Na_2SO_4$. The solvent was then distilled off under reduced pressure and the residue was purified by silica gel column chromatography (eluent: ethyl acetate-ethanol=10:1) to provide 3.82 g (yield 49.7%) of the title compound as brown solid.

$^1$H-NMR(200 MHz,$CDCl_3$) δ: 0.98–1.20(2H,m), 1.44 (9H,s), 1.32–1.53(2H,m), 1.57–1.72(2H,m), 1.79–1.98(3H, m), 2.56–2.75(2H,m), 3.98–4.17(4H,m), 6.87(1H,d,J=7.2 Hz), 7.65(1H,d,J=8.6 Hz), 7.78(1H,dd,J=8.6, 7.2 Hz), 8.36 (1H,s).

EXAMPLE 79

4,5-Dihydro-4-(1-tert-butoxycarbonylpiperidin-4-ylmethyl)-3H-1,4,8b-triazaacenaphthylen-3-one A solution prepared by dissolving 5.78 g (24.22 mM) of 3-carbethoxy-5-chloromethylimidazo[1,2-a]pyridine, 7.78 g (36.33 mM) of 1-tert-butoxycarbonyl-4-aminomethylpiperidine, and 6.75 ml (48.44 mM) of triethylamine in 100 ml of ethanol was refluxed under argon gas for 3 hours. After completion of the reaction, the solvent was distilled off under reduced pressure and the residue was extracted with 100 ml of chloroform. The organic layer was washed with saturated aqueous NaCl solution and dried over $MgSO_4$ and the solvent was distilled off under reduced pressure. The residue was purified by silica gel column chromatography (eluent: chloroform-methanol=20:1) to provide 6.50 g (yield 72.4%) of the title compound as yellow liquid.

$^1$H-NMR(200 MHz,$CDCl_3$) δ: 1.30–1.56(2H,m), 1.43 (9H,s), 1.79–91.95(2H,m), 1.96–2.15(1H,m), 2.58–2.82 (2H,m), 3.53–3.71(2H,m), 4.00–4.22(2H,m), 5.01(2H,s), 6.72(1H,d,J=6.7 Hz), 7.36(1H,dd,J=9.2, 6.7 Hz), 7.54(1H, d,J=9.2 Hz), 8.18(1H,s).

EXAMPLE 80

4,5-Dihydro-4-[2-(1-tert-butoxycarbonylpiperidin-4-yl)ethan-1-yl]-3H-1,4,8b-triazaacenaphthylen-3-one In 50 ml of acetonitrile was suspended 6.73 g (20.0 mM) of 3-carbethoxy-5-chloromethylimidazo[1,2-a]pyridine sulfate followed by addition of 5.97 ml (40.0 mM) of DBU at room temperature with stirring. To the resulting solution was added 4.57 g (20.0 mM) of 2-(1-tert-butoxycarbonylpiperidin-4-yl)-1-ethylamine as well as 5.54 ml (40.0 mM) of triethylamine and 3.00 g (20.0 mM) of sodium iodide and the mixture was stirred at room temperature for 16 hours. After completion of the reaction, the solvent was distilled off under reduced pressure and the residue was extracted with 100 ml of 2-butanone. The organic layer was washed with 100 ml of saturated aqueous NaCl solution and dried over $MgSO_4$ and the solvent was distilled off under reduced pressure. The residue was purified by silica gel column chromatography (eluent: ethyl acetate-ethanol=5:1) to provide 2.88 g (yield 37.5%) of the title compound as yellow oil.

$^1$H-NMR(200 MHz,$CDCl_3$) δ: 1.04–1.29(2H,m), 1.45 (9H,s), 1.52–1.78(3H,m), 1.78–1.84(2H,m), 2.58–2.82(2H, m), 3.54–3.72(2H,m), 3.98–4.20(2H,m), 5.00(2H,s), 6.74 (1H,d,J=6.6 Hz), 7.35(1H,dd,J=9.2, 6.6 Hz), 7.53(1H,d,J= 9.2 Hz), 8.17(1H,s).

EXAMPLE 81

4,5-Dihydro-4-[3-(1-tert-butoxycarbonylpiperidin-4-yl)propan-1-yl]-3H-1,4,8b-triazaacenaphthylen-3-one A solution prepared by dissolving 3.59 g (10.66 mM) of 3-carbethoxy-5-chloromethylimidazo[1,2-a]pyridine sulfate, 3.10 g (12.79 mM) of 3-(1-tert-butoxycarbonylpiperidin- 4-yl)-1-propylamine, and 5.94 ml (42.64 mM) of triethylamine in 30 ml of ethanol was refluxed for 5 hours. After completion of the reaction, the solvent was distilled off under reduced pressure and the residue was extracted with 100 ml of chloroform. The organic layer was washed with 100 ml of saturated aqueous NaCl solution and dried over $MgSO_4$ and the solvent was distilled off under reduced pressure. The residue was purified by silica gel column chromatography (eluent: chloroform-methanol=50:1) to provide 2.55 g (yield 62.1%) of the title compound as yellow oil.

$^1$H-NMR(200 MHz,$CDCl_3$) δ: 0.97–1.24(2H,m), 1.25–1.39(3H,m), 1.45(9H,s), 1.57–1.81(4H,m), 2.52–2.78 (2H,m), 3.57(2H,t,J=7.4 Hz), 3.96–4.18(2H,m), 5.01(2H,s), 6.74(1H,d,J=6.0 Hz), 7.33(1H,dd,J=9.2,7.0 Hz), 7.59(1H,d, J=9.2 Hz), 8.18(1H,s).

IR(Neat): 1678, 1533, 1161 $cm^{-1}$.

EXAMPLE 82

1,2-Dihydro-1-(1-trifluoromethanesulfonylpiperidin-4-ylmethyl)-1,4,7b-triazacyclopent[cd]inden-2-one i) Synthesis of 1,2-dihydro-1-(piperidin-4-ylmethyl)-1,4,7b-triazacyclopent[cd]inden-2-one dihydrochloride To a solution of 3.00 g (8.42 mM) of 1,2-dihydro-1-(1-tert-butoxycarbonylpiperidin-4-ylmethyl)-1,4,7b-triazacyclopento[cd]inden-2-one in 50 ml of ethanol was added 10 ml (122 mM) of 12N-hydrochloric acid and the mixture was stirred at room temperature for 1 hour. After completion of the reaction, the reaction mixture was concentrated under reduced pressure and the precipitate that formed was recovered by filtration. This precipitate was rinsed with small amounts of ethanol and ether to provide 2.30 g (yield 83.0%) of the title compound as brown solid.

$^1$H-NMR(200 MHz,DMSO-$d_6$) δ: 1.42–1.67(2H,m), 1.76– 1.95(2H,m), 2.05–2.29(1H,m), 2.66–2.93(2H,m), 3.14–3.34(2H,m), 4.04(2H,d,J=7.2 Hz), 7.63(1H,d,J=7.6 Hz), 7.87(1H,d,J=8.8 Hz), 8.20(1H,dd,J=8.8, 7.6 Hz), 8.92 (1H,s).

ii) Synthesis of 1,2-dihydro-1-(1-trifluoromethanesulfonylpiperidin-4-ylmethyl)-1,4,7b-triazacyclopent[cd]inden-2-one In 20 ml of acetonitrile was suspended 988 mg (3.0 mM) of 1,2-dihydro-1-(piperidin-4-ylmethyl)-1,4,7b-triazacyclopent[cd]inden-2-one dihydrochloride followed by addition of 0.9 ml (6.0 mM) of DBU at room temperature and thorough mixing. To the resulting solution was added 0.83 ml (6.0 mM) of triethylamine, followed by addition of 1.29 g (3.6 mM) of N-phenyltrifluoromethanesulfonimide, and the mixture was stirred at room temperature for 16 hours. After completion of the reaction, the solvent was distilled off under reduced pressure and the residue was extracted with 100 ml of ethyl acetate. The organic layer was washed with 100 ml of saturated aqueous NaCl solution and dried over $MgSO_4$ and the solvent was then distilled off under reduced pressure. The residue was purified by silica gel column chromatography (eluent: ethyl acetate-ethanol= 10:1) to provide 890 mg (yield 76.4%) of the title compound as light-yellow crystals.

$^1$H-NMR(200 MHz,$CDCl_3$) δ: 1.39–1.64(2H,m), 1.80–1.96(2H,m), 2.08–2.35(1H,m), 2.92–3.13(2H,m), 3.91–4.04(2H,m), 4.01(2H,d,J=7.0 Hz), 6.86(1H,d,J=8.6 Hz), 7.80(1H,dd,J=8.6, 6.8 Hz), 8.38(1H,s).

IR(KBr): 1698, 1507, 1383, 1227 $cm^{-1}$.

Elemental Analysis for $C_{15}H_{15}N_4O_3SF_3$:

Calcd.: C, 46.39; H, 3.89; N, 14.43. Found : C, 46.37; H, 3.66; N, 14.19.

EXAMPLE 83

1,2-Dihydro-1-[2-(1-(trifluoromethanesulfonyl)piperidin-4-yl)ethan-1-yl]-1,4,7b-triazacyclopent[cd]inden-2-one hydrochloride i) Synthesis of 1,2-dihydro-1-[2-(piperidin-4-yl)ethan-1-yl]-1,4,7b-triazacyclopent[cd]inden-2-one dihydrochloride To a solution prepared by dissolving 5.30 g (14.13 mM) of 1,2-dihydro-1-[2-(1-(tert-butoxycarbonyl)piperidin-4-yl)ethan-1-yl]-1,4,7b-triazacyclopent[cd]inden-2-one in 50 ml of ethanol was added 5.88 ml (71.53 mM) of 12N-hydrochloric acid and the mixture was stirred at room temperature for 1 hour. After completion of the reaction, the reaction mixture was concentrated under reduced pressure and the crystals that formed were collected by filtration and rinsed with small amounts of ethanol and ether to provide 3.51 g (yield of 71.5%) of the title compound as white crystals.

$^1$H-NMR(200 MHz,DMSO-$d_6$) δ: 1.32–1.68(3H,m), 1.68–1.84(2H,m), 1.84–2.02(2H,m), 2.64–2.93(2H,m), 3.15–3.33(2H,m), 4.14(2H,t,J=7.6 Hz), 7.62(1H,d,J=7.6 Hz), 7.86(1H,d,J=8.6 Hz), 8.18(1H,dd,J=8.6, 7.6 Hz), 8.90 (1H,m), 8.82–9.22(2H,br s,$NH_2$).

IR(KBr): 1714, 1645, 1549 $cm^{-1}$.

ii) Synthesis of 1,2-dihydro-1-[2-(1-(trifluoromethanesulfonyl)piperidin-4-yl)ethan-1-yl]-1,4,7b-triazacyclopent[cd]inden-2-one In 30 ml of acetonitrile was suspended 1.72 g (5.0 mM) of 1,2-dihydro-1-[2-(piperidin-4-yl)ethan-1-yl]-1,4,7b-triazacyclopent[cd]inden-2-one dihydrochloride, followed by addition of 1.5 ml (10.0 mM) of DBU and 1.4 ml (10.0 mM) of triethylamine. Then, 8.93 g (25.0 mM) of N-phenyltrifluoromethanesulfonimide was added and the mixture was stirred at room temperature for 16 hours. After completion of the reaction, the solvent was distilled off under reduced pressure and the residue was extracted with 100 ml of chloroform. The organic layer was washed with 100 ml of saturated aqueous NaCl solution and dried over MgSO$_4$ and the solvent was distilled off under reduced pressure. The residue was purified by silica gel column chromatography (eluent: ethyl acetate-ethanol=10:1) to provide 1.54 g (yield 76.3%) of the title compound as white solid. Recrystallization of the solid (1.54 g) from 10 ml of ethanol gave 1.23 g (recovery rate 80.0%) of prisms.

$^1$H-NMR(200 MHz,CDCl$_3$) δ: 1.24–1.67(3H,m), 1.78–2.06(4H,m), 2.92–3.13(2H,m), 3.88–4.04(2H,m), 4.16 (2H,t,J=7.0 Hz), 6.87(1H,d,J=7.0 Hz), 7.68(1H,d,J=8.6 Hz), 7.80(1H,dd,J=8.6, 7.0 Hz), 8.37(1H,s).

IR(KBr): 1689, 1624, 1504 cm$^{-1}$.

Elemental Analysis for C$_{16}$H$_{17}$N$_4$O$_3$SF$_3$:

Calcd.: C, 47.76; H, 4.26; N, 13.92. Found : C, 47.57; H, 4.23; N, 13.96.

iii) Synthesis of 1,2-dihydro-1-[2-(1-trifluoromethane-sulfonyl)piperidin-4-yl)ethan-1-yl]-1,4,7b-triazacyclopent[cd]inden-2-one hydrochloride To a solution prepared by dissolving 402 mg (1.0 mM) of 1,2-dihydro-1-[2-(1-trifluoromethanesulfonyl)piperidin-4-yl)ethan-1-yl]-1,4,7b-triazacyclopent[cd]inden-2-one in 10 ml of 2-propanol was added 0.16 ml (2.0 mM) of 12N-hydrochloric acid and the mixture was stirred and concentrated under reduced pressure. The resulting precipitate was recovered by filtration and rinsed with a small amount of ether to provide 378 mg (yield 86.2%) of the title compound as white crystals.

$^1$H-NMR(200 MHz,DMSO-d$_6$) δ: 1.12–1.38(2H,m), 1.48–1.79(1H,m), 1.79–1.84(2H,m), 1.84–2.02(2H,m), 2.98–3.23(2H,m), 3.69–3.88(2H,m), 4.06–4.22(2H,m), 7.61 (1H,d,J=7.6 Hz), 7.87(1H,d,J=8.6 Hz), 8.18(1H,dd,J=8.6, 7.6 Hz), 8.90(2H,s).

EXAMPLE 84

1,2-Dihydro-1-[3-(1-trifluoromethanesulfonylpiperidin-4-yl)propan-1-yl]-1,4,7b-triazacyclopent[cd]inden-2-one i) Synthesis of 1,2-dihydro-1-[3-(piperidin-4-ylmethyl)propan-1-yl]-1,4,7b-triazacyclopent[cd] inden-2-one dihydrochloride To a solution prepared by dissolving 3.82 g (9.94 mM) of 1,2-dihydro-1-[3-(1-tert-butoxycarbonylpiperidin-4-yl) propan-1-yl]-1,4,7b-triazacyclopent[cd]inden-2-one in 50 ml of ethanol was added 10 ml (122 mM) of 12N-hydrochloric acid and the mixture was stirred at room temperature for 1 hour. After completion of the reaction, the reaction mixture was concentrated under reduced pressure and the resulting precipitate was recovered by filtration. The precipitate was rinsed with small amounts of ethanol and ether to provide 2.99 g (yield 84.5%) of the title compound as brown solid.

$^1$H-NMR(200 MHz,DMSO-d$_6$) δ: 1.18–1.44(4H,m), 1.44–1.66(1H,m), 1.66–1.91(4H,m), 2.67–2.92(2H,m), 3.09–3.29(2H,m), 4.10(2H,t,J=7.0 Hz), 7.68(1H,d,J=7.8 Hz), 7.89(1H,d,J=8.8 Hz), 8.24(1H,dd,J=8.8, 7.8 Hz), 9.00 (1H,s), 8.87–9.26(2H,m).

ii) Synthesis of 1,2-dihydro-1-[3-(1-trifluoromethanesulfonylpiperidin-4-yl)propan-1-yl]-1,4,7b-triazacyclopent[cd]inden-2-one In 20 ml of acetonitrile was suspended 1072 mg (3.0 mM) of 1,2-dihydro-1-[3-(piperidin-4-yl)propan-1-yl]-1,4,7b-triazacyclopent[cd]inden-2-one dihydrochloride followed by addition of 0.9 ml (6.0 mM) of DBU at room temperature and thorough mixing. To the resulting solution was added 0.83 ml (6.0 mM) of triethylamine. Then, 1.29 g (3.6 mM) of N-phenyltrifluoromethanesulfonimide was added and the mixture was stirred at room temperature for 16 hours. After completion of the reaction, the solvent was distilled off under reduced pressure and the residue was extracted with 100 ml of ethyl acetate. The organic layer was washed with 100 ml of saturated aqueous NaCl solution and dried over MgSO$_4$ and the solvent was distilled off under reduced pressure. The residue was purified by silica gel column chromatography (eluent: ethyl acetate-ethanol=10:1) to provide 870 mg (yield 69.7%) of the title compound as light-brown crystals.

$^1$H-NMR(200 MHz,CDCl$_3$) δ: 1.25–1.64(5H,m), 1.64–2.02(4H,m), 2.90–3.11(2H,m), 3.84–4.02(2H,m), 4.09 (t,2H, J=7.4 Hz), 6.86 (d, 1H, J=7.0 Hz), 7.66 (1H,d,J=8.8 Hz), 7.78(1H,dd,J=8.8, 7.0 Hz), 8.36(1H,s).

IR(KBr): 1701, 1507, 1383, 1228 cm$^{-1}$.

Elemental Analysis for C$_{18}$H$_{19}$N$_4$O$_3$SF$_3$:

Calcd.: C, 49.03; H, 4.60; N, 13.45. Found : C, 49.12; H, 4.49; N, 13.43.

EXAMPLE 85

4,5-Dihydro-4-(1-trifluoromethanesulfonylpiperidin-4-ylmethyl)-3H-1,4,8b-triazaacenaphthylen-3-one hydrochloride i) Synthesis of 4,5-dihydro-4-(piperidin-4-ylmethyl)-3H-1,4,8b-triazaacenaphthylen-3-one dihydrochloride To a solution prepared by dissolving 3.71 g (10.0 mM) of 4,5-dihydro-4-(1-tert-butoxycarbonylpiperidin-4-ylmethyl)-3H-1,4,8b-triazaacenaphthylen-3-one in 50 ml of ethanol was added 4.11 ml of 12N-hydrochloric acid at room temperature. This mixture was stirred at room temperature for 1 hour and the resulting precipitate was recovered by filtration. The precipitate was rinsed with a small amount of ether and dried in vacuo to provide 3.24 g (yield 94.2%) of the title compound as white powders.

$^1$H-NMR(200 MHz,DMSO-d$_6$) δ: 1.24–1.42(2H,m), 1.76–1.92(2H,m), 1.94–2.20(1H,m), 2.64–2.90(2H,m), 3.11–3.30(2H,m), 3.46(2H,d,J=7.2 Hz), 5.25(2H,s), 7.42 (1H,d,J=7.0 Hz), 7.88(1H,d,J=8.7 Hz), 8.01(1H,dd,J=8.7, 7.0 Hz), 8.65(1H,s), 8.95–9.33(2H,m).

ii) Synthesis of 4,5-dihydro-4-(1-trifluoromethanesulfonylpiperidin-4-ylmethyl)-3H-1,4,8b-triazaacenaphthylen-3-one In 20 ml of THF was suspended 2.06 g (6.0 mM) of 4,5-dihydro-4-(piperidin-4-ylmethyl)-3H-1,4,8b-triazaacenaphthylen-3-one dihydrochloride and 3.35 ml (24.0 mM) of triethylamine and 1.51 ml (9.0 mM) of trifluoromethanesulfonic anhydride were added in that order at 0° C. The mixture was stirred at room temperature for 1 hour and the solvent was then distilled off under reduced pressure. The residue was extracted with 100 ml of chloroform and the organic layer was washed with 100 ml of saturated aqueous NaCl solution and dried over MgSO$_4$. The solvent was then distilled off under reduced pressure and the residue was purified by silica gel column chromatography (eluent: ethyl acetate-ethanol=10:1) to provide 1.71 g (yield 71.0%) of the title compound as light-yellow amorphous substance.

$^1$H-NMR(200 MHz,CDCl$_3$) δ: 1.32–1.58(2H,m), 1.78–1.96(2H,m), 1.96–2.17(1H,m), 2.93–3.17(2H,m), 3.51

(2H,d,J=7.4 Hz), 3.88–4.07(2H,m), 5.03(2H,s), 6.77(1H,d, J=7.0 Hz), 7.36(1H,dd,J=8.8, 7.0 Hz), 7.56(1H,d,J=8.8 Hz), 8.19(1H,s).

iii) Synthesis of 4,5-dihydro-4-(1-trifluoromethanesulfonylpiperidin-4-ylmethyl)-3H-1,4,8b-triazaacenaphthylen-3-one hydrochloride To a solution prepared by dissolving 580 mg (1.44 mM) of 4,5-dihydro-4-(1-trifluoromethanesulfonylpiperidin-4-ylmethyl)-3H-1,4,8b-triazaacenaphthylen-3-one in 10 ml of ethanol was added 0.24 ml (2.88 mM) of 12N-hydrochloric acid with stirring. The resulting solution was concentrated under reduced pressure and the precipitate was recovered by filtration. The precipitate was rinsed with a small amount of ether and dried in vacuo to provide 480 mg (yield 80.0%) of the title compound as white solid.

$^1$H-NMR(200 MHz,DMSO-$d_6$) δ: 1.24–1.41(2H,m), 1.75–1.94(2H,m), 1.96–2.22(2H,m), 3.04–3.26(2H,m), 3.48 (2H,d,J=7.4 Hz), 3.73–3.91(2H,m), 5.25(2H,s), 7.38(1H,d, J=7.0 Hz), 7.83(1H,d,J=8.6 Hz), 7.95(1H,dd,J=8.6, 7.0 Hz), 8.59(1H,s).

EXAMPLE 86

4,5-Dihydro-4-[2-(1-trifluoromethanesulfonylpiperidin-4-yl)ethan-1-yl]-3H-1,4,8b-triazaacenaphthylen-3-one i) Synthesis of 4,5-dihydro-4-[2-(piperidin-4-yl)ethan-1-yl]-3H-1,4,8b-triazaacenaphthylen-3-one dihydrochloride To a solution prepared by dissolving 2.88 g (7.49 mM) of 4,5-dihydro-4-[2-(1-tert-butoxycarbonylpiperidin-4-yl)ethan-1-yl]-3H-1,4,8b-triazaacenaphthylen-3-one in 30 ml of ethanol was added 6.25 ml (74.9 mM) of 12N-hydrochloric acid and the mixture was stirred at room temperature for 1 hour. After completion of the reaction, the reaction mixture was concentrated under reduced pressure and the precipitate was recovered by filtration. The precipitate was rinsed with small amounts of ethanol and ether to provide 2.13 g (yield 79.8%) of the title compound as light-yellow crystals.

$^1$H-NMR(200 MHz,DMSO-$d_6$) δ: 1.29–1.76(5H,m), 1.78–1.98(2H,m), 2.64–2.91(2H,m), 3.12–3.31(2H,m), 3.47–3.66(2H,m), 5.27(2H,s), 7.43(1H,d,J=7.0 Hz), 7.86 (1H,d,J=8.8 Hz), 8.00(1H,dd,J=8.8, 7.0 Hz), 8.64(1H,s), 8.93–9.31(2H,m).

ii) Synthesis of 4,5-dihydro-4-[2-(1-trifluoromethanesulfonylpiperidin-4-yl)ethan-1-yl]-3H-1,4,8b-triazaacenaphthylen-3-one In 15 ml of acetonitrile was suspended 713 mg (2.0 mM) of 4,5-dihydro-4-[2-(piperidin-4-yl)ethan-1-yl]-3H-1,4,8b-triazaacenaphthylen-3-one hydrochloride followed by addition of 0.6 ml (4.0 mM) of DBU at room temperature with stirring. To the resulting solution was added 0.83 ml (6.0 mM) of triethylamine as well as 0.37 ml (2.2 mM) of trifluoromethanesulfonic anhydride at 0° C. and the mixture was stirred at room temperature for 1 hour. After completion of the reaction, the solvent was distilled off under reduced pressure and the residue was extracted with 50 ml of 2-butanone. The organic layer was washed with 50 ml of saturated aqueous NaCl solution and dried over MgSO$_4$ and the solvent was distilled off under reduced pressure. The residue was purified by silica gel column chromatography (eluent: ethyl acetate-ethanol=9:1) to provide 434 mg (yield 35.0%) of the title compound as light-yellow amorphous substance.

$^1$H-NMR(200 MHz,CDCl$_3$) δ: 1.26–1.48(2H,m), 1.48–1.75(3H,m), 1.88–2.04(2H,m), 2.84–3.02(2H,m), 3.65 (2H,t,J=6.8 Hz), 3.88–4.04(2H,m), 5.04(2H,s), 6.81(1H,d, J=6.2 Hz), 7.38(1H,dd,J=9.2, 6.2 Hz), 7.54(1H,d,J=9.2 Hz), 8.14(1H,s).

IR(KBr): 1732, 1709, 1633, 1227 cm$^{-1}$.

EXAMPLE 87

4,5-Dihydro-4-[3-(1-trifluoromethanesulfonylpiperidin-4-yl)propan-1-yl]-3H-1,4,8b-triazaacenaphthylen-3-one hydrochloride i) Synthesis of 4,5-dihydro-4-[3-(piperidin-4-yl)propan-1-yl]-3H-1,4,8b-triazaacenaphthylen-3-one dihydrochloride To a solution prepared by dissolving 2.12 g (5.51 mM) of 4,5-dihydro-4-[3-(1-tert-butoxycarbonylpiperidin-4-yl)propan-1-yl]-3H-1,4,8b-triazaacenaphthylen-3-one in 30 ml of ethanol was added 1.40 ml of 12N-hydrochloric acid and the mixture was stirred at room temperature for 1 hour. After completion of the reaction, the solvent was distilled off under reduced pressure. To the residue was added 5 ml of ethanol and 5 ml of ether and the resulting precipitate was recovered by filtration. The precipitate was rinsed with small amounts of ethanol and ether to provide 1.87 g (yield 91.2%) of the title compound as light-yellow crystals.

$^1$H-NMR(200 MHz,DMSO-$d_6$) δ: 1.17–1.51(4H,m), 1.51–1.72(3H,m), 1.71–1.89(2H,m), 2.67–2.94(2H,m), 3.09–3.31(2H,m), 3.36–3.61(2H,m), 5.29(2H,s), 7.47(1H,d, J=6.4 Hz), 7.89(1H,d,J=9.0 Hz), 8.02(1H,d,J=7.4 Hz), 8.67 (1H,s), 8.82–9.28(2H,m,NH).

IR(KBr): 1653, 1599, 1443 cm$^{-1}$.

ii) Synthesis of 4,5-dihydro-4-[3-(1-trifluoromethanesulfonylpiperidin-4-yl)propan-1-yl]-3H-1,4,8b-triazaacenaphthylen-3-one In 20 ml of acetonitrile was suspended 1.37 g (3.69 mM) of 4,5-dihydro-4-[3-(piperidin-4-yl)propan-1-yl]-3H-1,4,8b-triazaacenaphthylen-3-one hydrochloride followed by addition of 1.1 ml (7.38 mM) of DBU at room temperature with stirring. To the resulting solution was added 1.0 ml (7.38 mM) of triethylamine as well as 6.59 g (18.45 mM) of N-phenyltrifluoromethanesulfonimide and the mixture was stirred at room temperature for 16 hour. After completion of the reaction, the solvent was distilled off under reduced pressure and the residue was extracted with 100 ml of chloroform. The organic layer was washed with 100 ml of saturated aqueous NaCl solution and dried over MgSO$_4$ and the solvent was distilled off under reduced pressure. The residue was purified by silica gel column chromatography (eluent: chloroform-methanol=50:1) to provide 1.08 g (yield 68.3%) of the title compound as light-yellow solid.

$^1$H-NMR(200 MHz,CDCl$_3$) δ: 1.16–1.61(4H,m), 1.61–1.91(5H,m), 2.92–3.11(2H,m), 3.58(2H,t,J=7.6 Hz), 3.87–4.03(2H,m), 5.01(2H,s), 6.75(1H,d,J=7.0 Hz), 7.36 (1H,dd,J=9.0, 7.0 Hz), 7.54(1H,d,J=9.0 Hz), 8.18(1H,s).

IR(KBr): 1647, 1543, 1387, 1182 cm$^{-1}$.

iii) Synthesis of 4,5-dihydro-4-[3-(1-trifluoromethanesulfonylpiperidin-4-yl)propan-1-yl]-3H-1,4,8b-triazaacenaphthylene-3-one hydrochloride To a solution prepared by dissolving 300 mg (0.70 mM) of 4,5-dihydro-4-[3-(1-trifluoromethanesulfonylpiperidin-4- yl)propan-1-yl]-3H-1,4,8b-triazaacenaphthylen-3-one in 10 ml of ethanol was added 0.12 ml (1.4 mM) of 12N hydrochloric acid at room temperature. After stirring, the solvent was distilled off under reduced pressure and 10 ml of 2-propanol was added to the residue. The precipitate that formed was recovered by filtration and rinsed with a small amount of ether to provide 265 mg (yield 81.1%) of the title compound as light-yellow solid.

$^1$H-NMR(200 MHz,DMSO-d$_6$) δ: 1.07–1.41(4H,m), 1.43–1.74(3H,m), 1.74–1.89(2H,m), 3.04–3.25(2H,m), 3.40–3.91(4H,m), 5.25(2H,s), 7.40(1H,d,J=7.2 Hz), 7.83 (1H,d,J=9.0 Hz), 7.96(1H,dd,J=9.0, 7.2 Hz), 8.60(1H,s).

IR(KBr): 1666, 1552, 1375, 1184 cm$^{-1}$.

m.p. 172–174° C.

Elemental Analysis for $C_{18}H_{22}N_4O_3SClF_3 \cdot H_2O$:

Calcd.: C, 44.58; H, 4.99; N, 11.55. Found : C, 44.31; H, 4.65; N, 11.17.

EXAMPLE 88

4,5-Dihydro-4-(1-trifluoroacetylpiperidin-4-ylmethyl)-3H-1,4,8b-triazaacenaphthylen-3-one hydrochloride i) Synthesis of 4,5-dihydro-4-(1-trifluoroacetylpiperidin-4-ylmethyl)-3H-1,4,8b-triazaacenaphthylen-3-one In 20 ml of acetonitrile was suspended 687 mg (2.0 mM) of 4,5-dihydro-4-(piperidin-4-ylmethyl)-3H-1,4,8b-triazaacenaphthylen-3-one dihydrochloride followed by addition of 2.23 ml (16.0 mM) of triethylamine and 1.41 ml (10.0 mM) of trifluoroacetic anhydride in the order mentioned. This mixture was stirred at room temperature for 1 hour and the solvent was then distilled off under reduced pressure. The residue was extracted with 50 ml of chloroform and the organic layer was washed with 50 ml of saturated aqueous NaCl solution and dried over MgSO$_4$. The solvent was then distilled off under reduced pressure and the residue was purified by silica gel column chromatography (eluent: ethyl acetate-ethanol=10:1) to provide 540 mg (yield 73.7%) of the title compound as light-yellow amorphous substance.

$^1$H-NMR(200 MHz,CDCl$_3$) δ: 1.13–1.40(2H,m), 1.82–2.00(2H,m), 2.05–2.26(2H,m), 2.66–2.85(1H,m), 3.02–3.24(1H,m), 3.30–3.42(1H,m), 3.54–3.68(1H,m), 4.00–4.11(1H,m), 4.45–4.60(1H,m), 5.00(1H,s), 6.75(1H,d, J=6.8 Hz), 7.35(1H,dd,J=8.8, 6.8 Hz), 7.57(1H,d,J=8.8 Hz), 8.20(1H,s).

ii) Synthesis of 4,5-dihydro-4-(1-trifluoroacetyl-piperidin-4-ylmethyl)-3H-1,4,8b-triazaacenaphthylen-3-one hydrochloride To a solution prepared by dissolving 540 mg (1.47 mM) of 4,5-dihydro-4-(1-trifluoroacetylpiperidin-4-yl-methyl)-3H-1,4,8b-triazaacenaphthylen-3-one in 10 ml of ethanol was added 0.24 ml (2.94 mM) of 12N-hydrochloric acid with stirring. The resulting solution was concentrated under reduced pressure and the precipitate that formed was recovered by filtration. The precipitate was rinsed with a small amount of ether and dried in vacuo to provide 330 mg (yield 55.7%) of the title compound as white solid.

$^1$H-NMR(200 MHz,DMSO-d$_6$) δ: 1.26–1.42(2H,m), 1.72–1.91(2H,m), 1.93–2.20(1H,m), 3.03–3.26(2H,m), 3.46 (2H,d,J=7.0 Hz), 3.73–3.88(2H,m), 5.22(2H,s), 7.38(1H,d, J=6.8 Hz), 7.86(1H,d,J=8.8 Hz), 7.95(1H,dd,J=8.8, 6.8 Hz), 8.61(1H,s).

EXAMPLE 89

4,5-Dihydro-4-[2-(1-trifluoroacetylpiperidin-4-yl) ethan-1-yl]-3H-1,4,8b-triazaacenaphthylen-3-one In 15 ml of acetonitrile was suspended 713 mg (2.0 mM) of 4-[2-(piperidin-4-yl)ethan-1-yl]-4,5-dihydro-3H-1,4,8b-triazaacenaphthylen-3-one hydrochloride followed by addition of 0.6 ml (4.0 mM) of DBU at room temperature with stirring. To the resulting solution was added 0.83 ml (6.0 mM) of triethylamine as well as 0.31 ml (2.2 mM) of trifluoroacetic anhydride at 0° C. and the mixture was stirred at room temperature for 1 hour. After completion of the reaction, the solvent was distilled off under reduced pressure and the residue was extracted with 50 ml of 2-butanone. The organic layer was washed with 50 ml of saturated aqueous NaCl solution and dried over MgSO$_4$ and the solvent was distilled off under reduced pressure. The residue was purified by silica gel column chromatography (eluent: ethyl acetate-ethanol=9:1) to provide 455 mg (yield 59.8%) of the title compound as light yellow solid.

$^1$H-NMR(200 MHz,CDCl$_3$) δ: 1.13–1.41(2H,m), 1.56–1.71(3H,m), 1.85–2.07(2H,m), 2.66–2.85(1H,m), 3.01–3.22(1H,m), 3.65(2H,t,J=7.0 Hz), 3.93–4.12(1H,m), 4.46–4.62(1H,m), 5.01(2H,s), 6.76(1H,d,J=7.0 Hz), 7.34 (1H,dd,J=7.0, 9.2 Hz), 7.56(1H,d,J=9.2 Hz), 8.19(1H,s).

IR(KBr): 1683, 1657, 1180, 1146 cm$^{-1}$.

EXAMPLE 90

4,5-Dihydro-4-(1-pentafluoropropionylpiperidin-4-ylmethyl)-3H-1,4,8b-triazaacenaphthylen-3-one hydrochloride i) Synthesis of 4,5-dihydro-4-(1-pentafluoropropionylpiperidin-4-ylmethyl)-3H-1,4, 8b-triazaacenaphthylen-3-one In 10 ml of acetonitrile was suspended 687 mg (2.0 mM) of 4,5-dihydro-4-(piperidin-4-ylmethyl)-3H-1,4,8b-triazaacenaphthylen-3-one dihydrochloride, followed by addition of 2.23 ml (16.0 mM) of triethylamine and 1.97 ml (10.0 mM) of pentafluoropropionic anhydride in the order mentioned. This mixture was stirred at room temperature for 1 hour and the solvent was then distilled off under reduced pressure. The residue was extracted with 50 ml of chloroform and the organic layer was washed with 50 ml of saturated aqueous NaCl solution and dried over MgSO$_4$. The solvent was distilled off under reduced pressure and the residue was purified by silica gel column chromatography (eluent: ethyl acetate-ethanol=10:1) to provide 526 mg (yield 63.2%) of the title compound as light-yellow amorphous substance.

$^1$H-NMR(200 MHz,CDCl$_3$) δ: 1.22–1.53(2H,m), 1.80–1.97(2H,m), 2.05–2.27(1H,m), 2.71–2.89(1H,m), 3.06–3.23(1H,m), 3.31–3.46(1H,m), 3.52–3.68(1H,m), 4.05–4.23(1H,m), 4.46≧4.62(1H,m), 5.04(2H,s), 6.77(1H, d,J=6.8 Hz), 7.36(1H,dd,J=9.2, 6.8 Hz), 7.57(1H,d,J=9.2 Hz), 8.20(1H,s).

ii) Synthesis of 4,5-dihydro-4-(1-pentafluoropropionylpiperidin-4-ylmethyl)-3H-1,4, 8b-triazaacenaphthylen-3-one hydrochloride To a solution of 526 mg (1.26 mM) of 4,5-dihydro-4-(1-pentafluoropropionylpiperidin-3-4-ylmethyl)-3H-1,4,8b-triazaacenaphthylen-3-one in 10 ml of ethanol was added 0.20 ml (2.52 mM) of 12N-hydrochloric acid with stirring. The resulting solution was concentrated under reduced pressure and the precipitate that formed was recovered by filtration. This precipitate was rinsed with a small amount of ether and dried in vacuo to provide 430 mg (yield 75.4%) of the title compound as white solid.

$^1$H-NMR(200 MHz,DMSO-d$_6$) δ: 1.23–1.40(2H,m), 1.73–1.93(2H,m), 1.95–2.22(1H,m), 3.02–3.25(2H,m), 3.46 (2H,d,J=7.2 Hz), 3.72–3.89(2H,m), 5.24(2H,s), 7.36(1H,d, J=7.0 Hz), 7.85(1H,d,J=8.8 Hz), 7.96(1H,dd,J=8.8, 7.0 Hz), 8.60(1H,s).

Reference Example 1

5-Ethoxycarbonyl-3-trichloroacetylimidazo[1,2-a] pyridine

To a solution of 25.22 g (0.133 mol) of 5-ethoxycarbonylimidazo[1,2-a]pyridine and 48.60 g (0.398 mol) of 4-dimethylaminopyridine was added dropwise 72.33 g (0.398 mol) of trichloroacetyl chloride. The mixture was heated for 63 hours under reflux. After cooling, the reaction mixture was washed with an aqueous solution of sodium hydrogencarbonate, dried over anhydrous magnesium sulfate. The solvent was distilled off, and the residue was purified by column chromatography (eluent: ethyl acetate/ n-hexane=1:1) to give 33.10 g of the desired compound (77.4%, yellow solid).

NMR(200 MHz,CDCl$_3$) δ: 1.40(3H,J=7.2 Hz), 4.46(2H, q,J=7.2 Hz), 7.57–7.72(2H,m), 7.98(1H,dd,J=8.0,2.0 Hz), 8.84(1H,s).

Reference Example 2

5-Ethoxycarbonyl-2-methyl-3-trichloroacetylimidazo[1,2-a]pyridine

To a solution of 8.03 g (39.3 mmol) of 5-ethoxycarbonyl-2-methylimidazo[1,2-a]pyridine and 14.41 g (118 mmol) of 4-dimethylaminopyridine in 80 ml of chloroform was added dropwise 21.45 g (118 mmol) of trichloroacetyl chloride. The mixture was heated for 15 hours under reflux. After cooling, the reaction mixture was washed with an aqueous solution of sodium hydrogencarbonate, drid over anhydrous magnesium sulfate. The solvent was distilled off, and the residue was purified by column chromatography (eluent:ethyl acetate/n-hexane=2:1) to give 8.29 g of the desired compound (60.3%, pale yellow solid).

NMR(200 MHz,CDCl$_3$) δ: 1.45(3H,J=7.2 Hz), 2.65(3H, s), 4.49(2H,q,J=7.2 Hz), 7.40(1H,dd,J=8.8,7.2 Hz), 7.77 (1H,dd,J=7.2,1.2 Hz), 7.84(1H,dd,J=8.8,1.2 Hz).

Reference Example 3

5-Amino-3-ethoxycarbonyl-2-methylimidazo[1,2-a] pyridine.hydrochloride

To a suspension of 43.7 g (0.40 mol) of 2,6-diaminopyridine in 400 ml of ethanol was added 131.7 g (0.8 mol) of ethyl 2-chloroacetoacetate. The mixture was heated for 18 hours under reflux. After cooling, the resulting crystals was collected by filtration, washed with ethanol and ether successively to give 58.4 g of the desired compound (57.1%, pale yellow crystals).

NMR(200 MHz,D$_2$O) δ: 1.41(3H,t,J=7.2 Hz), 2.61(3H,s), 4.42(2H,q,J=7.2 Hz), 6.53(1H,d,J=8.2 Hz), 6.87(1H,d,J=8.2 Hz), 7.68(1H,t,J=8.2 Hz).

Reference Example 4

1,2-Dihydro-3-methyl-1,4,7b-triazacyclopent[cd] inden-2-one

To a suspension of 4.8 g (120 mmol) of sodium hydride (60% dispersion in oil) in 60 ml of DMF was added 10.23 g (40 mmol) of 5-amino-3-ethoxycarbonyl-2-methylimidazo[1,2-a]pyridine.hydrochloride with small portions. The mixture was stirred for 0.5 hour, then for 0.5 hour at 100° C., which was left standing for cooling. To the reaction mixture was added 60 ml of water. The mixture was washed with chloroform, to which was added, while stirring at room temperature, conc. HCl to make the pH of the solution 8. The resulting precipitate was collected by filtration, washed with water and ether, successively to give 5.97 g of the desired compound (86.1%, pale brown solid).

NMR(200 MHz,DMSO-d$_6$) δ: 2.65(3H,s), 6.94(1H,d,J= 7.4 Hz), 7.48(1H,d,J=8.6 Hz), 7.76(1H,dd,J=8.6,7.4 Hz), 12.1(1H,br).

Reference Example 5

1,2-Dihydro-3-methyl-1-[5-(phthalimido)pentan-1-yl]-1,4,7b-triazacyclopent[cd]inden-2-one To a suspension of 5.20 g (30 mmol) of 1,2-dihydro-3-methyl-1,4,7b-triazacyclopent[cd]inden-2-one in 60 ml of DMF was added, while stirring under ice-cooling, 1.44 g (36 mmol) of 60% sodium hydride (dispersion in oil). The mixture was stirred for 15 minutes at the same temperature. To the reaction mixture was added a solution of 8.89 g (30 mmol) of N-(5-bromopentyl)phthalimide in DMF (20 ml). The mixture was stirred for 1.5 hour at 110° C. After cooling, the reaction mixture was poured into water, extracted with ethyl acetate. The extract solution was washed with water, dried over anhydrous magnesium sulfate and concentrated. The concentrate was purified by column chromatography (eluent: ethyl acetate/ethanol=10:1) to afford 6.93 g of the desired compound (59.4%, pale brown solid).

NMR(200 MHz,CDCl$_3$) δ: 1.46(2H,m), 1.76(2H,m), 1.91 (2H,m), 2.80(3H,s), 3.68(2H,t,J=7.0 Hz), 4.05(2H,t,J=7.2 Hz), 6.83(1H,d,J=7.4 Hz), 7.58(1H,d,J=8.6 Hz), 7.70(1H, dd,J=8.6,7.4 Hz), 7.66–7.85(4H,m).

Reference Example 6

1,2-Dihydro-3-methyl-1-[6-(phthalimido)hexan-1-yl]-1,4,7b-triazacyclopent[cd]inden-2-one To a suspension of 5.20 g (30 mmol) of 1,2-dihydro-3-methyl-1,4,7b-triazacyclopent[cd]inden-2-one in 60 ml of DMF was added, while stirring under ice-cooling, 1.44 g (36 mmol) of 60% sodium hydride (dispersion in oil). The mixture was stirred for 15 minutes at the same temperature. To the reaction mixture was added a DMF solution (20 ml) of 9.31 g (30 mmol) of N-(6-bromohexyl)phthalimide. The mixture was stirred for 1.5 hour at 110° C. After cooling, the reaction mixture was poured into water, which was extracted with ethyl acetate. The extract was washed with water, dried over anhydrous magnesium sulfate, and concentrated. The concentrate was purified by column chromatography (eluent: ethyl acetate/ethanol=10:1) to give 3.47 g of the desired compound (28.7%, pale brown solid). NMR(200 MHz,CDCl$_3$) δ: 1.33–1.56(4H,m), 1.68(2H,m), 1.85(2H,m), 2.82(3H,s), 3.67(2H,t,J=7.2 Hz), 4.04(2H,t,J=7.2 Hz), 6.78 (1H,d,J=7.4 Hz), 7.47(1H,d,J=8.6 Hz), 7.69(1H,dd,J=8.6, 7.4 Hz), 7.67–7.76(2H,m), 7.78–7.88(2H,m).

Reference Example 7

1,2-Dihydro-3-methyl-1-[3-(phthalimido)propan-1-yl]-1,4,7b-triazacyclopent[cd]inden-2-one To a suspension of 8.66 g (50 mmol) of 1,2-dihydro-3-methyl-1,4,7b-triazacyclopent[cd]inden-2-one in 100 ml of DMF was added, while stirring under ice-cooling, 2.20 g (55 mmol) of 60% sodium hydride (dispersion in oil). The mixture was stirred for 20 minutes at the same temperature. To the reaction mixture was added 13.14 g (50 mmol) of N-(3-bromopropyl)phthalimide. The mixture was stirred for 7 hours at 100° C. After cooling, the reaction mixture was poured into water, which was subjected to extraction with chloroform. The extract was dried over anhydrous magnesium sulfate, and, the solvent was then distilled off. The residue was crystallized from methylene chloride—ethanol to give 5.72 g of the desired compound (31.7%, pale brown solid substance).

NMR(200 MHz,CDCl$_3$) δ: 2.29(2H,m), 2.81(3H,s), 3.85 (2H,t,J=7.0 Hz), 4.16(2H,t,J=7.2 Hz), 6.86(1H,d,J=7.4 Hz), 7.48(1H,d,J=8.6 Hz), 7.79(1H,dd,J=8.6,7.4 Hz), 7.66–7.76 (4H,m).

Reference Example 8

1,2-Dihydro-3-methyl-1-[4-(phthalimido)butan-1-yl]-1,4,7b-triazacyclopent[cd]inden-2-one To a suspension of 8.66 g (50 mmol) of 1,2-dihydro-3-methyl-1,4,7b-triazacyclopent[cd]inden-2-one in 100 ml of DMF was added, while stirring under ice-cooling, 2.20 g (55 mmol) of 60% sodium hydride (dispersion in oil). The mixture was stirred for 15 minutes at the same temperature. To the reaction mixture was added 14.10 g (50 mmol) of phthalimide, which was stirred for 6 hours at 100° C. After cooling, the reaction mixture was then poured into water, extracted with chloroform. The extract solution was dried over anhydrous magnesium sulfate, the solvent was distilled off. The residue was purified by column chromatography (eluent: ethyl acetate) to give 11.43 g of the desired compound (61.1%, pale yellow solid).

NMR(200 MHz,CDCl$_3$) δ: 1.70–2.00(4H,m), 2.81(3H,s), 3.76(2H,t,J=6.6 Hz), 4.12(2H,t,J=6.8 Hz), 6.85(1H,d,J=7.6 Hz), 7.47(1H,d,J=8.6 Hz), 7.69(1H,dd,J=8.6,7.6 Hz), 7.65–7.88(4H,m).

Reference Example 9

1-[5-(Amino)pentan-1-yl]-1,2-dihydro-3-methyl-1,4,7b-triazacyclopent[cd]inden-2-one To a suspension of 6.26 g (16.1 mmol) of 1,2-dihydro-3-methyl-1-[5-(phthalimido)pentan-1-yl]-1,4,7b-triazacyclopent[cd]inden-2-one in 120 ml of ethanol was added 2.42 g (48.3 mmol) of hydrazine monohydrate. The mixture was heated for two hours under reflux. After cooling, the resulting precipitates were filtered off. The filtrate was concentrated to give the residue, water was added, extracted with chloroform (three times). The extract was dried over anhydrous magnesium sulfate. The solvent was distilled off to give 3.31 g of the desired compound (79.6%, pale yellow solid substance).

NMR(200 MHz,CDCl$_3$) δ: 1.34–1.60(6H,m), 1.88(2H, m), 2.70(2H,t,J=6.8 Hz), 2.83(3H,s), 4.07(2H,t,J=7.2 Hz), 6.79(1H,d,J=7.4 Hz), 7.48(1H,d,J=8.6 Hz), 7.70(1H,d,J=8.6,7.4 Hz).

Reference Example 10

1-[6-(Amino)hexan-1-yl]-1,2-dihydro-3-methyl-1,4,7b-triazacyclopent[cd]inden-2-one To a suspension of 2.94 g (7.31 mmol) of 1,2-dihydro-3-methyl-1-[6-(phthalimido)hexan-1-yl]-1,4,7b-triazacyclopent[cd]inden-2-one in 80 ml of ethanol was added 1.10 g (22.0 mmol) of hydrazine.monohydrate. The mixture was heated for 2 hours under reflux. After cooling, the resulting precipitates were filtered off. The filtrate was concentrated to give the residue, water was added, extracted with chloroform (three times). The extract was dried over anhydrous magnesium sulfate, then the solvent was distilled off to give 1.50 g of the desired compound (75.4%, pale yellow solid).

NMR(200 MHz,CDCl$_3$) δ: 1.25–1.52(8H,m), 1.86(2H, m), 2.68(2H,m), 2.83(3H,s), 4.06(2H,t,J=7.2 Hz), 6.79(1H, d,J=7.4 Hz), 7.48(1H,d,J=8.6 Hz), 7.70(1H,dd,J=8.6,7.4 Hz).

Reference Example 11

1-[3-(Amino)propan-1-yl]-1,2-dihydro-3-methyl-1,4,7b-triazacyclopent[cd]inden-2-one To a suspension of 3.47 g (9.63 mmol) of 1,2-dihydro-3-methyl-1-[3-(phthalimido)propan-1-yl]-1,4,7b-triazacyclopent[cd]inden-2-one in 70 ml of ethanol was added 1.45 g (29.0 mmol) of hydrazine monohydrate. The mixture was heated for 2 hours under reflux. After cooling, and the resulting precipitates were filtered off. The filtrate was concentrated to give the residue, water was added, extracted with chloroform (three times). The extract was dried over anhydrous magnesium sulfate, then the solvent was distilled off to give 1.68 g of the desired compound (75.8%, pale yellow solid substance).

NMR(200 MHz,CDCl$_3$) δ: 1.48(2H,br), 1.98(2H,m), 2.78 (2H,t,J=6.6 Hz), 2.83(3H,s), 4.18(2H,t,J=6.8 Hz), 6.86(1H, d,J=7.4 Hz), 7.49(1H,d,J=8.8 Hz), 7.70(1H,dd,J=8.8,7.4 Hz).

Reference Example 12

1-[4-(Amino)butan-1-yl]-1,2-dihydro-3-methyl-1,4,7b-triazacyclopent[cd]inden-2-one To a suspension of 5.99 g (16.0 mmol) of 1,2-dihydro-3-methyl-1-[4-(phthalimido)butan-1-yl]-1,4,7b-triazacyclopent[cd]inden-2-one in 150 ml of ethanol was added 2.40 g (48.0 mmol) of hydrazine monohydrate. The mixture was heated for one hour under reflux. After cooling, and the resulting precipitates were filtered off. The filtrate was concentrated to give the residue, water was water, extracted with chloroform (three times). The extract solution was dried over anhydrous magnesium sulfate. The solvent was distilled off to give 3.17 g of the desired compound (81.1%, pale yellow solid).

NMR(200 MHz,CDCl$_3$) δ: 1.37(2H,br), 1.56(2H,m), 1.91 (2H,m), 2.77(2H,t,J=7.0 Hz), 2.83(3H,s), 4.09(2H,t,J=7.0 Hz), 6.81(1H,d,J=7.4 Hz), 7.49(1H,d,J=8.8 Hz), 7.71(1H, dd,J=8.8,7.4 Hz).

Reference Example 13

1,2-Dihydro-3-methyl-1,4,7b-triazacyclopento[cd] indene-2-thione

A mixture of 8.66 g (50 mmol) of 1,2-dihydro-3-methyl-1,4,7b-triazacyclopent[cd]inden-2-one and 24.27 g (60 mmol) of a Lawesson's reagent in 200 ml of pyridine was stirred for 5 hours at 100° C. After cooling, the resulting precipitates were collected by filtration, washed with pyridine and ether in that order to give 6.90 g of the desired compound (72.9%, brown solid substance). This compound was used, in the subsequent reaction without further purification.

NMR(200 MHz,DMSO-$d_6$) δ: 2.75(3H,s), 7.24(1H,d,J=7.6 Hz), 7.68(1H,d,J=8.4 Hz), 7.93(1H,dd,J=8.4,7.6 Hz).

Reference Example 14

3-Methyl-2-[4-(phthalimido)butan-1-ylthio]-1,4,7b-triazacyclopent[cd]indene

A mixture of 5.68 g (30 mmol) of 1,2-dihydro-3-methyl-1,4,7b-triazacyclopent[cd]indene-2-thione, 8.47 g (30 mmol) of N-(4-bromobutyl)phthalimide and 6.27 ml (45 mmol) of triethylamine in 150 ml of DMF was stirred for 2 hours at 100° C. After cooling, the reaction mixture was poured into water, extracted with ethyl acetate. The extract solution was washed with water, dried over anhydrous magnesium sulfate and concentrated. The residue was crystallized from chloroform-ethanol to give 7.39 g of the desired compound (63.1%, pale brown solid)

NMR(200 MHz,CDCl$_3$) δ: 1.96(4H,m), 2.89(3H,s), 3.56(2H,m), 3.77(2H,m), 7.62–7.75(4H,m), 7.76–7.85(2H,m), 7.92(1H,m).

Reference Example 15

2-[4-(Amino)butan-1-ylthio]-3-methyl-1,4,7b-triazacyclopent[cd]indene

To a suspension of 3.90 g (10.0 mmol) of 3-methyl-[4-(phthalimido)butan-1-ylthio]-1,4,7b-triazacyclopent[cd]indene in 70 ml of ethanol was added 1.50 g (30.0 mmol) of hydrazine monohydrate. The mixture was heated for 2 hours under reflux. After cooling the resulting precipitates were filtered off. The filtrate was concentrated to give the residue, water was added, extracted with chloroform. The extract was dried over anhydrous magnesium sulfate, then the solvent was distilled off to give 1.89 g of the desired compound (72.7%, pale brown solid)

NMR(200 MHz,CDCl$_3$) δ: 1.51(2H,br), 1.69(2H,m), 1.96(2H,m), 2.79(2H,t,J=6.8 Hz), 2.90(3H,s), 3.54(2H,t,J=7.2 Hz), 7.66(1H,d,J=8.0 Hz), 7.71(1H,d,J=7.8 Hz), 7.93(1H,dd,J=8.0,7.8 Hz).

Reference Example 16

4-[4-(Amino)phenylmethyl]-4,5-dihydro-3H-1,4,8b-triazaacenaphthylene-3,5-dione

To a solution of 1.47 g (12.0 mmol) of 4-aminobenzylamine and 1.68 g (13.0 mmol) of N,N-diisopropylethylamine was added a solution of 3.50 g (10.0 mmol) of 5-ethoxycarbonyl-3-trichloroacetylimidazo[1,2-a]pyridine in 10 ml of acetonitrile. The mixture was stirred for 7 hours at room temperature. The resulting precipitate was collected by filtration, washed with acetonitrile and dried to afford 2.586 g of the desired compound (86.7%, a yellow crystals).

Elemental Analysis Calcd for $C_{16}H_{12}N_4O_2$:

Calcd.: C, 65.75; H, 4.14; N, 19.17. Found: C, 65.53; H, 3.94; N, 19.19.

NMR(200 MHz,DMSO-$d_6$)δ: 4.99(2H,br), 5.03(2H,s), 6.47(2H,d,J=8.4 Hz), 7.10(2H,d,J=8.4 Hz), 7.89(1H,dd,J=8.8, 7.4 Hz), 8.12(1H,dd,J=7.4, 1.0 Hz), 8.28(1H,dd,J=8.8, 1.0 Hz), 8.66(1H,s).

Reference Example 17

4-[2-[4-(Amino)phenyl]ethan-1-yl]-4,5-dihydro-3H-1,4,8b-triazaacenaphthylene-3,5-dione To a solution of 1.63 g (12.0 mmol) of 2-[4-(amino)phenyl]ethylamine and 1.68 g (13 mmol) of N,N-diisopropylethylamine in 40 ml of acetonitrile was added a solution of 3.50 g (10.0 mmol) of 5-ethoxycarbonyl-3-trichloroacetylimidazo[1,2-a]pyridine in 10 ml of acetonitrile. The mixture was stirred for one hour at room temperature. The resulting crystalline precipitates were collected by filtration, washed with acetonitrile and dried to afford 1.03 g of the desired compound (33.6%, a yellow crystals). The filtrate was concentrated. The residne was crystallized from acetonitrile-methylene chloride. Crystalline precipitatse were collected by filtration, washed with acetonitrile to afford 1.60 g of the desired compound (52.1%, a yellow crystals).

NMR(200 MHz,DMSO-$d_6$) δ: 2.71(2H,m), 4.12(2H,m), 4.89(2H,br), 6.51(2H,m), 6.92(2H,m), 7.90(1H,dd,J=8.8,7.4 Hz), 8.13(1H,dd,J=7.4, 0.8 Hz), 8.29(1H,dd,J=8.8,0.8 Hz), 8.66(1H,s).

Reference Example 18

3-Methyl-2-[5-(phthalimido)pentan-1-ylthio]-1,4,7b-triazacyclopent[cd]indene

To a suspension of 2.03 g (10.7 mmol) of 1,2-dihydro-3-methyl-1,4,7b-triazacyclopent[cd]inden-2-thione in 50 ml of N,N-dimethylformamide were added 3.18 g (10.7 mmol) of N-(5-bromopentyl)phthalimide and 2.24 ml (16.1 mmol) of triethylamine. The mixture was stirred for two hours at 100° C. After cooling, the resulting precipitates were collected by filtration, washed with N,N-dimethylformamide, ethanol, and diethylether, successively, dried to afford 3.44 g of the desired compound (79.3%, a pale brown solid).

NMR(200 MHz,CDCl$_3$) δ: 1.48–1.88(4H,m), 1.96(2H,m), 2.89(3H,s), 3.51(2H,t,J=7.2 Hz), 3.73(2H,t,J=7.0 Hz), 7.62–7.87(6H,m), 7.94(1H,dd,J=8.0, 7.8 Hz).

Reference Example 19

3-Methyl-2-[5-(amino)pentan-1-ylthio]-1,4,7b-triazacyclopent[cd]indene

To a suspension of 2.50 g (6.2 mmol) of 3-methyl-2-[5-(phthalimido)pentan-1-ylthio]-1,4,7b-triazacyclopent[cd]indene in 50 ml of ethanol was added 928 mg (18.5 mmol) of hydrazinemonohydrate. The mixture was heated for two hours under reflux. After cooling, the resulting precipitates were collected by filtration and washed with ethanol. The filtrate and washing were combined and concentrated to give the residue. Water was added, extracted with methylene chloride, dried over anhydrous magnesium sulfate. The solvent was distilled off to afford 1.197 g of the desired compound (70.6%, a greenish brown solid).

NMR(200 MHz,CDCl$_3$) δ: 1.44(2H,br), 1.56(4H,m), 1.93(2H,m), 2.73(2H,m), 2.91(3H,s), 3.54(2H,t,J=7.2 Hz), 7.67(1H,d,J=7.8 Hz), 7.73(1H,d,J=8.0 Hz), 7.94(1H,dd,J=8.0, 7.8 Hz).

Reference Example 20

3-Dimethylaminomethyl-5-ethoxycarbonylimidazo[1,2-a]pyridine

To a solution of 1.90 g (10.0 mmol) of 5-ethoxycarbonylimidazo[1,2-a]pyridine in 40 ml of acetonitrile was added 2.41 g (13.0 mmol) of N,N-dimethylmethyleneammonium iodide. The mixture was heated for two hours under reflux. The solvent was distilled off. To the residue was added methylene chloride. The mixture was washed with an aqueous solution of sodium thiosulfate and an aqueous solution of sodium hydrogencarbonate, successively, dried over anhydrous magnesium sulfate. The solvent was distilled off, and the residue was purified by column chromatography (eluent: ethyl acetate) to afford 1.496 g of the desired compound (60.6%, a pale yellow solid). This product was recrystallized from ethyl acetate to afford the desired compound (colorless crystals), m.p.117.0–118.0° C.

Elemental Analysis Calcd for $C_{13}H_{17}N_3O_2$:

Calcd.: C, 63.14; H, 6.93; N, 16.99. Found: C, 63.09; H, 6.68; N, 16.94.

NMR(200 MHz,CDCl$_3$) δ: 1.45(3H,t,J=7.2 Hz), 1.96(6H, s), 3.72(2H,s), 4.45(2H,q,J=7.2 Hz), 7.20(1H,dd,J=8.8,7.0 Hz), 7.28(1H,dd,J=7.0, 1.6 Hz), 7.59(1H,s), 7.78(1H,dd,J=8.8, 1.6 Hz).

IR(KBr): 1718, 1714, 1626.

Reference Example 21

5-Ethoxycarbonylimidazo[1,2-a]pyridin-3-ylmethyl trimethylammonium iodide

To a solution of 6.15 g (24.9 mmol) of 3-dimethyl aminomethyl-5-ethoxycarbonylimidazo[1,2-a]pyridine was added a solution of 3.71 g (26.1 mmol) of methyl iodide in 5 ml of acetonitrile. The mixture was stirred for 66 hours at room temperature. The solvent was distilled off, to give 10.50 g of the desired compound (quantitative, a yellow solid). This product was used in the subsequent reaction without further purification.

NMR(200 MHz,DMSO-d$_6$) δ: 1.42(3H,t,J=7.2 Hz), 2.94 (9H,s), 4.57(2H,q,J=7.2 Hz), 5.13(2H,s), 7.55(1H,dd,J=9.0, 7.2 Hz), 7.82(1H,dd,J=7.2, 1.4 Hz), 8.06(1H,dd,J=9.0,1.4 Hz), 8.09(1H,s).

Reference Example 22

5-Ethoxycarbonyl-3-nitroimidazo[1,2-a]pyridine

To a solution of 19.02 g (0.10 mol) of 5-ethoxycarbonylimidazo[1,2-a]pyridine in 50 ml of conc. sulfuric acid was added dropwise, while stirring under ice-cooling, 40 ml of conc. nitric acid. The mixture was stirred for 20 minutes at the same temperature. The reaction mixture was poured into ice-water, which was neutralized with a 10% aqueous solution of NaOH. The resulting precipitates were collected by filtration, washed with water and dried to afford 20.38 g of the desired compound (86.6%, a pale yellow solid).

NMR(200 MHz,CDCl$_3$) δ: 1.41(3H,t,J=7.2 Hz), 4.48(2H, q,J=7.2 Hz), 7.62–7.74(2H,m), 7.98(1H,m), 8.55(1H,s).

Reference Example 23

3-Amino-5-ethoxycarbonylimidazo[1,2-a]pyridine

To a solution of 2.35 g of 5-ethoxycarbonyl-3-nitroimidazo[1,2-a]pyridine in 100 ml of ethanol was added 10% Pd—C (wet, 470 mg). The mixture was stirred for 110 hours at room temperature under hydrogen atmosphere. The catalyst was filtered off and washed with ethanol. The filtrate and the washing were combined, and the solvent was distilled off. The residue was purified by column chromatography (eluent: ethyl acetate) to afford 891 mg of the desired compound (43.4%, a dark reddish oil).

NMR(200 MHz,CDCl$_3$) δ: 1.46(3H,t,J=7.2 Hz), 4.22(2H, br), 4.48(2H,q,J=7.2 Hz), 7.04(1H,dd,J=8.8, 7.2 Hz), 7.24 (1H,s), 7.54(1H,dd,J=7.2, 1.2 Hz), 7.74(1H,dd,J=8.8,1.2 Hz).

Reference Example 24

3,4-Dihydro-1,3,7b-triazacyclopent[cd]inden-4-one

To a suspension of 343 mg (8.58 mmol) of 60% sodium hydride (dispersion in oil) in 3 ml of DMF was added, while stirring at room temperature, a solution of 880 mg (4.29 mmol) of 3-amino-5-ethoxycarbonylimidazo[1,2-a]pyridine in 5 ml of DMF. The mixture was stirred for 30 minutes at 100° C. After cooling, the reaction mixture was poured into ice-water, washed with ethyl acetate. The aqueous layer was neutralized by the addition of 6N-HCl. The resulting precipitates were collected by filtration, washed with water, and dried to afford 100 mg of the desired compound (14.7%, a brown solid). The filtrate was extracted with chloroform, dried over anhydrous magnesium sulfate. The solvent was distilled off, and the residue was purified by column chromatography (eluent:ethyl acetate/ethanol=10:1) to afford 27 mg of the desired compound (4.0%, a yellow solid)

NMR(200 MHz,CDCl$_3$) δ: 7.67(1H,s), 7.75(1H,dd,J=8.6, 7.0 Hz), 7.99(1H,d,J=7.0 Hz), 8.08(1H,d,J=8.6 Hz), 9.92 (1H,br).

Reference Example 25

3,4-Dihydro-3-[5-(phthalimido)pentan-1-yl]-1,3,7b-triazacyclopent[cd]inden-4-one To a suspension of 81 mg (0.51 mmol) of 3,4-dihydro-1, 3,7b-triazacyclopent[cd]inden-4-one in 1 ml of DMF was added, while stirring under ice-cooling, 25 mg (0.63 mmol) of 60% sodium hydride (dispersion in oil). The mixture was stirred for 15 minutes at the same temperature. To the reaction mixture was added a solution of 151 mg (0.51 mmol) of N-(5-bromopentyl)phthalimide in 1 ml of DMF. The mixture was stirred for two hours at 110° C. After cooling, the reaction mixture was poured into water, extracted with ethyl acetate. The extract was washed with an aqueous saline solution and dried over anhydrous magnesium sulfate. The solvent was distilled off, and the residue was purified by column chromatography (eluent:ethyl acetate/ethanol=10:1) to afford 40 mg of the desired compound (20.9%, a colorless solid).

NMR(200 MHz,CDCl$_3$) δ: 1.30–1.85(6H,m), 2.95(1H, m), 3.71(2H,t,J=7.0 Hz), 4.44(1H,m), 6.88(1H,d,J=7.0 Hz), 7.16(1H,dd,J=9.2, 7.0 Hz), 7.16(1H,s), 7.38(1H,d,J=9.2 Hz), 7.67–7.90(4H,m).

Reference Example 26

5-Ethoxycarbonyl-2-methyl-3-nitroimidazo[1,2-a] pyridine

To a solution of 1.02 g (5.0 mmol) of 5-ethoxycarbonyl-2-methyl-imidazo[1,2-a]pyridine in 2.5 ml of conc. sulfuric acid was added dropwise, while stirring under ice-cooling, 2.0 ml of conc. nitric acid. The mixture was stirred for 10 minutes at the same temperature. The reaction mixture was poured into ice-water, whose pH was adjusted to 3–4 with a 10% aqueous solution of NaOH. The resulting crystalline precipitates were collected by filtration, washed with water and dried, followed by further purification by column chromatography (eluent: ethyl acetate) to afford 752 mg of the desired compound (60.4%, a yellow solid).

NMR(200 MHz,CDCl$_3$) δ: 1.41(3H,t,J=7.2 Hz), 2.81(3H, s), 4.46(2H,q,J=7.2 Hz), 7.58–7.68(2H,m), 7.84(1H,m).

Reference Example 27

3-Amino-5-ethoxycarbonyl-2-methyl-imidazo[1,2-a] pyridine

To a solution of 300 mg of 5-ethoxycarbonyl-2-methyl-3-nitroimidazo[1,2-a]pyridine in 20 ml of methanol was added 10% Pd—C (wet, 90 mg). The mixture was stirred for two hours at room temperature under hydrogen atmosphere. The catalyst was filtered off and washed with methanol. The filtrate and the washing were combined, and the solvent was filtered off. The residue was purified by column chromatography (eluent: ethyl acetate) to afford 184 mg of the object product (69.7%, an orange solid)

NMR(200 MHz,CDCl$_3$) δ: 1.46(3H,t,J=7.2 Hz), 2.45(3H, s), 4.02(2H,br), 4.48(2H,q,J=7.2 Hz), 6.99(1H,dd,J=8.8,7.2 Hz), 7.52(1H,dd,J=7.2, 1.2 Hz), 7.66(1H,dd,J=8.8,1.2 Hz).

Reference Example 28

3,4-Dihydro-2-methyl-1,3,7b-triazacyclopent[cd]inden-4-one

To a suspension of 610 mg (15.3 mmol) of 60% sodium hydride (dispersion in oil) in 5 ml of DMF was added, while stirring at room temperature, a solution of 1.67 g (7.62 mmol) of 3-amino-5-ethoxycarbonyl-2-methyl-imidazo[1,2-a]pyridine in 5 ml of DMF. The mixture was stirred for 10 minutes, then for 30 minutes at 100° C. After cooling, the reaction mixture was poured into ice-water, and washed with chloroform. To the aqueous layer was added 6N-HCl to adjust the pH to 5–6. The resulting precipitates were collected by filtration, washed with water and diethyl ether, successively, and dried to afford 357 mg of the desired compound (27.0%, a brown solid).

NMR(200 MHz,CDCl$_3$) δ: 2.02(3H,s), 7.02–7.40(3H,m), 10.45(1H,br).

Reference Example 29

3,4-Dihydro-3-[5-(phthalimido)pentan-1-yl]-2-methyl-1,3,7b-triazacyclopent[cd]inden-4-one To a suspension of 277 mg (1.60 mmol) of 3,4-dihydro-2-methyl-1,3,7b-triazacyclopent[cd]inden-4-one in 3 ml of DMF was added, while stirring under ice-cooling, 77 mg (1.93 mmol) of 60% sodium hydride (dispersion in oil). The mixture was stirred for 15 minutes at the same temperature. To the reaction mixture was added 521 mg (1.76 mmol) of N-(5-bromopentyl)phthalimide. The mixture was stirred for one hour at 110° C. After cooling, the reaction mixture was poured into water, and extracted with ethyl acetate. The extract solution was washed with an aqueous saline solution, and dried over anhydrous magnesium sulfate. The solvent was distilled off, and the residue was purified by column chromatography (eluent: ethyl acetate/ethanol=10:1) to afford 410 mg of the desired compound (66.0%, a pale brown solid).

NMR(200 MHz,CDCl$_3$) δ: 1.25–1.80(6H,m), 2.06(3H,s), 2.99(1H,m), 3.67(2H,t,J=7.0 Hz), 4.31(1H,m), 6.94(1H,dd, J=6.8, 1.2 Hz), 7.13(1H,dd,J=9.0, 6.8 Hz), 7.29(1H,dd,J=9.0, 1.2 Hz), 7.66–7.90(4H,m).

Reference Example 30

4,5-Dihydro-3H-1,4,8b-triazaacenaphthylene-3,5-dione

To a solution of 2.64 g (7.55 mmol) of 5-ethoxycarbonyl-3-trichloroacetylimidazo[1,2-a]pyridine in 20 ml of acetonitrile was added 2.5 ml of 25% aqueous ammonia. The mixture was stirred for 5 hours at room temperature. The resulting crystals were collected by filtration and washed with acetonitrile to give 393 mg of the desired compound (27.8%, pale brown solid).

NMR(200 MHz,DMSO-d$_6$) δ: 7.84(1H,dd,J=8.8, 7.4 Hz), 8.01(1H,dd,J=7.4, 1.0 Hz), 8.22(1H,dd,J=8.8, 1.0 Hz), 8.53 (1H,s).

Reference Example 31

5-[2-[4-(Amino)phenyl]ethan-1-ylamino]-3-ethoxycarbonyl-2-methylimidazo[1,2-a]pyridine A mixture of 4.07 g (17.1 mmol) of 5-chloro-3-ethoxycarbonyl-2-methylimidazo[1,2-a]pyridine, 3.48 g (25.6 mmol) of 2-(4-aminophenyl)ethylamine and 4.41 g (34.1 mmol) of N,N-diisopropylethylamine in 60 ml of acetonitrile was heated for 64 hours under reflux with stirring. After cooling, the solvent was distilled off. To the residue was added chloroform. The residue was washed with water and dried over anhydrous magnesium sulfate. The solvent was distilled off. The residue was purified by column chromatography (eluent: chloroform/methanol=30:1) and recrystallized from ethyl acetate-n-hexane to give 4.37 g of the desired compound (75.7%, pale brown crystals).

NMR(200 MHz,CDCl$_3$) δ: 1.44(3H,t,J=7.2 Hz), 2.66(3H, s), 2.95(2H,m), 3.42(2H,m), 3.62(2H,br), 4.39(2H,q,J=7.2 Hz), 5.95(1H,dd,J=8.0, 1.2 Hz), 6.65(2H,m), 6.91(1H,dd,J=8.4, 1.2 Hz), 7.15(2H,m), 7.33(1H,dd,J=8.4, 8.0 Hz), 8.75 (1H,br).

Reference Example 32

1-[2-[4-(Amino)phenyl]ethan-1-yl]-1,2-dihydro-3-methyl-1,4,7b-triazacyclopent[cd]inden-2-one To a suspension of 80 mg (2.0 mmol) of 60% sodium hydride (dispension in oil) in 10 ml of DMF was added, while stirring at room temperature, 338 mg (1.0 mmol) of 5-[2-[4-(amino)phenyl]ethan-1-ylamino]-3-ethoxycarbonyl-2-methylimidazo[1,2-a]pyridine. The mixture was stirred for 30 minutes. The reaction mixture was poured into water, extracted with ethyl acetate. The extract was washed with an aqueous saline solution, dried over anhydrous magnesium sulfate. The solvent was distilled off. The residue was purified by column chromatography (eluent: ethyl acetate) to give 151 mg of the desired compound (51.7%, pale brown solid).

NMR(200 MHz,CDCl$_3$) δ: 2.82(3H,s), 3.01(2H,t,J=7.0 Hz), 3.61(2H,br), 4.21(2H,t,J=7.0 Hz), 6.39(1H,d,J=7.4 Hz), 6.55(2H,m), 6.93(2H,m), 7.41(1H,d,J=8.6 Hz), 7.58(1H,dd, J=8.6, 7.4 Hz).

Reference Example 33

5-Chloro-3-trichloroacetylimidazo[1,2-a]pyridine

To a solution of 45.77 g (0.30 mol) of 5-chloroimidazo[1,2-a]pyridine and 120.9 g (0.99 mol) of 4-dimethylaminopyridine in 500 ml of chloroform was added dropwise 163.5 g (0.90 mol) of trichloroacetyl chloride. The mixture was heated for 43 hours under reflux. After cooling, the reaction mixture was washed with an aqueous solution of sodium hydrogencarbonate, dried over anhydrous magnesium sulfate. The solvent was distilled off, and the residue was purified by column chromatography (eluent: ethyl acetate/n-hexan=1:1) to give 7.41 g of the desired compound (8.3%, pale brown solid).

NMR(200 MHz,CDCl$_3$) δ: 7.24(1H,dd,J=7.4, 1.2 Hz), 7.58(1H,dd,J=8.8, 7.4 Hz), 7.82(1H,dd,J=8.8, 1.2 Hz), 8.79 (1H,s).

Reference Example 34

N-(5-Imidazo[1,2-a]pyridylmethyl)hexamethylenetetraminium.chloride

To a suspension of 5.78 g (28.46 mmol) of 5-chloromethylimidazo[1,2-a]pyridine.hydrochloride and 4.79 g (34.16 mmol) of hexamethylenetetramin in 100 ml of acetonitrile was heated for 30 minutes under reflux. The reaction mixture was cooled to room temperature.

The resulting precipitates were collected by filtration, washed with 20 ml of acetonitrile and 20 ml of ether, and dried under reduced pressure to give 8.61 g of the desired compound (98.6 %, white solid).

NMR(200 MHz,DMSO-$d_6$) δ: 4.41–4.78(12H,m), 5.40 (2H,s), 7.30(1H,d,J=7.0 Hz), 7.48(1H,dd,J=8.6, 7.0 Hz), 7.83–7.89(2H,m), 8.68(1H,s).

IR(KBr): 2831, 1460, 1375 $cm^{-1}$

Reference Example 35

5-(tert-Butoxycarbonylamino)methylimidazo[1,2-a]pyridine

To a solution of 20 ml of purified water, 100 ml of ethanol and 24 ml of 12N HCl was added 8.61 g (28.06 mmol) of N-(5-imidazo[1,2-a]pyridylmethyl) hexamethylenetetraminium.chloride. The reaction mixture was stirred for 12 hours at 50° C. The reaction mixture was concentrated to 30 ml of volume under reduced pressure. The resulting precipitates anmmonium chloride were collected by filtration. The filtrate was completely concentrated under reduced pressure. To the residue was added 50 ml of purified water and 50 ml of THF, to give the homogeneous solution. To the solution was added 12 ml (84.18 mmol) of triethylamine and 7.35 g (33.67 mmol) of di-tert-butyl dicarbonate. The mixture was stirred for one hour at room temperature. To the reaction mixture was added 100 ml of purified water and 100 ml of ethyl acetate, and the mixture was extracted. The organic layer was washed with 100 ml of a saturated saline, dried over magnesium sulfate. The solvent was distilled off under reduced pressure. The residue was purified by silica gel column chromatography (eluent: chloroform/methanol=20:1) to give 4.20 g of the desired compound (60.5%, white solid).

NMR(200 MHz,$CDCl_3$) δ: 1.47(9H,s), 4.61(2H,d,J=6.0 Hz), 5.13(1H,brs), 6.76(1H,d,J=6.6 Hz), 7.18(1H,dd,J=8.8, 6.6 Hz), 7.61(1H,d,J=8.8 Hz), 7.69(2H,s).

IR(KBr): 1707, 1450, 1269, 1167 $cm^{-1}$

Reference Example 36

4,5-Dihydro-4-(tert-butoxycarbonyl)-3H-1,4,8b-triazaacenaphthylen-3-one

To a solution of 989 mg (4.0 mmol) of 5-(tert-butoxycarbonylamino)methylimidazo[1,2-a]pyridine and 2200 mg (18.0 mmol) of 4-(N,N-dimethylamino)pyridine in 25 ml of chloroform was added dropwise 1.34 ml (12.0 mmol) of trichloroacetyl chloride at room temperature. The reaction mixture was heated for 5 hours under reflux. The reaction mixture was poured into ice-water. The mixture was neutralized with a saturated aqueous solution of sodium hydrogencarbonate. To the mixture was added 100 ml of chloroform for extraction of the desired compound. The organic layer was washed with 100 ml of a saturated saline, and dried over magnesium sulfate. The solvent was distilled off under reduced pressure. The residue was purified by silica gel column chromatography (eluent: chloroform:methanol=20:1) to give 492 mg of the desired compound (45.0%, pale yellow solid).

NMR(200 MHz,$CDCl_3$) δ: 1.58(9H,s), 5.28(2H,s), 6.92 (1H,d,J=7.0 Hz), 7.45(1H,dd,J=9.2, 7.0 Hz), 7.65(1H,d,J= 9.2 Hz), 8.39(1H,s).

IR(KBr): 1714, 1515, 1309, 1149 $cm^{-1}$

Reference Example 37

4,5-Dihydro-3H-1,4,8b-triazaacenaphthylene-3-one.hydrochloride

To a solution of 95.7 mg (0.35 mmol) of 4,5-dihydro-4-(tert-butoxycarbonyl)-3H-1,4,8b-triazaacenaphthylen-3-one in 100 ml of ethanol was added 0.09 ml (1.05 mmol) of 12N HCl. The mixture was stirred for one hour at room temperature. The resulting crystalline precipitates were collected by filtration, washed with a small volume of ethanol and ether and dried to give 56.1 mg of the desired compound (76.4%, white solid).

NMR(200 MHz,DMSO-$d_6$) δ: 5.12(2H,s), 7.44(1H,d,J= 7.4 Hz), 7.85(1H,d,J=9.2 Hz), 7.99(1H,dd,J=9.2, 7.4 Hz), 8.50(1H,brs), 8.62(1H,s).

IR(KBr): 1677, 1479, 1360 $cm^{-1}$

Reference Example 38

1,2-Dihydro-1,4,7b-triazacyclopent[cd]inden-2-one.2NaCl i) Synthesis of 5-amino-3-carbethoxyimidazo[1,2-a]pyridine In 1250 ml of ether was suspended 56.0 g (500 mM) of potassium tert-butoxide and while the suspension was stirred vigorously, a solution of 37.0 g (500 mM) of ethyl formate and 61.3 g (500 mM) of ethyl chloroacetate in 100 ml of ether was added dropwise at room temperature over 15 minutes. The reaction mixture was stirred at room temperature for 30 minutes and the precipitate that formed was recovered by filtration. The precipitate was rinsed with 50 ml of ether and dried in vacuo to give 93.13 g of ethyl 2-chloro-2-formylacetate potassium salt as light-yellow solid. In 40 ml of ethanol was suspended 7.59 g (40.0 mM) of this ethyl 2-chloro-2-formylacetate potassium salt as well as 2.18 g (20.0 mM) of 2,6-diaminopyridine and following addition of 2.3 ml (40 mM) of acetic acid, the mixture was refluxed for 3 hours. After completion of the reaction, the precipitate that formed was recovered by filtration and rinsed with 10 ml of ethanol. The filtrate and the washes were pooled and neutralized with aqueous $NaCO_3$ solution, and the solvent was distilled off under reduced pressure. The residue was extracted with 100 ml of ethyl acetate and the organic layer was washed with 100 ml of saturated aqueous NaCl solution and dried over $MgSO_4$. The solvent was distilled off under reduced pressure and the residue was washed with ether to provide 1.65 g of the title compound as light-yellow solid. The washes were concentrated and the residue was purified by silica gel column chromatography (eluent: ethyl acetate) to provide 0.61 g of the title compound (total yield 2.26 g, percent yield 55.1%).

$^1$H-NMR(200 MHz,$CDCl_3$) δ: 1.42(3H,t,J=7.2 Hz), 4.37 (2H,q, J=7.2 Hz), 6.10(1H,dd,J=7.2, 1.0 Hz), 6.84(2H,br s,$NH_2$), 7.07(1H,dd,J=8.6, 1.2 Hz), 7.32(1H,t,J=8.6 Hz), 8.39(1H,s).

IR(KBr): 3225, 1689, 1647 $cm^{-1}$.

ii) Synthesis of 1,2-dihydro-1,4,7b-triazacyclopent[cd]inden-2-one.2NaCl

To a solution prepared by dissolving 1.44 g (7.0 mM) of 3-carbomethoxy-5-aminoimidazo[1,2-a]pyridine in 10 ml of acetonitrile followed by addition of 3.2 ml (14.0 mM) of 25% sodium methoxide-methanol and the mixture was refluxed for 1 hour. After completion of the reaction, 1.15 ml (14.0 mM) of 12N-hydrochloric acid was added to the reaction mixture under ice-cooling and the solvent was thoroughly distilled off under reduced pressure to provide 2.01 g (yield 100%) of a crude product as tan-colored solid.

$^1$H-NMR(200 MHz,DMSO-d$_6$) δ: 7.05 (1H,d,J=7.4 Hz), 7.66 (1H,d,J=8.6 Hz), 7.85(1H,dd,J=8.6, 7.4 Hz), 8.41(1H, s).

IR(KBr): 3452, 1699, 1668 cm$^{-1}$.

Reference Example 39

1,2-Dihydro-1,4,7b-triazacyclopent[cd]inden-2-one sodium salt

To a solution prepared by dissolving 51.3 g (25.0 mM) of 5-amino-3-carbethoxyimidazo[1,2-a]pyridine in 500 ml of ethanol was added 114 ml (50.0 mM) of 25% sodium methoxide-methanol and the mixture was refluxed for 3 hours. After completion of the reaction, the precipitate that formed was recovered by filtration, rinsed with 50 ml of ethanol, and dried in vacuo to provide 32.66 g (yield 72.1%) of the title compound as gray powders.

$^1$H-NMR(200 MHz,DMSO-d$_6$) δ: 6.47(1H,d,J=7.4 Hz), 7.02(1H,d,J=8.4 Hz), 7.45(1H,dd,J=8.4, 7.4 Hz), 7.78(1H, s).

Reference Example 40

3-Carbethoxy-5-chloromethylimidazo[1,2-a]pyridine sulfate i) Synthesis of 3-carbethoxy-5-methylimidazo[1,2-a]pyridine In 10 ml of ether was suspended 560 mg (5.0 mM) of potassium tert-butoxide and while the suspension was vigorously stirred, a solution of ethyl formate:370 mg (5.00 mM) and ethyl chloroformate: 613 mg (5.00 mM) in 10 ml of ether was added dropwise over 3 minutes at room temperature. This mixture was stirred at room temperature for 30 minutes and the precipitate that formed was recovered by filtration and rinsed with a small amount of ether. This precipitate was dried in vacuo to give 700 mg (yield 73.8%) of ethyl 2-chloro-2-formylacetate potassium salt as light-yellow solid. Then, 700 mg (3.69 mM) of ethyl 2-chloro-2-formylacetate potassium salt and 399 mg (3.69 mM) of 6-amino-2-methylpyridine were mixed with 20 ml of ethanol and after addition of 0.53 ml (9.23 mM) of acetic acid, the whole mixture was refluxed for 3 hours. After completion of the reaction, the solvent was distilled off under reduced pressure and the residue was diluted with 20 ml of ethyl acetate and 20 ml of purified water. Then, saturated aqueous NaHCO$_3$ solution was added until the water layer became pH 8. This mixture was extracted with 40 ml of ethyl acetate and the organic layer was washed with 30 ml of saturated aqueous NaCl solution and dried over MgSO$_4$. The solvent was then distilled off under reduced pressure and the residue was purified by silica gel column chromatography (eluent: ethyl acetate) to provide 430 mg (yield 57.1%) of the title compound as light-yellow liquid.

$^1$H-NMR(200 MHz,CDCl$_3$) δ: 1.42(3H,t,J=7.0 Hz), 2.82 (3H,s), 4.38(2H,q,J=7.0 Hz), 6.81(1H,d,J=7.0 Hz), 7.36(1H, dd,J=8.8, 7.0 Hz), 7.62(1H,d,J=8.8 Hz), 8.30(1H,s).

ii) Synthesis of 3-carboethoxy-5-chloromethylimidazo[1,2-a]pyridine

To a solution prepared by dissolving 430 mg (2.06 mM) of 3-carbethoxy-5-methylimidazo[1,2-a]pyridine in 10 ml of ethyl acetate was added 330 mg (2.67 mM) of N-chlorosuccinimide. Then, 1.03 ml (1.03 mM) of 1N-trifluoroacetic acid-ethyl acetate was added dropwise at room temperature. The mixture was stirred under argon gas at room temperature for 14 hours. After the reaction, the reaction mixture was poured in 30 ml of saturated aqueous NaHCO$_3$ solution with ice-cooling and the mixture was extracted with 20 ml of ethyl acetate. The organic layer was washed with 30 ml of saturated aqueous NaCl solution and dried over MgSO$_4$. The solvent was then distilled off under reduced pressure and the residue was purified by silica gel column chromatography (eluent: ethyl acetate) to provide 350 mg (yield 71.2%) of the title compound as yellow liquid.

$^1$H-NMR(200 MHz,CDCl$_3$) δ: 1.45(3H,t,J=7.2 Hz), 4.44 (2H,q,J=7.2 Hz), 5.44(2H,s), 7.08(1H,d,J=7.0 Hz), 7.42(1H, dd,J=8.8, 7.0 Hz), 7.80(1H,d,J=8.8 Hz), 8.35(1H,s).

iii) Synthesis of 3-carbethoxy-5-chloromethylimidazo[1,2-a]pyridine sulfate

To a solution prepared by dissolving 43.91 g (215.03 mM) of 3-carbethoxy-5-methylimidazo[1,2-a]pyridine in 200 ml of ethyl acetate was added 31.58 g (236.53 mM) of N-chlorosuccinimide. Then, 1.66 ml (21.50 mM) of trifluoroacetic acid was added dropwise at room temperature. This mixture was stirred under argon gas at room temperature for 14 hours. After completion of the reaction, the reaction mixture was poured in 300 ml of saturated aqueous NaHCO$_3$ solution with ice-cooling and extracted with 200 ml of ethyl acetate. The organic layer was washed with 300 ml of saturated aqueous NaCl solution and dried over MgSO$_4$ and the solvent was distilled off under reduced pressure to recover 22.15 g of crude 3-carbethoxy-5-chloromethylimidazo[1,2-a]pyridine as tan-colored liquid. To a solution prepared by dissolving 22.15 g of this crude 3-carbethoxy-5-chloromethylimidazo[1,2-a]pyridine in 200 ml of acetonitrile was added 4.95 ml (92.80 mM) of sulfuric acid with ice-cooling and the mixture was stirred. The purified precipitate was recovered by filtration, rinsed with a small amount of acetonitrile, and dried in vacuo to provide 16.20 g (yield 22.4%) of the title compound as orchre powders.

$^1$H-NMR(200 MHz,DMSO-d$_6$) δ: 1.38(3H,t,J=7.0 Hz), 4.41(2H,q,J=7.0 Hz), 5.60(2H,s), 7.62(1H,d,J=7.0 Hz), 7.83 (1H,dd,J=7.6, 7.0 Hz), 8.00(1H,d,7.6 Hz), 8.61(1H,s).

| Preparation Example 1 (as one coated tablet) | |
|---|---|
| (1) Compound of Example 1 | 10.0 mg |
| (2) Lactose | 60.0 mg |
| (3) Corn starch | 35.0 mg |
| (4) Gelatin | 3.0 mg |
| (5) Magnesium stearate | 2.0 mg |

A mixture of 10.0 mg of the compound of Example 1, 60.0 mg of lactose and 35.0 mg of corn starch was granulated through a 1 mm mesh screen, using 0.03 ml of an aqueous solution of 10 weight % gelatin (3.0 mg in terms of gelatin), which was dried at 40° C. and screened again. The granules thus obtained were mixed with 2.0 mg of magnesium stearate and compressed. The core tablet thus obtained was coated with a suspension of sucrose, titanium dioxide and talc in gum arabic, which was polished with bees wax.

| Preparation Example 2 (as one tablet) | |
|---|---|
| (1) Compound of Example 1 | 10.0 mg |
| (2) Lactose | 70.0 mg |
| (3) Corn starch | 50.0 mg |
| (4) Soluble starch | 7.0 mg |
| (5) Magnesium stearate | 3.0 mg |

A mixture of 10.0 mg of the compound of Example 1 and 3.0 mg of magnesium stearate was granulated with 0.07 ml of an aqueous solution of soluble starch (7.0 mg in terms of soluble starch), which was dried and, then mixed with 70.0 mg of lactose and 50.0 mg of corn starch. The mixture was compressed to obtain a tablet.

| Preparation Example 3 | |
|---|---|
| (1) Compound of Example 1 | 5.0 mg |
| (2) Common salt | 20.0 mg |
| (3) Distilled water to make the whole volume | 2 ml |

In distilled water were dissolved 5.0 mg of the compound of Example 1 and 20.0 mg of common salt. To the solution was added distilled water to make the whole volume 2.0 ml. The solution was subjected to filtration, which was filled into a 20 ml-ampoule under sterile conditions. The ampoule was sterilized and sealed to provide an injectable solution.

Industrial Applicability

The present invention relates to a novel tricyclic compound, which is useful as a medicine having an excellent activity of inhibiting platelet-derived growth factor (PDGF), antihypertensive activity, ameliorating activity of renal failure and lowering the cholesterol level, a process for producing the compound, and a pharmaceutical composition containing the compound.

What is claimed is:

1. A compound of the formula:

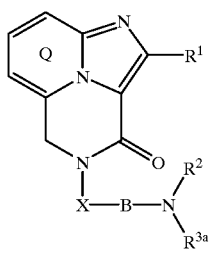

wherein:

ring Q is optionally substituted with one to three substituents selected from (i) halogen atom, (ii) alkyl group, (iii) halogeno-alkyl group, (iv) alkoxy group, (v) halogeno-alkoxy group, (vi) alkylthio group, (vii) halogeno-alkylthio group, (viii) hydroxyl group, (ix) carboxyl group, (x) cyano group, (xi) nitro group, (xii) amino group, (xiii) mono-alkyl amino group, (xiv) di-alkyl amino group, (xv) formyl group, (xvi) mercapto group, (xvii) alkyl-carbonyl group, (xviii) alkoxy-carbonyl group, (xix) sulfo group, (xx) alkyl-sulfonyl group, (xxi) carbamoyl group, (xxii) mono-alkyl-carbamoyl group, or (xxiii) di-alkyl-carbamoyl group; with the proviso that when Q is substituted by more than one substituent selected from (ix) carboxyl group, (x) cyano group, (xi) nitro group, (xv) formyl group, (xvii) alkyl-carbonyl group, (xviii) alkoxy-carbonyl group, (xix) sulfo group or (xx) alkylsulfonyl group, these substituents are substituted in the meta position to each other and there is a maximum of two of these substituents present on ring Q;

B is an optionally substituted divalent $C_{1-16}$ hydrocarbon selected from the group consisting of a $C_{1-15}$ alkylene group, $C_{2-16}$ alkenylene group, $C_{2-16}$ alkynylene group, phenylene group and a combination thereof;

X is a bond;

$R^2$ is a hydrogen atom or an optionally substituted $C_{1-18}$ hydrocarbon group selected from an alkyl group, a cycloalkyl group, an alkenyl group, an aralkyl group, or an aryl group; and $R^{3a}$ is an electron withdrawing group selected from (i) —$SO_2R^4$ wherein $R^4$ is an optionally substituted hydrocarbon group, (ii) —CO—$R^5$ wherein $R^5$ is a hydrogen atom or an optionally substituted hydrocarbon group, (iii) —$COOR^6$ wherein $R^6$ is an optionally substituted hydrocarbon group, (iv) —$CON(R^7)R^8$ wherein $R^7$ and $R^8$ respectively are a hydrogen atom or an optionally substituted hydrocarbon group, or, $R^7$ and $R^8$ form a ring together with the adjacent nitrogen atom, (v) a nitro group or (vi) a cyano group;

$R^2$ and $R^{3a}$ may form a ring together with the adjacent nitrogen atom to form a 5 or 6 membered ring selected from the group consisting of 2-, 3-, or 4-piperidyl, 2- or 3-pyrrolyl, and 1,2- 1,4-dihydro-4-pyridyl rings; and $R^1$ is a hydrogen atom, a halogen atom, an optionally substituted $C_{1-18}$ hydrocarbon group selected from an alkyl group, a cycloalkyl group, an alkenyl group, an aralkyl group, or an aryl group, or an $C_{1-6}$ acyl group;

wherein when the hydrocarbon group of $R^1$ or $R^2$ is substituted, then the hydrocarbon group is substituted as follows:

the alkyl, cycloalkyl, alkenyl and alkynyl groups are substituted with one to five substituents selected from the group consisting of (i) nitro group, (ii) hydroxyl group, (iii) cyano group, (iv) carbamoyl group, (v) mono-alkyl-carbamoyl group, (vi) di-alkyl-carbamoyl group, (vii) carboxyl group, (viii) alkoxy-carbonyl group, (ix) sulfo group, (x) halogen atom, (xi) alkoxy group, (xii) phenoxy group, (xiii) halogenophenoxy group, (xiv) alkylthio group, (xv) mercapto group, (xvi) phenylthio group, (xvii) pyridylthio group, (xviii) alkylsulfinyl group, (xix) alkylsulfonyl group, (xx) amino group, (xxi) acylamino group, (xxii) mono-alkylamino group, (xxiii) di-alkylamino group, (xxiv) 4 to 6 member cyclic amino group, (xxv) acyl group, (xxvi) benzoyl group and (xxvii) 5 to 10 member heterocyclic group;

the aralkyl group is substituted with one to four substituents selected from the group consisting of (i) halogen atom, (ii) alkyl group, (iii) halogeno-alkyl group, (iv) alkenyl group, (v) acyl group (vi) alkoxy group, (vii) nitro group (viii) cyano group, (ix) hydroxyl group, (x) alkoxy-carbonyl group, (xi) carbamoyl group, (xii) mono-alkyl-carbamoyl group, (xiii) di-alkyl-carbamoyl, (xiv) mono- alkenyl-carbamoyl group, and (xv) di-alkenyl-carbamoyl group; and the aryl group is substituted with one to four substituents selected from the group consisting of (i) halogen atom, (ii) alkyl group, (iii) halogeno-alkyl group, (iv)

alkenyl group, (v) acyl group, (vi) alkoxy group, (vii) nitro group, (viii) cyano group, (ix) hydroxyl group, (x) alkoxy-carbonyl group, (xi) carbamoyl group, (xii) mono-alkyl-carbamoyl group, (xiii) di-alkyl-carbamoyl, (xiv) mono- alkenyl-carbamoyl group, (xv) di-alkenyl-carbamoyl group and (xvi) oxo group; and wherein when the divalent $C_{1-16}$ hydrocarbon of B is substituted, the divalent $C_{1-16}$ hydrocarbon is substituted as follows:

the alkylene, alkenylene and alkynylene groups are substituted with an optionally substituted alkyl group, optionally substituted aralkyl group, or optionally substituted aryl group, and the phenylene group is substituted with one to four substituents selected from (i) halogen atom, (ii) alkyl group, (iii) alkoxy group, (iv) alkylthio group, (v) hydroxyl group, (vi) carboxyl group, (vii) cyano group, (viii) nitro group, (ix) amino group, (x) mono-alkyl amino group, (xi) di-alkyl amino group, (xii) formyl group, (xiii) mercapto group, (xiv) alkyl-carbonyl group, (xv) alkoxy-carbonyl group, (xvi) sulfo group, (xvii) alkylsulfonyl group, (xviii) carbamoyl group, (xix) mono-alkyl-carbamoyl group, or (xx) di-alkyl-carbamoyl group; with the proviso that when the phenylene group is substituted by more than one substituent selected from (vi) carboxyl group, (vii) cyano group, (viii) nitro group, (xii) formyl group, (xiv) alkyl-carbonyl group, (xv) alkoxy-carbonyl group, (xvi) sulfo group or (xvii) alkylsulfonyl group, these substituents are substituted in the meta position to each other and there is a maximum of two of these substituents present on the phenylene group; or a pharmaceutically acceptable salt thereof.

2. The compound of claim 1, wherein X is a direct bond.

3. A compound of the formula:

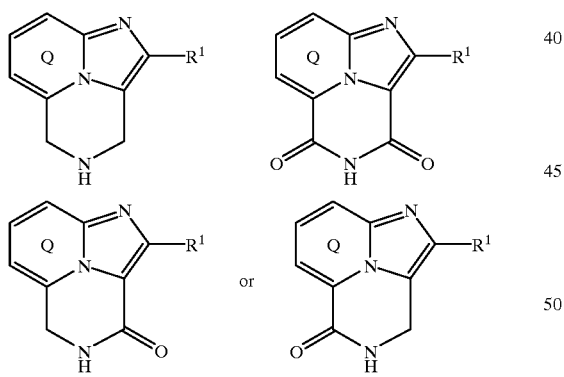

wherein ring Q is optionally substituted with one to three substituents selected from (i) halogen atom, (ii) alkyl group, (iii) halogeno-alkyl group, (iv) alkoxy group, (v) halogeno-alkoxy group, (vi) alkylthio group, (vii) halogeno-alkylthio group, (viii) hydroxyl group, (ix) carboxyl group, (x) cyano group, (xi) nitro group, (xii) amino group, (xiii) mono-alkyl amino group, (xiv) di-alkyl amino group, (xv) formyl group, (xvi) mercapto group, (xvii) alkyl-carbonyl group, (xviii) alkoxy-carbonyl group, (xix) sulfo group, (xx) alkyl-sulfonyl group, (xxi) carbamoyl group, (xxii) mono-alkyl-carbamoyl group, or (xxiii) di-alkyl-carbamoyl group; with the proviso that when Q is substituted by more than one substituent selected from (ix) carboxyl group, (x) cyano group, (xi) nitro group, (xv) formyl group, (xvii) alkyl-carbonyl group, (xviii) alkoxy-carbonyl group, (xix) sulfo group, (xx) alkylsulfonyl group, these substituents are substituted in the meta position to each other and there is a maximum of two of these substituents present on ring Q;

$R^1$ is a hydrogen atom, a halogen atom, an optionally substituted $C_{1-18}$ hydrocarbon group selected from an alkyl group, a cycloalkyl group, an alkenyl group, an aralkyl group, or an aryl group, or an $C_{1-6}$ acyl group;

wherein hydrocarbon group of $R^1$ is substituted, then the hydrocarbon group is substituted as follows:

the alkyl, cycloalkyl, alkenyl and alkynyl groups are substituted with one to five substituents selected from the group consisting of (i) nitro group, (ii) hydroxyl group, (iii) cyano group, (iv) carbamoyl group, (v) mono-alkyl-carbamoyl group, (vi) di-alkyl-carbamoyl group, (vii) carboxyl group, (viii) alkoxy-carbonyl group, (ix) sulfo group, (x) halogen atom, (xi) alkoxy group, (xii) phenoxy group, (xiii) halogenophenoxy group, (xiv) alkylthio group, (xv) mercapto group, (xvi) phenylthio group, (xvii) pyridylthio group, (xviii) alkylsulfinyl group, (xix) alkylsulfonyl group, (xx) amino group, (xxi) acylamino group, (xxii) mono-alkylamino group, (xxiii) di-alkylamino group, (xxiv) 4 to 6 member cyclic amino group, (xxv) acyl group, (xxvi) benzoyl group and (xxvii) 5 to 10 member heterocyclic group;

the aralkyl group is substituted with one to four substituents selected from the group consisting of (i) halogen atom, (ii) alkyl group, (iii) halogeno-alkyl group, (iv) alkenyl group, (v) acyl group, (vi) alkoxy group, (vii) nitro group, (vii) cyano group, (ix) hydroxyl group, (x) alkoxy-carbonyl group, (xi) carbamoyl group, (xii) mono-alkyl-carbamoyl group, (xiii) di-alkyl-carbamoyl group, (xiv) mono-alkenyl-carbamoyl group and (xv) di-alkenyl-carbamoyl group; and the aryl group is substituted with one to four substituents selected from the group consisting of (i) halogen atom, (ii) alkyl group, (iii) halogeno-alkyl group, (iv) alkenyl group, (v) acyl group, (vi) alkoxy group, (vii) nitro group, (viii) cyano group, (ix) hydroxyl group, (x) alkoxy-carbonyl group, (xi) carbamoyl group, (xii) mono-alkyl carbamoyl group, (xiii) di-alkyl-carbamoyl group, (xiv) mono-alkenyl-carbamoyl group, (xv) di-alkenyl-carbamoyl group and (xvi) oxo group; or a pharmaceutically acceptable salt thereof.

4. A compound of the formula:

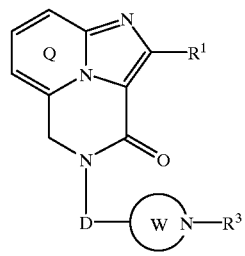

wherein $R^1$ is a hydrogen atom, a halogen atom, an optionally substituted $C_{1-18}$ hydrocarbon group selected from an alkyl group, a cycloalkyl group, an alkenyl group, an aralkyl group, an aryl group or an $C_{1-6}$ acyl group; $R^3$ is (i) —$SO_2R^4$ wherein $R^4$ is an optionally substituted hydrocarbon group, (ii) —$COR^5$ wherein $R^5$ is a hydrogen atom or an optionally substituted hydrocarbon group, (iii) —$COOR^6$ wherein $R^6$ is an optionally substituted hydrocarbon group, (iv) —$CON(R^7)R^8$ wherein $R^7$ and $R^8$ respectively are a hydrogen atom or an optionally substituted hydrocarbon group, (v) a nitro group or (vi) a cyano group; ring Q is optionally substituted with one to three substituents selected from (i) halogen atom, (ii) alkyl group, (iii) halogeno-alkyl group, (iv) alkoxy group, (v) halogeno-alkoxy group, (vi) alkylthio group, (vii) halogeno-alkylthio group, (viii) hydroxyl group, (ix) carboxyl group, (x) cyano group, (xi) nitro group, (xii) amino group, (xiii) mono-alkyl amino group, (xiv) di-alkyl amino group, (xv) formyl group, (xvi) mercapto group, (xvii) alkyl-carbonyl group, (xviii) alkoxy-carbonyl group, (xix) sulfo group, (xx) alkylsulfonyl group, (xxi) carbamoyl group, (xxii) mono-alkyl-carbamoyl group or (xxiii) di-alkyl-carbamoyl group; with the proviso that when Q is substituted by more than one substituent selected from (ix) carboxyl group, (x) cyano group, (xi) nitro group, (xv) formyl group, (xvii) alkyl-carbonyl group, (xviii) alkoxy-carbonyl group, (xix) sulfo group, (xx) alkylsulfonyl group, these substituents are substituted in the meta position to each other and there is a maximum of two of these substituents present on ring Q; D is a bond or an optionally substituted divalent $C_{1-16}$ hydrocarbon group selected from the group consisting of a $C_{1-15}$ alkylene group, $C_{2-16}$ alkenylene group, $C_{2-16}$ alkylene group, phenylene group and a combination thereof; ring W is

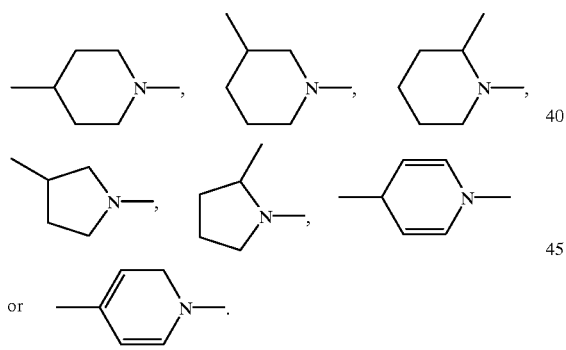

which is optionally substituted;
wherein when the hydrocarbon group of $R^1$ is substituted, then the hydrocarbon group is substituted as follows:
the alkyl, cycloalkyl, alkenyl and alkynyl groups are substituted with one to five substituents selected from the group consisting of (i) nitro group, (ii) hydroxyl group, (iii) cyano group, (iv) carbamoyl group, (v) mono-alkyl-carbamoyl group, (vi) di-alkyl-carbamoyl group, (vii) carboxyl group, (viii) alkoxy-carbonyl group, (ix) sulfo group, (x) halogen atom, (xi) alkoxy group, (xii) phenoxy group, (xiii) halogenophenoxy group, (xiv) alkylthio group, (xv) mercapto group, (xvi) phenylthio group, (xvii) pyridylthio group, (xviii) alkylsulfinyl group, (xix) alkylsulfonyl group, (xx) amino group, (xxi) acylamino group, (xxii) mono-alkylamino group, (xxiii) di-alkylamino group, (xxiv) 4 to 6 member cyclic amino group, (xxv) acyl group, (xxvi) benzoyl group and (xxvii) 5 to 10 member heterocyclic group;

the aralkyl group is substituted with one to four substituents selected from the group consisting of (i) halogen atom, (ii) alkyl group, (iii) halogeno-alkyl group, (iv) alkenyl group, (v) acyl group, (vi) alkoxy group, (vii) nitro group, (viii) cyano group, (ix) hydroxyl group, (x) alkoxy-carbonyl group, (xi) carbamoyl group, (xii) mono-alkyl-carbamoyl group, (xiii) di-alkyl-carbamoyl group, (xiv) mono-alkenyl-carbamoyl group and (xv) di-alkenyl-carbamoyl group; and the aryl group is substituted with one to four substituents selected from the group consisting of (i) halogen atom, (ii) alkyl group, (iii) halogeno-alkyl group, (iv) alkenyl group, (v) acyl group, (vi) alkoxy group, (vii) nitro group, (viii) cyano group, (ix) hydroxyl group, (x) alkoxy-carbonyl group, (xi) carbamoyl group, (xii) mono-alkyl-carbamoyl group, (xiii) di-alkyl-carbamoyl group, (xiv) mono-alkenyl-carbamoyl group, (xv) di-alkenyl-carbamoyl group and (xvi) oxo group;

wherein when the divalent $C_{1-16}$ hydrocarbon of D is substituted, the divalent $C_{1-16}$ hydrocarbon is substituted as follows:
the alkylene, alkenylene and alkynylene groups are substituted with an optionally substituted alkyl, optionally substituted aralkyl or optionally substituted aryl as defined for $R^1$,
the phenylene group is substituted with one to four substituents selected from the group consisting of (i) halogen atom, (ii) alkyl group, (iii) alkoxy group, (iv) alkylthio group, (v) hydroxyl group, (vi) carboxyl group, (vii) cyano group, (viii) nitro group, (ix) amino group, (x) mono-alkyl amino group, (xi) di-alkyl amino group, (xii) formyl group, (xiii) mercapto group, (xiv) alkyl-carbonyl group, (xv) alkoxy-carbonyl group, (xvi) sulfo group, (xvii) alkylsulfonyl group, (xviii) carbamoyl group, (xix) mono-alkyl-carbamoyl group or (xx) di-alkyl-carbamoyl group; with the proviso that when the phenylene group is substituted by more than one substituent selected from (vi) carboxyl group, (vii) cyano group, (viii) nitro group, (xii) formyl group, (xiv) alkyl-carbonyl group, (xv) alkoxy-carbonyl group, (xvi) sulfo group, (xvii) alkylsulfonyl group, these substituents are substituted in the meta position to each other and there is a maximum of two of these substituents present on the phenylene group; and wherein ring W is optionally substituted with one to three substituents selected from (i) halogen atom, (ii) alkyl group, (iii) halogeno-alkyl group, (iv) alkoxy group, (v) halogeno-alkoxy group, (vi) alkylthio group, (vii) halogeno-alkylthio group, (viii) hydroxyl group, (ix) carboxyl group, (x) cyano group, (xi) nitro group, (xii) amino group, (xiii) mono-alkyl amino group, (xiv) di-alkyl amino group, (xv) formyl group, (xvi) mercapto group, (xvii) alkyl-carbonyl group, (xviii) alkoxy-carbonyl group, (xix) sulfo group, (xx) alkylsulfonyl group, (xxi) carbamoyl group, (xxii) mono-alkyl-carbamoyl group or (xxiii) di-alkyl-carbamoyl group; or pharmaceutically acceptable salt thereof.

5. A compound of claim 1, wherein the ring Q is optionally substituted with one to three substituents selected from the group consisting of (i) halogen atom, (ii) a $C_{1-4}$ alkyl group, (iii) a $C_{1-4}$ alkoxy group, (iv) a $C_{1-4}$ alkylthio group, (v) a hydroxyl group, (vi) a carboxyl group, (vii) a cyano group, (viii) a nitro group, (ix) an amino group, (x) a mono- or di-$C_{1-4}$ alkyl group, (xi) a formyl group, (xii) a mercapto group, (xiii) a $C_{1-4}$ alkyl-carbonyl group, (xiv) a $C_{1-4}$ alkoxy-carbonyl group, (xv) a sulfo group, (xvi) a $C_{1-4}$ alkyl sulfonyl group, (xvii) a carbamoyl group and (xviii) a mono- or di-$C_{1-4}$ alkyl-carbamoyl group; with the proviso that when Q is substituted by more than one substituent selected from (vi) a carboxyl group, (vii) a cyano group, (viii) a nitro group, (xi) a formyl group, (xiii) a $C_{1-4}$ alkyl-carbonyl group, (xiv) a $C_{1-4}$ alkoxy-carbonyl group, (xv) a sulfo group, or (xvi) a $C_{1-4}$ alkyl sulfonyl group, these substituents are substituted in the meta position to each other and there is a maximum of two of these substituents present on ring Q.

6. A compound of claim 1, wherein the ring Q is unsubstituted.

7. A compound of claim 1, wherein $R^1$ is a hydrogen atom, an optionally substituted alkyl group, an optionally substituted alkenyl group, an optionally substituted aralkyl group, an optionally substituted aryl group, an alkoxy carbonyl group, an alkyl carbamoyl group or an alkanoyl group.

8. A compound of claim 1, wherein $R^1$ is a hydrogen atom, a $C_{1-6}$ alkyl group or a phenyl group.

9. A compound of claim 1, wherein $R^2$ is a hydrogen atom, an optionally substituted alkyl group or an optionally substituted alkenyl group.

10. A compound of claim 1, wherein B is a $C_{2-10}$ alkylene group.

11. A compound of claim 1, wherein B is a group of the formula:

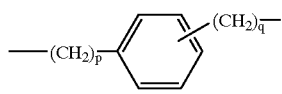

wherein p and q are independently an integer of 0 to 5.

12. A compound of claim 1, wherein B is a $C_{3-8}$ alkylene group.

13. A compound of claim 2, wherein the ring Q is unsubstituted.

14. A compound of claim 2, wherein $R^1$ is a hydrogen atom, an optionally substituted alkyl group or an optionally substituted alkenyl group.

15. A compound of claim 2, wherein $R^1$ is a hydrogen atom or a $C_{1-6}$ alkyl group.

16. A compound of claim 2, wherein $R^2$ is a hydrogen atom or a $C_{1-6}$ alkyl group.

17. A compound of claim 2, wherein $R^2$ is a hydrogen atom.

18. A compound of claim 2, wherein B is a $C_{2-10}$ alkylene group.

19. A compound of claim 2, wherein B is a $C_{3-8}$ alkylene group.

20. A compound of claim 2, wherein the electron-withdrawing group represented by $R^3$ is —$SO_2R^{4a}$ wherein $R^{4a}$ is an optionally substituted alkyl group, an optionally substituted alkenyl group, an optionally substituted aralkyl group or an optionally substituted aryl group.

21. A compound of claim 20, wherein $R^{4a}$ is a halogeno-$C_{1-6}$ alkyl group.

22. A compound of claim 4, wherein D is an optionally substituted divalent hydrocarbon.

23. A compound of claim 4, wherein $R^3$ is —$SO_2R^4$ wherein $R^4$ is an optionally substituted hydrocarbon group, —$COR^5$ wherein $R^5$ is a hydrogen atom or an optionally substituted hydrocarbon group, —$COOR^6$ wherein $R^6$ is an optionally substituted hydrocarbon group or —$CON(R^7)R^8$ wherein $R^7$ and $R^8$ respectively are a hydrogen atom or an optionally substituted hydrocarbon group.

24. A compound of claim 4, wherein ring Q is unsubstituted.

25. A compound of claim 4, wherein ring W is

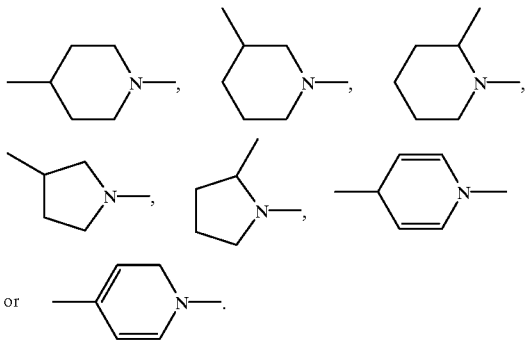

26. A compound of claim 4, wherein D is $C_{1-6}$ alkylene.
27. A compound of claim 4, wherein D is $C_{1-6}$ alkylene.
28. A compound of claim 4, wherein D is ethylene.
29. A compound of claim 4, wherein ring W is

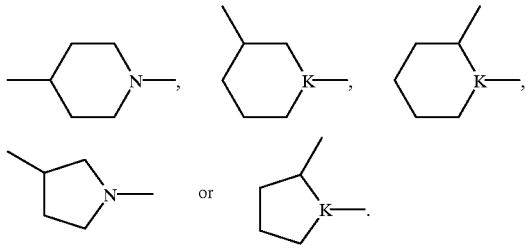

30. A compound of claim 4, wherein $R^3$ is —$SO_2R^4$ wherein $R^4$ is an optionally substituted hydrocarbon group.

31. A compound of claim 30, wherein $R^4$ is an optionally halogenated $C_{1-6}$ alkyl group.

32. A compound of claim 4, wherein ring W is

33. A compound of claim 1, which is 4,5-dihydro-4-(1-trifluoromethanesulfonylpiperidine-4-ylmethyl)-3H-1,4,8b-triazaacenaphthylene-3-one, or a pharmaceutically acceptable salt thereof.

34. A compound of claim 1, which is 4,5-dihydro-4-[2-(1-trifluoromethanesulfonylpiperidin-4-ylmethyl)-3H-1,4,8b-triazaacenaphthylene-3-one, or a pharmaceutically acceptable salt thereof.

35. A compound of claim 1, which is 4,5-dihydro-4-[4-(trifluoromethanesulfonamido)butan-1-yl]-3H-1,4,8b-triazaacenaphthylen-3-one or a pharmaceutically acceptable salt thereof, or 1,2-dihydro-3-methyl-1-[5-(trifluoromethanesulfonamido)pentan-1-yl]-1,4,7b-triazacyclopento[cd]inden-2-one or a pharmaceutically acceptable salt thereof.

36. A process for producing a compound of claim 1, which comprises reacting a compound of the formula:

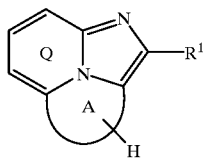

wherein Q, R¹ and A are as defined in claim 1, or a salt thereof with a compound of the formula:

E¹—Y wherein E¹ is a leaving group and the Y is as defined in claim 1, or a salt thereof.

37. A composition which consists of a compound of claim 1 in a pharmaceutically acceptable carrier or diluent.

38. A pharmaceutical composition comprising an effective amount of the compound of claim 1, in a pharmaceutically acceptable carrier or diluent.

39. A therapeutic composition for inhibiting platelet-derived growth factor, which comprises an effective amount of the compound of claim 1, in a pharmaceutically acceptable carrier or diluent.

40. A therapeutic composition for a hypertension disease, which comprises an effective amount of the compound of claim 1, in a pharmaceutically acceptable carrier or diluent.

41. A therapeutic composition for a renal disease, which comprises an effective amount of the compound of claim 1 in a pharmaceutically acceptable carrier or diluent.

42. A pharmaceutical composition for lowering lipid level, which comprises an effective amount of the compound of claim 1, in a pharmaceutically acceptable carrier or diluent.

43. A method for treating a disease derived from platelet-derived growth factor which comprises administering an effective amount of a compound of claim 1 together with a pharmaceutecally acceptable carrier or diluent to mammal.

44. A method for inhibiting platelet-derived growth factor in a mammal, which comprises administering to said mammal in need thereof an effective amount of a compound of claim 1 or a pharmaceutically acceptable salt thereof.

45. A method for treating hypertension in a mammal, which comprises administering to said mammal in need thereof an effective amount of a compound of claim 1 or a pharmaceutically acceptable salt thereof.

46. A method for treating a renal disease in a mammal, which comprises administering to said mammal in need thereof an effective amount of a compound of claim 1 or a pharmaceutically acceptable salt thereof.

47. A method for lowering lipid level in a mammal, which comprises administering to said mammal in need thereof an effective amount of a compound of claim 1 or a pharmaceutically acceptable salt thereof.

* * * * *